US009963427B2

(12) United States Patent
Johnson et al.

(10) Patent No.: US 9,963,427 B2
(45) Date of Patent: *May 8, 2018

(54) DITHIOL MUCOLYTIC AGENTS

(71) Applicant: PARION SCIENCES, INC., Durham, NC (US)

(72) Inventors: Michael R. Johnson, Chapel Hill, NC (US); William R. Thelin, Chapel Hill, NC (US); Ronald A. Aungst, Jr., Clifton Park, NY (US)

(73) Assignee: PARION SCIENCES, INC., Durham, NC (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/067,472

(22) Filed: Mar. 11, 2016

(65) Prior Publication Data

US 2016/0194278 A1  Jul. 7, 2016

Related U.S. Application Data

(62) Division of application No. 14/458,898, filed on Aug. 13, 2014, now Pat. No. 9,346,753.

(60) Provisional application No. 61/869,378, filed on Aug. 23, 2013.

(51) Int. Cl.
| | | |
|---|---|---|
| A61K 31/145 | (2006.01) | |
| A61K 31/155 | (2006.01) | |
| A61K 31/165 | (2006.01) | |
| A61K 31/27 | (2006.01) | |
| A61K 31/382 | (2006.01) | |
| A61K 31/4965 | (2006.01) | |
| A61K 33/14 | (2006.01) | |
| A61K 45/06 | (2006.01) | |
| A61K 9/00 | (2006.01) | |
| C07C 323/16 | (2006.01) | |
| C07D 241/32 | (2006.01) | |
| C07D 339/08 | (2006.01) | |
| A61K 31/047 | (2006.01) | |
| A61K 31/138 | (2006.01) | |
| A61K 31/7004 | (2006.01) | |

(52) U.S. Cl.
CPC .......... *C07C 323/16* (2013.01); *A61K 9/0043* (2013.01); *A61K 9/0073* (2013.01); *A61K 9/0082* (2013.01); *A61K 31/047* (2013.01); *A61K 31/138* (2013.01); *A61K 31/145* (2013.01); *A61K 31/155* (2013.01); *A61K 31/165* (2013.01); *A61K 31/27* (2013.01); *A61K 31/382* (2013.01); *A61K 31/4965* (2013.01); *A61K 31/7004* (2013.01); *A61K 33/14* (2013.01); *A61K 45/06* (2013.01); *C07D 241/32* (2013.01); *C07D 339/08* (2013.01)

(58) Field of Classification Search
CPC .................................................. A61K 31/145
See application file for complete search history.

(56) References Cited

U.S. PATENT DOCUMENTS

| | | | |
|---|---|---|---|
| 3,663,690 A | 5/1972 | Eichel et al. | |
| 6,858,614 B2 | 2/2005 | Johnson | |
| 6,858,615 B2 | 2/2005 | Johnson | |
| 6,903,105 B2 | 6/2005 | Johnson | |
| 6,995,160 B2 | 2/2006 | Johnson | |
| 7,026,325 B2 | 4/2006 | Johnson | |
| 7,030,117 B2 | 4/2006 | Johnson | |
| 7,064,129 B2 | 6/2006 | Johnson et al. | |
| 7,186,833 B2 | 3/2007 | Johnson | |
| 7,189,719 B2 | 3/2007 | Johnson | |
| 7,192,958 B2 | 3/2007 | Johnson | |
| 7,192,959 B2 | 3/2007 | Johnson | |
| 7,192,960 B2 | 3/2007 | Johnson | |
| 7,241,766 B2 | 7/2007 | Johnson | |
| 7,247,636 B2 | 7/2007 | Johnson | |
| 7,247,637 B2 | 7/2007 | Johnson et al. | |
| 7,317,013 B2 | 1/2008 | Johnson | |
| 7,332,496 B2 | 2/2008 | Johnson | |
| 7,345,044 B2 | 3/2008 | Johnson | |
| 7,368,447 B2 | 5/2008 | Johnson et al. | |
| 7,368,450 B2 | 5/2008 | Johnson | |
| 7,368,451 B2 | 5/2008 | Johnson et al. | |
| 7,375,107 B2 | 5/2008 | Johnson | |
| 7,388,013 B2 | 6/2008 | Johnson et al. | |
| 7,399,766 B2 | 7/2008 | Johnson | |
| 7,410,968 B2 | 8/2008 | Johnson et al. | |
| 7,745,442 B2 | 6/2010 | Johnson et al. | |
| 7,807,834 B2 | 10/2010 | Johnson et al. | |
| 7,820,678 B2 | 10/2010 | Johnson | |
| 7,842,697 B2 | 11/2010 | Johnson | |

(Continued)

FOREIGN PATENT DOCUMENTS

| | | |
|---|---|---|
| CN | 101415405 | 4/2009 |
| WO | WO 2003/088961 | 10/2003 |
| WO | WO 2005/094269 | 10/2005 |
| WO | WO 2010/086099 | 8/2010 |
| WO | WO 2012/035076 | 3/2012 |

OTHER PUBLICATIONS

Firooznia, Bioorganic & Medicinal Chemistry Letters 12 (2002) 3059-3062.*
Written Opinion dated Oct. 17, 2016 in Singaporean Patent Application No. 11201601291Q.
English translation of International Search Report and Written Opinion dated Nov. 14, 2014, in PCT/US 14/50877 filed Aug. 13, 2014.
J. Stolk, et al., "In vitro effect of a mucolytic thiol agent on the activity of polymorphonuclear leucocyte elastase and antileucoprotease", Thorax, vol. 41, 1986, pp. 840-845.
Office Action dated Jul. 14, 2016 in Israeli Patent Application No. 244112 (submitting English translation only).

(Continued)

*Primary Examiner* — Layla D Berry
(74) *Attorney, Agent, or Firm* — Cooley LLP

(57) ABSTRACT

Provided are dithiol mucolytic agents. These agents increase the liquefaction of mucus in a patient with excessive mucus or mucus with increased viscoelastic, cohesive, or adhesive properties. Also provided are a variety of methods of treatment using these inventive mucolytic agents.

36 Claims, 8 Drawing Sheets

(56) References Cited

U.S. PATENT DOCUMENTS

Figure 1:
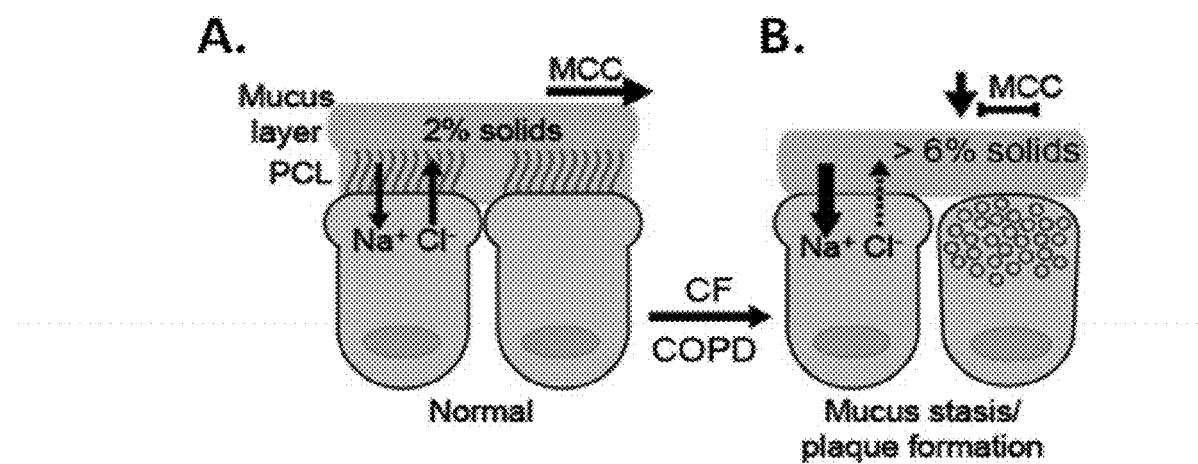
Figure 2:
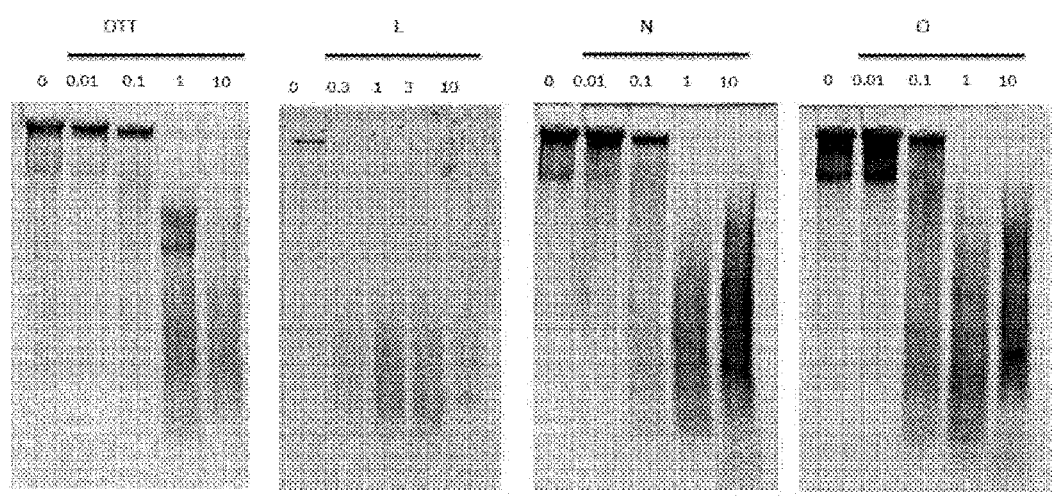

| | | |
|---|---|---|
| 7,868,010 B2 | 1/2011 | Johnson et al. |
| 7,875,619 B2 | 1/2011 | Johnson |
| 7,956,059 B2 | 6/2011 | Johnson |
| 7,981,898 B2 | 7/2011 | Johnson et al. |
| 8,008,494 B2 | 8/2011 | Johnson |
| 8,022,210 B2 | 9/2011 | Johnson |
| 8,058,278 B2 | 11/2011 | Johnson et al. |
| 8,124,607 B2 | 2/2012 | Johnson |
| 8,143,256 B2 | 3/2012 | Johnson |
| 8,163,758 B2 | 4/2012 | Johnson et al. |
| 8,198,286 B2 | 6/2012 | Johnson |
| 8,211,895 B2 | 7/2012 | Johnson et al. |
| 8,227,474 B2 | 7/2012 | Johnson |
| 8,288,391 B2 | 10/2012 | Johnson et al. |
| 8,314,105 B2 | 11/2012 | Johnson |
| 8,324,218 B2 | 12/2012 | Johnson |
| 8,431,579 B2 | 4/2013 | Johnson et al. |
| 8,507,497 B2 | 8/2013 | Johnson et al. |
| 8,551,534 B2 | 10/2013 | Boucher et al. |
| 8,575,176 B2 | 11/2013 | Johnson |
| 8,669,262 B2 | 3/2014 | Johnson |
| 8,846,688 B2 | 9/2014 | Johnson |
| 8,980,898 B2 | 3/2015 | Johnson et al. |
| 9,029,382 B2 | 5/2015 | Johnson |
| 9,072,738 B2 | 7/2015 | Johnson |
| 9,346,753 B2 | 5/2016 | Johnson et al. |
| 2001/0037037 A1 | 11/2001 | Dietliker et al. |
| 2004/0147748 A1 | 7/2004 | Chen et al. |
| 2005/0059639 A1 | 3/2005 | Wei |
| 2005/0090505 A1 | 4/2005 | Johnson et al. |
| 2005/0131063 A1 | 6/2005 | Stamler et al. |
| 2006/0142306 A1 | 6/2006 | Johnson |
| 2007/0265280 A1 | 11/2007 | Johnson |
| 2008/0103148 A1 | 5/2008 | Johnson |
| 2008/0131500 A1 | 6/2008 | Chang |
| 2008/0167466 A1 | 7/2008 | Johnson et al. |
| 2008/0176863 A1 | 7/2008 | Johnson et al. |
| 2008/0200476 A1 | 8/2008 | Johnson |
| 2008/0293740 A1 | 11/2008 | Johnson et al. |
| 2009/0018144 A1 | 1/2009 | Johnson et al. |
| 2009/0062308 A1 | 3/2009 | Johnson |
| 2009/0163572 A1 | 6/2009 | Born |
| 2009/0192227 A1 | 7/2009 | Tirouvanziam et al. |
| 2009/0253714 A1 | 10/2009 | Johnson et al. |
| 2009/0324724 A1 | 12/2009 | Johnson |
| 2010/0074881 A1 | 3/2010 | Boucher et al. |
| 2010/0183587 A1 | 7/2010 | Dana et al. |
| 2010/0272814 A1 | 10/2010 | Skogvall |
| 2011/0195973 A1 | 8/2011 | Johnson |
| 2013/0060034 A1 | 3/2013 | Johnson |
| 2013/0324559 A1 | 12/2013 | Johnson et al. |
| 2014/0031371 A1 | 1/2014 | Johnson |
| 2014/0096765 A1 | 4/2014 | Boucher et al. |
| 2014/0107133 A1 | 4/2014 | Johnson |
| 2014/0142118 A1 | 5/2014 | Johnson |
| 2014/0170244 A1 | 6/2014 | Johnson |
| 2014/0171447 A1 | 6/2014 | Johnson |
| 2014/0179625 A1 | 6/2014 | Johnson |
| 2015/0056305 A1 | 2/2015 | Johnson et al. |
| 2015/0099764 A1 | 4/2015 | Johnson et al. |
| 2015/0166487 A1 | 6/2015 | Johnson |
| 2015/0166488 A1 | 6/2015 | Johnson |
| 2015/0290189 A1 | 10/2015 | Johnson |
| 2015/0299142 A1 | 10/2015 | Johnson |
| 2015/0307530 A1 | 10/2015 | Johnson et al. |
| 2015/0376145 A1 | 12/2015 | Johnson |
| 2015/0376146 A1 | 12/2015 | Johnson |
| 2016/0222023 A1 | 8/2016 | Johnson et al. |
| 2016/0318861 A1 | 11/2016 | Johnson et al. |

OTHER PUBLICATIONS

International Search Report and Written Opinion for International Application No. PCT/US2013/057588, dated Jan. 10, 2014, 8 pages.
Supplementary European Search Report for European Application No. 14838105.6, dated May 10, 2017, 6 pages.
Second Written Opinion for Singapore Application No. 11201601291Q, dated May 8, 2017, 7 pages.
International Search Report and Written Opinion for International Application No. PCT/US2016/015353, dated Jun. 10, 2016, 11 pages.
International Search Report and Written Opinion for International Application No. PCT/US2016/029729, dated Jul. 6, 2016, 7 pages.
Acros Organics N.V., "Acetylsalicylic acid," Material Safety Data Sheet, ACC# 00300, Retrieved from the Internet: <URL: https://fscimage.fishersci.com/msds/00300.htm>, Retrieved on Feb. 8, 2017, 6 pages.
Burns, J. A. et al., "Selective reduction of disulfides by tris(2-carboxyethyl)phosphine," J. Org. Chem. 56(8):2648-2650 (1991).
Cayman Chemical Company, "TCEP (hydrochloride)", Safety Data Sheet, Jan. 17, 2014, 6 pages.
CSID:11492484, http://www.chemspider.com/Chemical-Structure.11492484.html (accessed 18:59, Dec. 14, 2017), 3 pages.
Hospira Inc., "Acetylcysteine—acetylcysteine solution," Material Safety Data Sheet, Obtained by Global Safety Management, Inc., Oct. 17, 2012.
Jayaraman, S. et al, "Noninvasive in vivo fluorescence measurement of airway-surface liquid depth, salt concentration, and pH," The Journal of Clinical Investigation, Feb. 2001, 107(3):317-324.
Kermack, W. O. et al., "38. Attempts to find new antimalarials. Part XVIII. Derivatives of m-phenanthroline," Journal of the Chemical Society (Resumed), 1942, pp. 213-218.
Lee, R. L. et al., "Thioredoxin and dihydrolipoic acid inhibit elastase activity in cystic fibrosis sputum," American Journal of Physiology—Lung Cellular and Molecular Physiology, 289(5):L875-L882 (Nov. 2005).
Mindolli, P. B. et al., "Improved diagnosis of pulmonary tuberculosis using bleach microscopy method," J. Clin. Diagn. Res., Jul. 2013; 7(7):1336-1338.
Nash, E. F. et al., "Nebulized and oral thiol derivatives for pulmonary disease in cystic fibrosis (Review)," The Cochrane Collaboration, Cochrane Database of Systematic Reviews 2009, Issue 1, Art. No. CD007168. DOI: 10.1002/14651858.CD007168.pub2, 34 pages.
Optima Chemical, Trimethylphosphine 98% (TMP), CAS No. 594-09-2, 2 pages.
Pubchem: SID 162750564, May 22, 2013 [retrieved on Apr. 26, 2016]. Retrieved from the Internet. <URL: https://pubchem.ncbi.nlm.nih.gov/substance/162750564#section=Top>, 5 pages.
Pubchem: SID 55133019, Oct. 8, 2008. [retrieved on Feb. 3, 2016]. Retrieved from the Internet. <URL: https://pubchem.ncbi.nlm.nih.gov/substance/55133019#section=Top>, 5 pages.
Noszal, B. et al., "Population, Acid-Base, and Redox Properties of N-Acetylcysteine Conformers," J. Med. Chem. 2000, 43(11):2176-2182.

* cited by examiner

DITHIOL MUCOLYTIC AGENTS

CONTINUING APPLICATION INFORMATION

This application is a Divisional of U.S. application Ser. No. 14/458,898, filed on Aug. 13, 2014, which claims benefit to 61/869,378, filed on Aug. 23, 2013.

BACKGROUND OF THE INVENTION

Field of the Invention

The present invention relates to novel dithiol mucolytic agents. The present invention also includes a variety of methods of treatment using these inventive mucolytic agents.

Description of the Background

The mucosal surfaces at the interface between the environment and the body have evolved a number of "innate defense", i.e., protective mechanisms. The mucus transport system is the fundamental defense of the airways against inhaled particulates/infectious agents. Inhaled particles are trapped in the mucus layer and subsequently propelled out of the lungs via mucus clearance. The mucus transport system requires that mucus be well hydrated to facilitate cilliary clearance. In the absence of sufficient mucus hydration, the mucus becomes excessively viscous and adherent, which can lead to airway mucus accumulation and infection.

Typically, the quantity of the liquid layer on a mucosal surface reflects the balance between epithelial liquid secretion, often reflecting anion ($Cl^-$ and/or $HCO_3^-$) secretion coupled with water (and a cation counter-ion), and epithelial liquid absorption, often reflecting $Na^+$ absorption, coupled with water and counter anion ($Cl^-$ and/or $HCO_3^-$). Many diseases of mucosal surfaces are caused by too little protective liquid on those mucosal surfaces created by an imbalance between secretion (too little) and absorption (relatively too much). The defective salt transport processes that characterize these mucosal dysfunctions reside in the epithelial layer of the mucosal surface.

Abnormalities in the mucus transport system characterize a complex of muco-obstructive airway diseases that include cystic fibrosis (CF) and chronic bronchitis (CB). Normal mucus clearance requires 1) adequate hydration of the airway surface and 2) an absence of strong adhesive and cohesive interactions between mucus and cell surface. Hydration is defined by the concentrations of mucins in the periciliary and mucus layers. Ion transport properties regulate the amount of salt and water (i.e. the solvent) and goblet cells and glands control the quantity of mucins on the airway surface. Subjects with mucus-obstructive diseases including cystic fibrosis (CF), chronic bronchitis associated with cigarette smoke exposure, i.e., COPD, and asthma exhibit increases in mucus concentration as quantified by % solids (FIG. 1), as a result of reduced airway hydration and mucin hypersecretion, consequent to goblet cell and glandular hyperplasia. Both as a function of disease severity, and in acute exacerbations, raised mucin concentrations produce adherent mucus that sticks to epithelial cells, impairs clearance, triggering inflammatory responses and airway wall injury, and serves as a growth medium for pathogenic microorganisms. Clearly, enhancing the clearance of such thickened/adhered mucus from the airways is likely to benefit patients with mucus-obstructive diseases.

Chronic bronchitis (CB), including the most common lethal genetic form of chronic bronchitis, cystic fibrosis (CF), are diseases that reflect the body's failure to clear mucus normally from the lungs, which ultimately produces chronic airways infection. In the normal lung, the primary defense against chronic intrapulmonary airways infection (chronic bronchitis) is mediated by the continuous clearance of mucus from bronchial airway surfaces. This function in health effectively removes from the lung potentially noxious toxins and pathogens. Recent data indicate that the initiating problem, i.e., the "basic defect," in both CB and CF is the failure to clear mucus from airway surfaces. The failure to clear mucus reflects an imbalance between the amount of liquid and mucin on airway surfaces. This "airway surface liquid" (ASL) is primarily composed of salt and water in proportions similar to plasma (i.e., isotonic). Mucin macromolecules organize into a well-defined "mucus layer" which normally traps inhaled bacteria and is transported out of the lung via the actions of cilia which beat in a watery, low viscosity solution termed the "periciliary liquid" (PCL). In the disease state, there is an imbalance in the quantities of mucus and ASL on airway surfaces. This results in a relative reduction in ASL which leads to mucus concentration, reduction in the lubricant activity of the PCL, and a failure to clear mucus via ciliary activity to the mouth. The reduction in mechanical clearance of mucus from the lung leads to chronic bacterial colonization of mucus adherent to airway surfaces. It is the chronic retention of bacteria, the failure of local antimicrobial substances to kill mucus-entrapped bacteria on a chronic basis, and the consequent chronic inflammatory responses of the body to this type of surface infection, that lead to the syndromes of CB and CF.

The current afflicted population in the U.S. is 12,000,000 patients with the acquired (primarily from cigarette smoke exposure) form of chronic bronchitis and approximately 30,000 patients with the genetic form, cystic fibrosis. Approximately equal numbers of both populations are present in Europe. In Asia, there is little CF but the incidence of CB is high and, like the rest of the world, is increasing.

There is currently a large, unmet medical need for products that specifically treat CB and CF at the level of the basic defect that cause these diseases. The current therapies for chronic bronchitis and cystic fibrosis focus on treating the symptoms and/or the late effects of these diseases. Thus, for chronic bronchitis, β-agonists, inhaled steroids, anti-cholinergic agents, and oral theophyllines and phosphodiesterase inhibitors are all in development. However, none of these drugs treat effectively the fundamental problem of the failure to clear mucus from the lung. Similarly, in cystic fibrosis, the same spectrum of pharmacologic agents is used. These strategies have been complemented by more recent strategies designed to clear the CF lung of the DNA ("Pulmozyme"; Genentech) that has been deposited in the lung by neutrophils that have futilely attempted to kill the bacteria that grow in adherent mucus masses and through the use of inhaled antibiotics ("TOBI") designed to augment the lungs' own killing mechanisms to rid the adherent mucus plaques of bacteria. A general principle of the body is that if the initiating lesion is not treated, in this case mucus retention/obstruction, bacterial infections became chronic and increasingly refractory to antimicrobial therapy. Thus, a major unmet therapeutic need for both CB and CF lung diseases is an effective means of mobilizing airway mucus and promoting its clearance, with bacteria, from the lung.

Other mucosal surfaces in and on the body exhibit subtle differences in the normal physiology of the protective surface liquids on their surfaces but the pathophysiology of disease reflects a common theme, i.e., too little protective surface liquid and impaired mucus clearance. For example, in xerostomia (dry mouth) the oral cavity is depleted of liquid due to a failure of the parotid sublingual and submandibular glands to secrete liquid. Similarly, keratoconjunctivitis sicca (dry eye) is caused insufficient tear volume resulting from the failure of lacrimal glands to secrete liquid or excessive evaporative fluid loss. In rhinosinusitis, there is an imbalance, as in CB, between mucin secretion, relative airway surface liquid depletion, and mucus stasis. Finally, in the gastrointestinal tract, failure to secrete Cl− (and liquid) in the proximal small intestine, combined with increased $Na^+$ (and liquid) absorption in the terminal ileum leads to the distal intestinal obstruction syndrome (DIOS). In older patients excessive $Na^+$ (and volume) absorption in the descending colon produces constipation and diverticulitis.

The high prevalence of both acute bronchitis and chronic bronchitis indicates that this disease syndrome is a major health problem in the U.S. Despite significant advancements in the etiology of mucus obstructive diseases, pharmacotherapy of both CF and COPD have been characterized by an aging array of therapies, typically including inhaled steroids and bronchodilators for maintenance, and antibiotics and high-dose steroids for exacerbations. Clearly, what are needed are drugs that are more effective at restoring the clearance of mucus from the lungs of patients with CB/CF. The value of these new therapies will be reflected in improvements in the quality and duration of life for both the CF and the CB populations.

One approach to increase mucus clearance is to enhance the transportability of mucins via the disruption of the polymeric mucus structure. Mucin proteins are organized into high molecular weight polymers via the formation of covalent (disulfide) and non-covalent bonds. Disruption of the covalent bonds with reducing agents is a well-established method to reduce the viscoelastic properties of mucus in vitro and is predicted to minimize mucus adhesiveness and improve clearance in vivo. Reducing agents are well known to decrease mucus viscosity in vitro and commonly used as an aid to processing sputum samples (Hirsch, S. R., Zastrow, J. E., and Kory, R. C. Sputum liquefying agents: a comparative in vitro evaluation. *J. Lab. Clin. Med.* 1969. 74:346-353). Examples of reducing agents include sulfide containing molecules capable of reducing protein di-sulfide bonds including, but not limited to, N-acetyl cysteine, N-acystelyn, carbocysteine, cysteamine, glutathione, dithiothreitol (DTT), and thioredoxin containing proteins.

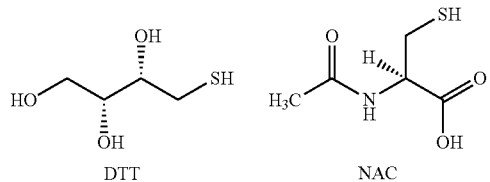

N-acetyl cysteine (NAC) is approved for use in conjunction with chest physiotherapy to loosen viscid or thickened airway mucus. Clinical studies evaluating the effects of oral or inhaled NAC in CF and COPD have reported improvements in the rheologic properties of mucus and trends toward improvements in lung function and decreases in pulmonary exacerbations (Duijvestijn Y C M and Brand P L P.; Systematic review of N-acetylcysteine in cystic fibrosis. Acta Peadiatr 88: 38-41. 1999). However, the preponderance of clinical data suggests that NAC is at best a marginally effective therapeutic agent for treating airway mucus obstruction when administered orally or as an inhalation aerosol. A recent Cochrane review of the existing clinical literature on the use of NAC found no evidence to support the efficacy of NAC for CF (Nash E F, Stephenson A, Ratjen F, Tullis E.; Nebulized and oral thiol derivatives for pulmonary disease in cystic fibrosis. Cochrane Database Syst Rev. 2009; 21(1):CD007168.).

NAC, as a topical pulmonary therapeutic agent, is not optimal for the reduction of mucin disulfide bonds. Specifically, NAC does not possess the basic properties of an effective pulmonary drug as NAC (1) is a relatively inefficient reducing agent the airway surface environment (e.g. CF pH 6.5-7.2); and (2) is rapidly metabolized and cleared from the airway surface (Jayaraman S, Song Y, Vetrivel L, Shankar L, Verkman A S. Noninvasive in vivo fluorescence measurement of airway-surface liquid depth, salt concentration, and pH.

Figure 3:
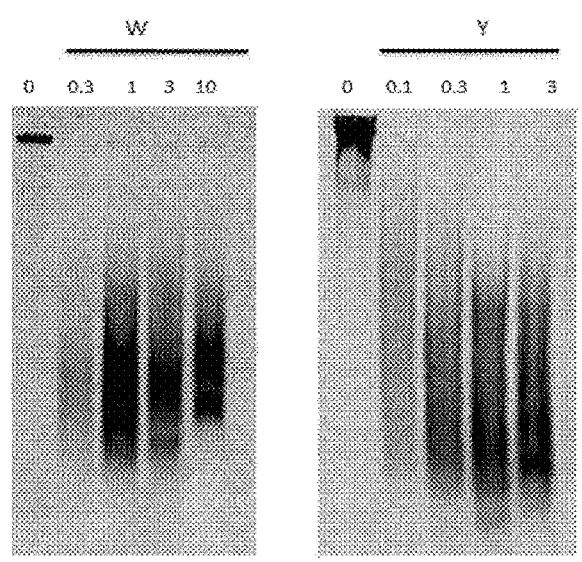
Figure 4:
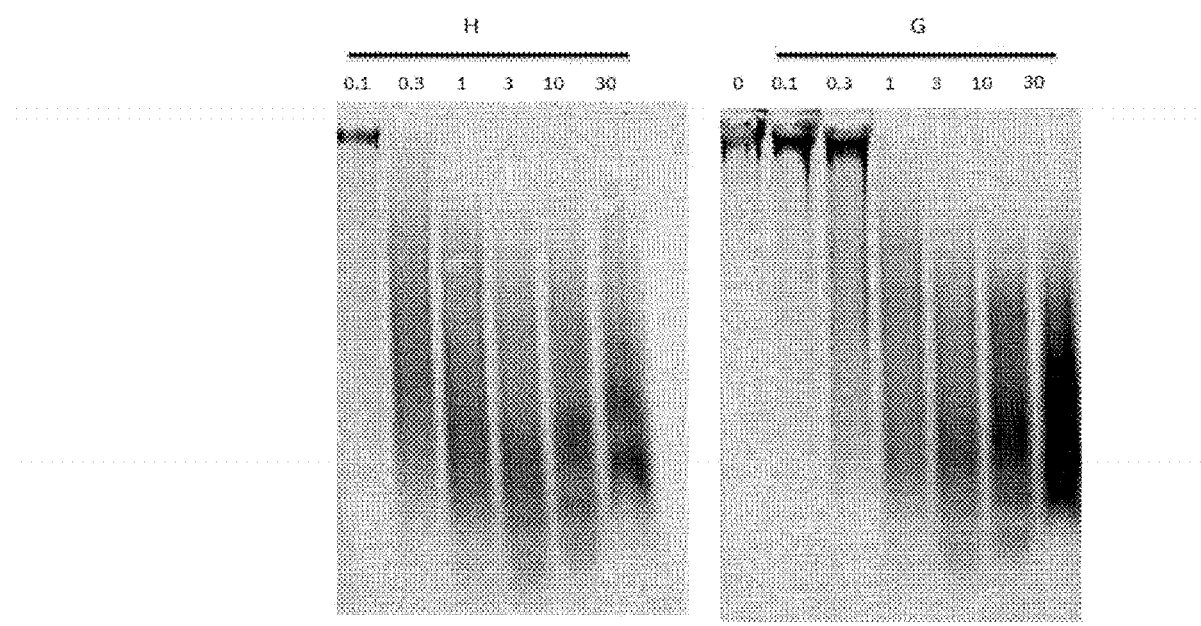
Figure 5:
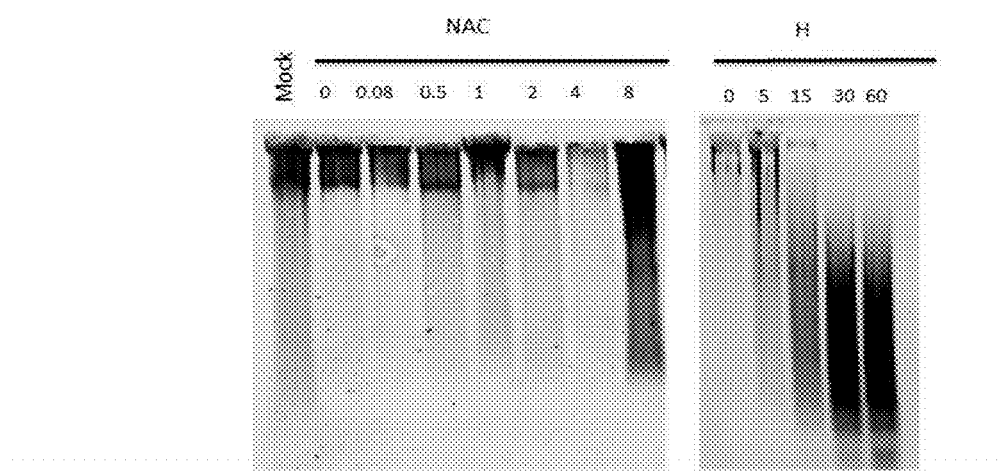
Figure 6:
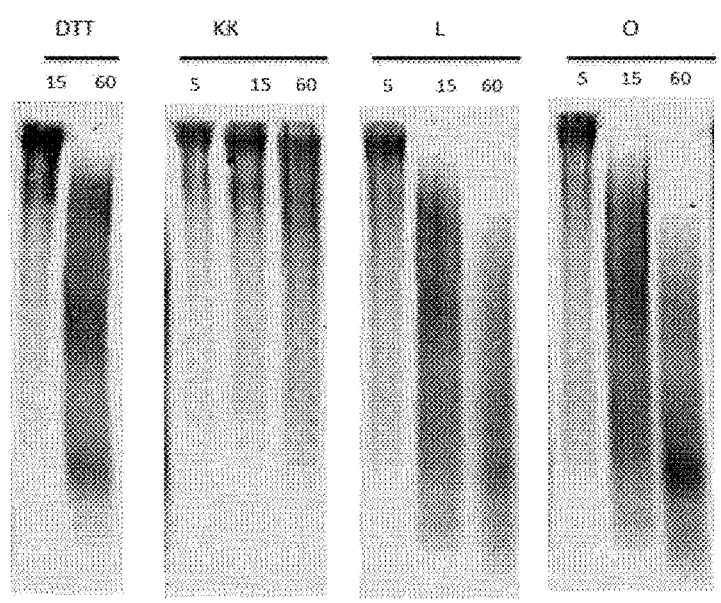
Figure 7:
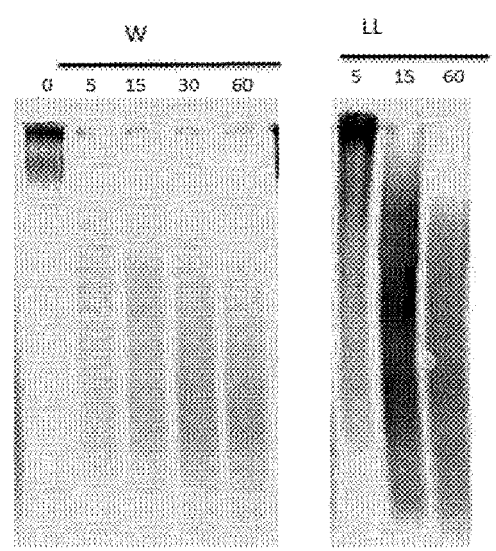
Figure 8:
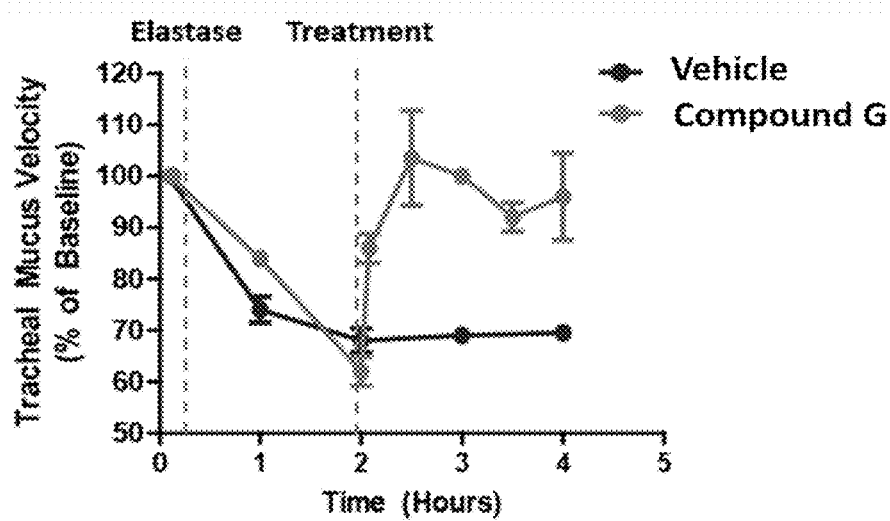

J Clin Invest. 2001; 107(3):317-24). For example, in the pH environment of the airway surface (measured in the range of pH 6.0 to 7.2 in CF and COPD airways), NAC exists only partially in its reactive state as a negatively charge thiolate (Jayaraman S, Song Y, Vetrivel L, Shankar L, Verkman A S. Noninvasive in vivo fluorescence measurement of airway-surface liquid depth, salt concentration, and pH. J Clin Invest. 2001; 107(3):317-24) (FIG. 3). Furthermore, in animal studies, $^{14}C$-labled NAC, administered by inhalation, exhibits rapid elimination from the lungs with a half-life of approximately 20 minutes (unpublished observation). The relatively low reducing activity at of NAC physiologic airway pH and a the short half-life of NAC on the lung surface provide an explanation for the lack of strong clinical evidence for effective mucus reduction in mucus obstructive diseases.

Additionally, NAC is most commonly administered as a concentrated inhalation solution (Mucomyst® is a 20% or 1.27M solution). However, the administration of concentrated NAC solutions impact the tolerability of NAC as it exaggerates (1) the unpleasant sulfur taste/odor; and (2) pulmonary side effects including irritation and bronchoconstriction which can require co-administration of rescue medications such as bronchodilators. Although Mucomyst was approved by the FDA in 1963, no other reducing agents administered as an inhalation aerosol are currently available to treat muco-obstructive diseases. What are needed are effective, safe, and well-tolerated reducing agents for the treatment of diseases characterized by impaired mucus clearance

SUMMARY OF THE INVENTION

One object of the present invention relates to a method to increase the liquefaction of mucus in a patient with excessive mucus or mucus with increased viscoelastic, cohesive, or adhesive properties. The method includes the step of contacting the mucus of a patient with abnormal or excessive mucus with a composition comprising a mucolytic compound containing a dithiol group to decrease mucus viscoelasticity through the reduction of mucin disulfide bonds.

It is an object of the present invention to provide mucolytic compounds that are more effective, and/or absorbed less rapidly from mucosal surfaces, and/or are better tolerated as compared to N-acetylcysteine (NAC) and DTT.

It is another object of the present invention to provide compounds which are more active in the physiologic environment of the airway surface.

It is another object of the present invention to provide compounds that are more potent and/or absorbed less rapidly, as compared to compounds such as N-acetylcysteine and DTT. Therefore, such compounds will give a prolonged pharmacodynamic half-life on mucosal surfaces as compared to NAC and DTT.

It is another object of the present invention to provide methods of treatment that take advantage of the pharmacological properties of the compounds described above.

In particular, it is an object of the present invention to provide methods of treatment which rely on promoting mucus clearance from mucosal surfaces.

It is an object of the present invention to provide compounds that are more potent and/or absorbed less rapidly from mucosal surfaces, and/or are less reversible as compared to known compounds.

Therefore, the compounds will give a prolonged pharmacodynamic half-life on mucosal surfaces as compared to known compounds.

It is another object of the present invention to provide compounds which are (1) absorbed less rapidly from mucosal surfaces, especially airway surfaces, as compared to known compounds and; (2) It is another object of the present invention to provide compounds that are more potent and/or absorbed less rapidly and/or exhibit less reversibility, as compared to compounds such as DTT and NAC. Therefore, such compounds will give a prolonged pharmacodynamic half-life on mucosal surfaces as compared to previous compounds.

It is another object of the present invention to provide methods of treatment that take advantage of the pharmacological properties of the compounds described above.

In particular, it is an object of the present invention to provide methods of treatment which rely on rehydration of mucosal surfaces.

The objects of the present invention may be accomplished with a class of dithiols represented by compounds of Formula I which embraces structures (Ia)-(Id):

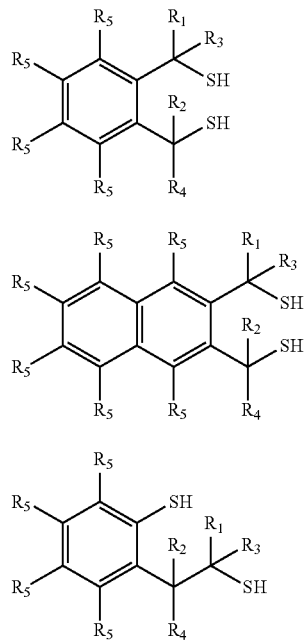

wherein $R^1$ and $R^2$ are each, independently, hydrogen, lower alkyl, halogen or triflouromethyl;

$R^3$ and $R^4$ are each, independently, hydrogen, lower alkyl, hydroxyl-lower alkyl, phenyl, (phenyl)-lower alkyl, (halophenyl)-lower alkyl, ((lower-alkyl)phenyl)-lower-alkyl, ((lower-alkoxy)phenyl)-lower-alkyl, (naphthyl)-lower-alkyl, or (pyridyl)-lower-alkyl;

each $R^5$ is, independently, hydrogen, halogen, trifluoromethyl, lower alkyl, unsubstituted or substituted phenyl, lower alkyl-thio, phenyl-lower alkyl-thio, lower alkyl-sulfonyl, or phenyl-lower alkyl-sulfonyl, OH, —$(CH_2)_m$—$OR^8$, —O—$(CH_2)_m$—$OR^8$, —$(CH_2)_n$—$NR^7R^{10}$, —$(CH_2)_n$—$NR^7R^7$, —O—$(CH_2)_m$—$NR^7R^{10}$, —O—$(CH_2)_m$—$NR^7R^7$, —$(CH_2)_n$ $(CHOR^8)(CHOR^8)_n$—$CH_2OR^8$, —O—$(CH_2)_m$ $(CHOR^8)(CHOR^8)_n$—$CH_2OR^8$, —$(CH_2CH_2O)_m$—$R^8$, —O—$(CH_2CH_2O)_m$—$R^8$, —$(CH_2CH_2O)_m$—$CH_2CH_2NR^7R^{10}$, —O—$(CH_2CH_2O)_m$—$CH_2CH_2NR^7R^{10}$, —$(CH_2)_n$—$C(=O)NR^7R^{10}$, —O—$(CH_2)_m$—$C(=O)NR^7R^{10}$, —$(CH_2)_n$—$(Z)_g$—$R^7$, —O—$(CH_2)_m$—$(Z)_g$—$R^7$, —$(CH_2)_n$—$NR^{10}$—$CH_2(CHOR^8)(CHOR^8)_n$—$CH_2OR^8$, —O—$(CH_2)_m$—$NR^{10}$—$CH_2(CHOR^8)(CHOR^8)_n$—$CH_2OR^8$, —$(CH_2)_n$—$CO_2R^7$, —O—$(CH_2)_m$—$CO_2R^7$, —$OSO_3H$, —O-glucuronide, —O-glucose,

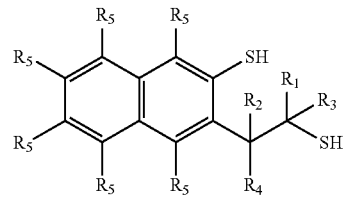

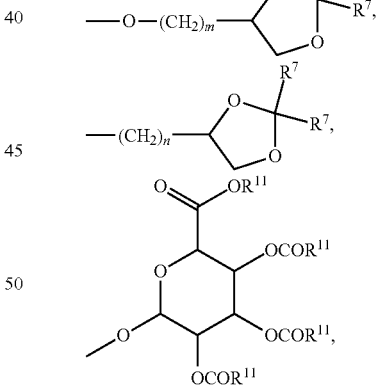

-Link-$(CH_2)_m$-CAP, -Link-$(CH_2)_n(CHOR^8)(CHOR^8)_n$-CAP, -Link-$(CH_2CH_2O)_m$—$CH_2$-CAP, -Link-$(CH_2CH_2O)_m$—$CH_2CH_2$-CAP, -Link-$(CH_2)_m$—$(Z)_g$-CAP, -Link-$(CH_2)_n$ $(Z)_g$—$(CH_2)_m$-CAP, -Link-$(CH_2)_n$—$NR^{13}$—$CH_2(CHOR^8)$ $(CHOR^8)_n$-CAP, -Link-$(CH_2)_n$—$(CHOR^8)_m CH_2$—$NR^{13}$—$(Z)_g$-CAP, -Link-$(CH_2)_n NR^{13}$—$(CH_2)_m(CHOR^8)_n$ $CH_2NR^{13}$—$(Z)_g$-CAP, -Link-$(CH_2)_m$—$(Z)_g$—$(CH_2)_m$-CAP, -Link-NH—C(=O)—NH—$(CH_2)_m$-CAP, -Link-$(CH_2)_m$—C(=O)$NR^{13}$—$(CH_2)_m$-CAP, -Link-$(CH_2)_n$—$(Z)_g$—$(CH_2)_m$—$(Z)_g$-CAP, or -Link-$Z_g$—$(CH_2)_m$-Het-$(CH_2)_m$-CAP with the proviso that at least one $R^5$ group contains at least one basic nitrogen;

each $R^7$ is, independently, hydrogen, lower alkyl, phenyl, substituted phenyl, lower alkyl phenyl or —$CH_2(CHOR^8)_m$—$CH_2OR^8$;

each $R^8$ is, independently, hydrogen, lower alkyl, lower alkyl phenyl, —C(=O)—$R^{11}$, glucuronide, 2-tetrahydropyranyl, or

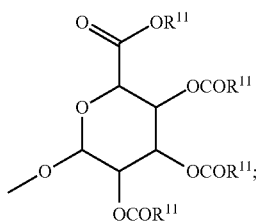

each $R^9$ is, independently, —$CO_2R^7$, —$CON(R^7)_2$, —$SO_2CH_3$, —$C(=O)R^7$, —$CO_2R^{13}$, —$CON(R^{13})_2$, —$SO_2CH_2R^{13}$, or —$C(=O)R^{13}$;

each $R^{10}$ is, independently, —H, —$SO_2CH_3$, —$CO_2R^7$, —$C(=O)NR^7R^9$, —$C(=O)R^7$, or —$CH_2$—$(CHOH)_n$—$CH_2OH$;

each Z is, independently, —(CHOH)—, —C(=O)—, —(CHNR$^7$R$^{10}$)—, —(C=NR$^{10}$)—, —NR$^{10}$—, —(CH$_2$)$_n$—, —(CHNR$^{13}$R$^{13}$)—, —(C=NR$^{13}$)—, or —NR$^{13}$—;

each $R^{11}$ is, independently, hydrogen, lower alkyl, phenyl lower alkyl or substituted phenyl lower alkyl;

each $R^{12}$ is, independently, —$SO_2CH_3$, —$CO_2R^7$, —$C(=O)NR^7R^9$, —$C(=O)R^7$, —$CH_2(CHOH)_n$—$CH_2OH$, —$CO_2R^{13}$, —$C(=O)NR^{13}R^{13}$, or —$C(=O)R^{13}$;

each $R^{13}$ is, independently, hydrogen, lower alkyl, phenyl, substituted phenyl or —$CH_2(CHOR^8)_m$—$CH_2OR^8$, —$SO_2CH_3$, —$CO_2R^7$, —$C(=O)NR^7R^9$, —$C(=O)R^7$, —$CH_2$—$(CHOH)_n$—$CH_2OH$, —$(CH_2)_m$—$NR^7R^{10}$, —$(CH_2)_m$—$NR^7R^7$, —$(CH_2)_m$—$NR^{11}R^{11}$, —$(CH_2)_m$—$(NR^{11}R^{11}R^{11})^+$, $(CH_2)_m$—$(CHOR^8)_m$—$(CH_2)_mNR^{11}R^{11}$, —$(CH_2)_m$—$(CHOR^8)_m$—$(CH_2)_mNR^7R^{10}$, —$(CH_2)_m$—$NR^{10}R^{10}$, —$(CH_2)_m$—$(CHOR^8)_m$—$(CH_2)_m$—$(NR^{11}R^{11}R^{11})^+$, —$(CH_2)_m$—$(CHOR^8)_m$—$(CH_2)_mNR^7R^7$;

each g is, independently, an integer from 1 to 6;
each m is, independently, an integer from 1 to 7;
each n is, independently, an integer from 0 to 7;
each -Het- is, independently, —N(R$^7$)—, —N(R$^{10}$)—, —S—, —SO—, —SO$_2$—; —O—, —SO$_2$NH—, —NHSO$_2$—, —NR$^7$CO—, —CONR$^7$—, —N(R$^{13}$)—, —SO$_2$NR$^{13}$—, —NR$^{13}$CO—, or —CONR$^{13}$—;

each Link is, independently, —O—, —(CH$_2$)$_n$—, —O(CH$_2$)$_m$—, —NR$^{13}$—C(=O)—NR$^{13}$—, —NR$^{13}$—C(=O)—(CH$_2$)$_m$—, —C(=O)NR$^{13}$—(CH$_2$)$_m$—, —(CH$_2$)$_n$—(Z)$_g$—(CH$_2$)$_n$—, —S—, —SO—, —SO$_2$—, —SO$_2$NR$^7$—, —SO$_2$NR$^{10}$—, or -Het-;

each CAP is, independently

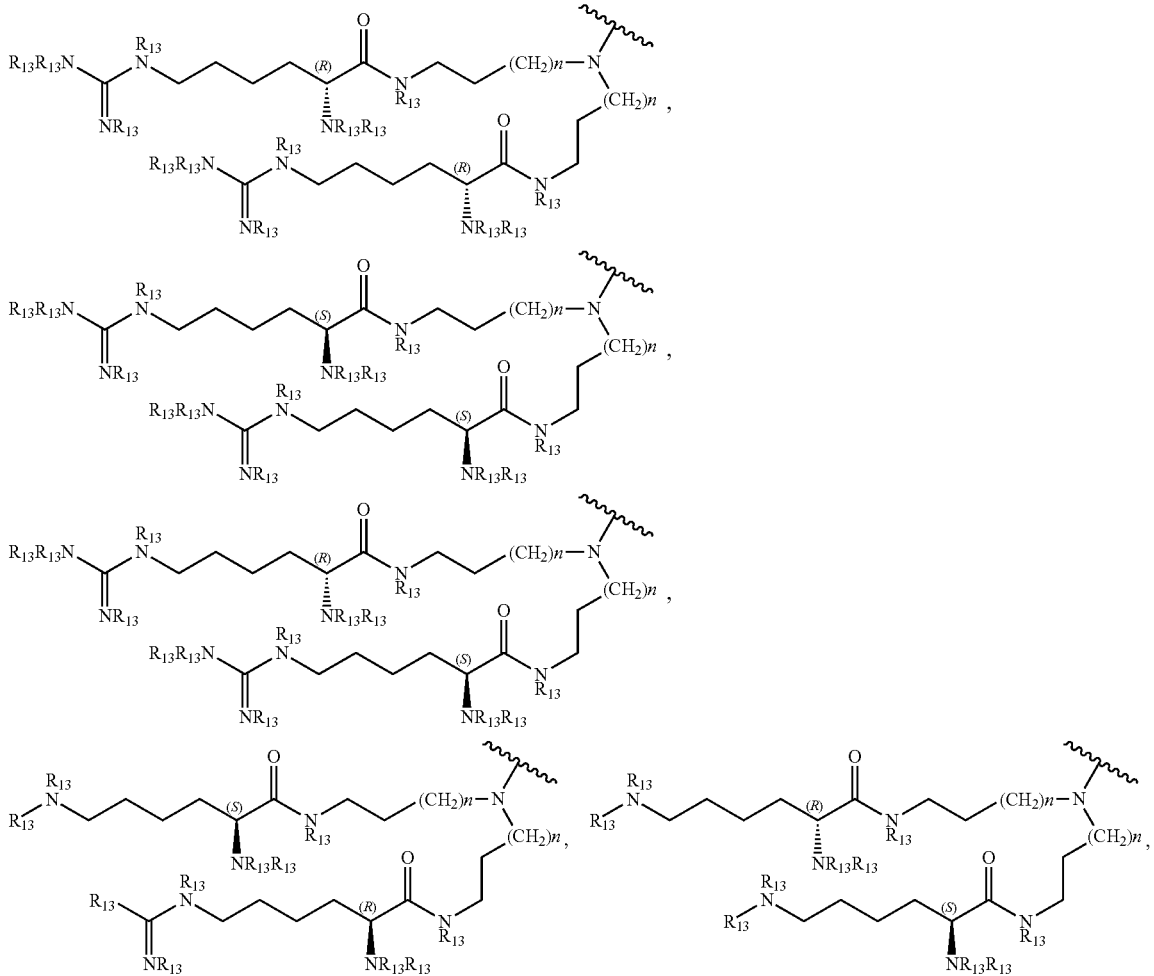

-continued

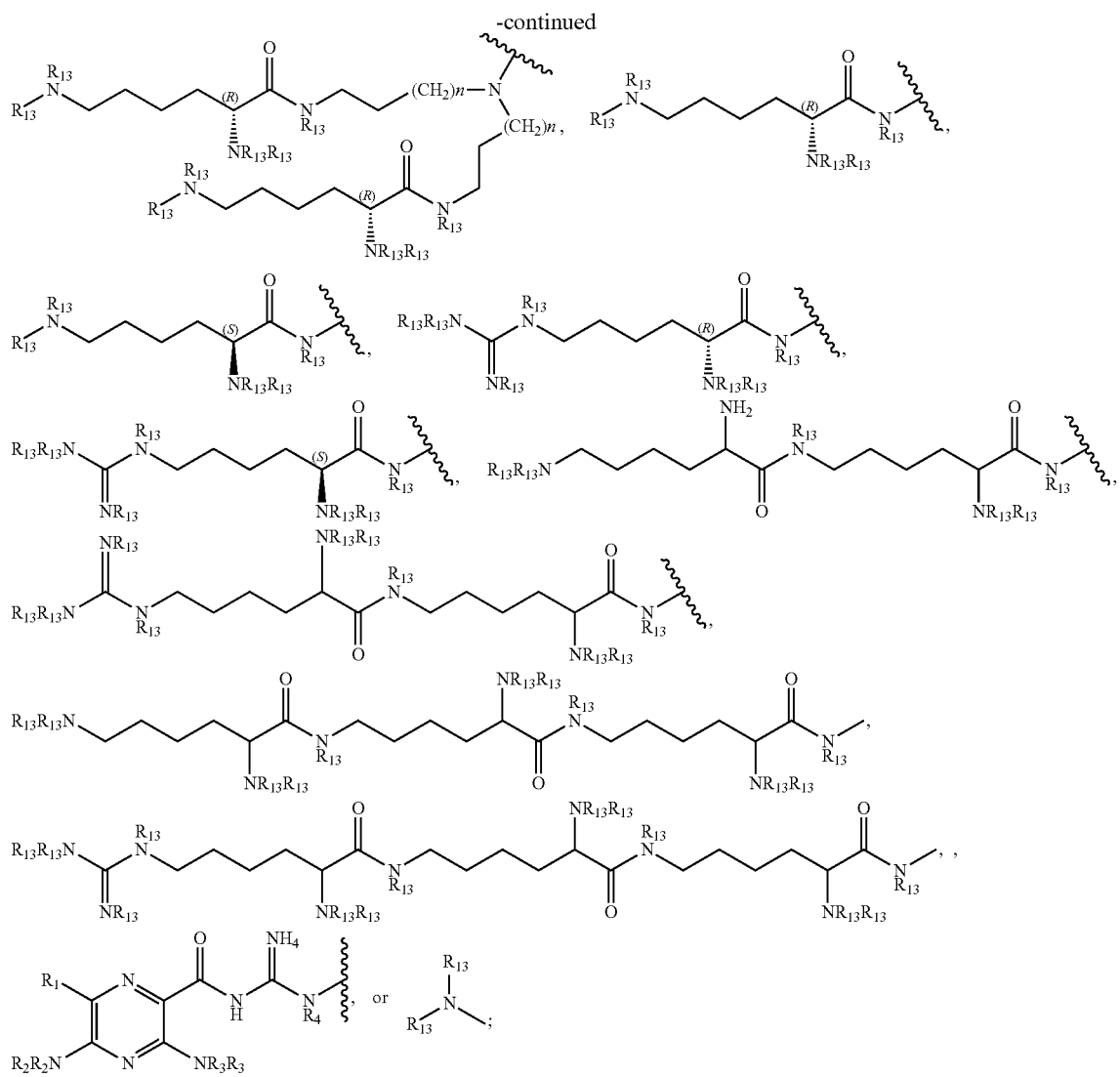

with the proviso that when any —CHOR$^8$— or —CH$_2$OR$^8$ groups are located 1,2- or 1,3- with respect to each other, the R$^8$ groups may, optionally, be taken together to form a cyclic mono- or di-substituted 1,3-dioxane or 1,3-dioxolane;

and racemates, enantiomers, diastereomers, tautomers, polymorphs, pseudopolymorphs and pharmaceutically acceptable salts, thereof.

The present invention also provides pharmaceutical compositions which comprise a compound as described herein.

The present invention also provides a method of restoring mucosal defense, comprising:

contacting mucus with an effective amount of compound described herein to a subject in need thereof.

The present invention also provides a method of decreasing mucus viscoelasticity, comprising:

administering an effective amount of a compound described herein to a mucosal surface of a subject.

The present invention also provides a method of decreasing mucus viscoelasticity on a mucosal surface, comprising:

administering an effective amount of a compound described herein to a mucosal surface of a subject.

The present invention also provides a method of scavenging free radicals on a mucosal surface, comprising:

administering an effective amount of a compound described herein to a mucosal surface of a subject.

The present invention also provides a method of decreasing inflammation on a mucosal surface, comprising:

administering an effective amount of a compound described herein to a mucosal surface of a subject.

The present invention also provides a method of reducing inflammatory cells on a mucosal surface, comprising:

administering an effective amount of a compound described herein to a mucosal surface of a subject.

The present invention also provides a method treating mucus obstructive diseases, comprising:

contacting mucus with an effective amount of compound described herein to a subject in need thereof.

The present invention also provides a method treating mucus adhesion, comprising:

contacting mucus with an effective amount of compound described herein to a subject in need thereof.

The present invention also provides a method of treating chronic bronchitis, comprising:

administering an effective amount of a compound described herein to a subject in need thereof.

The present invention also provides a method of treating cystic fibrosis, comprising:

administering an effective amount of compound described herein to a subject in need thereof.

The present invention also provides a method of treating cystic fibrosis exacerbations, comprising:
administering an effective amount of compound described herein to a subject in need thereof.

The present invention also provides a method of treating bronchiectasis, comprising:
administering an effective amount of a compound described herein to a subject in need thereof.

The present invention also provides a method of treating chronic obstructive pulmonary disease, comprising:
administering an effective amount of a compound described herein to a subject in need thereof.

The present invention also provides a method of treating chronic obstructive pulmonary disease exacerbations, comprising:
administering an effective amount of a compound described herein to a subject in need thereof.

The present invention also provides a method of treating asthma, comprising:
administering an effective amount of a compound described herein to a subject in need thereof.

The present invention also provides a method of treating asthma exacerbations, comprising:
administering an effective amount of a compound described herein to a subject in need thereof.

The present invention also provides a method of treating esophagitis, comprising:
administering an effective amount of a compound described herein to a subject in need thereof.

The present invention also provides a method of treating ventilator-induced pneumonia, comprising:
administering an effective compound described herein to a subject by means of a ventilator.

The present invention also provides a method of treating primary ciliary dyskinesia, comprising:
administering an effective amount of a compound described herein to a subject in need thereof.

The present invention also provides a method of treating emphysema, comprising:
administering an effective amount of a compound described herein to a subject in need thereof.

The present invention also provides a method of treating pneumonia, comprising:
administering an effective amount of a compound described herein to a subject in need thereof.

The present invention also provides a method of treating rhinosinusitis, comprising:
administering an effective amount of a compound described herein to a subject in need thereof.

The present invention also provides a method of treating nasal dehydration, comprising:
administering an effective amount of a compound described herein to the nasal passages of a subject in need thereof.

In a specific embodiment, the nasal dehydration is brought on by administering dry oxygen to the subject.

The present invention also provides a method of treating sinusitis, comprising:
administering an effective amount of a compound described herein to a subject in need thereof.

The present invention also provides a method of treating dry eye, comprising:
administering an effective amount of a compound described herein to the eye of the subject in need thereof.

The present invention also provides a method of promoting ocular hydration, comprising:
administering an effective amount of a compound described herein to the eye of the subject.

The present invention also provides a method of promoting corneal hydration, comprising:
administering an effective amount of a compound described herein to the eye of the subject.

The present invention also provides a method of treating excessive eye discharge produced by, but not limited to blepharitis, allergies, conjunctivitis, corneal ulcer, trachoma, congenital herpes simplex, corneal abrasions, ectropion, eyelid disorders, gonococcal conjunctivitis, herpetic keratitis, ophthalmitis, Sjogren's Syndrome, Stevens-Johnson Syndrome comprising:
administering an effective amount of a compound described herein to the eye of the subject.

The present invention also provides a method of treating Sjogren's disease, comprising:
administering an effective amount of compound described herein to a subject in need thereof.

The present invention also provides a method of treating dry mouth (xerostomia), comprising:
administering an effective amount of compound described herein to the mouth of the subject in need thereof.

The present invention also provides a method of treating vaginal dryness, comprising:
administering an effective amount of a compound described herein to the vaginal tract of a subject in need thereof.

The present invention also provides a method of treating constipation, comprising:
administering an effective amount of a compound described herein to a subject in need thereof. In one embodiment of this method, the compound is administered either orally or via a suppository or enema.

The present invention also provides a method of treating distal intestinal obstruction syndrome, comprising:
administering an effective amount of compound described herein to a subject in need thereof.

The present invention also provides a method of treating chronic diverticulitis comprising:
administering an effective amount of a compound described herein to a subject in need thereof.

The present invention also provides a method of inducing sputum for diagnostic purposes, comprising:
administering an effective amount of compound described herein to a subject in need thereof.

The present invention also provides a method of treating inhaled pathogens, comprising:
administering an effective amount of a compound described herein to a subject in need thereof.

The present invention also provides a method of treating inhaled irritants, comprising:
administering an effective amount of a compound described herein to a subject in need thereof.

The present invention also provides a method of treating inhaled particles, comprising:
administering an effective amount of a compound described herein to a subject in need thereof.

In a specific embodiment, the inhaled particles are insoluble particles including dust, debris, or radioactive material.

The objects of the invention may also be accomplished with a method of treating anthrax, comprising administering an effective amount of a compound of Formula I as defined herein and an osmolyte to a subject in need thereof.

The objects of the invention may also be accomplished with a method of prophylactic, post-exposure prophylactic, preventive or therapeutic treatment against diseases or conditions caused by pathogens, particularly pathogens which may be used in bioterrorism, comprising administering an effective amount of a compound of Formula I to a subject in need thereof.

It is further an object of the present invention to provide treatments comprising the use of osmolytes together with mucolytics of Formula I that are more potent, more specific, and/or absorbed less rapidly from mucosal surfaces as compared to compounds such as NAC.

It is another aspect of the present invention to provide treatments using mucolytics of Formula I that are more potent and/or absorbed less rapidly and/or exhibit less reversibility, as compared to compounds such as NAC when administered with an osmotic enhancer. Therefore, such mucolytics when used in conjunction with osmolytes will give an increased pharmacodynamic effect on mucosal surfaces as compared to either compound used alone.

It is another object of the present invention to provide treatments using mucolytics of Formula I and osmolytes together which are absorbed less rapidly from mucosal surfaces, especially airway surfaces than NAC. It is another object of the invention to provide compositions which contain mucolytics of Formula I and osmolytes.

The objects of the invention may be accomplished with a method of treating a disease ameliorated by increased mucus clearance and mucosal hydration comprising administering an effective amount of a compound of Formula I as defined herein and an osmolyte to a subject in need of increased mucociliary clearance and/or mucosal hydration.

BRIEF DESCRIPTION OF THE DRAWINGS

FIG. 1. Role of mucus dehydration in pathogenic sequence of CF/COPD. Disease-related dehydration of mucus (panel B, ↑ % solids), leads to a collapse of the periciliary layer (PCL), reduction or cessation of mucus clearance, and adhesion of the mucus layer to the cell surface.

FIG. 2. Reduction of human salivary mucin by compounds L, N, and O. Human saliva was exposed to a range of concentrations of compounds L, N and O or DTT, as indicated, electrophoresed, transferred to a nitrocellulose membrane, and probed for Muc5b. Concentrations are indicated in mM and reduction reactions were performed for 30 min at 25° C. Reactions were quenched with NEM prior to electrophoresis.

FIG. 3. Reduction of human salivary mucin by compounds W and Y. Human saliva was exposed to a range of concentrations of compounds W and Y, as indicated, electrophoresed, transferred to a nitrocellulose membrane, and probed for Muc5b. Concentrations are indicated in mM and reduction reactions were performed for 30 min at 25° C. Reactions were quenched with NEM prior to electrophoresis.

FIG. 4. Reduction of human salivary mucin by compounds H and G. Human saliva was exposed to a range of concentrations of compounds H and G, as indicated, electrophoresed, transferred to a nitrocellulose membrane, and probed for Muc5b. Concentrations are indicated in mM and reduction reactions were performed for 30 min at 25° C. Reactions were quenched with NEM prior to electrophoresis.

FIG. 5. Reduction of human salivary mucin by compounds H and NAC. Human saliva was exposed to 10 mM of compounds H or NAC, as indicated, electrophoresed, transferred to a nitrocellulose membrane, and probed for Muc5b. Reduction reactions were performed for a range of times, as indicated in min., at 25° C. Reactions were quenched with NEM prior to electrophoresis.

FIG. 6. Reduction of human salivary mucin by compounds KK, L, and O. Human saliva was exposed to 1 mM of compounds KK, L and O or DTT, as indicated, electrophoresed, transferred to a nitrocellulose membrane, and probed for Muc5b. Reduction reactions were performed for a range of times, as indicated in min., at 25° C. Reactions were quenched with NEM prior to electrophoresis.

FIG. 7. Reduction of human salivary mucin by compounds W and LL. Human saliva was exposed to 0.3 mM (left panel) or 1 mM (right panel) of compounds W and LL, as indicated, electrophoresed, transferred to a nitrocellulose membrane, and probed for Muc5b. Reduction reactions were performed for a range of times, as indicated in min., at 25° C. Reactions were quenched with NEM prior to electrophoresis.

FIG. 8. Tracheal Mucus Velocity in sheep for compound G.

DETAILED DESCRIPTION OF THE INVENTION

As used herein, the following terms are defined as indicated.

"A compound of the invention" means a compound of Formula I or a salt, particularly a pharmaceutically acceptable salt thereof.

"A compound of Formula I" means a compound having the structural formula designated herein as Formula I. Compounds of Formula I include solvates and hydrates (i.e., adducts of a compound of Formula I with a solvent). In those embodiments wherein a compound of Formula I includes one or more chiral centers, the phrase is intended to encompass each individual stereoisomer including optical isomers (enantiomers and diastereomers) and geometric isomers (cis-/trans-isomerism) and mixtures of stereoisomers. In addition, compounds of Formula I also include tautomers of the depicted formula(s).

Throughout the description and examples, compounds are named using standard IUPAC naming principles, where possible, including the use of the ChemDraw Ultra 11.0 software program for naming compounds, sold by CambridgeSoft Corp./PerkinElmer.

In some chemical structure representations where carbon atoms do not have a sufficient number of attached variables depicted to produce a valence of four, the remaining carbon substituents needed to provide a valence of four should be assumed to be hydrogen. Similarly, in some chemical structures where a bond is drawn without specifying the terminal group, such bond is indicative of a methyl (Me, $—CH_3$) group, as is conventional in the art.

The present invention is based on the discovery that the compounds of Formula I are more potent and/or, absorbed less rapidly, achieve higher concentrations and have higher residence time in the mucosal surfaces, especially airway surfaces, and/or are better tolerated compared to NAC and DTT. Therefore, the compounds of Formula I have a greater activity and/or produce less cellular toxicity on mucosal surfaces as compared to NAC and DTT.

The present invention is based on the discovery that the compounds of formula (I) are more potent and/or, absorbed less rapidly from mucosal surfaces, especially airway surfaces, and/or less reversible from interactions as compared to compounds such as NAC and DTT. Therefore, the compounds of formula (I) have a longer half-life on mucosal surfaces as compared to these compounds.

In the compounds represented by formula I which embraces structures (Ia)-(Id):

$R^1$ is independently hydrogen, lower alkylkoxy, halogen or triflouromethyl;

$R^2$ is, independently hydrogen or lower alkyl;

$R^3$ and $R^4$ are each, independently, hydrogen, lower alkyl, hydroxyl-lower alkyl, phenyl, (phenyl)-lower alkyl, (halophenyl)-lower alkyl, ((lower-alkyl)phenyl)-lower-alkyl, ((lower-alkoxy)phenyl)-lower-alkyl, (naphthyl)-lower-alkyl, or (pyridyl)-lower-alkyl;

each $R^5$ is, independently, hydrogen, halogen, trifluoromethyl, lower alkyl, unsubstituted or substituted phenyl, lower alkyl-thio, phenyl-lower alkyl-thio, lower alkyl-sulfonyl, or phenyl-lower alkyl-sulfonyl, OH, —$(CH_2)_m$—$OR^8$, —O—$(CH_2)_m$—$OR^8$, —$(CH_2)_n$—$NR^7R^{10}$, —$(CH_2)_n$—$NR^7R^7$, —O—$(CH_2)_m$—$NR^7R^{10}$, —O—$(CH_2)_m$—$NR^7R^7$, —$(CH_2)_n$ $(CHOR^8)(CHOR^8)_n$—$CH_2OR^8$, —O—$(CH_2)_m$ $(CHOR^8)(CHOR^8)_n$—$CH_2OR^8$, —$(CH_2CH_2O)_m$—$R^8$, —O—$(CH_2CH_2O)_m$—$R^8$, —$(CH_2CH_2O)_m$—$CH_2CH_2NR^7R^{10}$, —O—$(CH_2CH_2O)_m$—$CH_2CH_2NR^7R^{10}$, —$(CH_2)_n$—$C(=O)NR^7R^{10}$, —O—$(CH_2)_m$—$C(=O)NR^7R^{10}$, —$(CH_2)_n$—$(Z)_g$—$R^7$, —O—$(CH_2)_m$—$(Z)_g$—$R^7$, —$(CH_2)_n$—$NR^{10}$—$CH_2(CHOR^8)(CHOR^8)_n$—$CH_2OR^8$, —O—$(CH_2)_m$—$NR^{10}$—$CH_2(CHOR^8)(CHOR^8)_n$—$CH_2OR^8$, —$(CH_2)_n$—$CO_2R^7$, —O—$(CH_2)_m$—$CO_2R^7$, —$OSO_3H$, —O-glucuronide, —O-glucose,

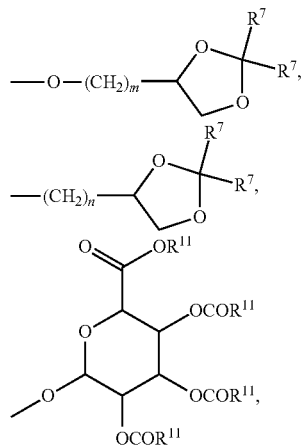

-Link-$(CH_2)_m$-CAP, -Link-$(CH_2)_n(CHOR^8)(CHOR^8)_n$-CAP, -Link-$(CH_2CH_2O)_m$—$CH_2$-CAP, -Link-$(CH_2CH_2O)_m$—$CH_2CH_2$-CAP, -Link-$(CH_2)_m$—$(Z)_g$-CAP, -Link-$(CH_2)_n$ $(Z)_g$—$(CH_2)_m$-CAP, -Link-$(CH_2)_n$—$NR^{13}$—$CH_2(CHOR^8)$ $(CHOR^8)_n$-CAP, -Link-$(CH_2)_n$—$(CHOR^8)_m$ $CH_2$—$NR^{13}$—$(Z)_g$-CAP, -Link-$(CH_2)NR^{13}$—$(CH_2)_m(CHOR^8)_n$ $CH_2NR^{13}$—$(Z)_g$-CAP, -Link-$(CH_2)_m$—$(Z)_g$—$(CH_2)_m$-CAP, -Link-NH—C(=O)—NH—$(CH_2)_m$-CAP, -Link-$(CH_2)_m$—C(=O)$NR^{13}$—$(CH_2)_m$-CAP, -Link-$(CH_2)_n$—$(Z)_g$—$(CH_2)_m$—$(Z)_g$-CAP, or -Link-$Z_g$—$(CH_2)_m$-Het-$(CH_2)_m$-CAP with the proviso that at least one $R^5$ group contains at least one basic nitrogen;

The term —O-glucuronide, unless otherwise specified, means a group represented by

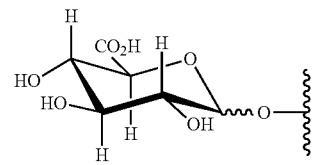

wherein the ⌇O means the glycosidic linkage can be above or below the plane of the ring.

The term —O-glucose, unless otherwise specified, means a group represented by

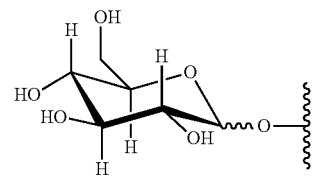

wherein the ⌇O means the glycosidic linkage can be above or below the plane of the ring.

In a preferred embodiment $R^5$ is one of the following:

hydrogen, halogen, trifluoromethyl, lower alkyl, unsubstituted or substituted phenyl, lower alkyl-thio, phenyl-lower alkyl-thio, lower alkyl-sulfonyl, or phenyl-lower alkyl-sulfonyl, OH, —$(CH_2)_m$—$OR^8$, —O—$(CH_2)_m$—$OR^8$, —$(CH_2)_n$—$NR^7R^{10}$, —O—$(CH_2)_m$—$NR^7R^{10}$, —$(CH_2)_n$ $(CHOR^8)(CHOR^8)_n$—$CH_2OR^8$, —O—$(CH_2)_m(CHOR^8)$ $(CHOR^8)_n$—$CH_2OR^8$, —$(CH_2CH_2O)_m$—$R^8$, —O—$(CH_2CH_2O)_m$—$R^8$, —$(CH_2CH_2O)_m$—$CH_2CH_2NR^7R^{10}$, —O—$(CH_2CH_2O)_m$—$CH_2CH_2NR^7R^{10}$, —$(CH_2)_n$—C(=O)$NR^7R^{10}$, —O—$(CH_2)_m$—C(=O)$NR^7R^{10}$, —$(CH_2)_n$—$(Z)_g$—$R^7$, —O—$(CH_2)_m$—$(Z)_g$—$R^7$, —$(CH_2)_n$—$NR^{10}$—$CH_2(CHOR^8)(CHOR^8)_n$—$CH_2OR^8$, —O—$(CH_2)_m$—$NR^{10}$—$CH_2(CHOR^8)(CHOR^8)_n$—$CH_2OR^8$, —$(CH_2)_n$—$CO_2R^7$, —O—$(CH_2)_m$—$CO_2R^7$, —$OSO_3H$, —O-glucuronide, —O-glucose,

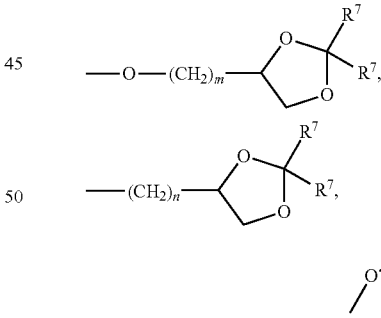

In a preferred embodiment, each —$(CH_2)_n$—$(Z)_g$—$R^7$ falls within the scope of the structures described above and is, independently,

—$(CH_2)$—NH—C(=NH)$NH_2$,

In another a preferred embodiment, each —O—$(CH_2)_m$—$(Z)_g$—$R^7$ falls within the scope of the structures described above and is, independently, —O—$(CH_2)_m$—NH—C(=NH)—$N(R^7)_2$, or —O—$(CH_2)_m$—$CHNH_2$—$CO_2NR^7R^{10}$.

In another preferred embodiment, $R^5$ is —OH, —O—$(CH_2)_m(Z)_gR^{12}$, -Het-$(CH_2)_m$—NH—C(=$NR^{13}$)—

NR$^{13}$R$^{13}$, -Het-(CH$_2$)$_n$—(Z)$_g$—(CH$_2$)$_m$NH—C(=NR$^{13}$)—NR$^{13}$R$^{13}$, -Link-(CH$_2$)$_m$—(Z)$_g$—(CH$_2$)$_m$-CAP, Link-(CH$_2$)$_n$—CR$^{11}$R$^{11}$-CAP, -Het-(CH$_2$)$_m$—CONR$^{13}$R$^{13}$, —(CH$_2$)$_n$—NR$^{12}$R$^{12}$, —O—(CH$_2$)$_m$NR$^{11}$R$^{11}$, —O—(CH$_2$)$_m$—N$^{\oplus}$—(R$^{11}$)$_3$, —(CH$_2$)$_n$—(Z)$_g$—(CH$_2$)$_m$—NR$^{10}$R$^{10}$, -Het-(CH$_2$)$_m$—(Z)$_g$—NH—C(=NR$^{13}$)—NR$^{13}$R$^{13}$, —O—(CH$_2$)$_m$(CHOR$^8$)(CHOR$^8$)$_n$—CH$_2$OR$^8$, —O—(CH$_2$)$_m$—C(=O)NR$^7$R$^{10}$, —O—(CH$_2$)$_m$—(Z)$_g$—R$^7$, or —O—(CH$_2$)$_m$—NR$^{10}$—CH$_2$(CHOR$^8$)(CHOR$^8$)$_n$—CH$_2$OR$^8$.

In a particularly preferred embodiment, R$^5$ is -Link-(CH$_2$)$_m$-CAP, -Link-(CH$_2$)$_n$(CHOR$^8$)(CHOR$^8$)$_n$-CAP, -Link-(CH$_2$CH$_2$O)$_m$—CH$_2$-CAP, -Link-(CH$_2$CH$_2$O)$_m$—CH$_2$CH$_2$-CAP, -Link-(CH$_2$)$_m$—(Z)$_g$-CAP, -Link-(CH$_2$)$_n$(Z)$_g$—(CH$_2$)$_m$-CAP, -Link-(CH$_2$)$_n$—NR$^{13}$—CH$_2$(CHOR$^8$)(CHOR$^8$)$_n$-CAP, -Link-(CH$_2$)$_n$—(CHOR$^8$)$_m$CH$_2$—NR$^{13}$—(Z)$_g$-CAP, -Link-(CH$_2$)$_n$NR$^{13}$—(CH$_2$)$_m$(CHOR$^8$)$_n$CH$_2$NR$^{13}$—(Z)$_g$-CAP, -Link-(CH$_2$)$_m$—(Z)$_g$—(CH$_2$)$_m$-CAP, -Link-NH—C(=O)—NH—(CH$_2$)$_m$-CAP, -Link-(CH$_2$)$_m$—C(=O)NR$^{13}$—(CH$_2$)$_m$-CAP, -Link-(CH$_2$)$_n$—(Z)$_g$—(CH$_2$)$_m$—(Z)$_g$-CAP, or -Link-Z$_g$—(CH$_2$)$_m$-Het-(CH$_2$)$_m$-CAP.

Selected substituents within the compounds of the invention are present to a recursive degree. In this context, "recursive substituent" means that a substituent may recite another instance of itself. Because of the recursive nature of such substituents, theoretically, a large number of compounds may be present in any given embodiment. For example, R$^9$ contains a R$^{13}$ substituent. R$^{13}$ can contain an R$^{10}$ substituent and R$^{10}$ can contain a R$^9$ substituent. One of ordinary skill in the art of medicinal chemistry understands that the total number of such substituents is reasonably limited by the desired properties of the compound intended. Such properties include, by way of example and not limitation, physical properties such as molecular weight, solubility or log P, application properties such as activity against the intended target, and practical properties such as ease of synthesis.

By way of example and not limitation, R$^5$, R$^{13}$ and R$^{10}$ are recursive substituents in certain embodiments. Typically, each of these may independently occur 20, 19, 18, 17, 16, 15, 14, 13, 12, 11, 10, 9, 8, 7, 6, 5, 4, 3, 2, 1, or 0, times in a given embodiment. More typically, each of these may independently occur 12 or fewer times in a given embodiment. More typically yet, R$^9$ will occur 0 to 8 times in a given embodiment, R$^{13}$ will occur 0 to 6 times in a given embodiment and R$^{10}$ will occur 0 to 6 times in a given embodiment. Even more typically yet, R$^9$ will occur 0 to 6 times in a given embodiment, R$^{13}$ will occur 0 to 4 times in a given embodiment and R$^{10}$ will occur 0 to 4 times in a given embodiment.

Recursive substituents are an intended aspect of the invention. One of ordinary skill in the art of medicinal chemistry understands the versatility of such substituents. To the degree that recursive substituents are present in an embodiment of the invention, the total number will be determined as set forth above.

Each -Het- is, independently, —N(R$^7$)—, —N(R$^{10}$)—, —S—, —SO—, —SO$_2$—; —O—, —SO$_2$NH—, —NHSO$_2$—, —NR$^7$CO—, —CONR$^7$—, —N(R$^{13}$)—, —SO$_2$NR$^{13}$—, —NR$^{13}$CO—, or —CONR$^{13}$—. In a preferred embodiment, -Het- is —O—, —N(R$^7$)—, or —N(R$^{10}$)—. Most preferably, -Het- is —O—.

Each -Link- is, independently, —O—, —(CH$_2$)$_n$—, —O(CH$_2$)$_m$—, —NR$^{13}$—C(=O)—NR$^{13}$—, —NR$^{13}$—C(=O)—(CH$_2$)$_m$—, —C(=O)NR$^{13}$—(CH$_2$)$_m$—, —(CH$_2$)$_n$—(Z)$_g$—(CH$_2$)$_n$—, —S—, —SO—, —SO$_2$—, —SO$_2$NR$^7$—, —SO$_2$NR$^{10}$—, or -Het-. In a preferred embodiment, -Link- is —O—, —(CH$_2$)$_n$—, —NR$^{13}$—C(=O)—(CH$_2$)$_m$—, or —C(=O)NR$^{13}$—(CH$_2$)$_m$—.

Each -CAP is each CAP is, independently

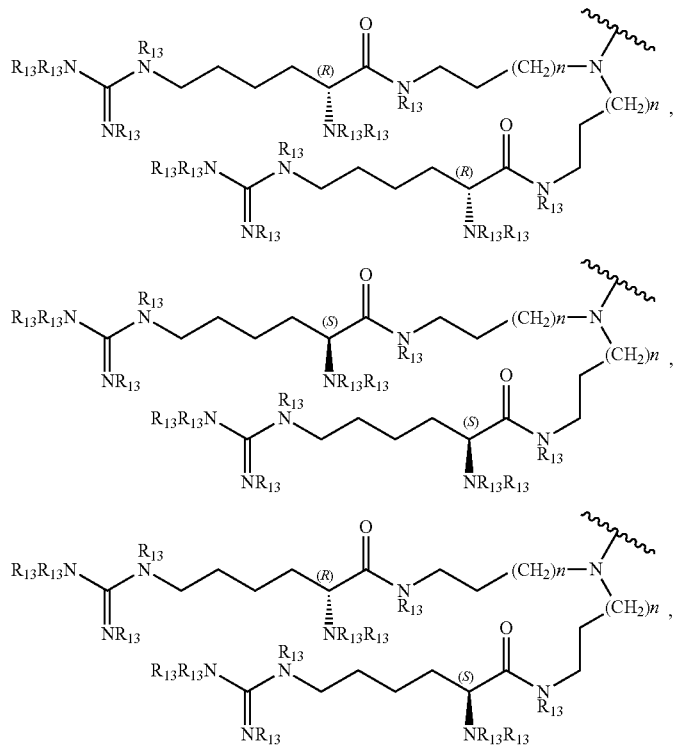

-continued

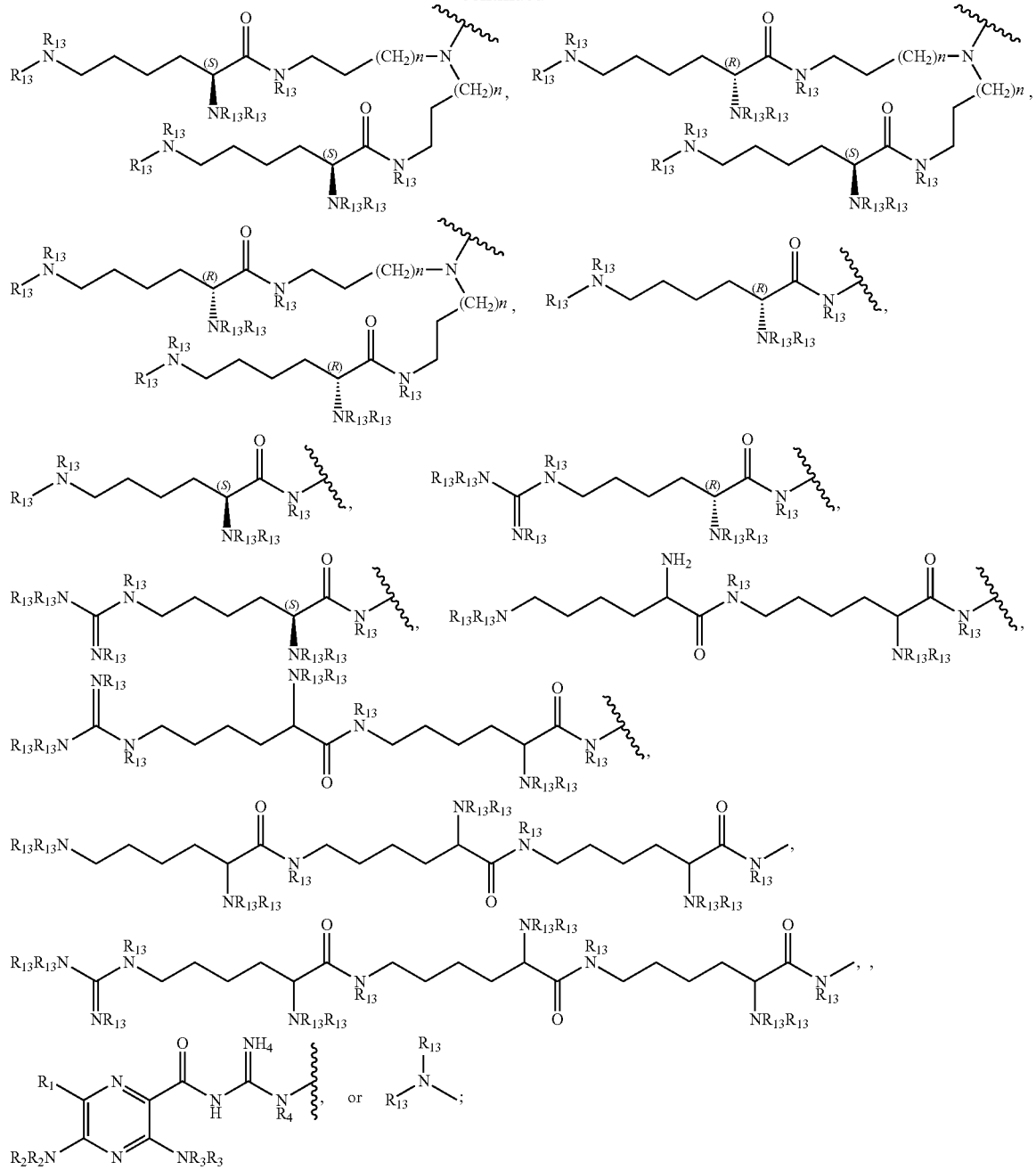

In a preferred embodiment, CAP is

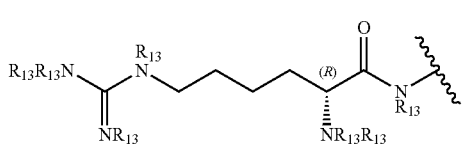

Each g is, independently, an integer from 1 to 6. Therefore, each g may be 1, 2, 3, 4, 5, or 6.

Each m is an integer from 1 to 7. Therefore, each m may be 1, 2, 3, 4, 5, 6, or 7.

Each n is an integer from 0 to 7. Therefore, each n may be 0, 1, 2, 3, 4, 5, 6, or 7.

Each Z is, independently, —(CHOH)—, —C(=O)—, —(CHNR$^7$R$^{10}$)—, —(C=NR$^{10}$)—, —NR$^{10}$—, —(CH$_2$)$_n$—, —(CHNR$^{13}$R$^{13}$)—, —(C=NR$^{13}$)—, or —NR$^{13}$—. As designated by (Z)$_g$ in certain embodiments, Z may occur one, two, three, four, five or six times and each occurrence of Z is, independently, —(CHOH)—, —C(=O)—, —(CHNR$^7$R$^{10}$)—, —(C=NR$^{10}$)—, —NR$^{10}$—, —(CH$_2$)$_n$—, —(CHNR$^{13}$R$^{13}$)—, —(C=NR$^{13}$)—, or —NR$^{13}$—. Therefore, by way of example and not by way of limitation, (Z)$_g$ can be —(CHOH)—(CHNR$^7$R$^{10}$)—, —(CHOH)—(CHNR$^7$R$^{10}$)—C(=O)—, —(CHOH)—(CHNR$^7$R$^{10}$)—C(=O)—

$-(CH_2)_n-$, $-(CHOH)-(CHNR^7R^{10})-C(=O)-(CH_2)_n-(CHNR^{13}R^{13})-$, $-(CHOH)-(CHNR^7R^{10})-C(=O)-(CH_2)_n-(CHNR^{13}R^{13})-C(=O)-$, and the like.

In any variable containing $-CHOR^8-$ or $-CH_2OR^8$ groups, when any $-CHOR^8-$ or $-CH_2OR^8$ groups are located 1,2- or 1,3- with respect to each other, the $R^8$ groups may, optionally, be taken together to form a cyclic mono- or di-substituted 1, 3-dioxane or 1,3-dioxolane.

The compounds described herein may be prepared and used as the free base. Alternatively, the compounds may be prepared and used as a pharmaceutically acceptable salt. Pharmaceutically acceptable salts are salts that retain or enhance the desired biological activity of the parent compound and do not impart undesired toxicological effects. Examples of such salts are (a) acid addition salts formed with inorganic acids, for example, hydrochloric acid, hydrobromic acid, sulfuric acid, phosphoric acid, nitric acid and the like; (b) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, malonic acid, sulfosalicylic acid, glycolic acid, 2-hydroxy-3-naphthoate, pamoate, salicylic acid, stearic acid, phthalic acid, mandelic acid, lactic acid and the like; and (c) salts formed from elemental anions for example, chlorine, bromine, and iodine.

It is to be noted that all enantiomers, diastereomers, and racemic mixtures, tautomers, polymorphs, pseudopolymorphs and pharmaceutically acceptable salts of compounds within the scope of formulae I (Ia-Id) are embraced by the present invention. All mixtures of such enantiomers and diastereomers are within the scope of the present invention.

A compound of formula I and its pharmaceutically acceptable salts may exist as different polymorphs or pseudopolymorphs. As used herein, crystalline polymorphism means the ability of a crystalline compound to exist in different crystal structures. The crystalline polymorphism may result from differences in crystal packing (packing polymorphism) or differences in packing between different conformers of the same molecule (conformational polymorphism). As used herein, crystalline pseudopolymorphism means the ability of a hydrate or solvate of a compound to exist in different crystal structures. The pseudopolymorphs of the instant invention may exist due to differences in crystal packing (packing pseudopolymorphism) or due to differences in packing between different conformers of the same molecule (conformational pseudopolymorphism). The instant invention comprises all polymorphs and pseudopolymorphs of the compounds of formula I-III and their pharmaceutically acceptable salts.

A compound of formula I and its pharmaceutically acceptable salts may also exist as an amorphous solid. As used herein, an amorphous solid is a solid in which there is no long-range order of the positions of the atoms in the solid. This definition applies as well when the crystal size is two nanometers or less. Additives, including solvents, may be used to create the amorphous forms of the instant invention. The instant invention comprises all amorphous forms of the compounds of formula I-III and their pharmaceutically acceptable salts.

The compounds of formula I may exist in different tautomeric forms. One skilled in the art will recognize that amidines, amides, guanidines, ureas, thioureas, heterocycles and the like can exist in tautomeric forms. All possible tautomeric forms of the amidines, amides, guanidines, ureas, thioureas, heterocycles and the like of all of the embodiments of formula I are within the scope of the instant invention.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., Stereochemistry of Organic Compounds (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l, D and L, or (+) and (−) are employed to designate the sign of rotation of plane-polarized light by the compound, with S, (−), or l meaning that the compound is levorotatory while a compound prefixed with R, (+), or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

A single stereoisomer, e.g. an enantiomer, substantially free of its stereoisomer may be obtained by resolution of the racemic mixture using a method such as formation of diastereomers using optically active resolving agents ("Stereochemistry of Carbon Compounds," (1962) by E. L. Eliel, McGraw Hill; Lochmuller, C. H., (1975) *J. Chromatogr.*, 113:(3) 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

The compounds described herein may be prepared and used as the free base. Alternatively, the compounds may be prepared and used as a pharmaceutically acceptable salt. Pharmaceutically acceptable salts are salts that retain or enhance the desired biological activity of the parent compound and do not impart undesired toxicological effects. Examples of such salts are (a) acid addition salts formed with inorganic acids, for example, hydrochloric acid, hydrobromic acid, sulfuric acid, phosphoric acid, nitric acid and the like; (b) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, malonic acid, sulfosalicylic acid, glycolic acid, 2-hydroxy-3-naphthoate, pamoate, salicylic acid, stearic acid, phthalic acid, mandelic acid, lactic acid and the like; and (c) salts formed from elemental anions for example, chlorine, bromine, and iodine.

It is to be noted that all enantiomers, diastereomers, and racemic mixtures, tautomers, polymorphs, pseudopolymorphs and pharmaceutically acceptable salts of compounds within the scope of formulae (X are embraced by the present invention. All mixtures of such enantiomers and diastereomers are within the scope of the present invention.

A compound of formula I and its pharmaceutically acceptable salts may exist as different polymorphs or pseudopolymorphs. As used herein, crystalline polymorphism means the ability of a crystalline compound to exist in different crystal structures. The crystalline polymorphism may result from differences in crystal packing (packing polymorphism) or differences in packing between different conformers of the same molecule (conformational polymorphism). As used herein, crystalline pseudopolymorphism means the ability of a hydrate or solvate of a compound to exist in different crystal structures. The pseudopolymorphs of the instant invention may exist due to differences in crystal packing (packing pseudopolymorphism) or due to differences in packing between different conformers of the same molecule (conformational pseudopolymorphism). The instant invention comprises all polymorphs and pseudopolymorphs of the compounds of formula I-III and their pharmaceutically acceptable salts.

A compound of formula I and its pharmaceutically acceptable salts may also exist as an amorphous solid. As used herein, an amorphous solid is a solid in which there is no long-range order of the positions of the atoms in the solid. This definition applies as well when the crystal size is two nanometers or less. Additives, including solvents, may be used to create the amorphous forms of the instant invention. The instant invention comprises all amorphous forms of the compounds of formula I and their pharmaceutically acceptable salts.

The compounds of formula I may exist in different tautomeric forms. One skilled in the art will recognize that amidines, amides, guanidines, ureas, thioureas, heterocycles and the like can exist in tautomeric forms. All possible tautomeric forms of the amidines, amides, guanidines, ureas, thioureas, heterocycles and the like of all of the embodiments of formula I-IV are within the scope of the instant invention.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., Stereochemistry of Organic Compounds (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l, D and L, or (+) and (−) are employed to designate the sign of rotation of plane-polarized light by the compound, with S, (−), or l meaning that the compound is levorotatory while a compound prefixed with R, (+), or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

A single stereoisomer, e.g. an enantiomer, substantially free of its stereoisomer may be obtained by resolution of the racemic mixture using a method such as formation of diastereomers using optically active resolving agents ("Stereochemistry of Carbon Compounds," (1962) by E. L. Eliel, McGraw Hill; Lochmuller, C. H., (1975) J. Chromatogr., 113:(3) 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

As discussed above, the compounds used to prepare the compositions of the present invention may be in the form of a pharmaceutically acceptable free base. Because the free base of the compound is generally less soluble in aqueous solutions than the salt, free base compositions are employed to provide more sustained release of active agent to the lungs. An active agent present in the lungs in particulate form which has not dissolved into solution is not available to induce a physiological response, but serves as a depot of bioavailable drug which gradually dissolves into solution.

In a preferred embodiment, the compound of formula (I) is

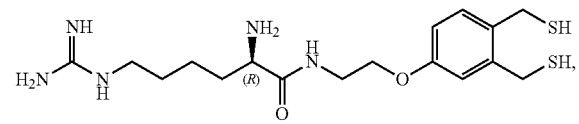

In another preferred embodiment, the compound of formula (I) is

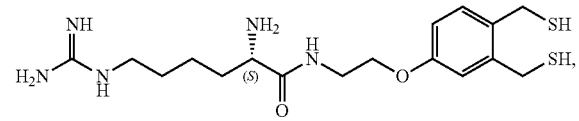

In another preferred embodiment, the compound of formula (I) is

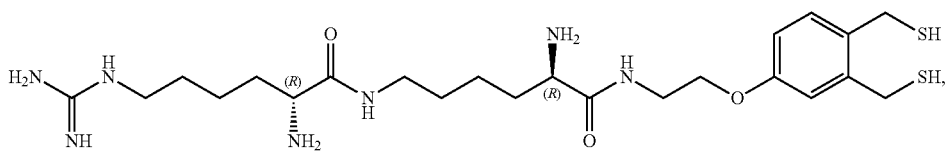

In another preferred embodiment, the compound of formula (I) is

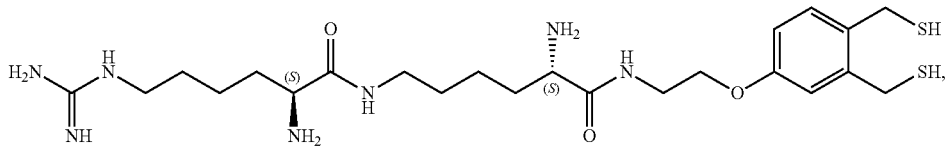

In another preferred embodiment, the compound of formula (I) is

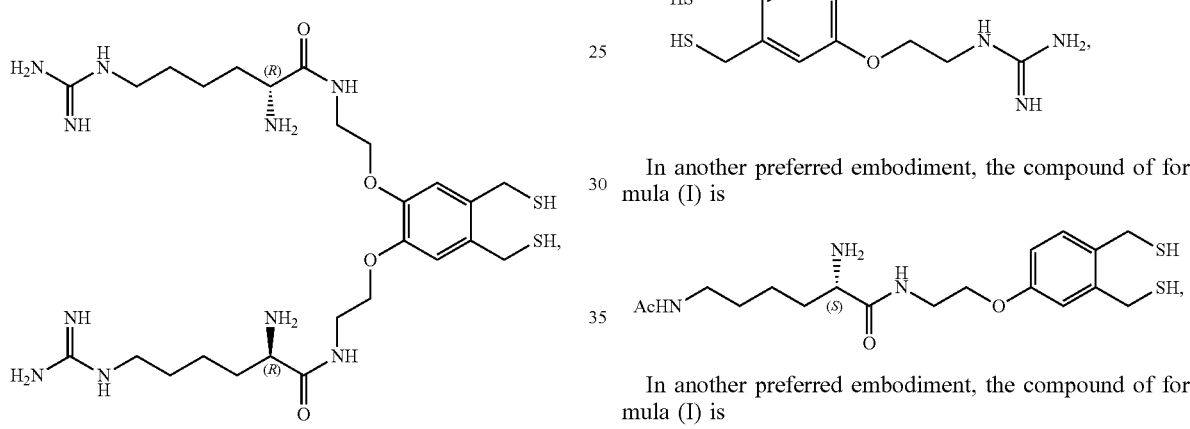

In another preferred embodiment, the compound of formula (I) is

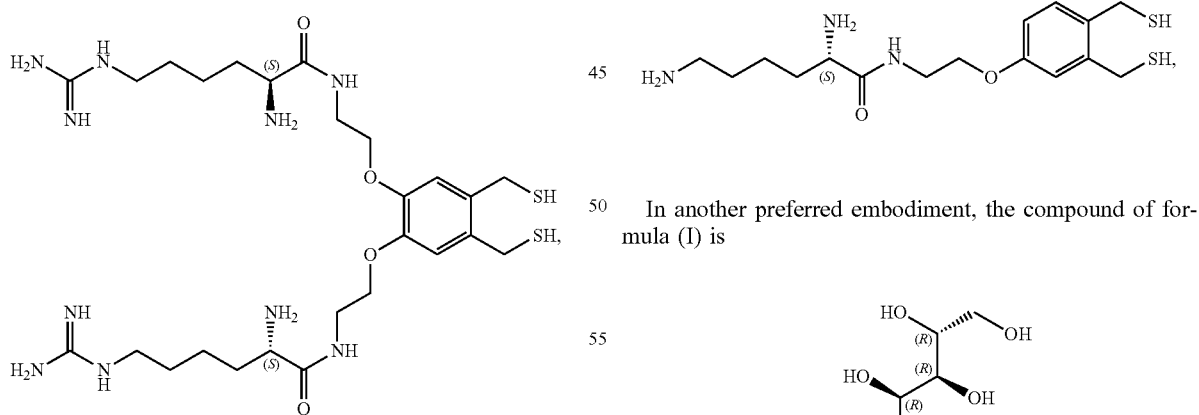

In another preferred embodiment, the compound of formula (I) is

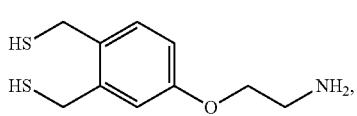

In another preferred embodiment, the compound of formula (I) is

In another preferred embodiment, the compound of formula (I) is

In another preferred embodiment, the compound of formula (I) is

In another preferred embodiment, the compound of formula (I) is

In another preferred embodiment, the compound of formula (I) is

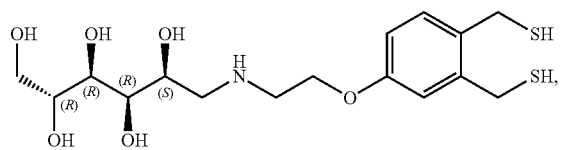
In another preferred embodiment, the compound of formula (I) is
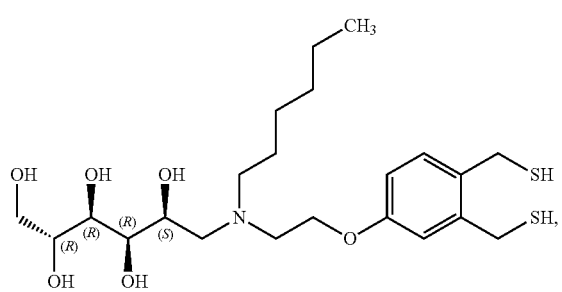
In another preferred embodiment, the compound of formula (I) is
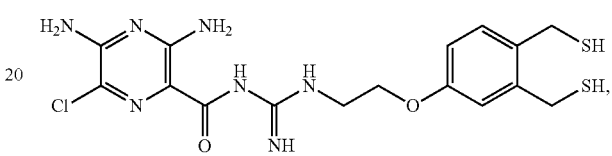
In another preferred embodiment, the compound of formula (I) is
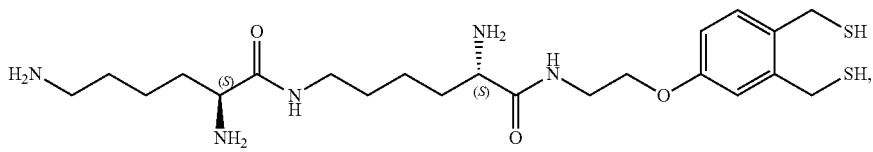
In another preferred embodiment, the compound of formula (I) is
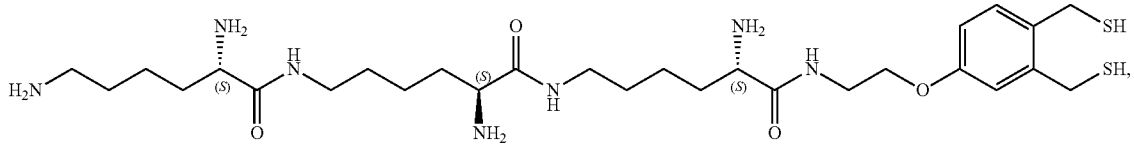
In another preferred embodiment, the compound of formula (I) is
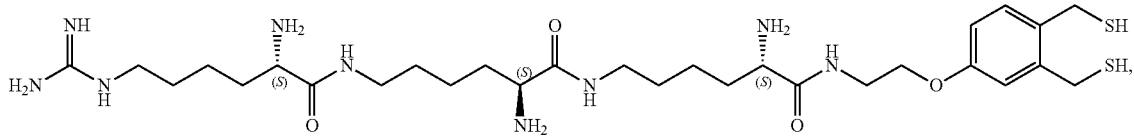

In another preferred embodiment, the compound of formula (I) is
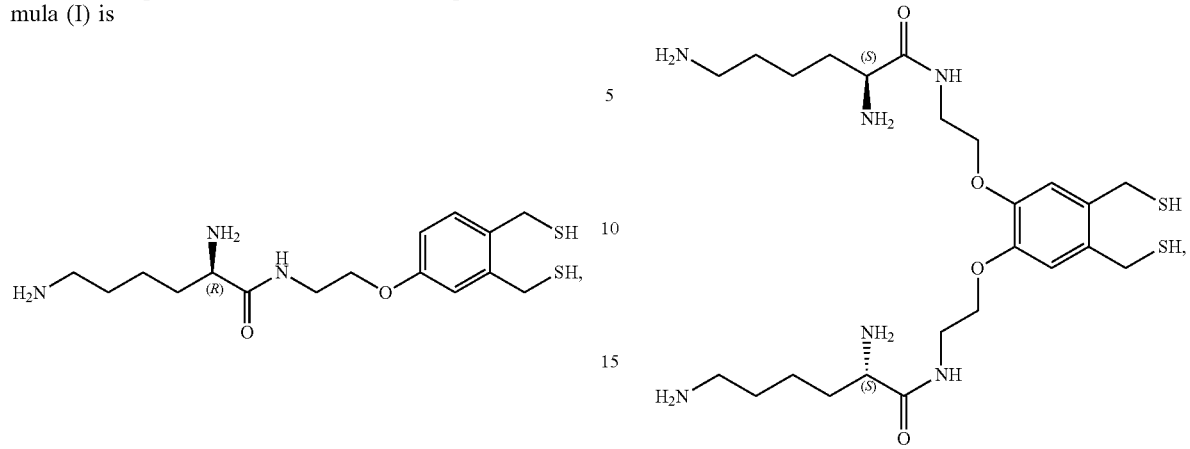
In another preferred embodiment, the compound of formula (I) is
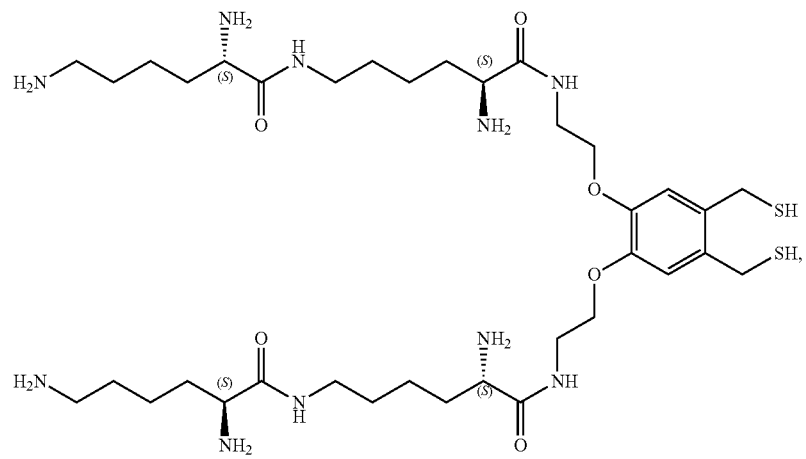
In another preferred embodiment, the compound of formula (I) is
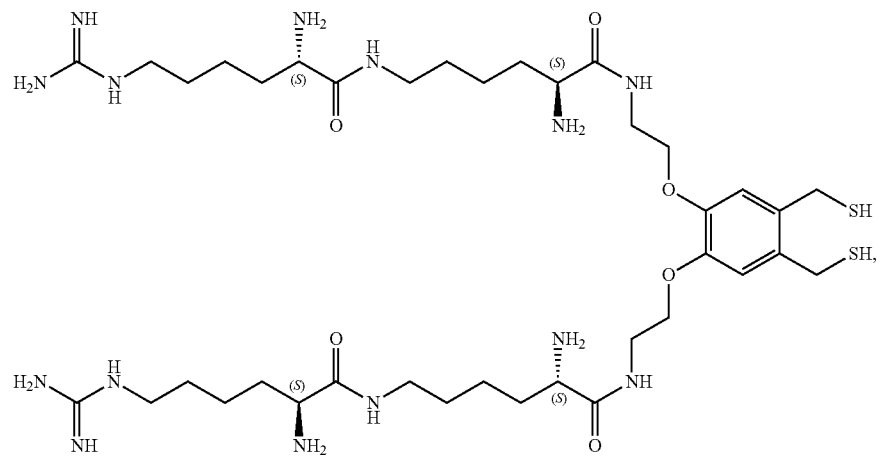

In another preferred embodiment, the compound of formula (I) is

The present invention also provides methods of treatment that take advantage of the properties of the compounds described herein as discussed above. Thus, subjects that may be treated by the methods of the present invention include, but are not limited to, patients afflicted with cystic fibrosis, asthma, primary ciliary dyskinesia, chronic bronchitis, bronchiectasis chronic obstructive airway disease, artificially ventilated patients, patients with acute pneumonia, etc. The present invention may be used to obtain a sputum sample from a patient by administering the active compounds to at least one lung of a patient, and then inducing or collecting a sputum sample from that patient. Typically, the invention will be administered to respiratory mucosal surfaces via aerosol (liquid or dry powders) or lavage.

Subjects that may be treated by the method of the present invention also include patients being administered supplemental oxygen nasally (a regimen that tends to dry the airway surfaces); patients afflicted with an allergic disease or response (e.g., an allergic response to pollen, dust, animal hair or particles, insects or insect particles, etc.) that affects nasal airway surfaces; patients afflicted with a bacterial infection e.g., staphylococcus infections such as Staphylococcus aureus infections, Hemophilus influenza infections, Streptococcus pneumoniae infections, Pseudomonas aeuriginosa infections, etc.) of the nasal airway surfaces; patients afflicted with an inflammatory disease that affects nasal airway surfaces; or patients afflicted with sinusitis (wherein the active agent or agents are administered to promote drainage of congested mucous secretions in the sinuses by administering an amount effective to promote drainage of congested fluid in the sinuses), or combined, Rhinosinusitis. The invention may be administered to rhinosinal surfaces by topical delivery, including aerosols and drops.

The present invention may be used to improve mucus clearance other than airway surfaces. Such other mucosal surfaces include gastrointestinal surfaces, oral surfaces, genito-urethral surfaces, and ocular surfaces or surfaces of the eye. For example, the active compounds of the present invention may be administered by any suitable means, including locally/topically, orally, or rectally, in an effective amount.

In another aspect, a post-exposure prophylactic treatment or therapeutic treatment method is provided for treating infection from an airborne pathogen comprising administering an effective amount of the compounds of formula (I-VII) to the lungs of an individual in need of such treatment against infection from an airborne pathogen. The pathogens which may be protected against by the prophylactic post exposure, rescue and therapeutic treatment methods of the invention include any pathogens which may enter the body through the mouth, nose or nasal airways, thus proceeding into the lungs. Typically, the pathogens will be airborne pathogens, either naturally occurring or by aerosolization. The pathogens may be naturally occurring or may have been introduced into the environment intentionally after aerosolization or other method of introducing the pathogens into the environment. Many pathogens which are not naturally transmitted in the air have been or may be aerosolized for use in bioterrorism. The pathogens for which the treatment of the invention may be useful includes, but is not limited to, category A, B and C priority pathogens as set forth by the NIAID. These categories correspond generally to the lists compiled by the Centers for Disease Control and Prevention (CDC). As set up by the CDC, Category A agents are those that can be easily disseminated or transmitted person-to-person, cause high mortality, with potential for major public health impact. Category B agents are next in priority and include those that are moderately easy to disseminate and cause moderate morbidity and low mortality. Category C consists of emerging pathogens that could be engineered for mass dissemination in the future because of their availability, ease of production and dissemination and potential for high morbidity and mortality. Particular examples of these pathogens are anthrax and plague. Additional pathogens which may be protected against or the infection risk therefrom reduced include influenza viruses, rhinoviruses, adenoviruses and respiratory syncytial viruses, and the like. A further pathogen which may be protected against is the coronavirus which is believed to cause severe acute respiratory syndrome (SARS).

The present invention also relates to the use of mucolytic agents of Formula I, or a pharmaceutically acceptable salt thereof, for preventing, mitigating, and/or treating deterministic health effects to the respiratory tract caused by exposure to radiological materials, particularly respirable aerosols containing radionuclides from nuclear attacks, such as detonation of radiological dispersal devices (RDD), or accidents, such as nuclear power plant disasters. As such, provided herein is a method for preventing, mitigating, and/or treating deterministic health effects to the respiratory tract and/or other bodily organs caused by respirable aerosols containing radionuclides in a recipient in need thereof, including in a human in need thereof, said method comprising administering to said human an effective amount of a compound of Formula (I), or a pharmaceutically acceptable salt thereof.

A major concern associated with consequence management planning for exposures of members of the public to respirable aerosols containing radionuclides from nuclear attacks, such as detonation of radiological dispersal devices (RDD), or accidents, such as nuclear power plant disasters is how to prevent, mitigate or treat potential deterministic health effects to the respiratory tract, primarily the lung. It is necessary to have drugs, techniques and procedures, and trained personnel prepared to manage and treat such highly internally contaminated individuals.

Research has been conducted to determine ways in which to prevent, mitigate or treat potential damage to the respiratory tract and various organs in the body that is caused by internally deposited radionuclides. To date, most of the research attention has focused on strategies designed to mitigate health effects from internally deposited radionuclides by accelerating their excretion or removal. These strategies have focused on soluble chemical forms that are capable of reaching the blood stream and are deposited at remote systemic sites specific to a given radioelement. Such approaches will not work in cases where the deposited radionuclide is in relatively insoluble form. Studies have shown that many, if not most of the physicochemical forms of dispersed radionuclides from RDDs, will be in relatively insoluble form.

The only method known to effectively reduce the radiation dose to the lungs from inhaled insoluble radioactive aerosols is bronchoalveolar lavage or BAL. This technique, which was adapted from that already in use for the treatment of patients with alveolar proteinosis, has been shown to be a safe, repeatable procedure, even when performed over an extended period of time. Although there are variations in procedure, the basic method for BAL is to anaesthetize the subject, followed by the slow introduction of isotonic saline into a single lobe of the lung until the function residual capacity is reached. Additional volumes are then added and drained by gravity.

The results of studies using BAL on animals indicate that about 40% of the deep lung content can be removed by a reasonable sequence of BALs. In some studies, there was considerable variability among animals in the amount of radionuclide recovered. The reasons for the variability are currently not understood.

Further, based on a study on animals, it is believed that a significant dose reduction from BAL therapy results in mitigation of health effects due to inhalation of insoluble radionuclides. In the study, adult dogs inhaled insoluble $^{144}$Ce-FAP particles. Two groups of dogs were given lung contents of $^{144}$Ce known to cause radiation pneumonitis and pulmonary fibrosis (about 2 MBq/kg body mass), with one group being treated with 10 unilateral lavages between 2 and 56 days after exposure, the other untreated. A third group was exposed at a level of $^{144}$Ce comparable to that seen in the BAL-treated group after treatment (about 1 MBq/kg), but these animals were untreated. All animals were allowed to live their lifespans, which extended to 16 years. Because there is variability in initial lung content of $^{144}$Ce among the dogs in each group, the dose rates and cumulative doses for each group overlap. Nevertheless, the effect of BAL in reducing the risk from pneumonitis/fibrosis was evident from the survival curves. In the untreated dogs with lung contents of 1.5-2.5 MBq/kg, the mean survival time was 370±65 d. For the treated dogs, the mean survival was 1270±240 d, which was statistically significantly different. The third group, which received lung contents of $^{144}$Ce of 0.6-1.4 MBq had a mean survival time of 1800±230, which was not statistically different from the treated group. Equally important to the increased survival, the dogs in the high-dose untreated group died from deterministic effects to lung (pneumonitis/fibrosis) while the treated dogs did not. Instead, the treated dogs, like the dogs in the low-dose untreated group, mostly had lung tumors (hemangiosarcoma or carcinoma). Therefore, the reduction in dose resulting from BAL treatment appears to have produced biological effects in lung that were predictable based on the radiation doses that the lungs received.

Based on these results, it is believed that decreasing the residual radiological dose further by any method or combination of methods for enhancing the clearance of particles from the lung would further decrease the probability of health effects to lung. However, BAL is a procedure that has many drawbacks. BAL is a highly invasive procedure that must be performed at specialized medical centers by trained pulmonologists. As such, a BAL procedure is expensive. Given the drawbacks of BAL, it is not a treatment option that would be readily and immediately available to persons in need of accelerated removal of radioactive particles, for example, in the event of a nuclear attack. In the event of a nuclear attack or a nuclear accident, immediate and relatively easily administered treatment for persons who have been exposed or who are at risk of being exposed is needed. Sodium channel blockers administered as an inhalation aerosol have been shown to restore hydration of airway surfaces. Such hydration of airway surfaces aids in clearing accumulated mucus secretions and associated particulate matter from the lung. As such, without being bound by any particular theory, it is believed that sodium channel blockers can be used in combination with mucolytic agents described in this invention to accelerate the removal of radioactive particles from airway passages.

As discussed above, the greatest risk to the lungs following a radiological attack, such as a dirty bomb, results from the inhalation and retention of insoluble radioactive particles. As a result of radioactive particle retention, the cumulative exposure to the lung is significantly increased, ultimately resulting in pulmonary fibrosis/pneumonitis and potentially death. Insoluble particles cannot be systemically cleared by chelating agents because these particles are not in solution. To date, the physical removal of particulate matter through BAL is the only therapeutic regimen shown to be effective at mitigating radiation-induced lung disease. As discussed above, BAL is not a realistic treatment solution for reducing the effects of radioactive particles that have been inhaled into the body. As such, it is desirable to provide a therapeutic regimen that effectively aids in clearing radioactive particles from airway passages and that, unlike BAL, is relatively simple to administer and scalable in a large-scale radiation exposure scenario. In addition, it is also desirable that the therapeutic regimen be readily available to a number of people in a relatively short period of time.

In an aspect of the present invention, a method for preventing, mitigating, and/or treating deterministic health effects to the respiratory tract and/or other bodily organs caused by respirable aerosols containing radionuclides comprises administering an effective amount of a mucolytic agent of Formula I or a pharmaceutically acceptable salt thereof to an individual in need. In a feature of this aspect, the mucolytic agent is administered in conjunction with an osmolyte. With further regard to this feature, the osmolyte is hypertonic saline. In a further feature, the mucolytic agent and the osmolyte are administered in conjunction with an ion transport modulator. With further regard to this feature, the ion transport modulator may be selected from the group consisting of β-agonists, CFTR potentiators, purinergic receptor agonists, lubiprostones, and protease inhibitors. In another feature of this aspect, the radionuclides are selected from the group consisting of Colbalt-60, Cesium-137, Iridium-192, Radium-226, Phospohrus-32, Strontium-89 and 90, Iodine-125, Thallium-201, Lead-210, Thorium-234, Uranium-238, Plutonium, Cobalt-58, Chromium-51, Americium, and Curium. In a further feature, the radionuclides are from a radioactive disposal device. In yet another feature, the mucolytic agent or pharmaceutically acceptable salt thereof is administered in an aerosol suspension of respirable particles which the individual inhales. In an additional feature, the mucolytic agent or a pharmaceutically acceptable salt thereof is administered post-exposure to the radionuclides.

The present invention is concerned primarily with the treatment of human subjects, but may also be employed for the treatment of other mammalian subjects, such as dogs and cats, for veterinary purposes.

Another aspect of the present invention is a pharmaceutical composition, comprising a compound of formula I in a pharmaceutically acceptable carrier (e.g., an aqueous carrier solution). In general, the compound of formula I is included in the composition in an amount effective to reduce the viscosity of mucus on mucosal surfaces.

An aspect of the present invention is the combination of mucolytic agents with other drugs or excipients to improve the efficacy and tolerability of the compounds described in the present invention.

Another aspect of the present invention is administering potent reducing agents in combination with osmolytes. A simple means to restore airway surface hydration in subjects with muco-obstructive diseases is to inhale hypertonic osmolyte solutions (most frequently 7% hypertonic saline (HS)), which draws water onto the airway surface. Rehydration of the lubricant periciliary layer (PCL) of the airway surface facilitates mucus clearance and, therefore, the removal of inhaled infectious agents.

Inhaled HS is a unique therapeutic agent as it is used by ~60% of CF patients nationwide, but is not FDA approved for daily use for pulmonary disease. As such, HS has not undergone the rigorous clinical testing to identify the dose and dosing frequency that are most efficacious and well tolerated. Instead, the HS regime has been optimized in practice by patients and physicians. Most commonly, HS is administered as two 15 minute inhalation treatments of 4 mL of 7% hypertonic saline per treatment. The tonicity of HS used by patients (7% NaCl) has been identified as a maximum concentration that is generally tolerated (i.e. minimal irritation or bronchoconstriction).

Another approach to replenish the protective liquid layer on mucosal surfaces is to "re-balance" the system by blocking $Na^+$ channel and liquid absorption. The epithelial protein that mediates the rate-limiting step of $Na^+$ and liquid absorption is the epithelial $Na^+$ channel (ENaC). ENaC is positioned on the apical surface of the epithelium, i.e. the mucosal surface-environmental interface. Other approaches to hydrate the airway surface include chloride ($Cl^-$) secretogogues that draw $Cl^-$ and water into the ASL.

The compounds of Formula I may also be used in conjunction with osmolytes thus lowering the dose of the compound needed to hydrate mucosal surfaces. This important property means that the compound will have a lower tendency to cause undesired side-effects. Active osmolytes of the present invention are molecules or compounds that are osmotically active (i.e., are "osmolytes"). "Osmotically active" compounds of the present invention are membrane-impermeable (i.e., essentially non-absorbable) on the airway or pulmonary epithelial surface. The terms "airway surface" and "pulmonary surface," as used herein, include pulmonary airway surfaces such as the bronchi and bronchioles, alveolar surfaces, and nasal and sinus surfaces. Active compounds of the present invention may be ionic osmolytes (i.e., salts), or may be non-ionic osmolytes (i.e., sugars, sugar alcohols, and organic osmolytes). It is specifically intended that both racemic forms of the active compounds that are racemic in nature are included in the group of active compounds that are useful in the present invention. It is to be noted that all racemates, enantiomers, diastereomers, tautomers, polymorphs and pseudopolymorphs and racemic mixtures of the osmotically active compounds are embraced by the present invention.

Active compounds of the present invention may be ionic osmolytes (i.e., salts), or may be non-ionic osmolytes (i.e., sugars, sugar alcohols, and organic osmolytes). It is specifically intended that both racemic forms of the active compounds that are racemic in nature are included in the group of active compounds that are useful in the present invention. It is to be noted that all racemates, enantiomers, diastereomers, tautomers, polymorphs and pseudopolymorphs and racemic mixtures of the osmotically active compounds are embraced by the present invention.

Active osmolytes useful in the present invention that are ionic osmolytes include any salt of a pharmaceutically acceptable anion and a pharmaceutically acceptable cation. Preferably, either (or both) of the anion and cation are non-absorbable (i.e., osmotically active and not subject to rapid active transport) in relation to the airway surfaces to which they are administered. Such compounds include but are not limited to anions and cations that are contained in FDA approved commercially marketed salts, see, e.g., Remington: The Science and Practice of Pharmacy, Vol. II, pg. 1457 (19.sup.th Ed. 1995), incorporated herein by reference, and can be used in any combination including their conventional combinations.

Pharmaceutically acceptable osmotically active anions that can be used to carry out the present invention include, but are not limited to, acetate, benzenesulfonate, benzoate, bicarbonate, bitartrate, bromide, calcium edetate, camsylate (camphorsulfonate), carbonate, chloride, citrate, dihydrochloride, edetate, edisylate (1,2-ethanedisulfonate), estolate (lauryl sulfate), esylate (1,2-ethanedisulfonate), fumarate, gluceptate, gluconate, glutamate, glycollylarsanilate (p-glycollamidophenylarsonate), hexylresorcinate, hydrabamine (N,N'-Di(dehydroabietyl)ethylenediamine), hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, nitrte, pamoate (embonate), pantothenate, phosphate or diphosphate, polygalacturonate, salicylate, stearate, subacetate, succinate, sulfate, tannate, tartrate, teoclate (8-chlorotheophyllinate), triethiodide, bicarbonate, etc. Particularly preferred anions include chloride sulfate, nitrate, gluconate, iodide, bicarbonate, bromide, and phosphate.

Pharmaceutically acceptable cations that can be used to carry out the present invention include, but are not limited to, organic cations such as benzathine (N,N'-dibenzylethylenediamine), chloroprocaine, choline, diethanolamine, ethylenediamine, meglumine (N-methyl D-glucamine), procaine, D-lysine, L-lysine, D-arginine, L-arginine, triethylammonium, N-methyl D-glycerol, and the like. Particularly preferred organic cations are 3-carbon, 4-carbon, 5-carbon and 6-carbon organic cations. Metallic cations useful in the practice of the present invention include but are not limited to aluminum, calcium, lithium, magnesium, potassium, sodium, zinc, iron, ammonium, and the like. Particularly preferred cations include sodium, potassium, choline, lithium, meglumine, D-lysine, ammonium, magnesium, and calcium.

Specific examples of osmotically active salts that may be used with the sodium channel blockers described herein to carry out the present invention include, but are not limited to, sodium chloride, potassium chloride, choline chloride, choline iodide, lithium chloride, meglumine chloride, L-lysine chloride, D-lysine chloride, ammonium chloride, potassium sulfate, potassium nitrate, potassium gluconate, potassium iodide, ferric chloride, ferrous chloride, potassium bromide, etc. Either a single salt or a combination of different osmotically active salts may be used to carry out the present invention. Combinations of different salts are preferred. When different salts are used, one of the anion or cation may be the same among the differing salts.

Osmotically active compounds of the present invention also include non-ionic osmolytes such as sugars, sugar-alcohols, and organic osmolytes. Sugars and sugar-alcohols useful in the practice of the present invention include but are not limited to 3-carbon sugars (e.g., glycerol, dihydroxyacetone); 4-carbon sugars (e.g., both the D and L forms of erythrose, threose, and erythrulose); 5-carbon sugars (e.g., both the D and L forms of ribose, arabinose, xylose, lyxose, psicose, fructose, sorbose, and tagatose); and 6-carbon sugars (e.g., both the D and L forms of altose, allose, glucose, mannose, gulose, idose, galactose, and talose, and the D and L forms of allo-heptulose, allo-hepulose, gluco-heptulose, manno-heptulose, gulo-heptulose, ido-heptulose, galacto-heptulose, talo-heptulose). Additional sugars useful in the practice of the present invention include raffinose, raffinose series oligosaccharides, and stachyose. Both the D and L forms of the reduced form of each sugar/sugar alcohol useful in the present invention are also active compounds within the scope of the invention. For example, glucose, when reduced, becomes sorbitol; within the scope of the invention, sorbitol and other reduced forms of sugar/sugar alcohols (e.g., mannitol, dulcitol, arabitol) are accordingly active compounds of the present invention.

Osmotically active compounds of the present invention additionally include the family of non-ionic osmolytes termed "organic osmolytes." The term "organic osmolytes" is generally used to refer to molecules used to control intracellular osmolality in the kidney. See e.g., J. S. Handler et al., Comp. Biochem. Physiol, 117, 301-306 (1997); M. Burg, Am. J. Physiol. 268, F983-F996 (1995), each incorporated herein by reference. Although the inventor does not wish to be bound to any particular theory of the invention, it appears that these organic osmolytes are useful in controlling extracellular volume on the airway/pulmonary surface. Organic osmolytes useful as active compounds in the present invention include but are not limited to three major classes of compounds: polyols (polyhydric alcohols), methylamines, and amino acids. The polyol organic osmolytes considered useful in the practice of this invention include, but are not limited to, inositol, myo-inositol, and sorbitol. The methylamine organic osmolytes useful in the practice of the invention include, but are not limited to, choline, betaine, carnitine (L-, D- and DL forms), phosphorylcholine, lyso-phosphorylcholine, glycerophosphorylcholine, creatine, and creatine phosphate. The amino acid organic osmolytes of the invention include, but are not limited to, the D- and L-forms of glycine, alanine, glutamine, glutamate, aspartate, proline and taurine. Additional osmolytes useful in the practice of the invention include tihulose and sarcosine. Mammalian organic osmolytes are preferred, with human organic osmolytes being most preferred. However, certain organic osmolytes are of bacterial, yeast, and marine animal origin, and these compounds are also useful active compounds within the scope of the present invention.

Under certain circumstances, an osmolyte precursor may be administered to the subject; accordingly, these compounds are also useful in the practice of the invention. The term "osmolyte precursor" as used herein refers to a compound which is converted into an osmolyte by a metabolic step, either catabolic or anabolic. The osmolyte precursors of this invention include, but are not limited to, glucose, glucose polymers, glycerol, choline, phosphatidylcholine, lyso-phosphatidylcholine and inorganic phosphates, which are precursors of polyols and methylamines. Precursors of amino acid osmolytes within the scope of this invention include proteins, peptides, and polyamino acids, which are hydrolyzed to yield osmolyte amino acids, and metabolic precursors which can be converted into osmolyte amino acids by a metabolic step such as transamination. For example, a precursor of the amino acid glutamine is poly-L-glutamine, and a precursor of glutamate is poly-L-glutamic acid.

In one embodiment of this invention, mucolytic agents are utilized to provide access to other therapeutic agents through the mucus layer to the airway epithelium. Mucus forms a diffusion barrier which can prevent therapeutic molecules from reaching their intended site of action.

The access of the following therapeutic agents to their site of action in the airway epithelium could be enhanced by the pre- or co-treatment with the mucolytic agents described in this invention.

Sodium Channel Blockers:

Coordinated ion transport by the airway epithelia directly regulates the hydration level of the mucosal surface. Importantly, sodium absorption through the epithelial sodium channel (ENaC) provides the rate-limiting step in hydration. In human subjects with loss of function mutation in ENaC have 'wet' airway surfaces and extraordinarily fast mucous clearance (Kerem et al., N Engl J Med. 1999 Jul. 15; 341(3):156-62). Conversely, increased sodium absorption through ENaC has been shown to be the underlying cause of mucous dehydration and the formation of mucous plugs in the lungs CF patients. Furthermore, transgenic mice that overexpress ENaC in the lungs have dehydrated airway surfaces and reduced/absent mucous clearance that results in death (Hummler et al., Proc Natl Acad Sci USA. 1997 Oct. 14; 94(21):11710-5). As predicted from clinical and experimental data, pharmacological blockade of ENaC conserves liquid on airway surfaces and increases mucus clearance (Hirsh et al., J Pharmacol Exp Ther. 2008; 325(1):77-88). Particular examples include, but are not limited to:

Small molecule channel blockers: Small molecule ENaC blockers are capable of directly preventing sodium transport through the ENaC channel pore. ENaC blocker that can be administered by the methods of this invention include, but are not limited to, amiloride, benzamil, phenamil, and amiloride analogues as exemplified by U.S. Pat. Nos. 6,858, 614, 6,858,615, 6,903,105, 6,995,160, 7,026,325, 7,030,117, 7,064,129, 7,186,833, 7,189,719, 7,192,958, 7,192,959, 7,241,766, 7,247,636, 7,247,637, 7,317,013, 7,332,496, 7,345,044, 7,368,447, 7,368,450, 7,368,451, 7,375,107, 7,399,766, 7,410,968, 7,820,678, 7,842,697, 7,868,010, 7,875,619, 7,956,059, 8,008,494, 8,022,210, 8,124,607, 8,143,256, 8,163,758, 8,198,286, 8,211,895, 8,324,218, 8,507,497, 8,575,176, 8,669,262, 7,956,059, 8,008,494, 8,022,210, 8,124,607, 8,143,256, 8,163,758, 8,198,286, 8,211,895, 8,324,218, 8,507,497, 8,575,176, 8,669,262, 7,956,059, 8,008,494, 8,022,210, U.S. Patent Application Publication No. US2014/0142118-A1, U. S. Patent Application No. US20140170244-A1, and U. S. Patent Application No. US20140171447-A1.

Protease inhibitors: ENaC proteolysis is well described to increase sodium transport through ENaC. Protease inhibitor block the activity of endogenous airway proteases, thereby preventing ENaC cleavage and activation. Protease that cleave ENaC include furin, meprin, matriptase, trypsin, channel associated proteases (CAPs), and neutrophil elastases. Protease inhibitors that can inhibit the proteolytic activity of these proteases that can be administered by the methods of this invention include, but are not limited to, camostat, prostasin, furin, aprotinin, leupeptin, and trypsin inhibitors.

Nucleic acids and Small Interfering RNAs (siRNA): Any suitable nucleic acid (or polynucleic acid) can be used to carry out the present invention, including but not limited to antisense oligonucleotide, siRNA, miRNA, miRNA mimic, antagomir, ribozyme, aptamer, and decoy oligonucleotide nucleic acids. See, e.g., US Patent Application Publication No. 20100316628. In general, such nucleic acids may be from 17 or 19 nucleotides in length, up to 23, 25 or 27 nucleotides in length, or more.

Any suitable siRNA active agent can be used to carry out the present invention. Examples include, but are not limited to, those described in U.S. Pat. No. 7,517,865 and US Patent Application Nos. 20100215588; 20100316628; 20110008366; and 20110104255. In general, the siRNAs are from 17 or 19 nucleotides in length, up to 23, 25 or 27 nucleotides in length, or more.

Secretogogues:

Mutations in the cystic fibrosis (CF) gene result in abnormal ion transport across the respiratory epithelium (Matsui et al., Cell 1998; 95:1005-15). Excessive absorption of sodium and the inability to secrete chloride by the airway epithelium in patients with CF drives water absorption down an osmotic gradient generated by inappropriate salt absorption, dehydrating airway mucous secretions and reducing the volume of liquid in the PCL. In COPD, cigarette smoke impairs CFTR function, thus creating an acquired phenotype similar to CF.

$P2Y_2$ Receptor Agonists: Agents that that may be administered in combination with the methods and molecules described in the present invention include a group of $P2Y_2$ agonists. Purinergic ($P2Y_2$) receptors are abundant on luminal surface of human bronchial epithelium (HBE) and are known to stimulate Cl⁻ secretion and inhibit Na⁺ absorption (Goralski et al., Curr Opin Pharmacol. 2010 June; 10(3): 294-9). UTP is an example of an endogenous $P2Y_2$ receptor agonist that provides a robust stimulation of chloride secretion, inhibition of sodium absorption and increase in airway surface liquid layer in airway epithelium, thus increasing the mucus clearance which is the primary defense mechanism of the lung. Early studies using uridine-5-triphosphate (UTP) delivered via aerosol to airway surfaces of CF and primary cilia dyskinesia (PCD) patients suggested the usefulness of UTP in enhancing MC and improving mean cough clearance rates.

Suitable $P2Y_2$ receptor agonists are described in, but are not limited to, U.S. Pat. Nos. 6,264,975, 5,656,256, 5,292,498, 6,348,589, 6,818,629, 6,977,246, 7,223,744, 7,531,525 and U.S. Pat. AP. 2009/0306009 each of which is incorporated herein by reference.

Activators of Alternative Chloride Channels such as CaCCs and ClC-2 Class Channels: CaCCs are broadly expressed in mammalian cells where they are involved in a wide range of physiological functions, including transepithelial fluid secretion, oocyte fertilization, olfactory and sensory signal transduction, smooth muscle contraction, and neuronal and cardiac excitation. Whole cell current analysis indicates several common features between CaCC subfamilies, including slow activation following membrane depolarization, outwardly rectifying steady state currents and greater iodide than chloride permeability. Single channel analysis has suggested four or more distinct CaCC subclasses, with a wide range of reported single channel conductances from less than 2 pS in cardiac myocytes to 50 pS in airway epithelial cells.

The consequences of CaCC activation are cell type specific, for example, chloride secretion in epithelial cells, action potential generation in olfactory receptor neurons, smooth muscle contraction, and prevention of polyspermia in oocytes. In some cell types, such as smooth muscle cells, membrane depolarization activates voltagegated calcium channels, increasing intracellular calcium concentration. Although CaCCs were functionally characterized nearly three decades ago, their molecular identity has remained unclear until recently, with potential candidates including bestrophins (BEST1-BEST4) (Sun et al., *Proc Natl Acad Sci USA* 99, 4008-4013 (2002) and Tsunenari et al., *J Biol Chem* 278, 41114-41125 (2003)), the calcium activated chloride channel ClCA family proteins (Gruber et al., *Genomics* 1998; 54:200-214) and ClC3 (Huang P et al. (2001) Regulation of human CLC-3 channels by multifunctional Ca2+/calmodulin-dependent protein kinase. JBC 276: 20093-100). Three independent laboratories have identified TMEM16A, also called anoctaminl, as a strong candidate for a CaCC (Yang Y D et al. (2008) TMEM16A confers receptor-activated calcium-dependent chloride conductance. *Nature.* 455: 1210-15; Caputo A et al. (2008) TMEM16A, a membrane protein associated with calcium-dependent chloride channel activity. *Science.* 322: 590-4; Schroeder B C et al. (2008) Expression cloning of TMEM16A as a calcium-activated chloride channel subunit. *Cell.* 134: 1019-29). Three different strategies were used: database searching for membrane proteins with multiple transmembrane segments and unknown function (Yang Y D et al. (2008) TMEM16A confers receptor-activated calcium-dependent chloride conductance. *Nature.* 455: 1210-15), functional genomics following the observation that interleukin 4 (Il4) treated bronchial epithelial cells show increased CaCC activity (Caputo A et al. (2008) TMEM16A, a membrane protein associated with calcium-dependent chloride channel activity. *Science.* 322: 590-4), and expression cloning using axolotl oocytes that do not have endogenous CaCC activity (Schroeder B C et al. (2008) Expression cloning of TMEM16A as a calcium-activated chloride channel subunit. *Cell.* 134: 1019-29). There is strong evidence to suggest TMEM16A is a key component of CaCC, including similarity to native CaCCs in its electrophysiological properties, appearance of CaCC currents in various transfected cell systems, reduction in CaCC currents following RNAi knockdown, and its tissue distribution. TMEM16A has eight putative transmembrane segments without domains evidently involved in calcium regulation.

ClC2 is a ubiquitously expressed, inwardly rectifying chloride channel that is activated by cell swelling. ClC2 was thought to be involved in cell volume regulation, but it has different biophysical characteristics from the volume sensitive chloride channels that have been characterized in many tissues. Suitable alternative chloride channel activators are described in U.S. Pat. Nos. 6,015,828, 6,159,969 and 7,253, 295. The therapeutic efficacy of activators of Alternative Chloride Channels such as CaCCs and ClC-2 Class Channels can be enhanced by the administration of compounds and methods of this invention.

Modulators of CFTR asctivity The hereditary lethal disease cystic fibrosis is caused mutations in the gene encoding CFTR protein, a cAMP activated chloride channel expressed in the airway epithelia. Various mutations in CFTR cause ion transport dysfunction by limiting the chloride ion secretion to the surface of the airway epithelium via CFTR and by dys-regulation of sodium ion absorption, leading to excessive absorption of sodium cations. These defects in ion transport result in impaired hydration of airway surface liquid layer, decrease in mucus clearance and lead to progressive loss of lung function. Recently, it has been shown that CFTR functional defects are present in cigarette smoke exposed tissue, thus implying the role of CFTR dysfunction in COPD.

Over 1500 putative mutations have been described in CFTR, which can be divided into classes according to the molecular mechanism of the genetic defect (Rowe et al., Pulm Pharmacol Ther., 23(4):268-78 (2010)). An understanding of the biology of each of these mutations has led to therapeutic strategies based on the particular mutation type. Class 1 mutations include premature termination codons (PTCs, e.g. nonsense mutations) within the coding region of CFTR, which cause premature truncation of normal protein translation. These mutations are found in 10% of CF patients, but are particularly common in Ashkenazi Jews (75% of mutant CFTR alleles). Class II CFTR mutations include F508del CFTR, the most common mutation in humans (accounting for 75% of alleles and found in approximately 90% of CF patients). The deletion of phenylalanine at the 508 position causes CFTR to exhibit abnormal folding characterized by deficient stabilization by domain-domain interactions between the nucleotide binding domain 1 (NBD1) and the transmembrane domains. The misfolded protein is recognized by cellular chaperones within the endoplasmic reticulum (ER), directed to the proteasome, and rapidly degraded prior to reaching its active site at the cell surface. Because the cellular machinery responsible for the recognition and degradation of the misfolded protein is not 100% efficient, particular individuals exhibit low levels of surface expression of F508del CFTR, which may account for partial CFTR activity (and a more mild CF phenotype) observed in individuals homozygous for F508del CFTR, and could represent a population more amenable to protein repair. Even when at the cell surface, F508del CFTR exhibits reduced gating, suggesting that misfolded CFTR also exhibits reduced CFTR ion channel activity. Class III and IV CFTR mutations are characterized by full-length CFTR that reaches the cell surface but exhibit reduced ion transport activity owing to abnormal channel gating (Class III, e.g. G551D) or reduced conductivity of the ion channel pore (Class IV, e.g. R117H). Similarly, splicing mutants (Class V) and mutations within the C-terminus (Class VI) are also full length, but exhibit reduced activity owing to reduced numbers of active channels within the plasma membrane. Although the molecular basis of CFTR mutants is complex and as yet incomplete, the classification of CFTR mutants can be simplified into the therapeutically relevant groups based on the activity of agents in development. Both traditional and high-throughput drug discovery programs have resulted in discovery of novel compounds that address specific mutant CFTR alleles. These 'CFTR modulators' are pharmacological agents intended to repair the CFTR protein and are described in each section that follows.

Potentiators of cell-surface cystic fibrosis transmembrane conductance regulator CFTR mutation classes that result in dysfunctional CFTR that resides at the plasma membrane include Class III, IV, V, and VI mutations and represent potential targets for CFTR activators. G551D CFTR represents an archetype CFTR allele for this category of agents, as it exhibits normal surface expression and half-life, but confers a severe defect in channel gating owing to an amino acid substitution in the adenosine triphosphate (ATP) binding pocket within the nucleotide binding domains (Gregory, R. J. et al. (1991) Maturation and function of cystic fibrosis transmembrane conductance regulator variants bearing mutations in putative nucleotide-binding domains 1 and 2. *MCB* 11: 3886-93; Bompadre, S. G. et al. (2007) G551D and G1349D, two CF-associated mutations in the signature sequences of CFTR, exhibit distinct gating defects. *Gen Physiol.* 129: 285-298). Flavonoids are well known activators of mutant CFTR and were among the first to be studied for beneficial effects in human individuals (including topical administration). Although agents such as genistein were affected by lack of efficacy in the nasal airway, more recent efforts have demonstrated activity of the flavonoid quercetin in the nose. However, flavonoid agents are challenged by poor solubility and systemic absorption, and are poor development candidates for inhaled therapeutics. More recent discovery strategies have focused on identification of compounds that 'potentiate' CFTR activity, restoring endogenous regulation (e.g. cyclic adenosine monophosphate (cAMP)-dependent regulation) and ion transport without excessive, constitutive activation that may potentially be detrimental (such as excessive CFTR activation seen with certain diarrheal illnesses). Identification of agents of this type is amenable to high-throughput screening-based strategies to discover agents that activate mutant CFTR by measuring the effects on anion conductance in cell-based screening assays. A number of specific strategies have been used for screens of this sort, including chloride sensitive dyes, fluorescence resonance energy transfer-based analysis of membrane potential, and cell conductance of airway monolayers. Identification and characterization of small molecule potentiators of mutant CFTR have led to the development of agents with pronounced activity in vitro and in the clinic.

Significant effort has been directed toward the goal of correcting the folding of F508del CFTR, thus restoring ion channel activity to the misfolded protein. A diverse array of cellular targets have been explored, commensurate with the large number of proteins now known to interact with CFTR biogenesis. Agents such as 4-phenyl butyrate downregulate Hsc70 (or other cell chaperones) central to the folding process, and represent an early example of compounds tested in the clinic. Other more recent efforts have resulted from high-throughput library screens for chloride channel function following incubation of test compounds with F508del expressing cells. A number of these strategies have identified F508del correctors that may address cell biogenesis through chaperone pathways. Pharmacologic activity of such agents has also been reported to augment F508del CFTR half-life in the plasma membrane through altered surface recycling attributed to features of the cellular processing machinery or reduced endocytic trafficking. This class of agents may be potential drug development candidates if their safety in vivo is confirmed. Other compounds have been shown to directly interact with CFTR and may offer greater specificity than agents that alter general aspects of cell folding or cellular quality control. The global cellular response to misfolded protein may also represent a target. Histone deacetylases (HDAC) have far-ranging effects on gene expression, and specific members of the HDAC family are involved in the ER associated degradation pathway promoting degradation of F508del CFTR. Treatment of CF cells with HDAC inhibitors can modulate ER stress, and HDACs such as suberoylanilidehydroxamic acid, as well as siRNA-silencing of HDACs, increase levels of F508del CFTR in the cell membrane. The combination of approaches such as these reveal a number of potential pharmacologic agents for F508del correction. Additive or synergistic rescue of F508del CFTR using more than one such strategy may offer hope of achieving ion transport activity sufficient to confer a normal phenotype in CF respiratory epithelia.

Read-through of premature termination codons (PTCs) represents another exciting approach to address the underlying cause of CF, and many other genetic diseases caused by PTCs. Certain aminoglycosides and other agents have the capacity to interact with the eukaryotic rRNA within the ribosomal subunits. Although this interaction is much weaker than that seen in prokaryotes and is distinct from the primary cause of aminoglycoside toxicity in human individuals, it can modestly reduce the fidelity of eukaryotic translation by interrupting the normal proofreading function of the ribosome. Insertion of a near cognate amino acid at a premature stop codon allows protein translation to continue until one of several stop codons normally present at the end of the mRNA transcript is reached and properly utilized. The specificity of the strategy has been attributed to greater stop codon fidelity at the authentic end of mRNA and has been established in vitro by demonstrating no detectable elongation beyond native stop codons.

CFTR activity modulating compounds that can be administered in combination with the methods and molecules described in the present invention include, but are not limited to, compounds described in US 2009/0246137 A1, US 2009/0253736 A1, US 2010/0227888 A1, U.S. Pat. No. 7,645,789, US 2009/0246820 A1 US 2009/0221597 A1 US 2010/0184739 A1, US 2010/0130547 A1, US 2010/0168094 A1, U.S. Pat. Nos. 7,553,855, 7,772,259 B2, 7,405,233 B2, US 2009/0203752, and U.S. Pat. No. 7,499,570.

Anti-infective Agents:

Chronic obstructive pulmonary diseases are accompanied by both acute and chronic bacterial infections. Both acute and chronic infections lead to chronic inflammation that has acute flare-ups in the form of pulmonary exacerbations. The underlying inflammation is treated with variety of inhaled anti-inflammatory agents. For example, in cystic fibrosis the most common bacteria causing chronic infection is *Pseudomonas aeruginosa* (*P. aeruginosa*) and antibiotics that are effective against this bacteria are a major component of treatment (Flume, Am J Respir Crit Care Med. 176(10): 957-69 (2007)). Also bacteria such as *Staphylococcus aureus* (*S. aureus*), *Burkholderia cepacia* (*B. cepacia*) and other gram negative organisms as well as anaerobes are isolated from respiratory secretions and people with CF may benefit from treatment of these pathogens to maintain their lung health. Anaerobic bacteria are also recognized as a feature of CF airways, sinuses in subjects with chronic sinusitis, and likely airways of subjects with COPD. Similarly, aspirations or microaspirations, especially in elderly population and during sleep, are associated with a chemical pneumonitis, anaerobic infections and subsequent bronchiectasis. An ideal treatment of aspiration-related pneumonitis and anaerobic infection would be an immediate treatment. As such, antibiotics are used to eradicate early infections, during pulmonary exacerbations and as chronic suppressive therapy.

The primary measure of antibiotic activity is the minimum inhibitory concentration (MIC). The MIC is the lowest concentration of an antibiotic that completely inhibits the growth of a microorganism in vitro. While the MIC is a good indicator of the potency of an antibiotic, it indicates nothing about the time course of antimicrobial activity. PK parameters quantify the lung tissue level time course of an antibiotic. The three pharmacokinetic parameters that are most important for evaluating antibiotic efficacy are the peak tissue level (Cmax), the trough level (Cmin), and the Area Under the tissue concentration time Curve (AUC). While these parameters quantify the tissue level time course, they do not describe the killing activity of an antibiotic.

Integrating the PK parameters with the MIC gives us three PK/PD parameters which quantify the activity of an antibiotic: the Peak/MIC ratio, the T>MIC, and the 24 h-AUC/MIC ratio. The Peak/MIC ratio is simply the Cpmax divided by the MIC. The T>MIC (time above MIC) is the percentage of a dosage interval in which the serum level exceeds the MIC. The 24 h-AUC/MIC ratio is determined by dividing the 24-hour-AUC by the MIC. The three pharmacodynamic properties of antibiotics that best describe killing activity are time-dependence, concentration-dependence, and persistent effects. The rate of killing is determined by either the length of time necessary to kill (time-dependent), or the effect of increasing concentrations (concentration-dependent). Persistent effects include the Post-Antibiotic Effect (PAE). PAE is the persistent suppression of bacterial growth following antibiotic exposure.

Using these parameters, antibiotics can be divided into 3 categories:

| Pattern of Activity | Antibiotics | Goal of Therapy | PK/PD Parameter |
| --- | --- | --- | --- |
| Type I Concentration-dependent killing and Prolonged persistent effects | Aminoglycosides Daptomycin Fluoroquinolones Ketolides | Maximize concentrations | 24 h-AUC/MIC Peak/MIC |
| Type II Time-dependent killing and Minimal persistent effects | Carbapenems Cephalosporins Erythromycin Linezolid Penicillins | Maximize duration of exposure | T > MIC |
| Type III Time-dependent killing and Moderate to prolonged persistent effects. | Azithromycin Clindamycin Oxazolidinones Tetracyclines Vancomycin | Maximize amount of drug | 24 h-AUC/MIC |

For Type I antibiotics (AG's, fluoroquinolones, daptomycin and the ketolides), the ideal dosing regimen would maximize concentration, because the higher the concentration, the more extensive and the faster is the degree of killing. Therefore, the 24 h-AUC/MIC ratio, and the Peak/MIC ratio are important predictors of antibiotic efficacy. For aminoglycosides, it is best to have a Peak/MIC ratio of at least 8-10 to prevent resistence. For fluoroquinolonesvs gram negative bacteria, the optimal 24 h-AUC/MIC ratio is approximately 125. Versus gram positives, 40 appears to be optimal. However, the ideal 24 h-AUC/MIC ratio for FQ's varies widely in the literature.

Type II antibiotics (beta-lactams, clindamycin, erythromycin, carbapenems and linezolid) demonstrate the complete opposite properties. The ideal dosing regimen for these antibiotics maximizes the duration of exposure. The T>MIC is the parameter that best correlates with efficacy. For beta-lactams and erythromycin, maximum killing is seen when the time above MIC is at least 70% of the dosing interval.

Type III antibiotics (vancomycin, tetracyclines, azithromycin, and the dalfopristin-quinupristin combination) have mixed properties, they have time-dependent killing and moderate persistent effects. The ideal dosing regimen for these antibiotics maximizes the amount of drug received.

Therefore, the 24 h-AUC/MIC ratio is the parameter that correlates with efficacy. For vancomycin, a 24 h-AUC/MIC ratio of at least 125 is necessary.

Patients including, but not limited to, CF, COPD, non-CF bronchiectasis, aspiration pneumonia, asthma and VAP patients suffering from respiratory infection caused by bacteria susceptible to meropenem may benefit from such treatment. Examples of carbapenam antibiotics are: imipenam, panipenam, meropenam, doripenem, biapenam, MK-826, DA-1131, ER-35786, lenapenam, S-4661, CS-834 (prodrug of R-95867), KR-21056 (prodrug of KR-21012), L-084 (prodrug of LJC 11036) and CXA-101. The therapeutic efficacy of all antiinfective agents described can be enhanced by the pre- or co-administration of compounds and methods of this invention.

Exemplary Anti-Inflammatory Agents:

Inhaled corticosteroids are the standard of chronic care for asthma, COPD and other respiratory diseases characterized by acute and chronic inflammation leading to airflow limitation. Examples of anti-inflammatory agents suitable for administration in combination with the methods and molecules described in the present invention include beclomethasone, budesonide, and fluticasone and a group of anti-inflammatory medications that do not contain steroids known as non-steroiodal anti-inflammatory drugs (NSAIDs).

Products of arachidonic acid metabolism, specifically the leukotrienes (LTs), contribute to pulmonary inflammation. Cysteinylleukotrienes (LTC4, LTD4, and LTE4) are produced predominantly by eosinophils, mast cells, and macrophages. Examples of leukotriene modifiers suitable for administration by the method of this invention include monteleukast, zileuton and zafirlukast.

Mast cell stabilizers are cromone medications such as cromolyn (sodium cromoglycate) used to prevent or control certain allergic disorders. They block a calcium channel essential for mast cell degranulation, stabilizing the cell and thereby preventing the release of histamine and related mediators. As inhalers they are used to treat asthma, as nasal sprays to treat hay fever (allergic rhinitis) and as eye drops for allergic conjunctivitis. Finally, in oral form they are used to treat the rare condition of mastocytosis.

PDE4 inhibitors have been shown to modulate pulmonary inflammation and used for treatment of chronic obstructive pulmonary diseases. Examples of PDE4 inhibitors suitable for use in combination with the methods and molecules described in the present invention include, but is not limited to theophylline and roflumilast.

Exemplary Bronchodilators:

Nitric Oxide (NO) Donors: NO, NO Donors, NO and Peroxynitrite Scavengers and Inducible NO Synthase Activity Modulators. Nitric oxide is a potent endogenous vasodilator and bronchodilator that can be exogenously administered via inhalation. It is synthesized by the conversion of the terminal guanidine nitrogen atom of L-arginine via endothelial cell calcium dependent enzyme nitric oxide synthetase and then diffuses across the cell membrane to activate the enzyme guanylatecyclase. This enzyme enhances the synthesis of cyclic guanosine monophosphate (cGMP), causing relaxation of vascular and bronchial smooth muscle and vasodilatation of blood vessels (Palmer, Circ Res., 82(8):852-61 (1998)).

Nitric oxide synthesised in endothelial cells that line blood vessels has a wide range of functions that are vital for maintaining a healthy respiratory and cardiovascular systems (Megson I L et al Expert Opin Investig Drugs. 2002 May; 11(5):587-601.). Reduced nitric oxide availability is implicated in the initiation and progression of many diseases and delivery of supplementary nitric oxide to help prevent disease progression is an attractive therapeutic option. Nitric oxide donor drugs represent a useful means of systemic nitric oxide delivery and organic nitrates have been used for many years as effective therapies for symptomatic relief from angina. However, nitrates have limitations and a number of alternative nitric oxide donor classes have emerged since the discovery that nitric oxide is a crucial biological mediator.

In the respiratory tract, NO is produced by residential and inflammatory cells (Ricciardolo F L et al. Curr Drug Targets 2006 June; 7(6):721-35). NO is generated via oxidation of L-arginine that is catalysed by the enzyme NO synthase (NOS). NOS exists in three distinct isoforms: neuronal NOS (nNOS), inducible NOS (iNOS), and endothelial NOS (eNOS). NO derived from the constitutive isoforms of NOS (nNOS and eNOS) and other NO-adduct molecules (nitrosothiols) are able to modulate bronchomotor tone. NO derived from the inducible isoform of NO synthase, up-regulated by different cytokines via NF-kappaB-dependent pathway, seems to be a pro-inflammatory mediator with immunomodulatory effects. In aging CF patients, expression of iNOS is significantly reduced (Yoon et al., J Clin Invest. 2006 February; 116(2):436-46). This reduced expression of iNOS in chronic CF is associated with emergence of mucoid muc mutant subpopulation of *P. aeruginosa*. It has been suggested that 15 mM $NO_2^-$ kills mucA *P. Aeruginosa* in CF airways at pH 6.5. NO itself or as a precursor to iron-nitrosyl species has been implicated in this antimicrobial effect. Therefore inhaled $NO_2^-$, including but not limited inhaled $NaNO_2$, has an appeal as a CF therapy. The production of NO under oxidative stress conditions secondarily generates strong oxidizing agents (reactive nitrogen species) that may amplify the inflammatory response in asthma and COPD. Moreover, NO can be exhaled and levels are abnormal in stable atopic asthma and during exacerbations in both asthma and COPD. Exhaled NO might therefore be a non-invasive tool to monitor the underlying inflammatory process. It is suggested that NOS regulation provides a novel target in the prevention and treatment of chronic inflammatory diseases of the airways such as asthma and COPD.

Examples of NO, NO donors and NO synthase activity modulators suitable for administration in combination with the methods and molecules described in the present invention include inhaled NO, agents disclosed in Vallance et al. Fundam Clin Pharmacol. 2003 February; 17(1):1-10, Al-Sa'doni H H et al. Mini Rev Med Chem. 2005 March; 5(3):247-54, Miller M R et al. Br J Pharmacol. 2007 June; 151(3):305-21. Epub 2007 Apr. 2 and Katsumi H et al. Cardiovasc Hematol Agents Med Chem. 2007 July; 5(3): 204-8.

Under certain conditions, inducible NO synthase activity leads to overproduction of NO which in turn increases inflammation and tissue injury. Under these conditions, the following inducible NO synthase inhibitors, NO scavengers and peroxynitrite scavengers administered in combination with the methods and molecules described in the present invention are suitable: Bonnefous et al. *J. Med. Chem.*, 2009, 52 (9), pp 3047-3062, Muscara et al *AJP-GI* June 1999 vol. 276 no. 6 G1313-G1316 or Hansel et al. *FASEB Journal.* 2003; 17:1298-1300.

Beta 2-adrenergic receptor agonists: It has been established that administration of super-therapeutic concentrations of receptor agonists leads to receptor desensitization and loss of efficacy. For example, this phenomenon has been described for beta 2-adrenoceptor based bronchodilator agents (Duringer et al., Br J Pharmacol., 158(1):169-79 (2009)). High concentration of these receptor agonist agents leads to the receptor phosphorylation, internalization and potential degradation. Administration of receptor agonists, which cause tachyphylaxis following bolus administration via fast nebulizer, by inhalation over the course of 8 to 24 hours or overnight to a patient via nasal cannula improves the efficacy of such agents due to decreased extent of tachyphylaxis. Beta 2-adrenergic receptor agonsists include albuterol, levalbuterol, salbutamol, procaterol, terbutaline, pirbuterol, and metaproterenol. The therapeutic efficacy of beta 2-adrenergic receptor agonists can be enhanced by the pre- or co-administration of compounds and methods of this invention.

Exemplary Gene Carriers:

Examples of gene carriers for the administration of gene therapy include viruses, DNA:protein complexes, plasmids, DNAs, and RNAs.

Other Exemplary Therapeutic Agents:

Examples of other classes of therapeutic agents suitable for administration in combination with the methods and molecules described in the present invention include antivirals such as ribavirin, anti-fungal agents such as amphotericin, intraconazol and voriconazol, immunosuppressants, anti-rejection drugs such as cyclosporine, tacrolimus and sirolimus, bronchodilators including but not limited to anticholinergic agents such as ipratropium, tiotropium, aclidinium and others, PDE5 inhibitors siRNAs, gene therapy vectors, aptamers, endothelin-receptor antagonists, alpha-1-antitrypsin, prostacyclins, vaccines, PDE-4 and PDE-5 inhibitors and steroids such as beclamethasone, budesonide, ciclesonide, flunisolide, fluticasone, memetasone and triamcinolone.

Experimental Procedures and Biological Assays:

Compounds of Formula I: Compounds of formula I are readily prepared by methods well known in the art as exemplified and detailed below.

Mucin Agarose Gel Western Blots: Reducing agent stock solutions are made up in 100 mM Potassium Phosphate and are buffered to pH 6.5. The reducing agent stocks are diluted into saliva samples (pH 6.5) to achieve the final desired reducing agent concentration. Reactions are incubated at 25° C. for the desired time (0-120 minutes). The reactions are quenched using at least a 2-fold excess of N-ethylmaleimide and/or hydrogen peroxide. A 5× concentrated sample loading buffer is diluted into the samples to achieve a 1× concentration (1×TAE, 5% glycerol, 0.1% SDS, Bromophenol Blue). Samples (50 ug) are analyzed by electrophoresis on 0.9% agarose gels using a buffer system consisting of 1×TAE/0.1% SDS. The agarose gel is soaked for 15 min in 4×SSC (0.6 M NaCl, 60 mM Tri-sodium Citrate dihydrate) containing 10 mM DTT before transferring the samples from the gel onto a nitrocellulose membrane by vacuum blotter. Unreduced and reduced Muc5B are visualized using a polyclonal antibody directed towards Muc5B and a Protoblot II AP System with stabilized substrate. FIGS. 2-7 clearly show superiority of the dithiol compounds of the present invention over DTT and NAC.

BiP Induction: Reducing agents are made up in Hanks Balanced Salt Solution (HBSS)/25 mM HEPES pH 7.4. Each compound solution (10 uL) is added apically to primary hBEs for 6 hrs. The hBEs are lysed in RIPA buffer supplemented with protease inhibitor cocktail (Roche) and 1 mM PMSF. The samples are normalized to contain the same total amount of protein followed by addition of 2×SDS sample buffer (100 mM Tris-HCl (pH6.8)/4% SDS/0.05% Bromophenol Blue/20% glycerol). Samples (20□g) are analyzed by electrophoresis on a 10% SDS-PAGE gel and transferred to a nitrocellulose membrane. BiP levels are visualized using a polyclonal antibody directed towards BiP and the LiCor Odyssey imaging detection system. Thapsigargin (TG, 2.5 □M) served as a positive control for BiP induction.

DTNB ASSAY: This assay determines the rate which a mucolytic agent can reduce a disulfide bond using 5,5-Dithiobis(2-nitrobenzoic acid). DTNB in various pH buffers and allows comparison of the kinetic rates of reducing agents. First, reducing agent stock solutions (30 mM) were made up in DMSO. Each compound stock solution was diluted, 1.5 ml in 1 ml 50 mM Tris-HCl buffer, pH 7.5, and then added in a 1:1 volumetric ratio to a solution of 100 mM DTNB in 50 mM Tris-HCl buffer, pH 7.5. Max $Abs_{412}$ was measured and then utilized to calculate the activity concentration. If the observed activity concentrations differed from expected activity concentrations by more than 5%, the volume was accordingly adjusted to kinetically test the rate in the next step. After having added the reducing agents, diluted in a range of pH buffer solutions (pH 6.0-7.5), to 45 mM DTNB in 50 mM Tris-HCl and measured the $Abs_{412}$ for 5 min rates were calculated as a $2^{nd}$ order kinetic. Table I summarizes the results vs. NAC and DTT.

TABLE 1

Kinetic Reaction Rates of Reduction of DTNB by the dithiol Compounds of the present invention compared to DTT and NAC.

| Compound | pH | | | |
|---|---|---|---|---|
| | 6 | 6.5 | 7 | 7.5 |
| NAC | 10 | 26 | 69 | 230 |
| DTT | 69 | 176 | 382 | 2088 |
| I | 285 | 745 | 1916 | 7265 |
| J | 86 | 337 | 1043 | 2016 |
| K | 678 | 1820 | 3775 | 9143 |
| L | 1911 | 5565 | 8847 | 14566 |
| C | 2460 | 7122 | 12313 | 17317 |
| N | 952 | 2366 | 4382 | 9532 |
| O | 921 | 2500 | 5412 | 13547 |
| P | 1018 | 2701 | 6180 | 13243 |
| Q | 954 | 2984 | 6077 | 15927 |
| R | 2901 | 7382 | 13522 | 16870 |
| S | 4483 | 10715 | 13732 | 15469 |
| E | 5933 | 13718 | 16393 | 17109 |
| W | 4850 | — | — | — |
| H | 6835 | — | — | — |
| B | 1491 | — | — | — |
| T | 5144 | — | — | — |
| U | 5761 | — | — | — |
| X | 8029 | — | — | — |
| Y | 8718 | — | — | — |
| G | 5154 | — | — | — |
| V | 1419 | 4568 | 6192 | 10043 |
| Z | 7200 | 10420 | 10631 | 18513 |
| KK | 873 | 2411 | 5163 | 13896 |
| LL | 743 | 2352 | 4661 | 8241 |

TMV Studies in Sheep

Test articles were administered to the pulmonary surfaces as an inhalation aerosol. For human neutrophil Elastase (HNE) studies, tracheal mucus velocity (TMV) was measured at 1 and 2 hours after HNE (but before drug); and 1, 30, 60, 90, and 120 minutes post-aerosol administration of Compound G.

The measurements of TMV were made as follows: Eight to 10 radiopaque Teflon disks (~1 mm in diameter, 0.8 mm thick, and weighing between 1.5-2 mg) were introduced into the trachea via an endotracheal tube (ETT). The particles were insufflated by a catheter connected to a source of compressed air (flow rate of 3-4 ml/min at 50 psi). The catheter was removed following insufflation without contacting the tracheal surface. To minimize the ETT effects on TMV, the cuff was deflated throughout the study except for the period of drug delivery. The disk movements were recorded using videotaped fluoroscopy, and individual disk velocities were calculated by measuring the distance traveled by each disk over a 60-s period. A collar containing radiopaque markers of predetermined length was placed around the animal's neck, which was used as a standard to correct for magnification effects intrinsic to the fluoroscopy unit. The mean value of disk velocities was calculated for each time point. To avoid dehydration, the sheep were periodically gavaged with tap water via a nastrogastric tube. To avoid desiccation of the tracheal mucosa caused by sustained intubation, the inspired air was warmed and humidified by a Bennet Humidifier (Puritan-Bennett, Lenexa, Kans.).

The activity of Compound G (1 µmole/kg) was subsequently tested in this sheep model of "acute bronchitis" in which neutrophil elastase (NE) was administered via aerosol prior to dosing with Compound G. In sheep treated with NE, Compound G, but not vehicle, restored TMV to normal, pre-NE levels, which was sustained for 2h post-dosing.

1. Preparation of S,S'-(4-(2-aminoethoxy)-1,2-phenylene)bis(methylene)diethanethioate hydrochloride (A)

Preparation of Dimethyl 4-hydroxyphthalate (2)

A solution of 4-hydroxyphthalic acid 1 (25.0 g, 137 mmol) in MeOH (700 mL) was charged with $SOCl_2$ (30.0 mL, 412 mmol) at 0° C. and stirred at room temperature for 20 h. The solvent was removed and the residue was partitioned between saturated aqueous $NaHCO_3$ solution (100 mL) and $CH_2Cl_2$ (250 mL). The $CH_2Cl_2$ layer was separated and the aqueous layer was extracted with $CH_2Cl_2$ (2×250 mL). The combined organic extracts were washed with brine, dried over $Na_2SO_4$, and concentrated to afford compound 2 (26.5 g, 92%) as a colorless oil: $^1$H NMR (400 MHz, $CDCl_3$) δ 7.72 (d, J=8.5 Hz, 1H), 7.00 (d, J=2.6 Hz, 1H), 6.91 (dd, J=8.5, 2.6 Hz, 1H), 3.89 (s, 3H), 3.85 (s, 3H).

Preparation of Dimethyl 4-{2-[(tert-butoxycarbonyl)amino]ethoxy}phthalate (4)

A solution of compound 2 (6.00 g, 28.6 mmol) in DMF (30 mL) was charged with $K_2CO_3$ (15.7 g, 114 mmol) and stirred at room temperature for 5 min. The above reaction mixture was charged with compound 3 (9.98 g, 42.9 mmol) and the final reaction mixture was stirred at room temperature for 72 h. Water (300 mL) was added to the reaction mixture and extracted with $CH_2Cl_2$ (2×300 mL). The combined organic extracts were concentrated and the residue was purified by column chromatography (silica gel, 20% to 30% EtOAc in hexanes) to afford compound 4 (9.00 g, 89%) as a yellow oil: $^1$H NMR (400 MHz, DMSO-$d_6$) δ 7.78 (d, J=8.4 Hz, 1H), 7.17 (d, J=2.5 Hz, 1H), 7.01 (dd, J=8.4, 2.5 Hz, 1H), 7.01 (t, J=6.0 Hz, 1H), 4.08 (t, J=5.5 Hz, 2H), 3.80 (s, 3H), 3.78 (s, 3H), 3.31 (t, J=6.4 Hz, 2H), 1.37 (s, 9H).

Preparation of Tert-butyl {2-[3,4-bis(hydroxymethyl)phenoxy]ethyl}carbamate (5)

A solution of compound 4 (9.00 g, 25.5 mmol) in THF (200 mL) was charged with lithium aluminum hydride (1 M solution in diethyl ether, 102 mL, 102 mmol) at 0° C. The resulting reaction mixture was stirred at 0° C. for 1 h and quenched with ice-cold water at 0° C. The reaction mixture was diluted with chloroform (300 mL) and filtered through a Celite pad, and the Celite pad was washed with chloroform (2×300 ml). The filtrate was concentrated under vacuum to afford 5 (6.80 g, 90%) as a yellow oil: $^1$H NMR (400 MHz,

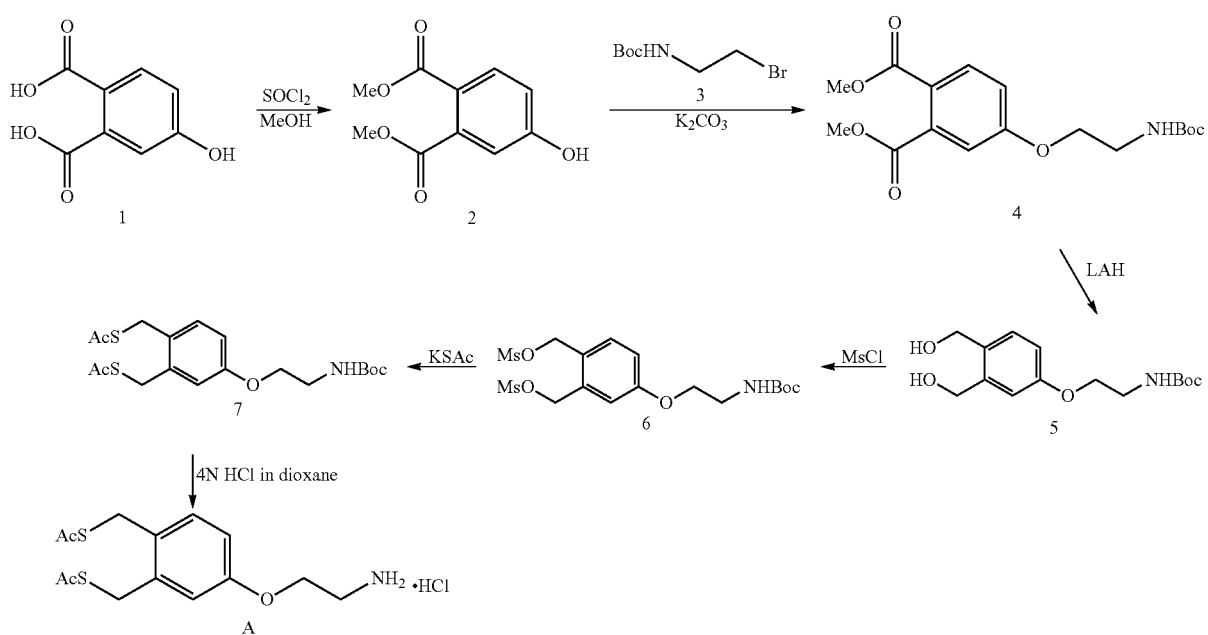

Scheme 1

CDCl$_3$) δ 7.23 (d, J=8.3 Hz, 1H), 6.89 (d, J=2.7 Hz, 1H), 6.78 (dd, J=8.3, 2.7 Hz, 1H), 5.10-5.01 (m, 1H), 4.65 (s, 2H), 4.64 (s, 2H), 3.99 (t, J=5.3 Hz, 2H), 3.49 (dd, J=10.6, 5.3 Hz, 2H), 1.44 (s, 9H).

Preparation of (4-{2-[(tert-butoxycarbonyl)amino]ethoxy}-1,2-phenylene)bis(methylene)dimethanesulfonate (6)

A solution of 5 (20.0 g, 67.3 mmol) in CH$_2$Cl$_2$ (500 mL) was charged with Et$_3$N (73.5 mL, 538 mmol) followed by methanesulfonyl chloride (20.8 mL, 270 mmol) at 0° C. and stirred at room temperature for 22 h. Water (200 mL) was added to the reaction mixture and extracted with CH$_2$Cl$_2$ (3×200 mL). The combined organic extracts were washed with brine, dried over Na$_2$SO$_4$, and concentrated to afford compound 6 (27.0 g, crude) as a brown oil, which was directly used for the next step without further purification.

Preparation of Compound 7

A solution of compound 6 (27.0 g, crude, 67.3 mmol) in a mixture of THF (200 ml) and DMF (40 mL) was charged with KSAc (19.2 g, 168 mmol) and stirred at room temperature for 20 h. The solvent was removed under reduced pressure and the reaction mixture was partitioned between water (100 mL) and CH$_2$Cl$_2$ (250 mL). The CH$_2$Cl$_2$ layer was separated and the aqueous layer was extracted with CH$_2$Cl$_2$ (2×300 mL). The combined organic extracts were concentrated and the residue was purified by column chromatography (silica gel, 10% to 20% EtOAc in hexanes) to afford compound 7 (16.2 g, 58% over two steps) as a yellow solid: $^1$H NMR (400 MHz, CDCl$_3$) δ 7.21 (d, 0.1=8.5 Hz, 1H), 6.84 (d, 0.1=2.6 Hz, 1H), 6.72 (dd, J=8.5, 2.6 Hz, 1H), 5.05-4.93 (m, 1H), 4.11 (s, 4H), 3.97 (t, J=5.2 Hz, 2H), 3.50 (dd, J=10.8, 6.1 Hz, 2H), 2.35 (s, 3H), 2.33 (s, 3H), 1.44 (s, 9H).

Preparation of compound A; S,S'-(4-(2-aminoethoxy)-1,2-phenylene)bis(methylene)diethanethioate hydrochloride Compound 7 (6.00 g, 14.5 mmol) was dissolved in 4 N HCl in dioxane (50 mL) at room temperature, and the solution was stirred at same temperature for 2 h. After removal of the solvent, the residue was triturated with MTBE to afford hydrochloric acid salt A (4.50 g, 88%) as an off-white solid: $^1$H NMR (400 MHz, CD$_3$OD) δ 7.24 (d, J=8.6 Hz, 1H), 6.97 (d, J=2.8 Hz, 1H), 6.85 (dd, J=8.6, 2.8 Hz, 1H), 4.20 (dd, J=4.9, 4.3 Hz, 2H), 4.14 (s, 2H), 4.13 (s, 2H), 2.35 (t, J=4.9 Hz, 2H), 2.32 (s, 3H), 2.31 (s, 3H).

2. Preparation of (R)-2-amino-N-(2-(3,4-bis(mercaptomethyl)phenoxy)ethyl)-6-guanidinohexanamide Hydochloride

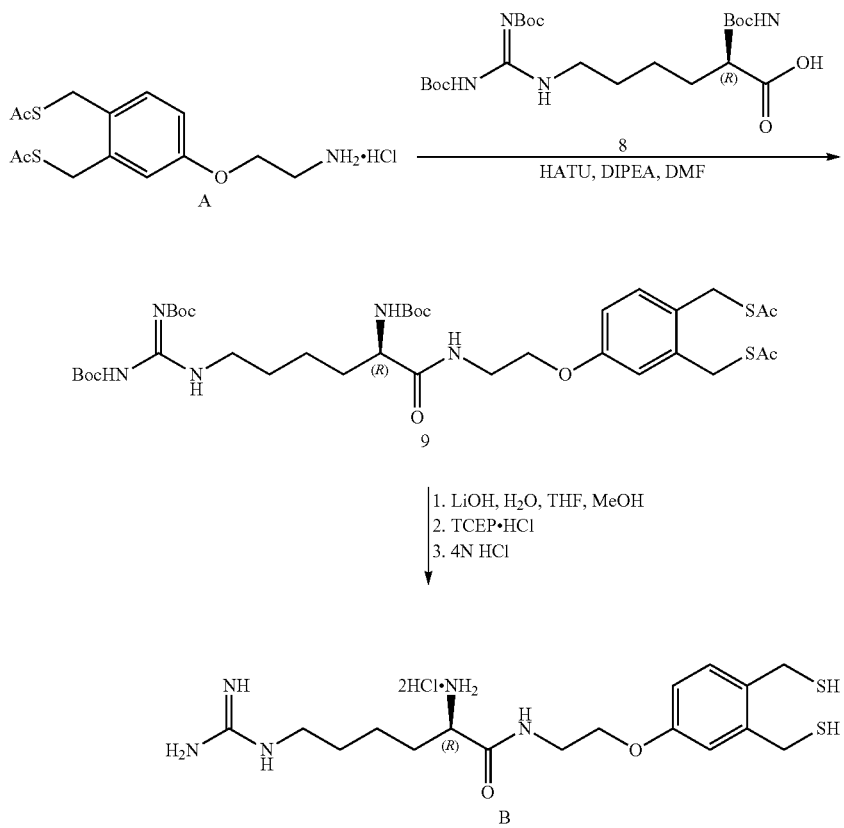

Scheme 2

Preparation of Compound 9

Compound A (450 mg, 1.26 mmol) and acid 8 (566 mg, 1.26 mmol) were dissolved in DMF (10 mL) and treated with DIPEA (0.88 mL, 5.04 mmol) and HATU (479 mg, 1.26 mmol). The reaction mixture was stirred at room temperature for 16 h. TLC analysis of the yellow reaction mixture showed the completion of the reaction. The solvent was removed under reduced pressure, the residue was dissolved in $CH_2Cl_2$ (100 mL), and the solution was quickly washed with saturated aqueous $NaHCO_3$ (2×50 mL) followed by brine (50 mL). The organic layer was dried over $Na_2SO_4$ and concentrated. The residue was purified by column chromatography (silica gel, 50% to 80% EtOAc in hexanes) to afford compound 9 (800 mg, 81%) as an off-white solid: $^1$H NMR (400 MHz, $CD_3OD$) δ 7.19 (d, J=8.3 Hz, 1H), 6.87 (d, J=2.8 Hz, 1H), 6.76 (dd, J=8.3, 2.8 Hz, 1H), 4.12 (s, 2H), 4.11 (s, 2H), 4.01 (t, J=5.2 Hz, 2H), 4.00-3.97 (m, 1H), 3.64 (dt, J=14.0, 5.1 Hz, 1H), 3.53-3.43 (m, 1H), 3.22 (t, J=7.0 Hz, 2H), 2.31 (s, 3H), 2.30 (s, 3H), 1.74-1.54 (m, 3H), 1.51 (s, 9H), 1.46 (s, 9H), 1.44-1.32 (3H), 1.41 (s, 9H).

Preparation of Compound B: (R)-2-amino-N-(2-(3,4-bis(mercaptomethyl)phenoxy)ethyl)-6-guanidinohexanamide Hydrochloride A solution of 9 (800 mg, 1.02 mmol) in a mixture of THF (20 mL), methanol (20 mL), and water (20 mL) was charged with solid $LiOH \cdot H_2O$ (171 mg, 4.08 mmol) and the reaction mixture was stirred at room temperature for 1 h. The above reaction mixture was charged with TCEP.HCl (146 mg, 0.51 mmol) and stirred for another 1 h. The organic solvent was removed and the residue was partitioned between saturated aqueous $NaHCO_3$ solution (10 mL) and $CH_2Cl_2$ (50 mL). The $CH_2Cl_2$ layer was separated and the aqueous layer was extracted with $CH_2Cl_2$ (2×30 mL). The combined organic layers were dried over $Na_2SO_4$, filtered, and concentrated. The final residue was dissolved in EtOH (20 mL) and 4 N HCl (20 mL) was added. After stirring at room temperature for 1 h, the reaction mixture was concentrated to afford compound B (crude HCl salt) as a yellow solid. The crude HCl salt was purified by reverse-phase column chromatography and lyophilized to afford 310 mg (66%) of pure compound B as a hygroscopic white solid: $^1$H NMR (400 MHz, $CD_3OD$) δ 7.20 (d, J=8.4 Hz, 1H), 6.90 (d, J=2.5 Hz, 1H), 6.78 (dd, J=8.4, 2.5 Hz, 1H), 4.08 (t, J=5.1 Hz, 2H), 3.89 (t, J=7.0 Hz, 1H), 3.82 (s, 2H), 3.80 (s, 2H), 3.71 (dt, J=14.0, 5.1 Hz, 1H), 3.61-3.63 (m, 1H), 3.08 (t, J=7.0 Hz, 2H), 1.93-1.79 (m, 2H), 1.64-1.53 (m, 2H), 1.50-1.40 (m, 2H); $^1$H NMR (400 MHz, DMSO-$d_6$) δ 8.88 (t, J=5.7 Hz, 1H), 8.33 (br s, 3H), 7.90 (t, J=5.8 Hz, 1H), 7.70-6.67 (m, 4H), 7.22 (d, J=8.5 Hz, 1H), 6.92 (d, J=2.6 Hz, 1H), 6.79 (dd, J=8.5, 2.6 Hz, 1H), 4.07-3.96 (m, 2H), 3.83-3.74 (m, 5H), 3.57-3.42 (m, 2H), 3.10-3.01 (m, 2H), 2.95 (t, J=7.4 Hz, 1H), 2.82 (t, J=7.0 Hz, 1H), 1.81-1.66 (m, 2H), 1.52-1.40 (m, 2H), 1.39-1.28 (m, 2H); HRMS (ESI-MS m/z) calculated for $C_{17}H_{29}N_5O_2S_2$ [M+H]$^+$, 400.1841; found 400.1855.

3. Preparation of C: (S)-2-amino-N-(2-(3,4-bis(mercaptomethyl)phenoxy)ethyl)-6-guanidinohexanamide

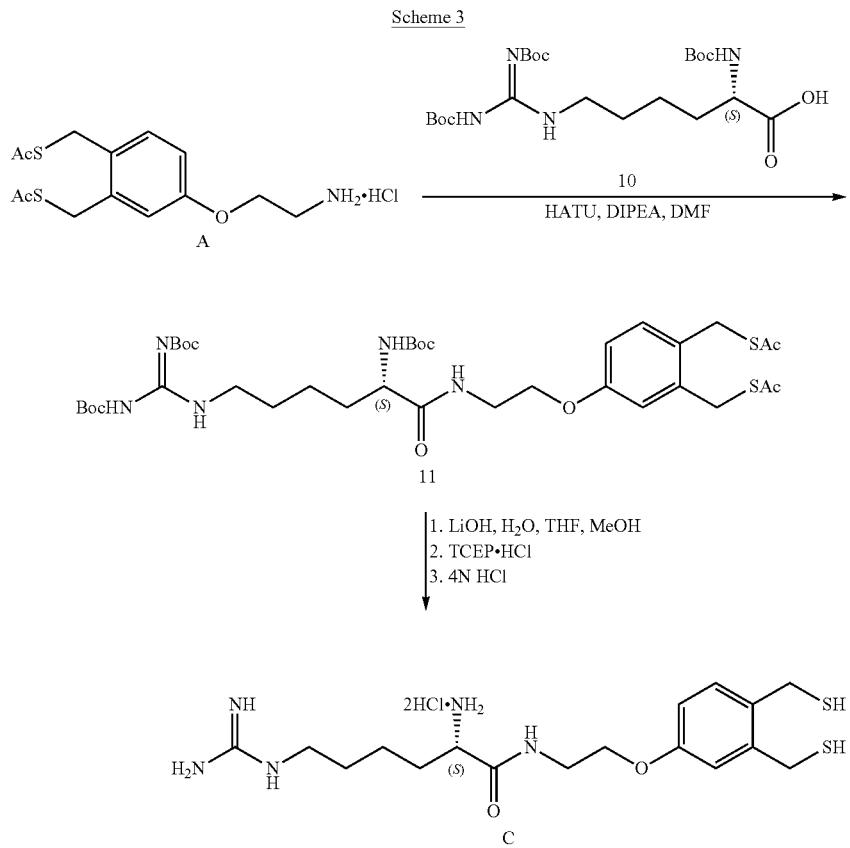

Scheme 3

Preparation of Compound 11

Compound A (429 mg, 1.12 mmol) and acid 10 (550 mg, 1.22 mmol) were dissolved in DMF (10 mL) and treated with DIPEA (0.78 mL, 4.48 mmol) and HATU (927 mg, 2.44 mmol). The reaction mixture was stirred at room temperature for 24 h. TLC analysis of the yellow reaction mixture showed the completion of the reaction. After the solvent was removed under reduced pressure, the residue was partitioned between $CH_2Cl_2$ (100 mL) and saturated aqueous $NaHCO_3$ (50 mL). The organic layer was separated, washed with brine (50 mL), and dried over $Na_2SO_4$. The organic layer was concentrated and the residue was purified by column chromatography (silica gel, 50% to 80% EtOAc in hexanes) to afford compound 11 (550 mg, 63%) as a yellow oil: $^1$H NMR (400 MHz, $CD_3OD$) δ 7.19 (d, 0.1=8.3 Hz, 1H), 6.87 (d, J=2.8 Hz, 1H), 6.77 (dd, J=8.3, 2.8 Hz, 1H), 4.12 (s, 2H), 4.11 (s, 2H), 4.01 (t, J=5.2 Hz, 2H), 4.00-3.97 (m, 1H), 3.64 (dt, J=14.0, 5.1 Hz, 1H), 3.53-3.43 (m, 1H), 3.22 (t, J=7.0 Hz, 2H), 2.32 (s, 3H), 2.30 (s, 3H), 1.74-1.54 (m, 3H), 1.51 (s, 9H), 1.46 (s, 9H), 1.44-1.32 (3H), 1.41 (s, 9H).

Preparation of compound C; [ALB-167699(a)]; (S)-2-amino-N-(2-(3,4-bis(mercaptomethyl)phenoxy)ethyl)-6-guanidinohexanamide A solution of 11 (800 mg, 1.02 mmol) in a mixture of THF (6.0 mL), methanol (6.0 mL), and water (6.0 mL) was charged with solid $LiOH.H_2O$ (129 mg, 3.06 mmol) and the reaction mixture was stirred at room temperature for 1 h. The above reaction mixture was charged with TCEP.HCl (146 mg, 0.51 mmol) and stirred for another 1 h. The solvent was removed and the residue was partitioned between saturated aqueous $NaHCO_3$ solution (10 mL) and $CH_2Cl_2$ (50 mL). The $CH_2Cl_2$ layer was separated and the aqueous layer was extracted with $CH_2Cl_2$ (2×30 mL). The combined organic layers were dried over $Na_2SO_4$, filtered, and concentrated to yield 600 mg of white, solid product. 400 mg of the crude product was dissolved in EtOH (5.0 mL) and 4 N HCl (20 mL) was added. After stirring at room temperature for 1 h, the reaction mixture was concentrated to afford compound C (crude HCl salt) as a yellow solid. The crude HCl salt was purified by reverse-phase column chromatography and lyophilized to afford 120 mg (45%) of pure compound C as a hygroscopic yellow solid: $^1$H NMR (400 MHz, $CD_3OD$) δ 7.20 (d, J=8.4 Hz, 1H), 6.90 (d, J=2.5 Hz, 1H), 6.78 (dd, J=8.4, 2.5 Hz, 1H), 4.08 (t, J=5.1 Hz, 2H), 3.86 (t, J=6.5 Hz, 1H), 3.82 (s, 2H), 3.80 (s, 2H), 3.71 (dt, J=14.0, 5.1 Hz, 1H), 3.61-3.63 (m, 1H), 3.07 (t, J=7.0 Hz, 2H), 1.93-1.79 (m, 2H), 1.64-1.53 (m, 2H), 1.48-1.38 (m, 2H); $^1$H NMR (400 MHz, DMSO-$d_6$) δ 8.84 (t, J=5.7 Hz, 1H), 8.32 (br s, 3H), 7.82 (t, J=5.7 Hz, 1H), 7.60-6.68 (m, 4H), 7.21 (d, 0.1=8.5 Hz, 1H), 6.91 (d, 0.1=2.6 Hz, 1H), 6.78 (dd, 0.1=8.5, 2.6 Hz, 1H), 4.06-398 (m, 2H), 3.82-3.72 (m, 5H), 3.56-3.43 (m, 2H), 3.09-2.99 (m, 2H), 2.93 (t, J=7.4 Hz, 1H), 2.80 (t, J=7.0 Hz, 1H), 1.76-1.68 (m, 2H), 1.50-1.41 (m, 2H), 1.38-1.27 (m, 2H); HRMS (ESI-MS m/z) calculated for $C_{17}H_{29}N_5O_2S_2$ $[M+H]^+$, 400.1835; found 400.1855.

4. Preparation of D: (R)-2-amino-N—((R)-5-amino-6-(2-(3,4-bis(mercaptomethyl)phenoxy)ethylamino)-6-oxohexyl)-6-guanidinohexanamide Hydrochloride Preparation of (R)-6-[2,3-bis(tert-butoxycarbonyl)guanidino]-2-[(tert-butoxycarbonyl)-amino]hexanoic acid (8)

A solution of N-α-Boc-D-lysine 12 (10.0 g, 40.6 mmol) in $CH_2Cl_2$ (200 mL) was charged with N,N'-bis-Boc-1-guanylpyrazole (11.3 g, 36.6 mmol) and triethylamine (11.0 mL, 81.3 mmol). The reaction mixture was stirred at room temperature for 16 h. The reaction mixture was washed with 10% aqueous citric acid (2×100 mL) and the solvent was removed under reduced pressure. The residue was dissolved in 1 N NaOH (300 mL), 1 N HCl was added to adjust the pH to 5-6, and the mixture was extracted with $CH_2Cl_2$ (500 ml). The $CH_2Cl_2$ layer was separated and the aqueous layer was extracted with $CH_2Cl_2$ (2×250 mL). The combined organic layers were dried over $Na_2SO_4$, filtered, and concentrated to afford compound 8 (18.5 g, 94%) as a white solid: $^1$H NMR (400 MHz, $CD_3OD$) δ 4.13-4.03 (m, 1H), 3.36 (t, J=6.8 Hz, 2H), 1.91-1.77 (m, 1H), 1.74-1.55 (m, 3H), 1.52 (s, 9H), 1.51-1.38 (m, 2H), 1.47 (s, 9H), 1.43 (s, 9H).

Preparation of (R)-methyl 6-amino-2-[(tert-butoxycarbonyl)amino]hexanoate (14)

A solution of N-α-Boc-D-lysine 12 (1.00 g, 4.06 mmol) in $CH_2Cl_2$ (20 mL) and MeOH (5.0 mL) was charged with TMS-diazomethane [$(CH_3)_3SiCHN_2$ 0.6 M solution in hexane, 13.5 mL, 8.12 mmol] at 0° C. and stirred at the same temperature for 1 h and at room temperature for another 1 h. The solvent was removed under reduced pressure to afford crude product 14 (1.04 g, crude) as a yellow oil, which was directly used for the next step without further purification: $^1$H NMR (400 MHz, $CD_3OD$) δ 4.12-4.05 (m, 1H), 3.70 (s, 3H), 2.62 (t, J=7.0 Hz, 2H), 1.82-1.70 (m, 1H), 1.69-1.58 (m, 1H), 1.54-1.32 (m, 4H), 1.43 (s, 9H).

Preparation of (12R,19R)-methyl 6,12,19-tris[(tert-butoxycarbonyl)amino]-2,2-dimethyl-4,13-dioxo-3-oxa-5,7,14-triazaicos-5-en-20-oate (15)

A stirred solution of acid 8 (1.95 g, 4.00 mmol) and amine 14 (1.04 g, 4.00 mmol) in $CH_2Cl_2$ (60 mL) was charged with NMM (2.64 mL, 24.0 mmol) and EEDQ (1.97 g, 8.00 mmol). The resulting mixture was stirred at room temperature for 16 h. Water (20 mL) was added to the reaction mixture and extracted with $CH_2Cl_2$ (3×50 mL). The combined organic extract was washed with brine and dried over $Na_2SO_4$. The solvent was removed and the residue was purified by column chromatography (silica gel, 20% to 40% EtOAc in hexanes) to afford amide 15 (2.15 g, 73% over two steps) as a white solid: $^1$H NMR (400 MHz, $CD_3OD$) δ 4.10-4.02 (m, 1H), 4.01-3.92 (m, 1H), 3.70 (s, 3H), 3.35 (t, J=6.8 Hz, 2H), 3.24-3.10 (m, 2H), 1.83-1.67 (m, 2H), 1.66-1.55 (m, 4H), 1.52 (s, 9H), 1.46 (s, 9H), 1.45-1.35 (m, 6H), 1.438 (s, 9H), 1.431 (s, 9H).

Scheme 4
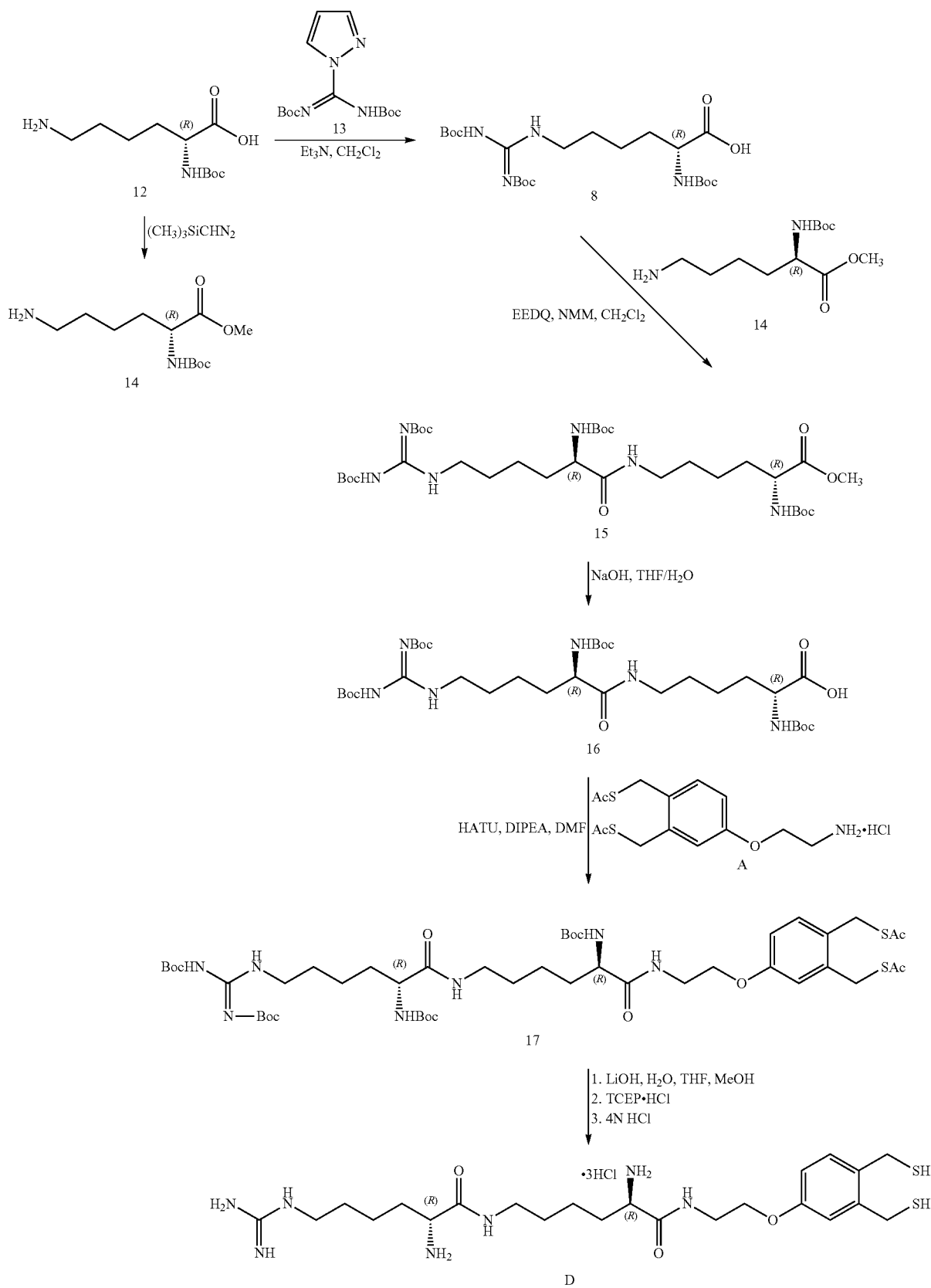

Preparation of (12R,19R)-6,12,19-tris[(tert-butoxy-carbonyl)amino]-2,2-dimethyl-4,13-dioxo-3-oxa-5,7,14-triazaicos-5-en-20-oic acid (16)

A solution of methyl ester 15 (2.15 g, 2.94 mmol) in MeOH/THF/H$_2$O (30 mL/30 mL/15 mL) was charged with NaOH (589 mg, 14.7 mmol) and the reaction mixture was stirred at room temperature for 1 h. After completion of the reaction, the mixture was concentrated under reduced pressure and the pH was adjusted to 5 with 1 N HCl. The suspension was partitioned between CH$_2$Cl$_2$ (50 mL) and water (50 mL). The organic layer was separated and the aqueous layer was extracted with CH$_2$Cl$_2$ (2×50 mL). The combined organic extracts were dried over Na$_2$SO$_4$ and concentrated to afford compound 16 (1.80 g, 86%) as a white solid, which was used directly in the next step: $^1$H NMR (400 MHz, CD$_3$OD) δ 4.07-4.00 (m, 1H), 4.00-3.91 (m, 1H), 3.35 (t, J=7.2 Hz, 2H), 3.25-3.10 (m, 2H), 1.89-1.23 (m, 12H), 1.52 (s, 9H), 1.46 (s, 9H), 1.438 (s, 9H), 1.436 (s, 9H).

Preparation of Compound 17

Compound A (700 mg, 1.96 mmol) and acid 16 (1.40 g, 1.96 mmol) were dissolved in DMF (10 mL) and treated with DIPEA (1.71 mL, 9.80 mmol) and HATU (745 mg, 1.96 mmol). The reaction mixture was stirred at room temperature for 16 h. TLC analysis of the yellow reaction mixture showed the completion of the reaction. After the solvent was removed under reduced pressure, the residue was partitioned between CH$_2$Cl$_2$ (100 mL) and saturated aqueous NaHCO$_3$ (50 mL). The organic layer was separated, washed with brine (50 mL), and dried over Na$_2$SO$_4$. The organic layer was concentrated and the residue was purified by column chromatography (silica gel, 50% to 80% EtOAc in hexanes) to afford compound 17 (1.30 g, 66%) as a pink solid: $^1$H NMR (400 MHz, CD$_3$OD) δ 7.19 (d, J=8.4 Hz, 1H), 6.87 (d, J=2.6 Hz, 1H), 6.76 (dd, J=8.4, 2.6 Hz, 1H), 4.12 (d, J=2.9 Hz, 4H), 4.00 (t, J=5.5 Hz, 2H), 3.99-3.92 (m, 2H), 3.67-3.57 (m, 1H), 3.56-3.45 (m, 1H), 3.34 (t, J=6.9 Hz, 2H), 3.20-3.01 (m, 2H), 2.33 (s, 3H), 2.31 (s, 3H), 1.78-1.54 (m, 6H), 1.51 (s, 9H), 1.46 (s, 9H), 1.45-1.27 (m, 6H), 1.43 (s, 9H), 1.40 (s, 9H).

Preparation of Compound D

A solution of 17 (1.30 g, 1.28 mmol) in a mixture of THF (20 mL), methanol (20 mL), and water (20 mL) was charged with solid LiOH.H$_2$O (216 mg, 5.14 mmol) and the reaction mixture was stirred at room temperature for 1 h. The above reaction mixture TCEP.HCl (183 mg, 0.64 mmol) was charged with and stirred for another 1 h. The solvent was removed and the residue was partitioned between saturated aqueous NaHCO$_3$ solution (10 mL) and CH$_2$Cl$_2$ (50 mL). The CH$_2$Cl$_2$ layer was separated and the aqueous layer was extracted with CH$_2$Cl$_2$ (2×30 mL). The organic layers were combined, dried over Na$_2$SO$_4$, filtered, and concentrated. The residue was dissolved in EtOH (20 mL) and 4 N HCl (20 mL) was added. After stirring at room temperature for 1 h, the reaction mixture was concentrated to afford compound D (820 mg, crude HCl salt) as a yellow solid. The crude HCl salt (600 mg) was purified by reverse-phase column chromatography and lyophilized to afford 325 mg (55%) of pure compound D as a hygroscopic white solid: $^1$H NMR (400 MHz, CD$_3$OD) δ 7.20 (d, J=8.4 Hz, 1H), 6.91 (d, J=2.7 Hz, 1H), 6.78 (dd, J=8.4, 2.7 Hz, 1H), 4.14-4.04 (m, 2H), 3.86 (td, J=6.7, 2.7 Hz, 2H), 3.83 (s, 2H), 3.80 (s, 2H), 3.75-3.66 (m, 1H), 3.62-3.52 (m, 1H), 3.21 (t, J=7.5 Hz, 2H), 3.17-3.08 (m, 2H), 1.96-1.75 (m, 4H), 1.71-1.59 (m, 2H), 1.58-1.34 (m, 6H); $^1$H NMR (400 MHz, DMSO-d$_6$) δ 8.84 (t, J=6.0 Hz, 1H), 8.68 (t, J=5.6 Hz, 1H), 8.43-8.15 (m, 5H), 7.84 (t, J=6.0 Hz, 1H), 7.65-6.61 (m, 4H), 7.22 (d, J=8.4 Hz, 1H), 6.91 (d, 0.1=2.6 Hz, 1H), 6.78 (dd, 0.1=8.4, 2.6 Hz, 1H), 4.08-3.96 (m, 2H), 3.79 (s, 2H), 3.77 (s, 2H), 3.74 (t, J=6.2 Hz, 1H), 3.60-3.40 (m, 2H), 3.16-3.01 (m, 4H), 2.98-2.75 (m, 2H), 1.80-1.62 (m, 4H), 1.54-1.39 (m, 4H), 1.39-1.27 (m, 4H); HRMS (ESI-MS m/z) calculated for C$_{23}$H$_{41}$N$_7$O$_3$S$_2$ [M+H]$^+$, 528.2791; found 528.2794. Elemental analysis: % calcd C, 43.36; H, 6.96; N, 14.11; found C, 41.23; H, 7.19; N, 15.39.

5. Preparation of E: (S)-2-amino-N-((S)-5-amino-6-(2-(3,4-bis(mercaptomethyl)phenoxy)ethylamino)-6-oxohexyl)-6-guanidinohexanamide Hydrochloride Scheme 5

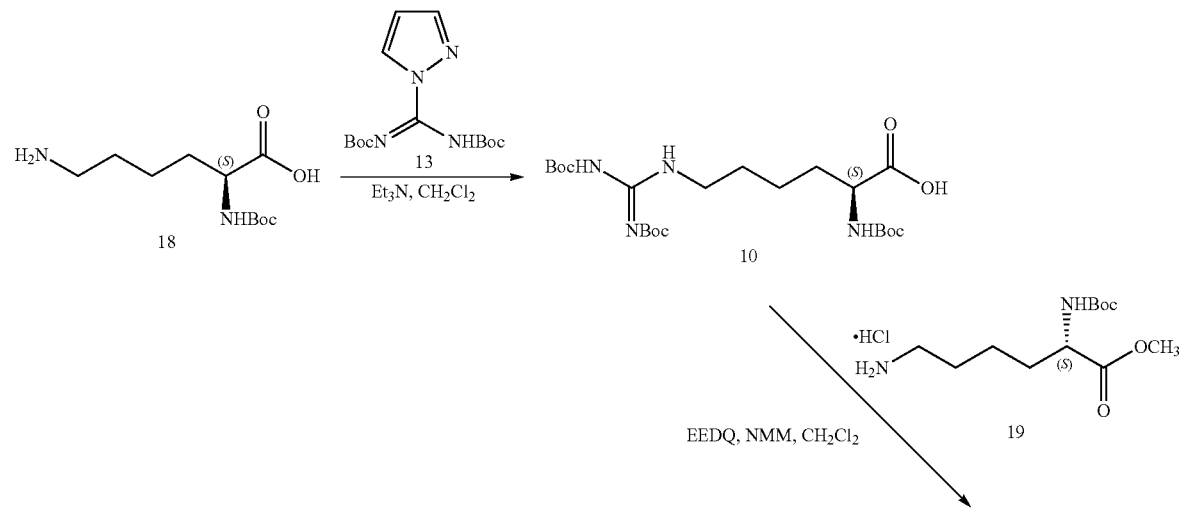

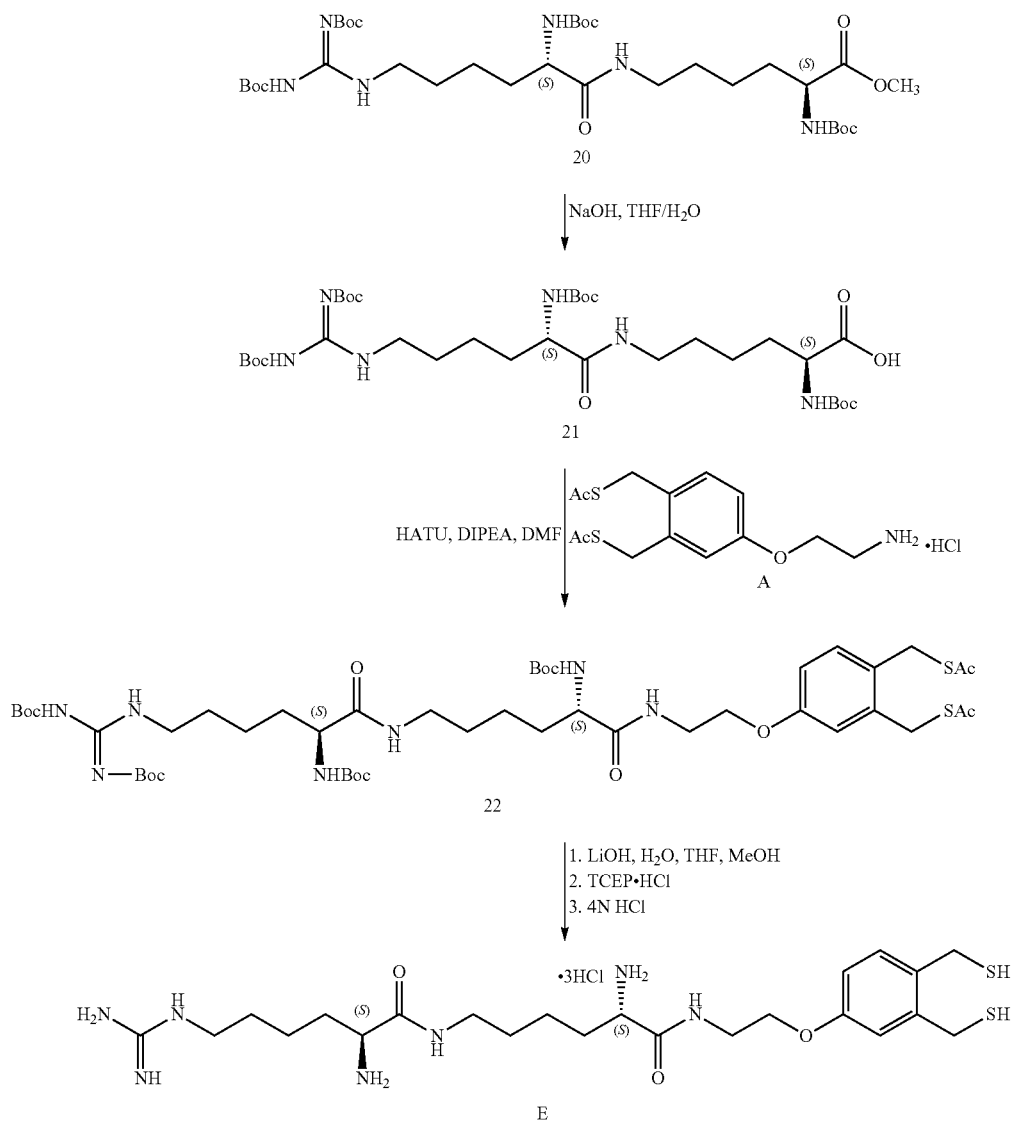

Preparation of (S)-6-[2,3-bis(tert-butoxycarbonyl)guanidino]-2-[(tert-butoxycarbonyl)amino]hexanoic acid (10)

A solution of N-α-Boc-L-lysine 18 (5.00 g, 20.3 mmol) in CH₂Cl₂ (100 mL) was charged with N,N'-bis-Boc-1-guanylpyrazole (5.10 g, 16.6 mmol) and triethylamine (5.54 mL, 40.6 mmol). The reaction mixture was stirred at room temperature for 48 h. The reaction mixture was washed with 10% aqueous citric acid (2×80 mL) and the solvent was removed under reduced pressure. The residue was dissolved in 1 N NaOH (200 mL), the pH of solution was adjusted to 5-6 with 1 N HCl, and the mixture was extracted with CH₂Cl₂ (300 ml). The CH₂Cl₂ layer was separated and the aqueous layer was extracted with CH₂Cl₂ (2×200 mL). The combined organic layers were dried over Na₂SO₄, filtered, and concentrated to afford compound 10 (9.00 g, 91%) as a white solid: ¹H NMR (400 MHz, CD₃OD) δ 4.10-4.02 (m, 1H), 3.36 (t, J=6.8 Hz, 2H), 1.90-1.78 (m, 1H), 1.73-1.56 (m, 3H), 1.52 (s, 9H), 1.45-1.31 (m, 2H), 1.47 (s, 9H), 1.43 (s, 9H).

Preparation of (12S,19S)-methyl 6,12,19-tris[(tert-butoxycarbonyl)amino]-2,2-dimethyl-4,13-dioxo-3-oxa-5,7,14-triazaicos-5-en-20-oate (20)

A stirred solution of acid 10 (5.00 g, 10.2 mmol) and amine 19 (3.04 g, 10.2 mmol) in CH₂Cl₂ (100 mL) was charged with NMM (6.75 mL, 61.5 mmol) and EEDQ (5.06 g, 20.5 mmol). The resulting mixture was stirred at room temperature for 16 h. The reaction mixture was charged with water (50 mL) and extracted with CH₂Cl₂ (3×100 mL). The combined organic extracts were washed with brine and dried over Na₂SO₄. The solvent was removed and the residue was purified by column chromatography (silica gel, 20% to 40% EtOAc in hexanes) to afford amide 20 (6.00 g, 80%) as a white solid: ¹H NMR (400 MHz, CD₃OD) δ 4.12-4.03 (m, 1H), 4.01-3.92 (m, 1H), 3.70 (s, 3H), 3.35 (t, J=7.0 Hz, 2H), 3.25-3.11 (m, 2H), 1.83-1.69 (m, 2H), 1.68-1.55 (m, 4H), 1.52 (s, 9H), 1.46 (s, 9H), 1.45-1.35 (m, 6H), 1.438 (s, 9H), 1.436 (s, 9H).

Preparation of (12S,19S)-6,12,19-tris[(tert-butoxycarbonyl)amino]-2,2-dimethyl-4,13-dioxo-3-oxa-5,7,14-triazaicos-5-en-20-oic acid, 21

A solution of methyl ester 20 (6.00 g, 8.21 mmol) in MeOH/THF/H$_2$O (100 mL/100 mL/50 mL) was charged with NaOH (1.64 g, 41.1 mmol) and the reaction mixture was stirred at room temperature for 1 h. After completion of the reaction, the mixture was concentrated under reduced pressure and the pH of the solution was adjusted to 5 with 1 N HCl. The suspension was partitioned between CH$_2$Cl$_2$ (150 mL) and water (100 mL). The organic layer was separated and the aqueous layer was extracted with CH$_2$Cl$_2$ (2×150 mL). The combined organic extracts were dried over Na$_2$SO$_4$ and concentrated to afford compound 21 (5.50 g, 94%) as a white solid, which was used directly in the next step: $^1$H NMR (400 MHz, CD$_3$OD) δ 4.06-4.00 (m, 1H), 4.00-3.93 (m, 1H), 3.35 (t, J=7.3 Hz, 2H), 3.26-3.07 (m, 2H), 1.85-1.56 (m, 6H), 1.53-1.32 (m, 6H), 1.52 (s, 9H), 1.46 (s, 9H), 1.438 (s, 9H), 1.435 (s, 9H).

Preparation of Compound 22

Compound A (1.20 g, 3.42 mmol) and acid 21 (2.44 g, 3.42 mmol) were dissolved in DMF (25 mL) and treated with DIPEA (2.98 mL, 17.1 mmol) and HATU (1.30 g, 3.42 mmol). The reaction mixture was stirred at room temperature for 16 h. TLC analysis of the yellow reaction mixture showed the completion of the reaction. After the solvent was removed under reduced pressure, the residue was dissolved in CH$_2$Cl$_2$ (100 mL). The solution was quickly washed with saturated aqueous NaHCO$_3$ (2×50 mL) and brine (50 mL) and dried over Na$_2$SO$_4$. The organic layer was concentrated and the residue was purified by column chromatography (silica gel, 50% to 80% EtOAc in hexanes) to afford compound 22 (1.50 g, 44%) as an orange solid: $^1$H NMR (400 MHz, CD$_3$OD) δ 7.19 (d, J=8.5 Hz, 1H), 6.87 (d, J=2.7 Hz, 1H), 6.76 (dd, J=8.5, 2.7 Hz, 1H), 4.12 (d, J=2.8 Hz, 4H), 4.00 (t, J=5.4 Hz, 2H), 3.99-3.92 (m, 2H), 3.65-3.56 (m, 1H), 3.55-3.45 (m, 1H), 3.34 (t, J=7.1 Hz, 2H), 3.21-3.04 (m, 2H), 2.33 (s, 3H), 2.31 (s, 3H), 1.78-1.54 (m, 6H), 1.51 (s, 9H), 1.46 (s, 9H), 1.43-1.29 (m, 6H), 1.43 (s, 9H), 1.40 (s, 9H).

Preparation of compound E: (S)-2-amino-N-((S)-5-amino-6-(2-(3,4-bis(mercaptomethyl)phenoxy)ethylamino)-6-oxohexyl)-6-guanidinohexanamide Hydrochloride A solution of 22 (1.50 g, 1.48 mmol) in a mixture of THF (10 mL), methanol (10 mL), and water (10 mL) was charged with solid LiOH.H$_2$O (249 mg, 5.93 mmol) and the reaction mixture was stirred at room temperature for 1 h. The above reaction mixture was charged with TCEP.HCl (212 mg, 0.74 mmol) and stirred for another 1 h. The solvent was removed and the residue was partitioned between saturated aqueous NaHCO$_3$ solution (10 mL) and CH$_2$Cl$_2$ (50 mL). The CH$_2$Cl$_2$ layer was separated and the aqueous layer was extracted with CH$_2$Cl$_2$ (2×30 mL). The combined organic layers were dried over Na$_2$SO$_4$, filtered, and concentrated. The residue was dissolved in EtOH (5.0 mL) and 4 N HCl (20 mL) was added. After stirring at room temperature for 1 h, the reaction mixture was concentrated to afford crude compound 2048 as a yellow solid. The crude HCl salt (E) was purified by reverse-phase column chromatography and lyophilized to afford 370 mg (39%) of pure compound E as a hygroscopic white solid: $^1$H NMR (400 MHz, CD$_3$OD) δ 7.20 (d, J=8.4 Hz, 1H), 6.91 (d, J=2.7 Hz, 1H), 6.78 (dd, J=8.4, 2.7 Hz, 1H), 4.14-4.04 (m, 2H), 3.87 (td, J=6.7, 2.7 Hz, 2H), 3.83 (s, 2H), 3.80 (s, 2H), 3.75-3.66 (m, 1H), 3.62-3.52 (m, 1H), 3.21 (t, J=7.5 Hz, 2H), 3.17-3.08 (m, 2H), 1.96-1.75 (m, 4H), 1.71-1.59 (m, 2H), 1.58-1.34 (m, 6H); $^1$H NMR (400 MHz, DMSO-d$_6$) δ 8.86 (t, J=5.6 Hz, 1H), 8.70 (t, J=5.6 Hz, 1H), 8.43-8.15 (m, 5H), 7.87 (t, J=5.7 Hz, 1H), 7.65-6.66 (m, 4H), 7.22 (d, J=8.4 Hz, 1H), 6.91 (d, J=2.6 Hz, 1H), 6.78 (dd, J=8.4, 2.6 Hz, 1H), 4.08-3.96 (m, 2H), 3.79 (s, 2H), 3.77 (s, 2H), 3.74 (t, J=6.2 Hz, 1H), 3.60-3.40 (m, 2H), 3.16-3.01 (m, 4H), 2.98-2.75 (m, 2H), 1.80-1.62 (m, 4H), 1.54-1.39 (m, 4H), 1.39-1.27 (m, 4H); HRMS (ESI-MS m/z) calculated for C$_{23}$H$_{41}$N$_7$O$_3$S$_2$ [M+H]$^+$, 528.2791; found 528.2793.

6. Preparation of Branched Precursor F: S,S'-(4,5-bis(2-aminoethoxy)-1,2-phenylene)bis(methylene) diethanethioate Hydrochloride Scheme 6

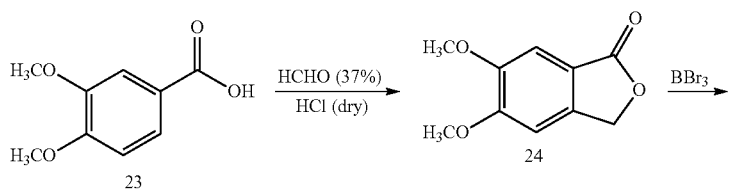

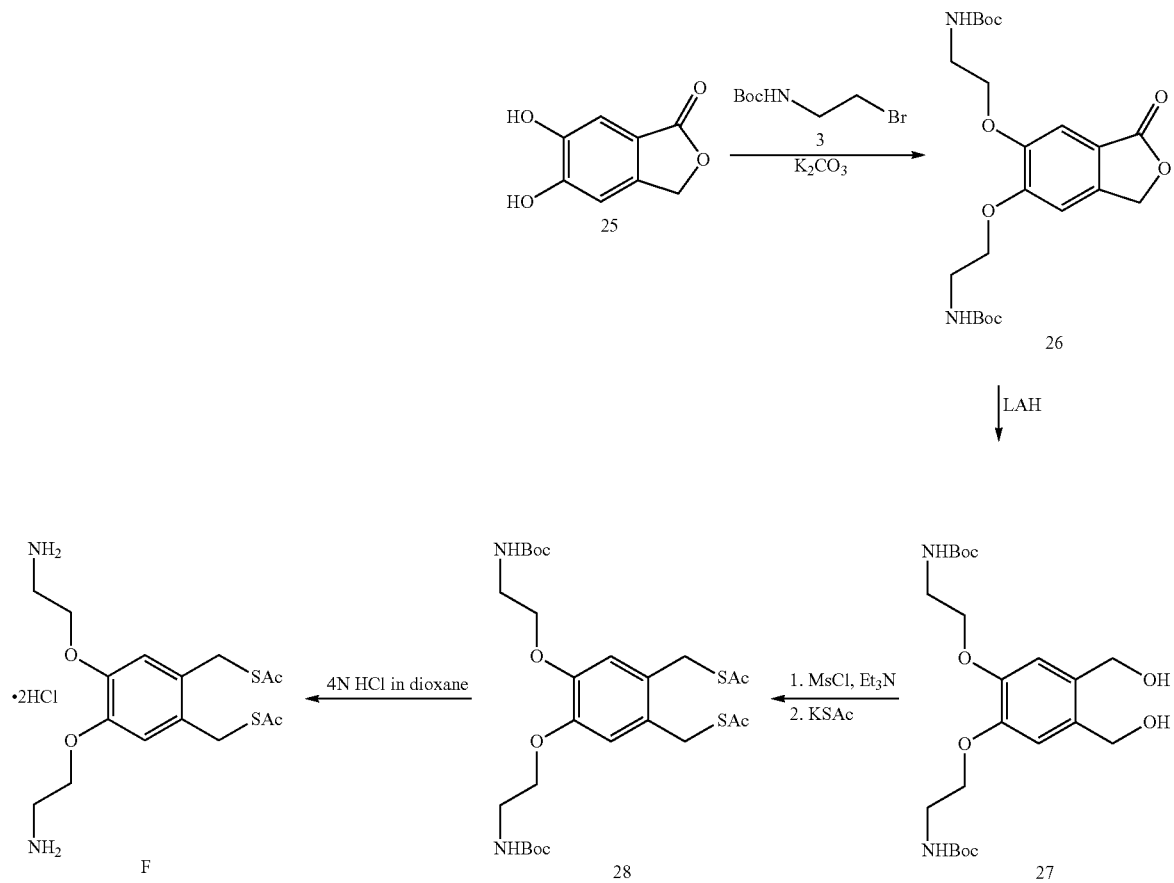

Preparation of 5,6-dimethoxyisobenzofuran-1(3H)-one (24)

HCl gas was bubbled through an aqueous formaldehyde (37%, 70 mL) at 0° C. and then at room temperature to get a saturated solution (1.5 h). This solution was charged with 3,4-dimethoxybenzoic acid 23 (9.00 g, 49.5 mmol) portionwise. The mixture was warmed to 70° C. and stirred at that temperature for 7 h; HCl gas was continuously bubbled through the solution during this period of time. The reaction mixture was stirred at room temperature for 16 h. The solvent was removed, water (100 mL) was added, and the mixture was neutralized with aqueous $NH_4OH$ solution. A solid formed, which was filtered and washed with water. Recrystallization of the product from ethanol yielded a brown solid (5.00 g, 52%). 2.0 g of impure 24 was isolated as well.

Alternative Preparation of 24

Concentrated HCl (37%, 150 mL) was added to 3,4-dimethoxybenzoic acid 23 (10.0 g, 54.9 mmol), followed by aqueous formaldehyde (37%, 75 mL). The mixture was warmed to 90° C. and stirred at that temperature for 5 h. The solvent was removed and the residue was portioned between water (100 mL) and EtOAc (250 ml). The organic layer was separated and the aqueous layer was extracted with EtOAc (3×200 mL). The combined organic layer was washed with 2.5 M NaOH, followed by water, and concentrated. The residue was purified by column chromatography (silica gel, 25 to 50% EtOAc in hexanes) to afford compound 24 (7.00 g, 66%) as an off-white solid: $^1H$ NMR (400 MHz, DMSO-$d_6$) δ 7.26 (s, 1H), 7.23 (s, 1H), 5.27 (s, 2H), 3.87 (s, 3H), 3.84 (s, 3H).

Preparation of 5,6-dihydroxyisobenzofuran-1(3H)-one (25)

A solution of compound 24 (7.00 g, 36.1 mmol) in $CH_2Cl_2$ (150 mL) was cooled to −78° C. and $BBr_3$ (8.52 mL, 90.2 mmol) was added at the same temperature. Stirring was continued at −78° C. for 30 min, and the reaction mixture was brought to room temperature and stirred for 16 h. The reaction mixture was quenched with MeOH at 0° C. and the solvent was removed. The residue was portioned between water (100 mL) and EtOAc (200 mL); the EtOAc layer was separated. The aqueous layer was extracted with EtOAc (3×200 mL). The combined organic layer was concentrated and the residue was purified by column chromatography (silica gel, 40-60% EtOAc in hexanes) to afford compound 25 (5.00 g, 83%) as an off-white solid: $^1H$ NMR (400 MHz, DMSO-$d_6$) δ 10.18 (br s, 1H), 9.65 (br s, 1H), 7.06 (s, 1H), 6.92 (s, 1H), 5.16 (s, 2H).

Preparation of di-tert-butyl {[(1-oxo-1,3-dihydroisobenzofuran-5,6-diyl)bis(oxy)]bis(ethane-2,1-diyl)}dicarbamate (26)

A solution of compound 25 (5.00 g, 30.1 mmol) in DMF (40 mL) was charged with $K_2CO_3$ (16.6 g, 120 mmol) and stirred at room temperature for 5 min. The above reaction mixture was charged with compound 3 (21.1 g, 90.4 mmol) and the reaction mixture was stirred at room temperature for 120 h. The reaction mixture was diluted with water (300 mL) and extracted with EtOAc (3×300 mL). The combined organic layer was concentrated and the residue was purified by column chromatography (silica gel, 30-60% EtOAc in hexanes) to afford compound 26 (8.00 g, 59%) as a white gum: $^1$H NMR (400 MHz, $CD_3OD$) δ 7.72 (s, 1H), 7.16 (s, 1H), 5.24 (s, 2H), 4.14 (t, J=5.7 Hz, 2H), 4.08 (t, J=5.7 Hz, 2H), 3.54-3.44 (m, 4H), 1.43 (s, 18H).

Preparation of di-tert-butyl ({[4,5-bis(hydroxymethyl)-1,2-phenylene]bis(oxy)}bis(ethane-2,1-diyl))dicarbamate (27)

A solution of compound 26 (5.00 g, 11.0 mmol) in THF (50 mL) was charged with lithium aluminum hydride (1 M solution in diethyl ether, 33.2 mL, 33.2 mmol) at 0° C. The resulting reaction mixture was stirred at 0° C. for 1 h and quenched with ice-cold water at 0° C. The reaction mixture was diluted with chloroform (300 mL) and filtered through a Celite pad, and the Celite pad was washed with chloroform (2×300 ml). The filtrate was concentrated under vacuum to afford 27 (4.50 g, 90%) as a colorless gum: $^1$H NMR (400 MHz, DMSO-$d_6$) δ 6.99 (s, 2H), 6.90 (t, J=5.9 Hz, 2H), 4.97 (brs, 2H), 4.44 (s, 4H), 3.92 (t, J=5.6 Hz, 4H), 3.30-3.22 (m, 4H), 1.38 (s, 18H).

Preparation of 28

A solution of 27 (4.50 g, 9.95 mmol) in $CH_2Cl_2$ (100 mL) was charged with $Et_3N$ (10.9 mL, 79.6 mmol) followed by methanesulfonyl chloride (3.00 mL, 39.8 mmol) at 0° C. and stirred at room temperature for 12 h. The reaction mixture was diluted with water (100 mL) and extracted with $CH_2Cl_2$ (3×150 mL). The combined organic extracts were washed with brine, dried over $Na_2SO_4$, and concentrated to afford the mesylated product (8.50 g, crude) as a yellow oil, which was directly used for the next step without further purification.

The above crude product (8.50 g, crude, 9.95 mmol) in a mixture of THF (200 ml) and DMF (50 mL) was charged with KSAc (2.84 g, 24.9 mmol) and stirred at room temperature for 16 h. The solvent was removed and the residue was partitioned between water (50.0 mL) and $CH_2Cl_2$ (100 mL). The $CH_2Cl_2$ layer was separated and the aqueous layer was extracted with $CH_2Cl_2$ (2×100 mL). The combined organic layer was concentrated and the residue was purified by column chromatography (silica gel, 10% to 15% EtOAc in hexanes) to afford compound 28 (4.20 g, 74% over two steps) as a yellow solid: $^1$H NMR (400 MHz, $CD_3OD$) δ 6.91 (s, 2H), 4.10 (s, 4H), 3.99 (t, J=5.7 Hz, 4H), 3.41 (t, J=5.6 Hz, 4H), 2.31 (s, 6H), 1.43 (s, 18).

Preparation of compound F; S,S'-(4,5-bis(2-aminoethoxy)-1,2-phenylene)bis(methylene)diethanethioate Hydrochloride Compound 28 (5.00 g, 8.74 mmol) was dissolved in 4 N HCl in dioxane (40 mL) at room temperature and the solution was stirred for 2 h. After concentration, the residue was triturated with MTBE to afford the hydrochloric acid salt F (3.50 g, 90%) as an off-white solid: $^1$H NMR (400 MHz, $CD_3OD$) δ 7.02 (s, 2H), 4.24 (t, J=5.2 Hz, 4H), 4.13 (s, 4H), 3.39 (t, J=5.3 Hz, 4H), 2.32 (s, 6H).

7. Preparation of G: (2R,2'R)-N,N'-(2,2'-(4,5-bis(mercaptomethyl)-1,2-phenylene)bis(oxy)bis(ethane-2,1-diyl))bis(2-amino-6-guanidinohexanamide)Hydrochloride

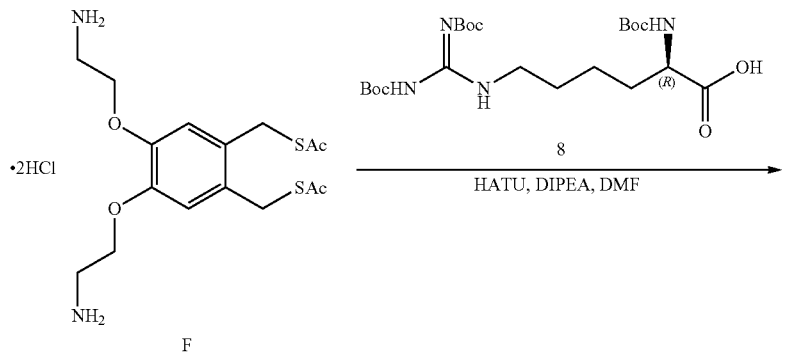

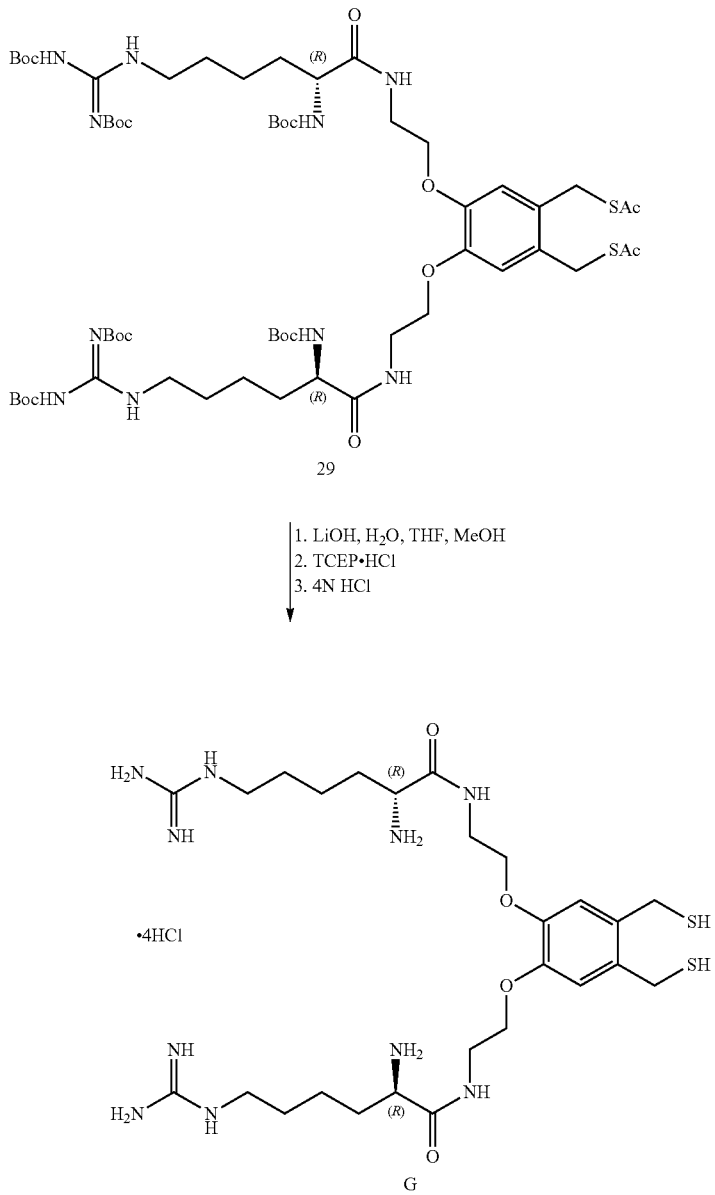

Preparation of Compound 29

Compound F (888 mg, 2.00 mmol) and acid 8 (1.95 g, 4.00 mmol) were dissolved in DMF (20 mL) and treated with DIPEA (3.49 mL, 20.0 mmol) and HATU (1.52 g, 4.00 mmol). The reaction mixture was stirred at room temperature for 16 h. TLC analysis of the yellow reaction mixture showed the completion of the reaction. The solvent was removed under reduced pressure and the residue was partitioned between $CH_2Cl_2$ (100 mL) and saturated aqueous $NaHCO_3$ (50 mL). The organic layer was separated, washed with brine (50 mL), and dried over $Na_2SO_4$. The organic layer was concentrated and the residue was purified by column chromatography (silica gel, 50% to 80% EtOAc in hexanes) to afford compound 29 (1.31 g, 50%) as a yellow solid: $^1$H NMR (400 MHz, $CD_3OD$) δ 6.88 (s, 2H), 4.09 (s, 4H), 4.08-3.98 (m, 6H), 3.69-3.53 (m, 4H), 3.23 (t, J=7.0 Hz, 4H), 2.31 (s, 6H), 1.79-1.57 (m, 6H), 1.57-1.30 (m, 6H), 1.51 (s, 18H), 1.46 (s, 18H), 1.40 (s, 18H).

Preparation of compound G: (2R,2'R)-N,N'-(2,2'-(4,5-bis(mercaptomethyl)-1,2-phenylene)bis(oxy)bis(ethane-2,1-diyl))bis(2-amino-6-guanidinohexanamide)Hydrochloride A solution of 29 (1.31 g, 1.00 mmol) in a mixture of THF (20 mL), methanol (20 mL), and water (20 mL) was charged with solid $LiOH·H_2O$ (168 mg, 4.00 mmol) and the reaction mixture was stirred at room temperature for 1 h. The above reaction mixture was charged with TCEP·HCl (143 mg, 0.50 mmol) and stirred for another 1 h. The solvent was removed and the residue was partitioned between $CH_2Cl_2$ (50 mL)

and saturated aqueous NaHCO$_3$ solution (10 mL). The CH$_2$Cl$_2$ layer was separated and the aqueous layer was extracted with CH$_2$Cl$_2$ (2×30 mL). The combined organic layers were dried over Na$_2$SO$_4$, filtered, and concentrated. The residue was dissolved in EtOH (20 mL) and 4 N HCl (20 mL) was added After stirring at room temperature for 1 h, the reaction mixture was concentrated to afford compound G (800 mg, crude HCl salt) as a yellow solid. The crude HCl salt (600 mg) was purified by reverse-phase column chromatography and lyophilized to afford 135 mg (23%) of pure compound G as a hygroscopic white solid: $^1$H NMR (400 MHz, CD$_3$OD) δ6.95 (s, 2H), 4.11 (t, J=5.8 Hz, 4H), 3.96 (t, J=6.8 Hz, 2H), 3.79 (s, 4H), 3.71 (dt, J=13.7, 5.8 Hz, 2H), 3.61 (dt, J=13.6, 5.0 Hz, 2H), 3.11 (t, J=7.0 Hz, 4H), 1.97-1.84 (m, 4H), 1.67-1.55 (m, 4H), 1.53-1.43 (m, 4H); $^1$H NMR (400 MHz, DMSO-d$_6$) δ9.03 (t, J=5.7 Hz, 2H), 8.35 (br s, 6H), 7.90 (t, J=5.4 Hz, 2H), 7.73-6.78 (m, 7H), 6.98 (s, 2H), 4.02 (t, J=5.8 Hz, 4H), 3.91-3.81 (m, 2H), 3.75 (s, 2H), 3.74 (s, 2H), 3.59-3.41 (m, 4H), 3.11-3.03 (m, 4H), 2.91 (t, J=7.7 Hz, 2H), 1.81-1.70 (m, 4H), 1.52-1.41 (m, 4H), 1.40-1.30 (m, 4H); HRMS (ESI-MS m/z) calculated for C$_{26}$H$_{48}$N$_{10}$O$_4$S$_2$ [M+H]$^+$, 629.3380; found 629.3377. Elemental analysis: % calcd C, 40.31; H, 6.77; N, 18.08; found C, 35.32; H, 7.40; N, 15.76.

8. Preparation of H: (2S,2'S)-N,N'-(2,2'-(4,5-bis(mercaptomethyl)-1,2-phenylene)bis(oxy)bis(ethane-2,1-diyl))bis(2-amino-6-guanidinohexanamide)Hydrochloride Preparation of Compound 30

Compound B (888 mg, 2.00 mmol) and acid 10 (1.95 g, 4.00 mmol) were dissolved in DMF (20 mL) and treated with DIPEA (3.49 mL, 20.0 mmol) and HATU (1.52 g, 4.00 mmol). The reaction mixture was stirred at room temperature for 16 h. TLC analysis of the yellow reaction mixture showed the completion of the reaction. After the solvent was removed under reduced pressure, the residue was partitioned between CH$_2$Cl$_2$ (100 mL) and NaHCO$_3$ (50 mL). The organic layer was separated, washed with brine (50 mL), and dried over Na$_2$SO$_4$. The organic layer was concentrated and the residue was purified by column chromatography (silica gel, 50% to 80% EtOAc in hexanes) to afford compound 30 (1.51 g, 57%) as an off-white solid: $^1$H NMR (400 MHz, CD$_3$OD) δ6.88 (s, 2H), 4.09 (s, 4H), 4.07-3.98 (m, 6H), 3.69-3.52 (m, 4H), 3.23 (t, J=7.0 Hz, 4H), 2.31 (s, 6H), 1.79-1.59 (m, 6H), 1.57-1.30 (m, 6H), 1.51 (s, 18H), 1.46 (s, 18H), 1.40 (s, 18H).

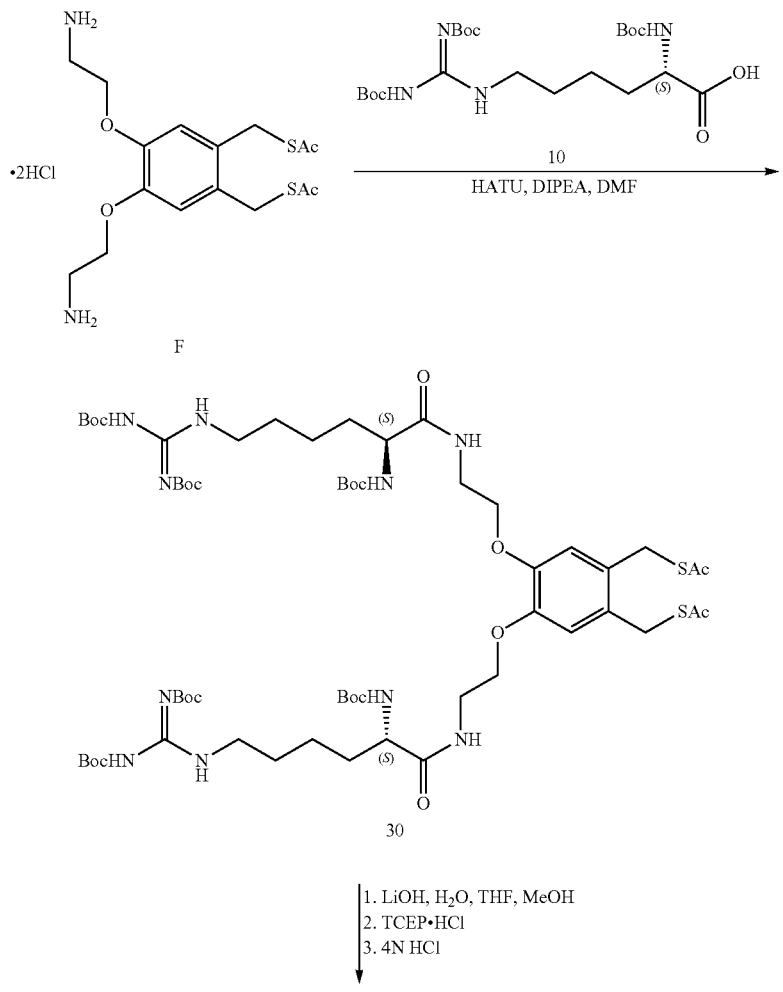

Scheme 8

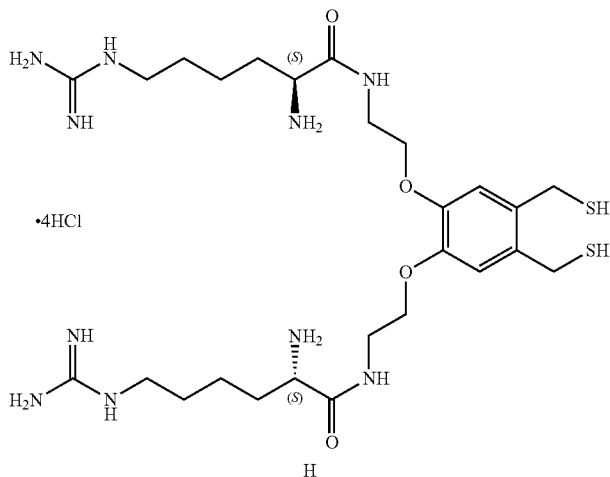

Preparation of Compound H; (2S,2'S)-N,N'-(2,2'-(4,5-bis(mercaptomethyl)-1,2-phenylene)bis(oxy)bis(ethane-2,1-diyl))bis(2-amino-6-guanidinohexanamide)Hydrochloride A solution of 30 (1.51 g, 1.14 mmol) in a mixture of THF (20 mL), methanol (20 mL), and water (20 mL) was charged with solid LiOH.H$_2$O (192 mg, 4.57 mmol) and the reaction mixture was stirred at room temperature for 1 h. The above reaction mixture was charged with TCEP.HCl (163 mg, 0.57 mmol) and stirred for another 1 h. The solvent was removed, the residue was dissolved in CH$_2$Cl$_2$ (50 mL), and the solution was washed with saturated aqueous NaHCO$_3$ solution (10 mL). The CH$_2$Cl$_2$ layer was separated and the aqueous layer was extracted with CH$_2$Cl$_2$ (2×30 mL). The combined organic layers were dried over Na$_2$SO$_4$, filtered, and concentrated to get 600 mg of crude, white, solid product. 400 mg of the crude product was dissolved in EtOH (5.0 mL), and 4 N HCl (20 mL) was added. After stirring at room temperature for 1 h, the reaction mixture was concentrated to afford compound H (crude HCl salt) as a yellow solid. The crude HCl salt was purified by reverse-phase column chromatography and lyophilized to afford 420 mg (48%) of pure compound H as a hygroscopic white solid: $^1$H NMR (400 MHz, CD$_3$OD) δ6.95 (s, 2H), 4.11 (t, J=5.8 Hz, 4H), 3.98 (t, J=6.8 Hz, 2H), 3.78 (s, 4H), 3.71 (dt, J=13.7, 5.8 Hz, 2H), 3.61 (dt, J=13.6, 5.0 Hz, 2H), 3.11 (t, J=7.0 Hz, 4H), 1.97-1.84 (m, 4H), 1.67-1.55 (m, 4H), 1.53-1.43 (m, 4H); $^1$H NMR (400 MHz, DMSO-d$_6$) δ8.98 (br s, 2H), 8.30 (br s, 6H), 7.83 (br s, 2H), 7.62-6.74 (m, 7H), 6.97 (s, 2H), 4.02 (t, J=5.8 Hz, 4H), 3.84 (t, J=6.9 Hz, 2H), 3.75 (br s, 4H), 3.57-3.41 (m, 4H), 3.11-3.02 (m, 4H), 2.96-2.83 (m, 2H), 1.81-1.70 (m, 4H), 1.52-1.41 (m, 4H), 1.40-1.30 (m, 4H); HRMS (ESI-MS m/z) calculated for C$_{26}$H$_{48}$N$_{10}$O$_4$S$_2$ [M+H]$^+$, 629.3380; found 629.3378.

9. Preparation of Compound I: tert-butyl 2-(3,4-bis(mercaptomethyl)phenoxy)ethylcarbamate

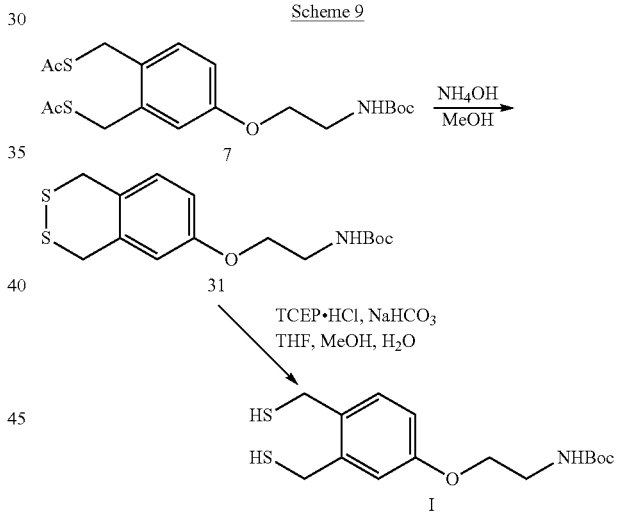

Preparation of Compound 31

A solution of 7 (12.9 g, 32.3 mmol) in methanol (250 mL) was charged with NH$_4$OH solution (40 mL, 37% in water) and the reaction mixture was stirred at room temperature for 74 h. Solvent was removed, the residue was partitioned between CH$_2$Cl$_2$ (250 mL) and water (100 mL). The CH$_2$Cl$_2$ layer was separated and the aqueous layer was extracted with CH$_2$Cl$_2$ (2×50 mL). The combined organic layers were dried over Na$_2$SO$_4$, filtered, and concentrated to get crude product which was purified by column chromatography (silica gel, 2% to 6% MeOH in CH$_2$Cl$_2$) to afford compound 31 (7.00 g, 66%, 80% pure by $^1$H NMR) as a white solid: $^1$H NMR (400 MHz, CDCl$_3$) δ7.04 (d, J=8.4 Hz, 1H), 6.79-6.72 (m, 1H), 6.71-6.65 (m, 1H), 5.33-5.07 (m, 1H), 3.98 (br s, 2H), 3.68 (s, 4H), 3.51 (br s, 2H), 1.43 (s, 9H).

Preparation of Compound I: tert-butyl 2-(3,4-bis(mercaptomethyl)phenoxy)ethylcarbamate A solution of 31 (500 mg, 1.52 mmol) in a mixture of THF (5.0 mL), methanol (5.0 mL), and NaHCO$_3$ saturated solution (5.0 mL) was charged with TCEP.HCl (656 mg, 2.29 mmol) and stirred for 2 h. The solvent was removed and the residue was partitioned between saturated aqueous NaHCO$_3$ solution (10 mL) and CH$_2$Cl$_2$ (50 mL). The CH$_2$Cl$_2$ layer was separated and the aqueous layer was extracted with CH$_2$Cl$_2$ (2×30 mL). The combined organic layers were dried over Na$_2$SO$_4$, filtered, and concentrated. The residue was purified by preparative HPLC and lyophilized to afford 240 mg (48%) of pure compound P-2035 as a light yellow liquid: $^1$H NMR (400 MHz, CD$_3$OD) δ7.17 (d, J=8.5 Hz, 1H), 6.88 (d, J=2.7 Hz, 1H), 6.76 (dd, J=8.5, 2.7 Hz, 1H), 3.98 (t, J=5.3 Hz, 2H), 3.81 (s, 2H), 3.80 (s, 2H), 3.40 (t, J=5.6 Hz, 2H), 1.43 (s, 9H); $^1$H NMR (400 MHz, DMSO-d$_6$) δ7.19 (d, J=8.4 Hz, 1H), 6.97 (t, J=5.3 Hz, 1H), 6.89 (d, J=2.7 Hz, 1H), 6.76 (dd, J=8.4, 2.7 Hz, 1H), 3.92 (t, J=6.0 Hz, 2H), 3.78 (d, J=4.5 Hz, 2H), 3.76 (d, J=4.5 Hz, 2H), 3.27 (q, J=5.8 Hz, 2H), 2.88 (t, J=7.5 Hz, 1H), 2.77 (t, J=7.5 Hz, 1H), 1.38 (s, 9H); ESI (m/z) [C$_{15}$H$_{23}$NO$_3$S$_2$+Na]$^+$ 352.

10. Preparation of J: (S)-tert-butyl 6-(2-(3,4-bis(mercaptomethyl)phenoxy)ethylamino)-6-oxo-hexane-1,5-diyldicarbamate compound 33 (3.0 g, 86%) as an colorless oil: $^1$H NMR (400 MHz, CD$_3$OD) δ7.19 (d, J=8.5 Hz, 1H), 6.87 (d, J=2.9 Hz, 1H), 6.76 (dd, J=8.5, 2.9 Hz, 1H), 4.13 (s, 2H), 4.12 (s, 2H), 3.99 (t, J=5.5 Hz, 2H), 3.98-3.95 (m, 1H), 3.61 (td, J=13.9, 4.9 Hz, 1H), 3.55-3.45 (m, 1H), 2.96 (t, J=6.9 Hz, 2H), 2.33 (s, 3H), 2.31 (s, 3H), 1.75-1.64 (m, 1H), 1.63-1.52 (m, 1H), 1.49-1.26 (m, 4H), 1.42 (s, 9H), 1.40 (s, 9H).

Preparation of Compound J: (S)-tert-butyl 6-(2-(3,4-bis(mercaptomethyl)phenoxy)ethylamino)-6-oxo-hexane-1,5-diyldicarbamate A solution of 33 (750 mg, 1.19 mmol) in a mixture of THF (5.0 mL), methanol (5.0 mL), and water (5.0 mL) was charged with solid LiOH.H$_2$O (151 mg, 3.50 mmol) and the reaction mixture was stirred at room temperature for 1 h. The above reaction mixture was charged with TCEP.HCl (170 mg, 0.59 mmol) and stirred for another 1 h. The solvent was removed and the residue was partitioned between saturated aqueous NaHCO$_3$ solution (10 mL) and CH$_2$Cl$_2$ (50 mL). The CH$_2$Cl$_2$ layer was separated and the aqueous layer was extracted with CH$_2$Cl$_2$ (2×30 mL). The combined organic layers were dried over Na$_2$SO$_4$, filtered, and concentrated. The residue was purified by preparative HPLC and lyophilized to afford 374 mg (56%) of pure compound J as a light yellow solid: $^1$H NMR (400 MHz, CD$_3$OD) δ7.18 (d, J=8.4 Hz, 1H), 6.88 (d, J=2.5 Hz, 1H), 6.78 (dd, J=8.4, 2.5

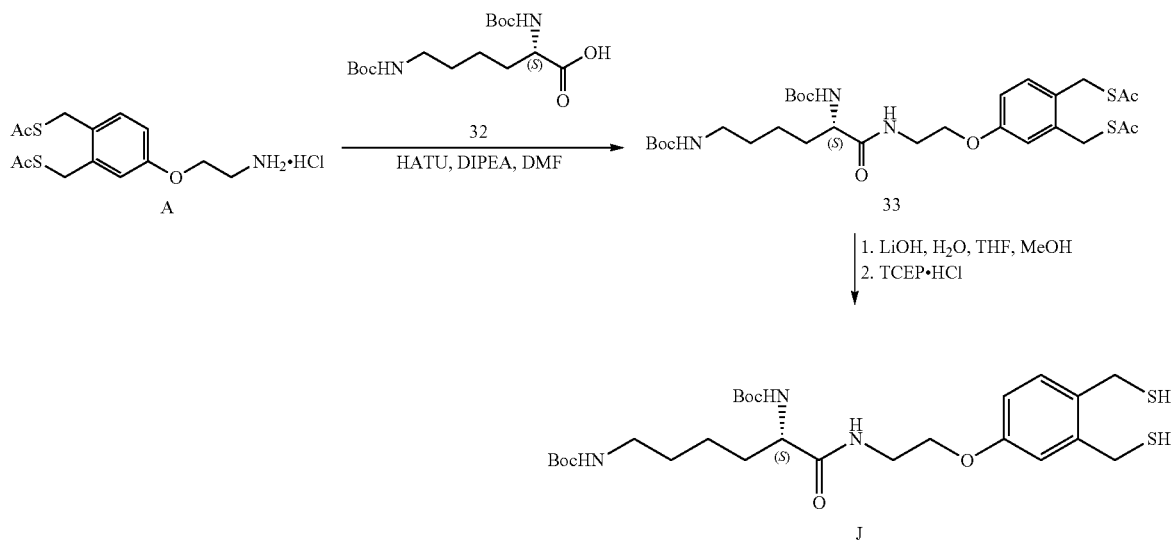

Scheme 10

Preparation of Compound 33

Compound A (1.96 g, 5.60 mmol) and acid 32 (1.94 g, 5.60 mmol) were dissolved in DMF (25 mL) and treated with DIPEA (4.89 mL, 28.0 mmol) and HATU (2.12 g, 5.60 mmol). The reaction mixture was stirred at room temperature for 24 h. TLC analysis of the yellow reaction mixture showed the completion of the reaction. After the solvent was removed under reduced pressure, the residue was dissolved in CH$_2$Cl$_2$ (100 mL). The solution was quickly washed with saturated aqueous NaHCO$_3$ (2×25 mL) and brine (25 mL) and dried over Na$_2$SO$_4$. The organic layer was concentrated and the residue was purified by column chromatography (silica gel, 50% to 80% EtOAc in hexanes) to afford Hz, 1H), 4.03 (t, J=5.3 Hz, 2H), 4.01-3.94 (m, 1H), 3.81 (s, 2H), 3.80 (s, 2H), 3.62 (td, J=14.1, 5.1 Hz, 1H), 3.53 (t, J=5.1 Hz, 1H), 2.96 (t, J=6.4 Hz, 2H), 1.75-1.63 (m, 1H), 1.63-1.51 (m, 1H), 1.50-1.24 (m, 4H), 1.42 (s, 18H); $^1$H NMR (400 MHz, DMSO-d$_6$) δ7.96 (t, J=5.3 Hz, 1H), 7.20 (d, J=8.4 Hz, 1H), 6.88 (d, J=2.7 Hz, 1H), 6.76 (dd, J=8.4, 2.7 Hz, 1H), 6.71-6.68 (m, 1H), 3.94 (t, J=6.1 Hz, 2H), 3.90-3.81 (m, 1H), 3.78 (d, J=4.9 Hz, 2H), 3.76 (d, J=4.4 Hz, 2H), 3.81-3.66 (m, 3H), 3.49-3.31 (m, 2H), 2.86 (t, J=7.5 Hz, 1H), 2.87-2.81 (m, 2H), 2.76 (t, J=7.3 Hz, 1H), 1.59-1.41 (m, 2H), 1.39-1.12 (m, 4H), 1.36 (s, 18H); HRMS (ESI-MS m/z) calculated for C$_{26}$H$_{43}$N$_3$O$_6$S$_2$ [M+H]$^+$, 558.2672; found 558.2678.

11. Preparation of K: (S)-6-acetamido-2-amino-N-(2-(3,4-bis(mercaptomethyl)phenoxy)ethyl)hexanamide 1.62-1.50 (m, 1H), 1.45-1.20 (m, 5H); HRMS (ESI-MS m/z) calculated for $C_{18}H_{29}N_3O_3S_2$ [M H]$^+$, 400.1729; found 400.1708.

Scheme 11

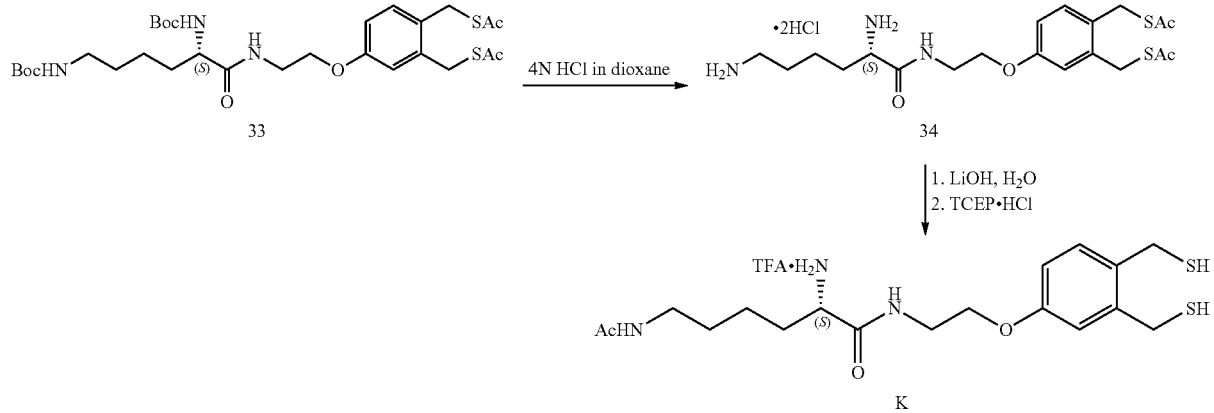

Preparation of Compound 34

Compound 33 (1.00 g, 1.59 mmol) was dissolved in 4 N HCl in dioxane (10 mL) at room temperature, and the solution was stirred at same temperature for 1 h. After removal of the solvent, the residue was triturated with ethyl acetate and n-hexane to afford hydrochloric acid salt 34 (800 mg, 98%) as an off-white solid: $^1$H NMR (400 MHz, CD$_3$OD) δ7.20 (d, J=8.5 Hz, 1H), 6.89 (d, J=2.6 Hz, 1H), 6.79 (dd, J=8.5, 2.6 Hz, 1H), 4.14 (s, 2H), 4.13 (s, 2H), 4.06 (t, J=5.3 Hz, 2H), 3.90 (t, J=6.5 Hz, 1H), 3.72-3.63 (m, 1H), 3.62-3.54 (m, 1H), 2.87 (t, J=8.0 Hz, 2H), 2.33 (s, 3H), 2.31 (s, 3H), 1.94-1.81 (m, 2H), 1.74-1.63 (m, 2H), 1.5-1.41 (m, 2H).

Preparation of Compound K: (S)-6-acetamido-2-amino-N-(2-(3,4-bis(mercaptomethyl)phenoxy)ethyl)hexanamide A solution of 34 (800 mg, 1.55 mmol) in water (10 mL) was charged with solid LiOH.H$_2$O (262 mg, 6.23 mmol) and the reaction mixture was stirred at room temperature for 1 h. The above reaction mixture was charged with TCEP.HCl (222 mg, 0.77 mmol) and stirred for another 1 h. The solvent was removed and the residue was partitioned between saturated aqueous NaHCO$_3$ solution (10 mL) and CH$_2$Cl$_2$ (100 mL). The CH$_2$Cl$_2$ layer was separated and the aqueous layer was extracted with CH$_2$Cl$_2$ (2×50 mL). The combined organic layers were dried over Na$_2$SO$_4$, filtered, and concentrated. The residue was purified by preparative HPLC and lyophilized to afford 90 mg (12%) of pure compound K as a colorless gum: $^1$H NMR (400 MHz, CD$_3$OD) δ7.18 (d, J=8.4 Hz, 1H), 6.89 (d, J=2.5 Hz, 1H), 6.77 (dd, J=8.4, 2.5 Hz, 1H), 4.05 (t, J=5.4 Hz, 2H), 3.81 (s, 2H), 3.80 (s, 2H), 3.63 (td, J=13.9, 5.1 Hz, 1H), 3.54 (td, J=14.1, 4.8 Hz, 1H), 3.36 (t, J=6.8 Hz, 1H), 3.13-3.01 (m, 2H), 1.89 (s, 3H), 1.75-1.52 (m, 2H), 1.51-1.41 (m, 2H), 1.39-1.22 (m, 2H); $^1$H NMR (400 MHz, DMSO-d$_6$) δ8.14 (t, J=5.7 Hz, 1H), 7.74 (t, J=5.3 Hz, 1H), 7.20 (d, J=8.4 Hz, 1H), 6.90 (d, J=2.7 Hz, 1H), 6.77 (dd, J=8.4, 2.7 Hz, 1H), 3.97 (t, J=5.6 Hz, 2H), 3.78 (s, 2H), 3.77 (2H), 3.49-3.39 (m, 2H), 3.22-3.16 (m, 2H), 3.12-2.83 (m, 2H), 2.96 (q, J=6.5 Hz, 2H), 1.76 (s, 3H),

12. Preparation of L: (S)-2,6-diamino-N-(2-(3,4-bis(mercaptomethyl)phenoxy)ethyl)hexanamide Scheme 12

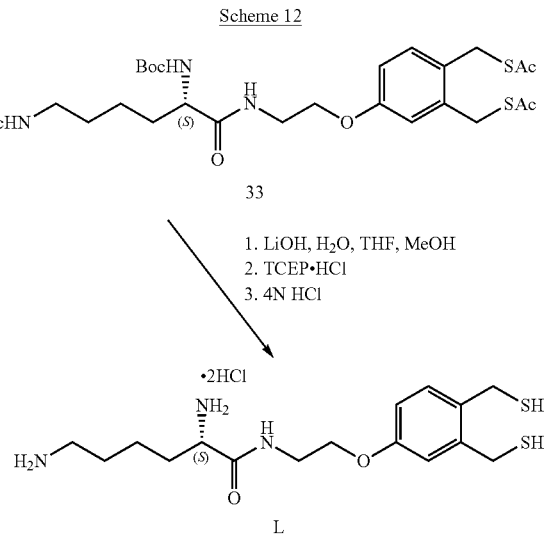

A solution of 33 (300 mg, 0.46 mmol) in a mixture of THF (5.0 mL), methanol (5.0 mL), and water (5.0 mL) was charged with solid LiOH.H$_2$O (59 mg, 1.40 mmol) and the reaction mixture was stirred at room temperature for 1 h. The above reaction mixture was charged with TCEP.HCl (66 mg, 0.23 mmol) and stirred for another 1 h. The solvent was removed and the residue was partitioned between saturated aqueous NaHCO$_3$ solution (10 mL) and CH$_2$Cl$_2$ (50 mL). The CH$_2$Cl$_2$ layer was separated and the aqueous layer was extracted with CH$_2$Cl$_2$ (2×20 mL). The combined organic layers were dried over Na$_2$SO$_4$, filtered, and concentrated. The residue was dissolved in EtOH (5.0 mL) and 4 N HCl (10 mL) was added. After stirring at room temperature for 1 h, the reaction mixture was concentrated to afford crude HCl salt which was purified by reverse-phase column chromatography and lyophilized to afford 90 mg (46%) of pure compound K as a hygroscopic yellow solid: $^1$H NMR (400 MHz, CD$_3$OD) δ7.20 (d, J=8.6 Hz, 1H), 6.90 (d, J=2.8 Hz, 1H), 6.78 (dd, J=8.6, 2.8 Hz, 1H), 4.12-4.04 (m, 2H), 3.89 (t, J=6.4 Hz, 1H), 3.83 (s, 2H), 3.81 (s, 2H), 3.70 (ddd, J=10.8, 5.8, 4.6 Hz, 1H), 3.58 (ddd, J=9.9, 6.2, 4.3 Hz, 1H), 2.83 (dd, J=8.8, 6.9 Hz, 2H), 1.94-1.79 (m, 2H), 1.72-1.61 (m, 2H), 1.52-1.40 (m, 2H); $^1$H NMR (400 MHz, DMSO-d$_6$) δ 8.84 (t, J=5.6 Hz, 1H), 8.30 (br s, 3H), 8.01 (br s, 3H), 7.22 (d, J=8.6 Hz, 1H), 6.91 (d, J=2.7 Hz, 1H), 6.78 (dd, J=8.6, 2.7 Hz, 1H), 4.07-3.97 (m, 2H), 3.80 (s, 2H), 3.78 (s, 2H), 3.83-3.71 (m, 1H), 3.58-3.41 (m, 2H), 3.01-2.90 (m, 1H), 2.86-2.78 (m, 1H), 2.76-2.64 (m, 2H), 1.80-1.67 (m, 2H), 1.63-1.50 (m, 2H), 1.42-1.29 (m, 2H); ESI (m/z) [C$_{16}$H$_{27}$N$_3$O$_2$S$_2$+H]$^+$ 358.

13. Preparation of M: (S)-tert-butyl 16-(3,4-bis(mercaptomethyl)phenoxy)-2,2-dimethyl-4,13-dioxo-3-oxa-5,7,14-triazahexadecan-12-yl-6-ylidenedicarbamate

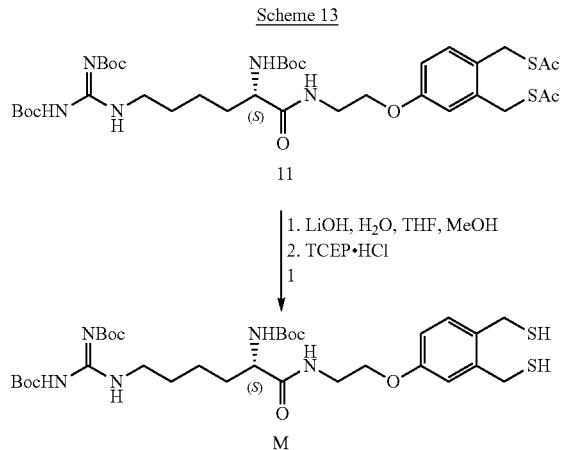

Scheme 13

Preparation of Compound M: (S)-tert-butyl 16-(3,4-bis(mercaptomethyl)phenoxy)-2,2-dimethyl-4,13-dioxo-3-oxa-5,7,14-triazahexadecan-12-yl-6-ylidenedicarbamate A solution of 11 (800 mg, 1.02 mmol) in a mixture of THF (6.0 mL), methanol (6.0 mL), and water (6.0 mL) was charged with solid LiOH.H$_2$O (129 mg, 3.06 mmol) and the reaction mixture was stirred at room temperature for 1 h. The above reaction mixture was charged with TCEP.HCl (146 mg, 0.51 mmol) and stirred for another 1 h. The solvent was removed and the residue was partitioned between saturated aqueous NaHCO$_3$ solution (10 mL) and CH$_2$Cl$_2$ (50 mL). The CH$_2$Cl$_2$ layer was separated and the aqueous layer was extracted with CH$_2$Cl$_2$ (2×30 mL). The combined organic layers were dried over Na$_2$SO$_4$, filtered, and concentrated to yield 600 mg of white, solid product. 200 mg of the crude product was purified by reverse-phase column chromatography and lyophilized to afford 96 mg (42%) of pure compound P-2040 as a hygroscopic white solid: $^1$H NMR (400 MHz, CD$_3$OD) δ7.17 (d, J=8.3 Hz, 1H), 6.88 (d, J=2.5 Hz, 1H), 6.76 (dd, J=8.3, 2.5 Hz, 1H), 4.03 (t, J=5.3 Hz, 2H), 4.02-3.98 (m, 1H), 3.81 (s, 2H), 3.79 (s, 2H), 3.64 (dt, J=14.2, 5.3 Hz, 1H), 3.54-3.44 (m, 1H), 3.24 (t, J=7.3 Hz, 2H), 1.76-1.66 (m, 1H), 1.64-1.56 (m, 1H), 1.56-1.48 (m, 2H), 1.51 (s, 9H), 1.46 (s, 9H), 1.44-1.31 (m, 2H), 1.41 (s, 9H); $^1$H NMR (400 MHz, DMSO-d$_6$) δ 11.48 (br s, 1H), 8.23 (t, J=5.1 Hz, 1H), 7.99 (t, J=5.4 Hz, 1H), 7.19 (d, J=8.5 Hz, 1H), 6.89 (d, J=2.6 Hz, 1H), 6.76 (dd, J=8.5, 2.6 Hz, 1H), 6.81-6.72 (m, 1H), 3.95 (t, J=5.6 Hz, 2H), 3.91-3.85 (m, 1H), 3.78 (d, J=5.3 Hz, 2H), 3.76 (d, J=4.7 Hz, 2H), 3.51-3.32 (m, 3H), 3.26-3.15 (m, 2H), 2.85 (t, J=7.6 Hz, 1H), 2.76 (t, J=7.4 Hz, 1H), 1.62-1.47 (m, 2H), 1.46 (s, 9H), 1.43-1.31 (m, 1H), 1.38 (s, 9H), 1.36 (s, 9H), 1.29-1.19 (m, 3H); ESI (m/z) [C$_{32}$H$_{53}$N$_5$O$_8$S$_2$+H]$^+$ 700.

14. Preparation of N: (2R,2'R,3R,3'R,4R,4'R,5S,5'S)-6,6'-(2-(3,4-bis(mercaptomethyl)phenoxy)ethylazanediyl)dihexane-1,2,3,4,5-pentaol hydrochloride

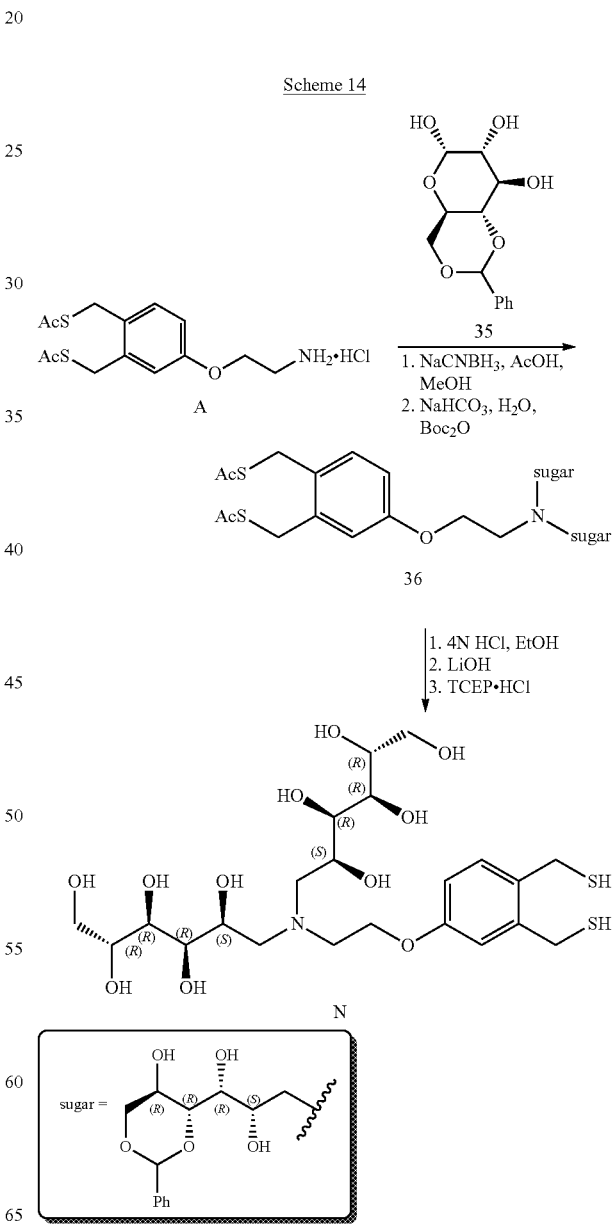

Scheme 14

Preparation of Compounds 36; SG-SJL-C-164

A solution of amine A (218 mg, 0.66 mmol) in methanol (10 mL) was charged with triol 35 (334 mg, 1.24 mmol) and acetic acid (0.2 mL, 3.30 mmol) successively and stirred at room temperature for 10 min. Sodium cyanoborohydride (78.0 mg, 1.24 mmol) was added to the above reaction mixture and the resulting reaction mixture was stirred at room temperature for 16 h. Additional 35 (2.0 equiv), AcOH (5.0 equiv), and NaCNBH$_3$ (2.0 equiv) were charged and the mixture was stirred for 24 h. Above reaction mixture was charged with NaHCO$_3$ (554 mg, 6.60 mmol) in water (5.0 ml) at 0° C. and stirred for 10 min., (Boc)$_2$O (288 mg, 1.32 mmol) was then added and the reaction mixture was stirred for 5 min at the same temperature, brought to room temperature, and stirred for another 1 h. After the solvent was removed under reduced pressure, the residue was dissolved in EtOAc (200 mL). The solution was quickly washed with saturated aqueous NaHCO$_3$ (2×50 mL) and brine (50 mL) and dried over Na$_2$SO$_4$ and purified by reverse-phase chromatography using a C18 Gold column to get pure 36 (255 mg, 47%) as a white solid; 100 mg corresponding monosugar Boc protected product (37) was isolated as well: $^1$H NMR (400 MHz, CD$_3$OD) δ7.46-7.39 (m, 4H), 7.31-7.25 (m, 6H), 7.14 (d, J=8.4 Hz, 1H), 6.83 (d, J=2.4 Hz, 1H), 6.67 (dd, J=8.4, 2.5 Hz, 1H), 5.45 (s, 2H), 4.21 (dd, J=10.8, 5.6 Hz, 2H), 4.10 (s, 2H), 4.08 (s, 2H), 4.07-3.99 (m, 4H), 3.97-3.91 (m, 2H), 3.90-3.87 (m, 2H), 3.72 (dd, J=9.6, 2.1 Hz, 2H), 3.57 (t, J=10.1 Hz, 2H), 3.16-3.07 (m, 2H), 3.01 (dd, J=13.6, 4.1 Hz, 2H), 2.90 (dd, J=12.9, 9.1 Hz, 2H), 2.30 (s, 3H), 2.29 (s, 3H).

Preparation of Compound N: (2R,2'R,3R,3'R,4R, 4'R,5S,5'S)-6,6'-(2-(3,4-bis(mercaptomethyl)phenoxy)ethylazanediyl)dihexane-1,2,3,4,5-pentaol hydrochloride A solution of 36 (100 mg, 0.12 mmol) in EtOH (1.0 mL) was charged with 4 N HCl (2.0 ml) and the reaction mixture was stirred at room temperature for 1 h. The solvent was removed and the residue was dissolved in water (5.0 mL) and charged with solid LiOH.H$_2$O (25.0 mg, 0.60 mmol) and the reaction mixture was stirred at room temperature for 1 h. The above reaction mixture was charged with TCEP.HCl (29 mg, 0.12 mmol) and stirred for another 1 h. The pH of above reaction mixture was brought to 2 by aqueous 4 N HCl and solvent was removed. The crude HCl salt was purified by reverse-phase column chromatography and lyophilized to afford 45 mg (63%) of pure compound P-2041 as a hygroscopic off-white solid: $^1$H NMR (400 MHz, CD$_3$OD) δ7.22 (d, J=8.5 Hz, 1H), 6.99 (d, J=2.5 Hz, 1H), 6.87 (dd, J=8.5, 2.5 Hz, 1H), 4.42-4.32 (m, 2H), 4.25-4.15 (m, 2H), 3.83 (s, 2H), 3.82 (s, 2H), 3.85-3.81 (m, 2H), 3.77 (dd, J=10.8, 3.1 Hz, 2H), 3.73-3.61 (m, 7H), 3.58-3.42 (m, 4H), 3.80-3.79 (m, 1H); $^1$H NMR (400 MHz, DMSO-d$_6$) δ8.63-8.52 (m, 1H), 7.22 (d, J=8.5 Hz, 1H), 6.97 (d, J=2.6 Hz, 1H), 6.85 (dd, J=8.5, 2.6 Hz, 1H), 5.52 (d, J=4.6 Hz, 1H), 5.44 (d, J=5.1 Hz, 1H), 4.81 (d, J=6.6 Hz, 2H), 4.64-4.50 (m, 4H), 4.46-4.39 (m, 2H), 4.37-4.29 (m, 2H), 4.12-3.99 (m, 2H), 3.80 (d, J=3.0 Hz, 2H), 3.79 (d, J=3.0 Hz, 2H), 3.74-3.65 (m, 4H), 3.64-3.56 (m, 2H), 3.55-3.37 (m, 10H), 2.89 (t, J=7.5 Hz, 1H), 2.81 (t, J=7.1 Hz, 1H); ESI (m/z) [C$_{22}$H$_{39}$NO$_{11}$S$_2$+ H]$^+$ 558.

15. Preparation of O: (2R,3R,4R,5S)-6-(2-(3,4-bis (mercaptomethyl)phenoxy)ethylamino)hexane-1,2,3, 4,5-pentaol hydrochloride

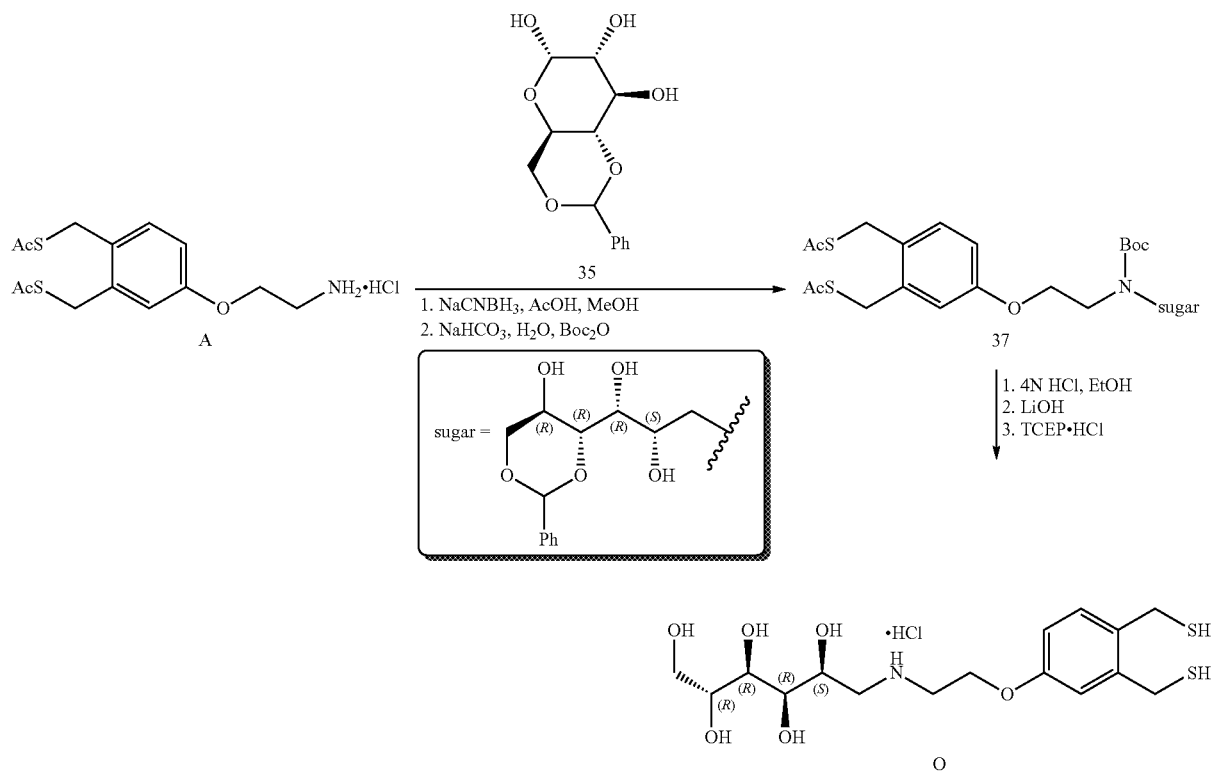

Scheme 15

Preparation of Compound 37

A solution of amine A (1.00 g, 2.85 mmol) in methanol (50 mL) was charged with triol 35 (992 mg, 3.70 mmol) and acetic acid (0.85 mL, 14.3 mmol) successively and stirred at room temperature for 10 min. Sodium cyanoborohydride (233 mg, 3.70 mmol) was added to the above reaction mixture and the resulting reaction mixture was stirred at room temperature for 65 h. Above reaction mixture was charged with saturated NaHCO$_3$ (50 mL) in water at 0° C. and stirred for 10 min., (Boc)$_2$O (1.24 g, 5.70 mmol) was then added and the reaction mixture was stirred for 5 min at the same temperature, brought to room temperature, and stirred for another 1 h. After the solvent was removed under reduced pressure, the residue was dissolved in EtOAc (250 mL). The solution was quickly washed with saturated aqueous NaHCO$_3$ (2×50 mL) and brine (50 mL) and dried over Na$_2$SO$_4$ and purified by column chromatography (silica gel, 40% to 80% EtOAc in hexanes) to afford compound 37 (1.15 g, 61%) as a white solid: $^1$H NMR (400 MHz, CD$_3$OD) δ7.52-7.43 (m, 2H), 7.33-7.25 (m, 3H), 7.16 (d, J=8.5 Hz, 1H), 6.84 (d, J=2.4 Hz, 1H), 6.71 (dd, J=8.5, 2.4 Hz, 1H), 5.54 (s, 1H), 4.23 (dd, J=10.9, 5.6 Hz, 1H), 4.118 (s, 2H), 4.110 (s, 2H), 4.10-4.03 (m, 3H), 3.93 (ddd, J=14.5, 9.6, 5.1 Hz, 1H), 3.83-3.77 (m, 1H), 3.76-3.70 (m, 1H), 3.68 (t, J=5.5 Hz, 1H), 3.67 (t, J=10.5 Hz, 2H), 3.63-3.57 (m, 1H), 3.45-3.33 (m, 1H), 2.314 (s, 3H), 2.311 (s, 3H), 1.42 (s, 9H).

Preparation of Compound O: (2R,3R,4R,5S)-6-(2-(3,4-bis(mercaptomethyl)phenoxy)ethylamino) hexane-1,2,3,4,5-pentaol hydrochloride A solution of 37 (1.15 g, 1.72 mmol) in EtOH (5.0 mL) was charged with 4 N HCl (20 ml) and the reaction mixture was stirred at room temperature for 1 h. The solvent was removed and the residue was dissolved in water (10 mL) and charged with solid LiOH.H$_2$O (1.00 g, 24.0 mmol) and the reaction mixture was stirred at room temperature for 1 h. The above reaction mixture was charged with TCEP.HCl (246 mg, 0.86 mmol) and stirred for another 1 h. The pH of above reaction mixture was brought to 2 by aqueous 4 N HCl and solvent was removed. The crude HCl salt was purified by reverse-phase column chromatography and lyophilized to afford 310 mg (42%) of pure compound O as a hygroscopic white solid: $^1$H NMR (400 MHz, CD$_3$OD) δ7.23 (d, J=8.7 Hz, 1H), 6.98 (d, J=2.7 Hz, 1H), 6.85 (dd, J=8.7, 2.7 Hz, 1H), 4.28 (t, J=5.1 Hz, 2H), 4.11 (ddd, J=9.6, 7.1, 4.6 Hz, 1H), 3.88 (dd, J=4.7, 1.1 Hz, 1H), 3.82 (s, 2H), 3.82 (s, 2H), 3.77 (dd, J=9.9, 2.5 Hz, 1H), 3.72-3.68 (m, 2H), 3.67-3.62 (m, 1H), 3.51-3.45 (m, 2H), 3.34-3.29 (m, 2H); $^1$H NMR (400 MHz, DMSO-d$_6$) δ 8.67 (br s, 2H), 7.24 (d, J=8.5 Hz, 1H), 6.96 (d, J=2.6 Hz, 1H), 6.82 (dd, J=8.5, 2.6 Hz, 1H), 5.40 (d, J=4.6 Hz, 1H), 4.85-4.75 (m, 1H), 4.66-4.55 (m, 1H), 4.60 (d, J=5.5 Hz, 1H), 4.44 (d, J=6.1 Hz, 1H), 4.23 (t, J=5.7 Hz, 2H), 3.99-3.91 (m, 1H), 3.80 (d, J=7.6 Hz, 2H), 3.78 (d, J=7.1 Hz, 2H), 3.73-3.67 (m, 1H), 3.63-3.56 (m, 1H), 3.54-3.38 (m, 3H), 3.34 (t, J=5.1 Hz, 2H), 3.20 (dd, J=13.2, 3.5 Hz, 1H), 3.06 (dd, J=12.4, 9.1 Hz, 1H), 2.91 (t, J=8.0 Hz, 1H), 2.81 (t, J=7.5 Hz, 1H); ESI (m/z) [C$_{16}$H$_{27}$NO$_6$S$_2$+H]$^+$ 394.

16. Preparation of P: (2R,3R,4R,5S)-6-((2-(3,4-bis(mercaptomethyl)phenoxy)ethyl)(hexyl)amino) hexane-1,2,3,4,5-pentaol hydrochloride

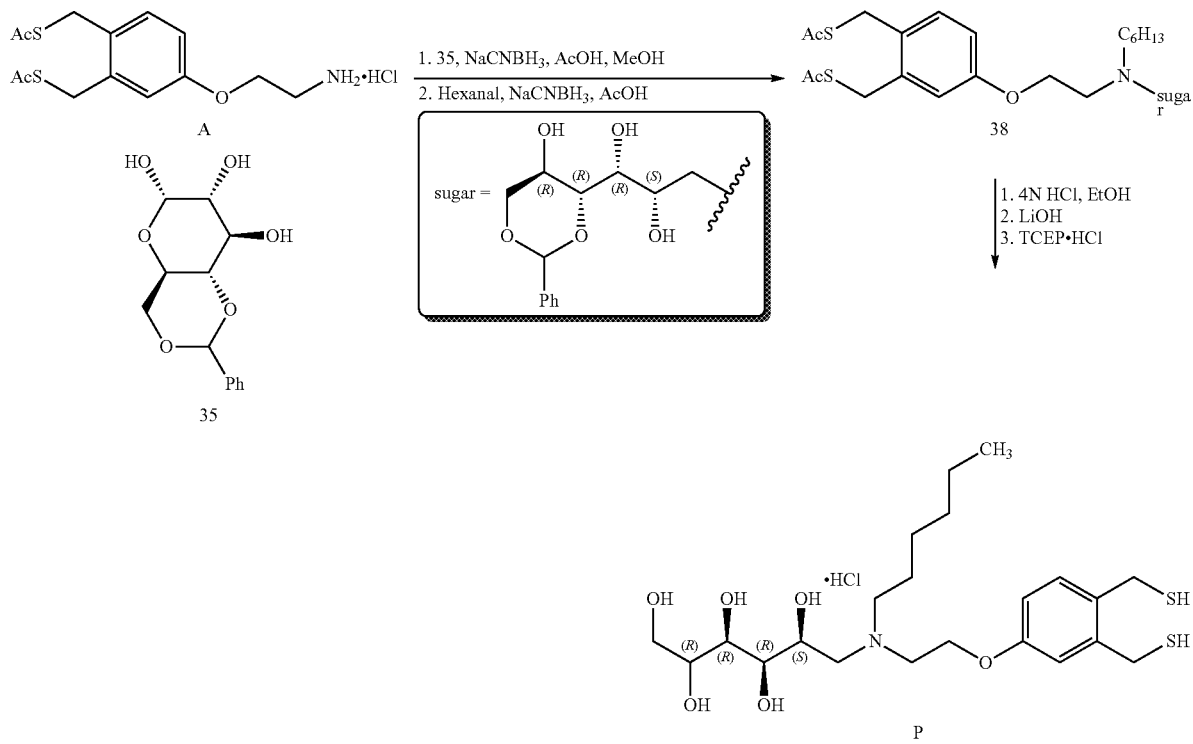

Preparation of Compounds 38; SG-SJL-C-176

A solution of amine A (700 mg, 2.00 mmol) in methanol (40 mL) was charged with triol (35) (697 mg, 2.60 mmol) and acetic acid (0.60 mL, 10.0 mmol) successively and stirred at room temperature for 10 min. Sodium cyanoborohydride (164 mg, 2.60 mmol) was added and the final reaction mixture was stirred at room temperature for 20 h. The above reaction mixture was charged with hexanal (0.60 mL, 5.00 mmol), acetic acid (0.60 ml, 10.0 mL) followed by NaCNBH$_3$ (315 mg, 5.00 mmol), stirred for 1 h. After the solvent was removed under reduced pressure, the residue was dissolved in EtOAc (150 mL). The solution was quickly washed with saturated aqueous NaHCO$_3$ (2×50 mL) and brine (50 mL) and dried over Na$_2$SO$_4$. Purification by normal chromatography using CMA system failed to give pure product, the mixture was then purified by reverse-phase chromatography using a C18 Gold column to get pure 38 (650 mg, 50%) as a gum: $^1$H NMR (400 MHz, CD$_3$OD) δ7.48-7.42 (m, 2H), 7.33-7.27 (m, 3H), 7.17 (d, J=8.5 Hz, 1H), 6.84 (d, J=2.4 Hz, 1H), 6.72 (dd, J=8.5, 2.4 Hz, 1H), 5.49 (s, 1H), 4.23 (dd, J=10.6, 5.3 Hz, 1H), 4.112 (s, 2H), 4.110 (s, 2H), 4.02-3.96 (m, 3H), 3.94 (dd, J=9.9, 5.1 Hz, 1H), 3.90 (dd, J=5.5, 2.2 Hz, 1H), 3.76 (dd, J=9.1, 2.2 Hz, 1H), 3.58 (t, J=10.1 Hz, 2H), 3.52-3.40 (m, 1H), 2.96-2.84 (m, 2H), 2.69 (dd, J=12.3, 7.3 Hz, 1H), 2.61 (dd, J=8.3, 5.9 Hz, 1H), 2.308 (s, 3H), 2.301 (s, 3H), 1.50-1.39 (m, 2H), 1.31-1.18 (m, 6H), 0.86 (t, J=6.8 Hz, 3H).

Preparation of Compound P: (2R,3R,4R,5S)-6-((2-(3,4-bis(mercaptomethyl)phenoxy)ethyl)(hexyl)amino)hexane-1,2,3,4,5-pentaol hydrochloride A solution of 38 (650 mg, 1.00 mmol) in EtOH (5.0 mL) was charged with 4 N HCl (20 ml) and the reaction mixture was stirred at room temperature for 1 h. The solvent was removed and the residue was dissolved in water (10 mL) and charged with solid LiOH.H$_2$O (600 mg, 14.0 mmol) and the reaction mixture was stirred at room temperature for 1 h. The above reaction mixture was charged with TCEP.HCl (143 mg, 0.50 mmol) and stirred for another 1 h. The pH of above reaction mixture was brought to 2 by aqueous 4 N HCl and solvent was removed. The crude HCl salt was purified by reverse-phase column chromatography and lyophilized to afford 230 mg (45%) of pure compound P as a hygroscopic off-white solid: $^1$H NMR (400 MHz, CD$_3$OD) δ7.27 (d, J=8.6 Hz, 1H), 6.96 (d, J=2.6 Hz, 1H), 6.87 (dd, J=8.6, 2.6 Hz, 1H), 4.38 (t, J=4.7 Hz, 2H), 4.24-4.14 (m, 1H), 3.79 (s, 2H), 3.78 (s, 2H), 3.77-3.74 (m, 2H), 3.73-3.63 (m, 3H), 3.63-3.56 (m, 2H), 3.49-3.36 (m, 2H), 3.30 (t, J=8.1 Hz, 2H), 1.80-1.64 (m, 2H), 1.37-1.12 (m, 6H), 0.78 (t, J=6.6 Hz, 3H); $^1$H NMR (400 MHz, DMSO-d$_6$) δ9.58 (d, J=14.5 Hz, 1H), 7.25 (d, J=8.5 Hz, 1H), 6.96 (d, J=1.6 Hz, 1H), 6.83 (dd, J=8.5, 1.6 Hz, 1H), 5.51 (br s, 1H), 4.83 (br s, 1H), 4.60 (br s, 1H), 4.50-4.38 (m, 1H), 4.36 (br s, 1H), 4.14-4.01 (m, 1H), 3.80 (d, J=5.6 Hz, 2H), 3.78 (d, J=5.6 Hz, 2H), 3.74-3.67 (m, 1H), 3.66-3.53 (m, 3H), 3.52-3.45 (m, 2H), 3.42 (dd, J=10.6, 4.6 Hz, 2H), 3.25-3.10 (m, 3H), 2.92 (t, J=7.6 Hz, 1H), 2.82 (t, J=6.8 Hz, 1H), 1.76-1.63 (m, 2H), 1.35-1.21 (m, 6H), 0.87 (t, J=6.8 Hz, 3H); HRMS (ESI-MS m/z) calculated for C$_{22}$H$_{39}$NO$_6$S$_2$ [M H]$^+$, 478.2297; found 478.2268.

17. Preparation of Q: (4-(2-(dimethylamino)ethoxy)-1,2-phenylene)dimethanethiol hydrochloride

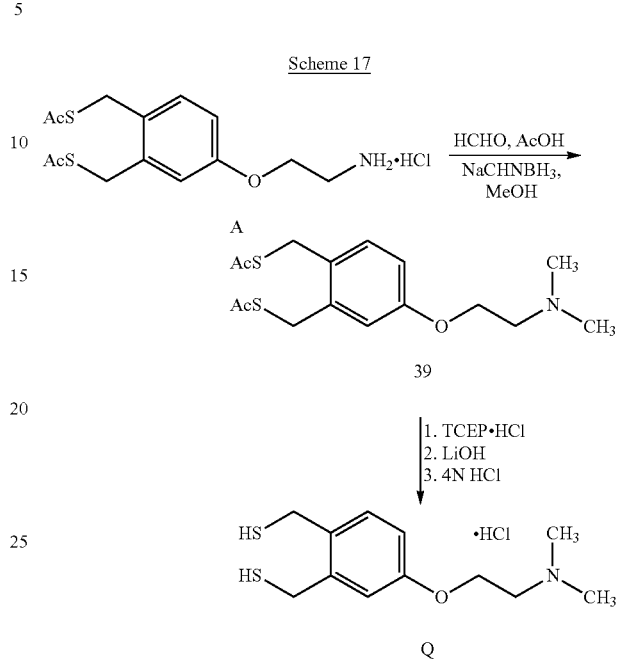

Scheme 17

Preparation of Compounds 39; SG-SJL-C-181

To a solution of compound A (700 mg, 2.00 mmol) and formaldehyde solution (30% in water, 1.20 mL, 12.0 mmol) in MeOH (20 mL) was added AcOH (1.20 mL, 20.0 mmol) and the reaction mixture was stirred at room temperature for 10 min. After NaCNBH$_3$ (756 mg, 12.0 mmol) was added, the solution was continued to be stirred at room temperature for 1 h. After removal of solvent, the residue was neutralized with saturated NaHCO$_3$ and the residue was partitioned between EtOAc (100 mL) and water (30 mL). The EtOAc layer was separated and aqueous layer was extracted with EtOAc (2×40 mL). The combined organic extracts were dried over Na$_2$SO$_4$ and concentrated under vacuum. The crude product 39 (700 mg) as a yellow liquid was directly used for the next step without any purification: $^1$H NMR (400 MHz, CD$_3$OD) δ7.20 (d, J=8.7 Hz, 1H), 6.89 (d, J=2.5 Hz, 1H), 6.78 (dd, J=8.7, 2.5 Hz, 1H), 4.13 (s, 2H), 4.12 (s, 2H), 4.09 (t, J=5.3 Hz, 2H), 2.84 (t, J=5.2 Hz, 2H), 2.40 (s, 6H), 2.32 (s, 3H), 2.31 (s, 3H).

Preparation of Compound Q: (4-(2-(dimethylamino)ethoxy)-1,2-phenylene)dimethanethiol hydrochloride A solution of 39 (700 mg, ~2.00 mmol) in a mixture of THF (10 mL), methanol (10 mL), and water (10 mL) was charged with solid LiOH.H$_2$O (420 mg, 10.0 mmol) and the reaction mixture was stirred at room temperature for 1 h. The above reaction mixture was charged with TCEP.HCl (572 mg, 2.00 mmol) and stirred for another 1 h. The solvent was removed and the residue was partitioned between saturated aqueous NaHCO$_3$ solution (10 mL) and CH$_2$Cl$_2$ (50 mL). The CH$_2$Cl$_2$ layer was separated and the aqueous layer was extracted with CH$_2$Cl$_2$ (2×25 mL). The combined organic layers were dried over Na$_2$SO$_4$, filtered, and concentrated. The above crude product was acidified with aqueous 4 N HCl and solvent was removed. The crude HCl salt was purified by reverse-phase column chromatography and lyophilized to afford 110 mg (19%, over two steps) of pure compound Q as a hygroscopic off-white solid: $^1$H NMR (400 MHz, CD$_3$OD) δ7.25 (d, J=8.5 Hz, 1H), 7.00 (d, J=2.8 Hz, 1H), 6.87 (dd, J=8.5, 2.5 Hz, 1H), 4.34 (t, J=4.9 Hz, 2H), 3.84 (s, 2H), 3.82 (s, 2H), 3.58 (t, J=5.1 Hz, 2H), 2.98 (s, 6H); $^1$H NMR (400 MHz, DMSO-d$_6$) δ10.31 (br s, 1H), 7.25 (d, J=8.2 Hz, 1H), 6.97 (d, J=2.8 Hz, 1H), 6.84 (dd, J=8.2, 2.8 Hz, 1H), 4.32 (t, J=5.2 Hz, 2H), 3.80 (d, J=7.2 Hz, 2H), 3.79 (d, J=6.6 Hz, 2H), 3.47 (t, J=5.4 Hz, 2H), 2.92 (t, J=7.4 Hz, 1H), 2.82 (t, J=7.6 Hz, 1H), 2.82 (s, 6H); ESI (m/z) [C$_{12}$H$_{19}$NOS$_2$+H]$^+$ 258.

18. Preparation of R: 3,5-diamino-N-(N-(2-(3,4-bis(mercaptomethyl)phenoxy)ethyl)carbamimidoyl)-6-chloropyrazine-2-carboxamide hydrochloride dine 41 (250 mg, impure) as a yellow solid; which was directly used for the next step; ESI (m/z) [C$_{20}$H$_{24}$ClN$_7$O$_4$S$_2$+H]$^+$526.

Preparation of Compound R: 3,5-diamino-N-(N-(2-(3,4-bis(mercaptomethyl)phenoxy)ethyl)carbamimidoyl)-6-chloropyrazine-2-carboxamide hydrochloride A solution of 41 (250 mg, ~0.47 mmol) in a mixture of THF (5.0 mL), methanol (5.0 mL), and water (5.0 mL) was charged with solid LiOH.H$_2$O (100 mg, 2.38 mmol) and the reaction mixture was stirred at room temperature for 1 h. The above reaction mixture was charged with TCEP.HCl (135 mg, 0.47 mmol) and stirred for another 1 h. The solvent was removed and the residue was partitioned between saturated aqueous NaHCO$_3$ solution (10 mL) and CH$_2$Cl$_2$ (50 mL). The CH$_2$Cl$_2$ layer was separated and the aqueous layer was extracted with CH$_2$Cl$_2$ (2×25 mL). The combined organic layers were dried over Na$_2$SO$_4$, filtered, and concentrated.

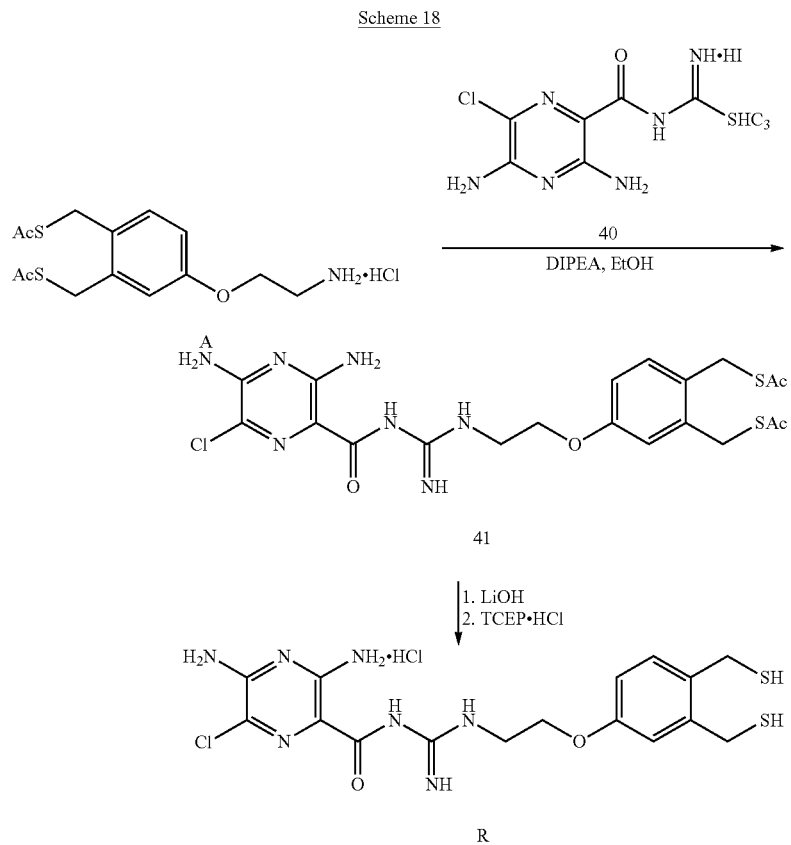

Preparation of Compounds 41; SG-SJL-C-184

A solution of amine salt A (700 mg, 2.00 mmol) and methyl 3,5-diamino-6-chloropyrazine-2-carbonylcarbamimidothioate (40, 1.24 g, 3.20 mmol) in EtOH (20 mL) was charged with DIPEA (2.84 mL, 16.0 mmol) at room temperature. The reaction mixture was heated at 60° C. in a sealed tube for 2 h, cooled to room temperature, and concentrated in vacuo. The residue was purified by column chromatography (silica gel, 80:18:2 CHCl$_3$/CH$_3$OH/NH$_4$OH) followed by reverse phase column to afford guani- The above crude product was acidified with 4 N HCl and solvent was removed. The crude HCl salt was purified by reverse-phase column chromatography and lyophilized to afford 65 mg (7.0%, over two steps) of pure compound P-2045 as a hygroscopic yellow solid: $^1$H NMR (400 MHz, CD$_3$OD) δ7.22 (d, J=8.6 Hz, 1H), 6.96 (d, J=2.5 Hz, 1H), 6.83 (dd, J=8.6, 2.5 Hz, 1H), 4.23 (t, J=5.1 Hz, 2H), 3.83 (s, 2H), 3.81 (s, 2H), 3.74 (t, J=4.8 Hz, 2H); $^1$H NMR (400 MHz, DMSO-d$_6$) δ10.57 (br s, 1H), 9.42 (br s, 1H), 9.16-8.77 (m, 2H), 7.43 (br s, 2H), 7.24 (d, J=8.5 Hz, 1H), 6.95 (d, J=2.6 Hz, 1H), 6.82 (dd, J=8.5, 2.6 Hz, 1H), 4.16 (t, J=5.3

Hz, 2H), 3.80 (s, 2H), 3.79 (s, 2H), 3.74-3.66 (m, 2H), 2.95-2.86 (m, 1H), 2.84-2.76 (m, 1H); ESI (m/z) $[C_{16}H_{20}ClN_7O_2S_2+H]^+$ 442.
19. Preparation of S: (S)-2,6-diamino-N-((S)-5-amino-6-(2-(3,4-bis(mercaptomethyl)phenoxy)ethyl-amino)-6-oxohexyl)hexanamide
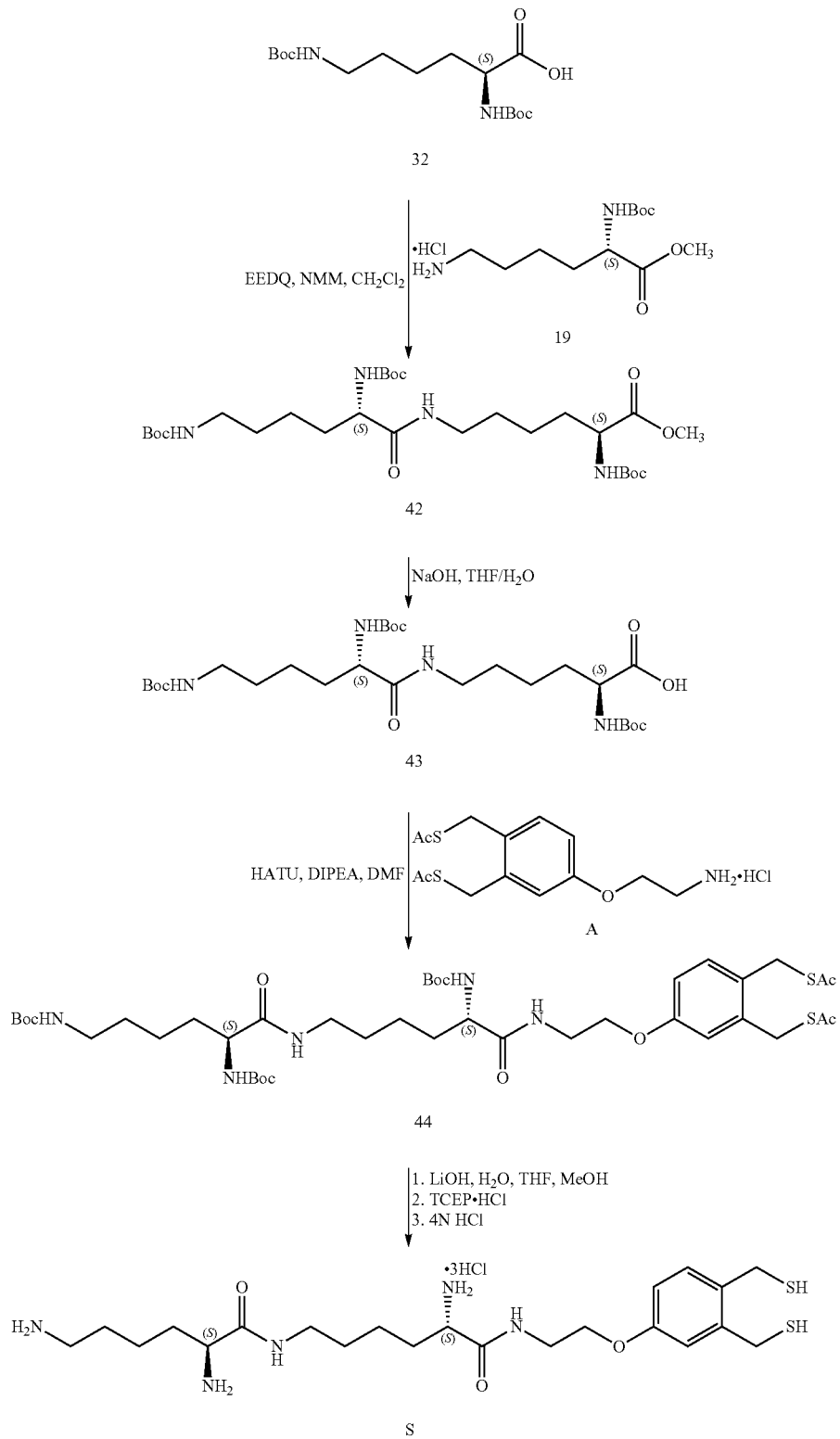

Preparation of (S)-methyl 6-((S)-2,6-bis((tert-butoxycarbonyl)amino)hexanamido)-2-((tert-butoxycarbonyl)amino)hexanoate (42); SG-SJL-D-77

A stirred solution of acid 32 (10.0 g, 28.9 mmol) and amine 19 (8.57 g, 28.9 mmol) in $CH_2Cl_2$ (200 mL) was charged with NMM (19.1 mL, 174 mmol) and EEDQ (14.3 g, 57.8 mmol). The resulting mixture was stirred at room temperature for 16 h. The reaction mixture was charged with water (50 mL) and extracted with $CH_2Cl_2$ (3×100 mL). The combined organic extracts were washed with brine and dried over $Na_2SO_4$. The solvent was removed and the residue was purified by column chromatography (silica gel, 20% to 40% EtOAc in hexanes) to afford amide 42 (14.6 g, 86%) as a white solid: $^1$H NMR (400 MHz, $CD_3OD$) δ 4.11-4.03 (m, 1H), 4.00-3.89 (m, 1H), 3.70 (s, 3H), 3.26-3.11 (m, 2H), 3.02 (t, J=6.6 Hz, 2H), 1.83-1.60 (m, 4H), 1.57-1.23 (m, 8H), 1.439 (s, 9H), 1.432 (s, 9H), 1.42 (s, 9H).

Preparation of (S)-6-((S)-2,6-bis((tert-butoxycarbonyl)amino)hexanamido)-2-((tert-butoxycarbonyl)amino)hexanoic acid (43); SG-SJL-D-81

A solution of methyl ester 42 (14.6 g, 24.8 mmol) in MeOH/THF/$H_2O$ (225 mL/225 mL/75 mL) was charged with NaOH (3.96 g, 99.2 mmol) and the reaction mixture was stirred at room temperature for 1 h. After completion of the reaction, the mixture was concentrated under reduced pressure and the pH of the solution was adjusted to 5 with 1 N HCl. The suspension was partitioned between $CH_2Cl_2$ (250 mL) and water (100 mL). The organic layer was separated and the aqueous layer was extracted with $CH_2Cl_2$ (2×250 mL). The combined organic extracts were dried over $Na_2SO_4$ and concentrated to afford compound 43 (13.8 g, 97%) as a white solid, which was used directly in the next step: $^1$H NMR (400 MHz, $CD_3OD$) δ4.09-4.00 (m, 1H), 3.98-3.90 (m, 1H), 3.27-3.10 (m, 2H), 3.02 (t, J=6.9 Hz, 2H), 1.87-1.74 (m, 2H), 1.73-1.61 (m, 2H), 1.60-1.23 (m, 8H), 1.48 (s, 18H), 1.42 (s, 9H).

Preparation of Compound 44; SG-SJL-D-10

Compound A (1.20 g, 3.42 mmol) and acid 43 (1.97 g, 3.42 mmol) were dissolved in DMF (25 mL) and treated with DIPEA (2.98 mL, 17.1 mmol) and HATU (1.30 g, 3.42 mmol). The reaction mixture was stirred at room temperature for 16 h. TLC analysis of the yellow reaction mixture showed the completion of the reaction. After the solvent was removed under reduced pressure, the residue was dissolved in $CH_2Cl_2$ (100 mL). The solution was quickly washed with saturated aqueous $NaHCO_3$ (2×50 mL) and brine (50 mL) and dried over $Na_2SO_4$. The organic layer was concentrated and the residue was purified by column chromatography (silica gel, 50% to 80% EtOAc in hexanes) to afford compound 44 (2.00 g, 67%) as an yellow solid: $^1$H NMR (400 MHz, $CD_3OD$) δ7.19 (d, J=8.4 Hz, 1H), 6.87 (d, J=2.6 Hz, 1H), 6.77 (dd, J=8.4, 2.6 Hz, 1H), 4.13 (s, 2H), 4.12 (s, 2H), 4.00 (t, J=5.8 Hz, 2H), 3.97-3.88 (m, 2H), 3.66-3.56 (m, 1H), 3.55-3.45 (m, 1H), 3.21-3.06 (m, 2H), 3.05-2.98 (m, 2H), 2.33 (s, 3H), 2.31 (s, 3H), 1.77-1.62 (m, 2H), 1.62-1.53 (m, 2H), 1.53-1.25 (m, 8H), 1.43 (s, 9H), 1.42 (s, 9H), 1.40 (s, 9H).

Preparation of Compound (S)-2,6-diamino-N-((S)-5-amino-6-(2-(3,4-bis(mercaptomethyl)phenoxy)ethylamino)-6-oxohexyl)hexanamide S A solution of 44 (1.25 g, 1.43 mmol) in a mixture of THF (10 mL), methanol (10 mL), and water (10 mL) was charged with solid LiOH.$H_2O$ (242 mg, 5.75 mmol) and the reaction mixture was stirred at room temperature for 1 h. The above reaction mixture was charged with TCEP.HCl (205 mg, 0.71 mmol) and stirred for another 1 h. The solvent was removed and the residue was partitioned between saturated aqueous $NaHCO_3$ solution (10 mL) and $CH_2Cl_2$ (50 mL). The $CH_2Cl_2$ layer was separated and the aqueous layer was extracted with $CH_2Cl_2$ (2×30 mL). The combined organic layers were dried over $Na_2SO_4$, filtered, and concentrated. The residue was dissolved in EtOH (5.0 mL) and 4 N HCl (20 mL) was added. After stirring at room temperature for 1 h, the reaction mixture was concentrated to afford crude compound S as a yellow solid. The crude HCl salt (S) was purified by reverse-phase column chromatography and lyophilized to afford 510 mg (60%) of pure compound S as a hygroscopic off-white solid: $^1$H NMR (400 MHz, $CD_3OD$) δ7.19 (d, J=8.5 Hz, 1H), 6.91 (d, J=2.7 Hz, 1H), 6.78 (dd, J=8.5, 2.7 Hz, 1H), 4.12-4.05 (m, 2H), 3.90 (q, J=6.6 Hz, 2H), 3.83 (s, 2H), 3.80 (s, 2H), 3.70 (ddd, J=10.5, 5.8, 4.6 Hz, 1H), 3.57 (ddd, J=10.4, 6.0, 4.6 Hz, 1H), 3.21 (dt, J=13.5, 6.5 Hz, 1H), 3.12 (dt, J=13.9, 6.8 Hz, 1H), 2.96 (t, J=7.6 Hz, 2H), 1.99-1.79 (m, 4H), 1.77-1.67 (m, 2H), 1.62-1.37 (m, 6H); $^1$H NMR (400 MHz, DMSO-$d_6$) δ8.90 (t, J=5.8 Hz, 1H), 8.76 (t, J=5.3 Hz, 1H), 8.55-7.92 (m, 10H), 7.22 (d, J=8.5 Hz, 1H), 6.92 (d, J=2.6 Hz, 1H), 6.78 (dd, J=8.5, 2.6 Hz, 1H), 4.09-3.99 (m, 2H), 3.79 (s, 2H), 3.78 (s, 2H), 3.78-3.24 (m, 2H), 3.55-3.41 (m, 2H), 3.06 (dd, J=12.8, 6.6 Hz, 2H), 3.01-2.91 (m, 1H), 2.90-2.79 (m, 1H), 2.75 (t, J=7.5 Hz, 2H), 1.80-1.68 (m, 4H), 1.65-1.54 (m, 2H), 1.49-1.29 (m, 6H); HRMS (ESI-MS m/z) calculated for $C_{22}H_{39}N_5O_3S_2$ [M+H]$^1$, 486.2573; found 486.2559. Elemental analysis: % calcd C, 44.4; H, 7.11; N, 11.77. found C, 43.84; H, 6.66; N, 11.16.

20. Preparation of T: (S)-2,6-diamino-N-((S)-5-amino-6-((S)-5-amino-6-(2-(3,4-bis(mercaptomethyl)phenoxy)ethylamino)-6-oxohexylamino)-6-oxohexyl)hexanamide
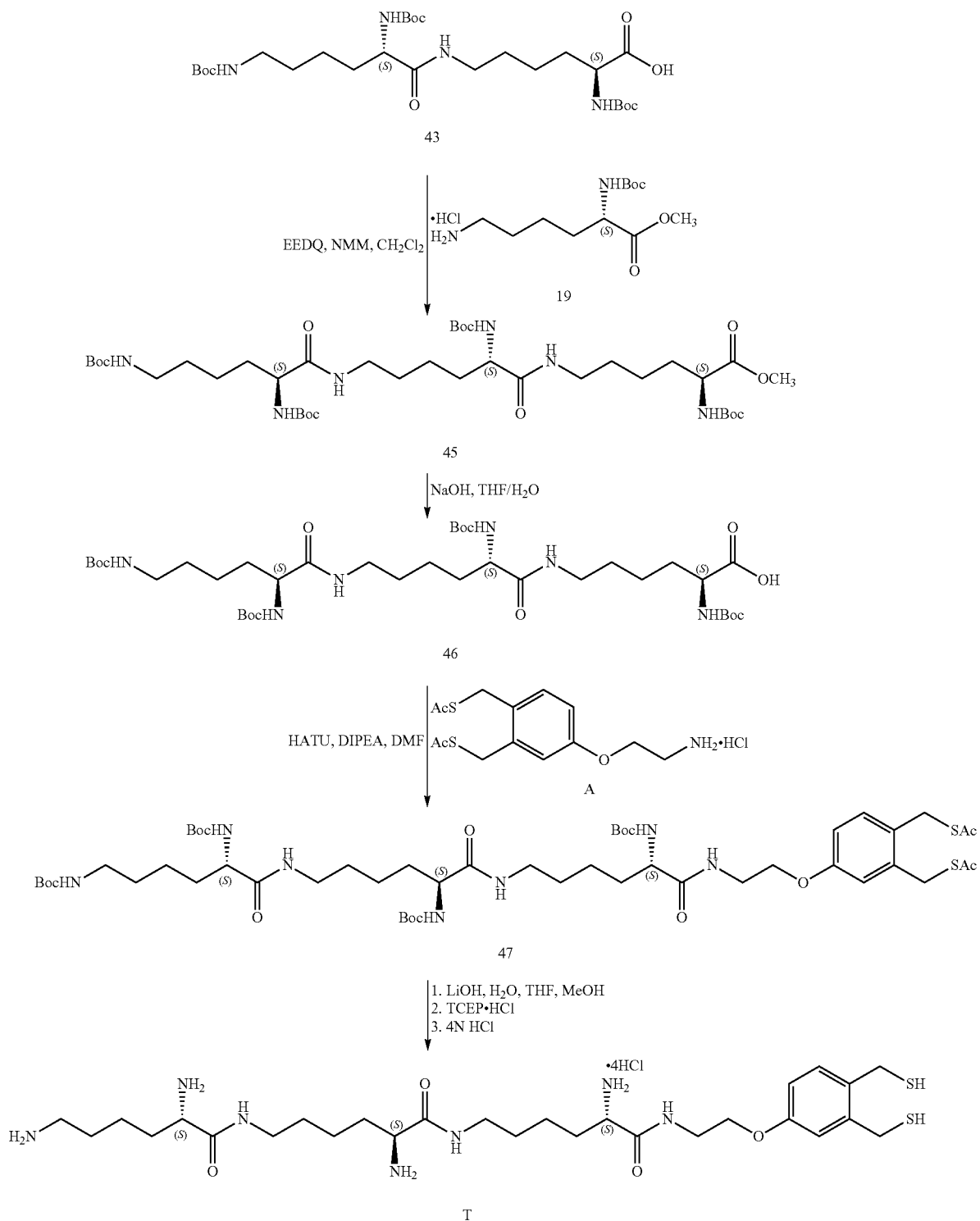

Preparation of (10S,17S,24S)-methyl 10,17,24-tris ((tert-butoxycarbonyl)amino)-2,2-dimethyl-4,11,18-trioxo-3-oxa-5,12,19-triazapentacosan-25-oate (45)

A stirred solution of acid 43 (1.50 g, 2.60 mmol) and amine 19 (775 mg, 2.60 mmol) in $CH_2Cl_2$ (30 mL) was charged with NMM (1.71 mL, 15.6 mmol) and EEDQ (1.28 g, 5.20 mmol). The resulting mixture was stirred at room temperature for 16 h. The reaction mixture was charged with water (20 mL) and extracted with $CH_2Cl_2$ (3×40 mL). The combined organic extracts were washed with brine and dried over $Na_2SO_4$. The solvent was removed and the residue was purified by column chromatography (silica gel, 40% to 80% EtOAc in hexanes) to afford amide 45 (2.00 g, 84%) as a white solid: $^1H$ NMR (400 MHz, $CD_3OD$) δ 4.10-4.02 (m, 1H), 3.98-3.88 (m, 2H), 3.70 (s, 3H), 3.26-3.10 (m, 4H), 3.06-3.00 (m, 2H), 1.82-1.63 (m, 4H), 1.62-1.26 (m, 14H), 1.439 (s, 18H), 1.431 (s, 9H), 1.42 (s, 9H).

Preparation of (10S,17S,24S)-10,17,24-tris((tert-butoxycarbonyl)amino)-2,2-dimethyl-4,11,18-trioxo-3-oxa-5,12,19-triazapentacosan-25-oic acid (46)

A solution of methyl ester 45 (2.00 g, 2.18 mmol) in $MeOH/THF/H_2O$ (60 mL/60 mL/20 mL) was charged with NaOH (436 mg, 10.9 mmol) and the reaction mixture was stirred at room temperature for 1 h. After completion of the reaction, the mixture was concentrated under reduced pressure and the pH of the solution was adjusted to 5 with 1 N HCl. The suspension was partitioned between $CH_2Cl_2$ (50 mL) and water (10 mL). The organic layer was separated and the aqueous layer was extracted with $CH_2Cl_2$ (2×50 mL). The combined organic extracts were dried over $Na_2SO_4$ and concentrated to afford compound 46 (1.90 g, 97%) as a white solid, which was used directly in the next step: $^1H$ NMR (400 MHz, $CD_3OD$) δ4.08-4.00 (m, 1H), 3.98-3.89 (m, 2H), 3.27-3.10 (m, 4H), 3.02 (t, J=6.6 Hz, 2H), 1.86-1.65 (m, 4H), 1.64-1.24 (m, 14H), 1.43 (s, 18H), 1.42 (s, 18H).

Preparation of Compound 47

Compound A (349 mg, 1.00 mmol) and acid 46 (902 mg, 1.00 mmol) were dissolved in DMF (10 mL) and treated with DIPEA (0.69 mL, 4.00 mmol) and HATU (380 mg, 1.00 mmol). The reaction mixture was stirred at room temperature for 16 h. TLC analysis of the yellow reaction mixture showed the completion of the reaction. After solvent was removed under reduced pressure, the residue was dissolved in $CH_2Cl_2$ (40 mL). The solution was quickly washed with saturated aqueous $NaHCO_3$ (2×25 mL) and brine (25 mL) and dried over $Na_2SO_4$. The organic layer was concentrated and the residue was purified by column chromatography (silica gel, 50% to 100% EtOAc in hexanes) to afford compound 47 (700 mg, 64%) as an yellow solid: $^1H$ NMR (400 MHz, $CD_3OD$) δ7.20 (d, J=8.5 Hz, 1H), 6.87 (d, J=2.7 Hz, 1H), 6.77 (dd, J=8.5, 2.7 Hz, 1H), 4.13 (s, 2H), 4.12 (s, 2H), 4.00 (t, J=5.8 Hz, 2H), 3.98-3.90 (m, 2H), 3.65-3.56 (m, 1H), 3.55-3.45 (m, 1H), 3.27-3.06 (m, 5H), 3.02 (t, J=7.0 Hz, 2H), 2.33 (s, 3H), 2.31 (s, 3H), 1.76-1.64 (m, 2H), 1.61-1.53 (m, 3H), 1.53-1.45 (m, 3H), 1.44-1.25 (m, 10H), 1.434 (s, 9H), 1.431 (s, 9H), 1.42 (s, 9H), 1.40 (s, 9H).

Preparation of Compound T: (S)-2,6-diamino-N-((S)-5-amino-6-((S)-5-amino-6-(2-(3,4-bis(mercaptomethyl)phenoxy)ethylamino)-6-oxohexylamino)-6-oxohexyl)hexanamide A solution of 10 (700 mg, 0.63 mmol) in a mixture of THF (20 mL), methanol (20 mL), and water (20 mL) was charged with solid $LiOH \cdot H_2O$ (107 mg, 2.55 mmol) and the reaction mixture was stirred at room temperature for 1 h. The above reaction mixture was charged with TCEP.HCl (90.0 mg, 0.31 mmol) and stirred for another 1 h. The solvent was removed and the residue was partitioned between saturated aqueous $NaHCO_3$ solution (10 mL) and $CH_2Cl_2$ (50 mL). The $CH_2Cl_2$ layer was separated and the aqueous layer was extracted with $CH_2Cl_2$ (2×30 mL). The combined organic layers were dried over $Na_2SO_4$, filtered, and concentrated. The residue was dissolved in EtOH (20 mL) and 4 N HCl (20 mL) was added. After stirring at room temperature for 1 h, the reaction mixture was concentrated to afford crude compound T as a yellow solid. The crude HCl salt (T) was purified by reverse-phase column chromatography and lyophilized to afford 320 mg (67%) of pure compound T as a hygroscopic white solid: $^1H$ NMR (400 MHz, $CD_3OD$) δ7.19 (d, J=8.4 Hz, 1H), 6.91 (d, J=2.9 Hz, 1H), 6.78 (dd, J=8.4, 2.9 Hz, 1H), 4.14-4.05 (m, 2H), 3.92 (t, J=7.0 Hz, 1H), 3.91-3.85 (m, 2H), 3.83 (s, 2H), 3.81 (s, 2H), 3.75-3.67 (m, 1H), 3.60-3.53 (m, 1H), 3.27-3.08 (m, 4H), 2.96 (dd, J=8.2, 7.8 Hz, 2H), 1.99-1.79 (m, 6H), 1.78-1.68 (m, 2H), 1.65-1.37 (m, 10H); $^1H$ NMR (400 MHz, DMSO-$d_6$) δ8.89 (t, J=5.2 Hz, 1H), 8.77 (dd, J=12.3, 5.8 Hz, 2H), 8.32 (br s, 8H), 8.10 (br s, 3H), 7.21 (d, J=8.6 Hz, 1H), 6.92 (d, J=2.4 Hz, 1H), 6.78 (dd, J=8.6, 2.4 Hz, 1H), 4.09-3.97 (m, 2H), 3.85-3.71 (m, 7H), 3.57-3.41 (m, 2H), 3.14-3.01 (m, 4H), 2.95 (t, J=8.0 Hz, 1H), 2.82 (t, J=7.7 Hz, 1H), 2.80-2.68 (m, 2H), 1.79-1.68 (m, 6H), 1.67-1.53 (m, 2H), 1.49-1.29 (m, 10H); HRMS (ESI-MS m/z) calculated for $C_{28}H_{51}N_7O_4S_2$ [M+H]$^+$, 614.3522; found 614.3530. Elemental analysis: % calcd C, 41.27; H, 7.3; N, 12.91; found C, 41.83; H, 7.62; N, 12.22.

21. Preparation of U: (S)-2-amino-6-((S)-2-amino-6-((S)-2-amino-6-guanidinohexanamido)hexanamido)-N-(2-(3,4-bis(mercaptomethyl)phenoxy)ethyl)hexanamide Hydrochloride
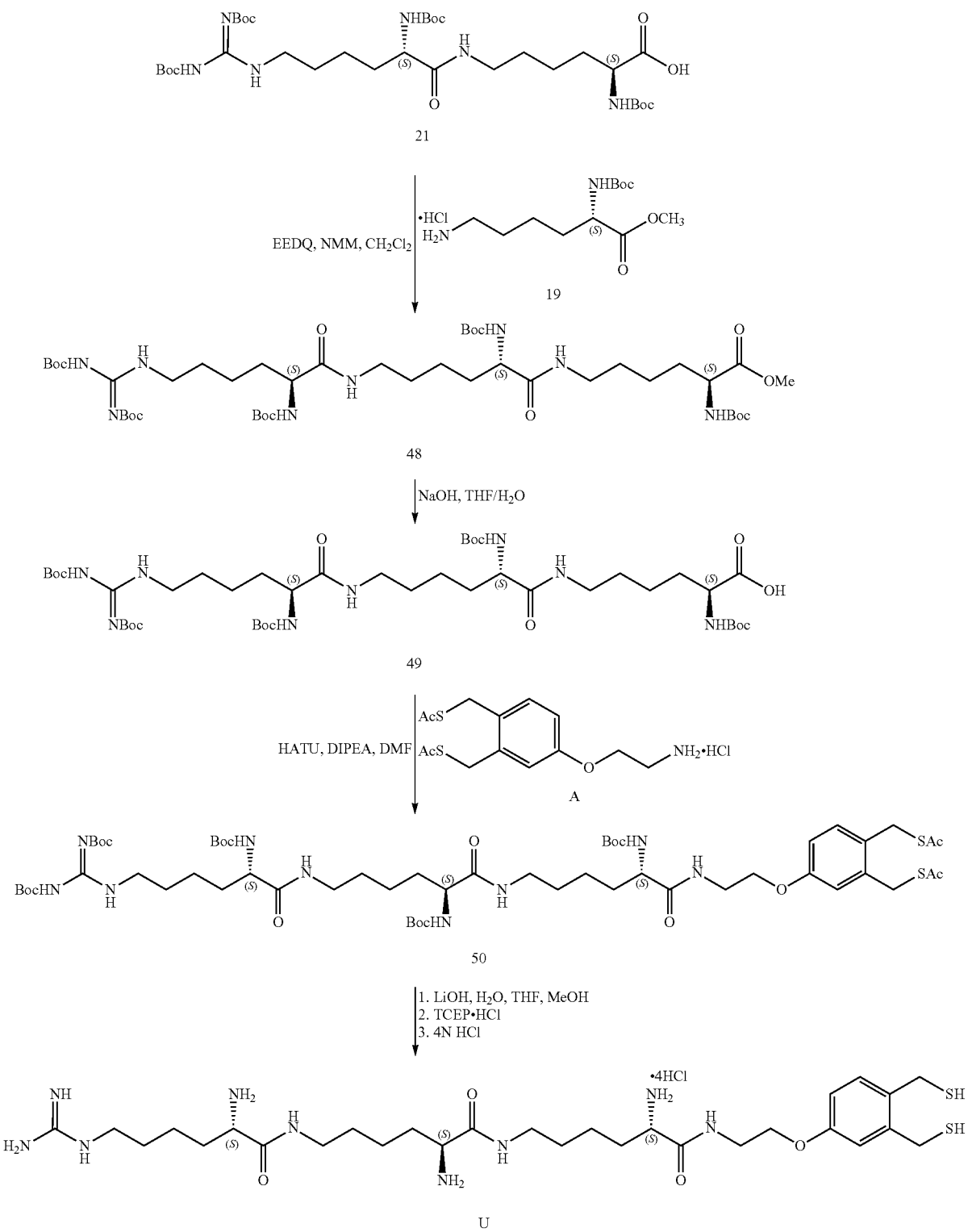
Scheme 21

Preparation of (12S,19S,26S)-methyl 6,12,19,26-tetrakis((tert-butoxycarbonyl)amino)-2,2-dimethyl-4,13,20-trioxo-3-oxa-5,7,14,21-tetraazaheptacos-5-en-27-oate (48)

A stirred solution of acid 21 (1.90 g, 2.60 mmol) and amine 19 (775 mg, 2.60 mmol) in CH$_2$Cl$_2$ (30 mL) was charged with NMM (1.71 mL, 15.6 mmol) and EEDQ (1.28 g, 5.20 mmol). The resulting mixture was stirred at room temperature for 16 h. The reaction mixture was charged with water (20 mL) and extracted with CH$_2$Cl$_2$ (3×40 mL). The combined organic extracts were washed with brine and dried over Na$_2$SO$_4$. The solvent was removed and the residue was purified by column chromatography (silica gel, 40% to 80% EtOAc in hexanes) to afford amide 48 (1.40 g, 51%) as a white solid: $^1$H NMR (400 MHz, CD$_3$OD) δ 4.11-4.02 (m, 1H), 4.01-3.86 (m, 2H), 3.70 (s, 3H), 3.35 (t, J=7.1 Hz, 2H), 3.24-3.12 (m, 4H), 1.81-1.67 (m, 3H), 1.66-1.54 (m, 5H), 1.53-1.30 (m, 10H), 1.52 (s, 9H), 1.46 (s, 9H), 1.438 (s, 9H), 1.437 (s, 9H), 1.432 (s, 9H).

Preparation of (12S,19S,26S)-6,12,19,26-tetrakis((tert-butoxycarbonyl)amino)-2,2-dimethyl-4,13,20-trioxo-3-oxa-5,7,14,21-tetraazaheptacos-5-en-27-oic acid (49)

A solution of methyl ester 48 (1.40 g, 1.32 mmol) in MeOH/THF/H$_2$O (45 mL/45 mL/15 mL) was charged with NaOH (265 mg, 6.61 mmol) and the reaction mixture was stirred at room temperature for 1 h. After completion of the reaction, the mixture was concentrated under reduced pressure and the pH of the solution was adjusted to 5 with aqueous 1 N HCl. The suspension was partitioned between CH$_2$Cl$_2$ (50 mL) and water (10 mL). The organic layer was separated and the aqueous layer was extracted with CH$_2$Cl$_2$ (2×50 mL). The combined organic extracts were dried over Na$_2$SO$_4$ and concentrated to afford compound 49 (1.20 g, 87%) as a white solid, which was used directly in the next step: $^1$H NMR (400 MHz, CD$_3$OD) δ4.06-3.89 (m, 3H), 3.35 (t, J=7.6 Hz, 2H), 3.25-3.11 (m, 4H), 1.86-1.66 (m, 3H), 1.64-1.55 (m, 5H), 1.54-1.30 (m, 10H), 1.52 (s, 9H), 1.46 (s, 9H), 1.43 (s, 27H).

Preparation of Compound 50

Compound A (200 mg, 0.57 mmol) and acid 49 (600 mg, 0.57 mmol) were dissolved in DMF (10 mL) and treated with DIPEA (0.39 mL, 2.28 mmol) and HATU (216 mg, 0.57 mmol). The reaction mixture was stirred at room temperature for 16 h. TLC analysis of the yellow reaction mixture showed the completion of the reaction. After the solvent was removed under reduced pressure, the residue was dissolved in CH$_2$Cl$_2$ (40 mL). The solution was quickly washed with saturated aqueous NaHCO$_3$ (2×25 mL) and brine (25 mL) and dried over Na$_2$SO$_4$. The organic layer was concentrated and the residue was purified by column chromatography (silica gel, 50% to 100% EtOAc in hexanes) to afford compound 50 (550 mg, 78%) as an brown oil: $^1$H NMR (400 MHz, CD$_3$OD) δ7.19 (d, J=8.5 Hz, 1H), 6.87 (d, J=2.7 Hz, 1H), 6.76 (dd, J=8.5, 2.7 Hz, 1H), 4.13 (s, 2H), 4.12 (s, 2H), 4.00 (t, J=5.8 Hz, 2H), 3.98-3.88 (m, 2H), 3.66-3.56 (m, 1H), 3.55-3.46 (m, 1H), 3.34 (t, J=7.0 Hz, 2H), 3.20-3.04 (m, 5H), 2.33 (s, 3H), 2.31 (s, 3H), 1.79-1.65 (m, 3H), 1.64-1.54 (m, 5H), 1.53-1.33 (m, 10H), 1.51 (s, 9H), 1.46 (s, 9H), 1.434 (s, 9H), 1.430 (s, 9H), 1.40 (s, 9H).

Preparation of Compound U: (S)-2-amino-6-((S)-2-amino-6-((S)-2-amino-6-guanidinohexanamido)hexanamido)-N-(2-(3,4-bis(mercaptomethyl)phenoxy)ethyl)hexanamide Hydrochloride A solution of 50 (550 mg, 0.44 mmol) in a mixture of THF (20 mL), methanol (20 mL), and water (20 mL) was charged with solid LiOH.H$_2$O (75.0 mg, 1.76 mmol) and the reaction mixture was stirred at room temperature for 1 h. The above reaction mixture was charged with TCEP.HCl (63.0 mg, 0.22 mmol) and stirred for another 1 h. The solvent was removed and the residue was partitioned between saturated aqueous NaHCO$_3$ solution (10 mL) and CH$_2$Cl$_2$ (50 mL). The CH$_2$Cl$_2$ layer was separated and the aqueous layer was extracted with CH$_2$Cl$_2$ (2×30 mL). The combined organic layers were dried over Na$_2$SO$_4$, filtered, and concentrated. The residue was dissolved in EtOH (20 mL) and 4 N HCl (20 mL) was added. After stirring at room temperature for 1 h, the reaction mixture was concentrated to afford crude compound U as a yellow solid. The crude HCl salt (U) was purified by reverse-phase column chromatography and lyophilized to afford 210 mg (60%) of pure compound P-2056 as a hygroscopic white solid: $^1$H NMR (400 MHz, CD$_3$OD) δ7.20 (d, J=8.6 Hz, 1H), 6.92 (d, J=2.6 Hz, 1H), 6.78 (dd, J=8.6, 2.6 Hz, 1H), 4.13-4.05 (m, 2H), 3.89 (t, J=6.9 Hz, 1H), 3.87-3.84 (m, 2H), 3.83 (s, 2H), 3.81 (s, 2H), 3.74-3.67 (m, 1H), 3.61-3.53 (m, 1H), 3.28-3.10 (m, 4H), 3.22 (t, J=6.8 Hz, 2H), 1.98-1.76 (m, 6H), 1.70-1.39 (m, 12H); $^1$H NMR (400 MHz, DMSO-d$_6$) δ8.83 (t, J=5.3 Hz, 1H), 8.77-8.68 (m, 2H), 8.39-8.19 (m, 8H), 7.83 (t, J=5.1 Hz, 1H), 7.22 (d, J=8.6 Hz, 1H), 6.91 (d, J=2.4 Hz, 1H), 6.78 (dd, J=8.6, 2.4 Hz, 1H), 4.07-3.98 (m, 2H), 3.78 (s, 2H), 3.77 (s, 2H), 3.83-3.69 (m, 3H), 3.55-3.45 (m, 2H), 3.15-3.01 (m, 6H), 2.92 (t, J=7.5 Hz, 1H), 2.81 (t, J=7.3 Hz, 1H), 1.78-1.66 (m, 6H), 1.53-1.39 (m, 6H), 1.35-1.26 (m, 6H); HRMS (ESI-MS m/z) calculated for C$_{29}$H$_{53}$N$_9$O$_4$S$_2$ [M+H]$^+$, 656.3740; found 656.3770. Elemental analysis: % calcd C, 43.44; H, 7.17; N, 15.72; found C, 39.51; H, 7.17; N, 14.23.

22. Preparation of V: (R)-2,6-diamino-N-(2-(3,4-bis(mercaptomethyl)phenoxy)ethyl)hexanamide Hydrochloride Scheme 22

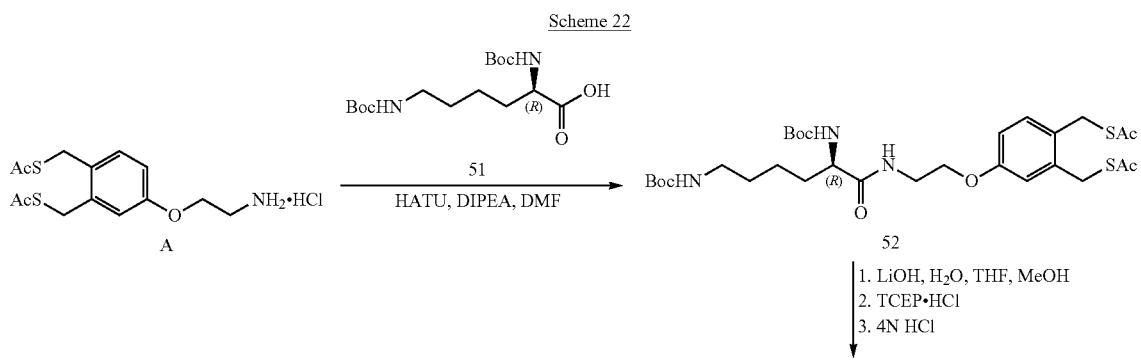

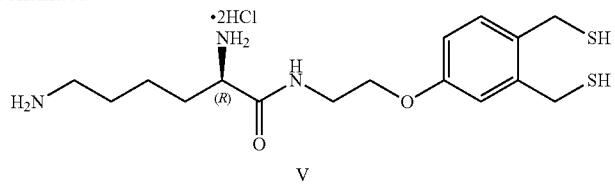

V

Preparation of Compound 52

Compound A (500 mg, 1.40 mmol) and acid 51 (486 mg, 1.40 mmol) were dissolved in DMF (10 mL) and treated with DIPEA (0.98 mL, 5.60 mmol) and HATU (532 mg, 1.40 mmol). The reaction mixture was stirred at room temperature for 16 h. TLC analysis of the yellow reaction mixture showed the completion of the reaction. After the solvent was removed under reduced pressure, the residue was dissolved in $CH_2Cl_2$ (40 mL). The solution was quickly washed with saturated aqueous $NaHCO_3$ (2×25 mL) and brine (25 mL) and dried over $Na_2SO_4$. The organic layer was concentrated and the residue was purified by column chromatography (silica gel, 50% to 100% EtOAc in hexanes) to afford compound 52 (640 mg, 71%) as an brown oil: $^1$H NMR (400 MHz, $CD_3OD$) δ7.19 (d, J=8.4 Hz, 1H), 6.87 (d, J=2.7 Hz, 1H), 6.76 (dd, J=8.4, 2.7 Hz, 1H), 4.13 (s, 2H), 4.12 (s, 2H), 4.00 (t, J=5.1 Hz, 2H), 3.98-3.93 (m, 1H), 3.61 (td, J=14.9, 5.5 Hz, 1H), 3.55-3.45 (m, 1H), 2.96 (t, J=6.5 Hz, 2H), 2.33 (s, 3H), 2.31 (s, 3H), 1.75-1.51 (m, 2H), 1.49-1.43 (m, 4H), 1.42 (s, 9H), 1.40 (s, 9H).

Preparation of Compound V: (R)-2,6-diamino-N-(2-(3,4-bis(mercaptomethyl)phenoxy)ethyl)hexanamide Hydrochloride A solution of 52 (640 mg, 1.00 mmol) in a mixture of THF (10 mL), methanol (10 mL), and water (10 mL) was charged with solid $LiOH·H_2O$ (168 mg, 4.00 mmol) and the reaction mixture was stirred at room temperature for 1 h. The above reaction mixture was charged with TCEP·HCl (143 mg, 0.50 mmol) and stirred for another 1 h. The solvent was removed and the residue was partitioned between saturated aqueous $NaHCO_3$ solution (10 mL) and $CH_2Cl_2$ (50 mL). The $CH_2Cl_2$ layer was separated and the aqueous layer was extracted with $CH_2Cl_2$ (2×30 mL). The combined organic layers were dried over $Na_2SO_4$, filtered, and concentrated. The residue was dissolved in EtOH (10 mL) and 4 N HCl (10 mL) was added. After stirring at room temperature for 1 h, the reaction mixture was concentrated to afford crude compound P-2059 as a yellow solid. The crude HCl salt (V) was purified by reverse-phase column chromatography and lyophilized to afford 230 mg (54%) of pure compound V as a hygroscopic white solid: $^1$H NMR (400 MHz, $CD_3OD$) δ7.20 (d, J=8.5 Hz, 1H), 6.90 (d, J=2.7 Hz, 1H), 6.78 (dd, J=8.5, 2.7 Hz, 1H), 4.12-4.04 (m, 2H), 3.89 (t, J=6.4 Hz, 1H), 3.83 (s, 2H), 3.81 (s, 2H), 3.70 (ddd, J=10.8, 5.8, 4.6 Hz, 1H), 3.58 (ddd, J=9.9, 6.2, 4.3 Hz, 1H), 2.83 (dd, J=8.8, 6.9 Hz, 2H), 1.94-1.79 (m, 2H), 1.72-1.61 (m, 2H), 1.52-1.40 (m, 2H); $^1$H NMR (400 MHz, DMSO-$d_6$) δ8.90 (t, J=5.2 Hz, 1H), 8.25 (br s, 5H), 7.22 (d, J=8.6 Hz, 1H), 6.92 (d, J=2.7 Hz, 1H), 6.78 (dd, J=8.6, 2.7 Hz, 1H), 4.07-3.97 (m, 2H), 3.80 (s, 2H), 3.78 (s, 2H), 3.79-3.75 (m, 1H), 3.58-3.41 (m, 2H), 3.12-2.73 (m, 2H), 2.69 (t, J=7.7 Hz, 2H), 1.81-1.67 (m, 2H), 1.63-1.50 (m, 2H), 1.41-1.29 (m, 2H); HRMS (ESI-MS m/z) calculated for $C_6H_{27}N_3O_2S_2$ $[M+H]^+$, 358.1623; found 358.1612. Elemental analysis: % calcd C, 44.64; H, 6.79; N, 9.76; found C, 42.85; H, 6.06; N, 9.17.

23. Preparation of W: (2S,2'S)-N,N'-(2,2'-(4,5-bis(mercaptomethyl)-1,2-phenylene)bis(oxy)bis(ethane-2,1-diyl))bis(2,6-diaminohexanamide)Hydrochloride

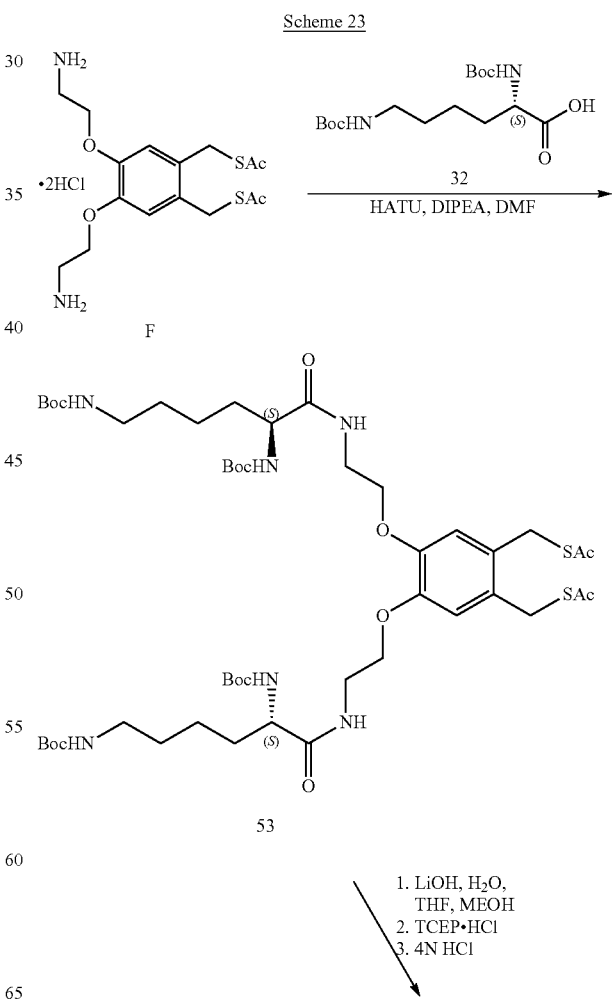

Scheme 23

-continued

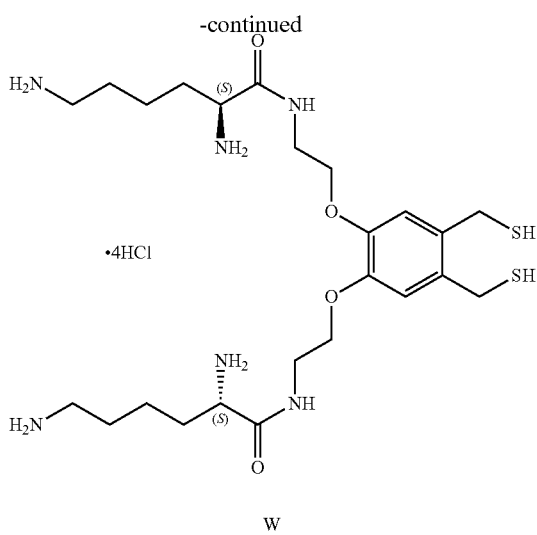

W

Preparation of Compound 53

Compound F (888 mg, 2.00 mmol) and acid 32 (1.38 g, 4.00 mmol) were dissolved in DMF (20 mL) and treated with DIPEA (3.49 mL, 20.0 mmol) and HATU (1.52 g, 4.00 mmol). The reaction mixture was stirred at room temperature for 16 h. TLC analysis of the yellow reaction mixture showed the completion of the reaction. After the solvent was removed under reduced pressure, the residue was partitioned between $CH_2Cl_2$ (100 mL) and $NaHCO_3$ (50 mL). The organic layer was separated, washed with brine (50 mL), and dried over $Na_2SO_4$. The organic layer was concentrated and the residue was purified by column chromatography (silica gel, 50% to 80% EtOAc in hexanes) to afford compound 53 (1.50 g, 73%) as an off-white solid: $^1$H NMR (400 MHz, $CD_3OD$) δ 6.88 (s, 2H), 4.10 (s, 4H), 4.09-3.96 (m, 6H), 3.63-3.55 (m, 4H), 2.97 (t, J=6.3 Hz, 4H), 2.31 (s, 6H), 1.78-1.67 (m, 2H), 1.65-1.55 (m, 2H), 1.50-1.25 (m, 8H), 1.42 (s, 18H), 1.40 (s, 18H).

Preparation of Compound W: (2S,2'S)-N,N'-(2,2'-(4,5-bis(mercaptomethyl)-1,2-phenylene)bis(oxy)bis(ethane-2,1-diyl))bis(2,6-diaminohexanamide)Hydrochloride A solution of 53 (1.50 g, 1.45 mmol) in a mixture of THF (20 mL), methanol (20 mL), and water (20 mL) was charged with solid $LiOH \cdot H_2O$ (245 mg, 5.83 mmol) and the reaction mixture was stirred at room temperature for 1 h. The above reaction mixture was charged with TCEP.HCl (207 mg, 0.73 mmol) and stirred for another 1 h. The solvent was removed, the residue was dissolved in $CH_2Cl_2$ (50 mL), and the solution was washed with saturated aqueous $NaHCO_3$ solution (10 mL). The $CH_2Cl_2$ layer was separated and the aqueous layer was extracted with $CH_2Cl_2$ (2×30 mL). The combined organic layers were dried over $Na_2SO_4$, filtered, and concentrated. The residue was dissolved in EtOH (5.0 mL), and 4 N HCl (20 mL) was added. After stirring at room temperature for 1 h, the reaction mixture was concentrated to afford compound W (crude HCl salt) as a yellow solid. The crude HCl salt was purified by reverse-phase column chromatography and lyophilized to afford 460 mg (46%) of pure compound P-W as a hygroscopic white solid: $^1$H NMR (400 MHz, $CD_3OD$) δ 6.96 (s, 2H), 4.11 (t, J=5.8 Hz, 4H), 3.96 (t, J=6.6 Hz, 2H), 3.79 (s, 4H), 3.71 (td, J=11.3, 5.8 Hz, 2H), 3.61 (td, J=11.3, 5.8 Hz, 2H), 2.86 (dd, J=8.9, 7.6 Hz, 4H), 1.97-1.84 (m, 4H), 1.73-1.63 (m, 4H), 1.54-1.44 (m, 4H); $^1$H NMR (400 MHz, DMSO-$d_6$) δ9.00 (t, J=5.5 Hz, 2H), 8.66-7.57 (m, 9H), 6.97 (s, 2H), 4.02 (t, J=6.0 Hz, 4H), 3.85 (t, J=6.5 Hz, 2H), 3.75 (s, 4H), 3.59-3.49 (m, 2H), 3.45-3.39 (m, 2H), 2.69 (t, J=7.8 Hz, 4H), 1.81-1.70 (m, 4H), 1.62-1.50 (m, 4H), 1.43-1.33 (m, 4H); HRMS (ESI-MS m/z) calculated for $C_{24}H_{44}N_6O_4S_2$ [M+H]$^+$, 545.2944; found 545.2940. Elemental analysis: % calcd C, 41.74; H, 7.01; N, 12.17; found C, 37.86; H, 7.32; N, 11.08.

24 Preparation of X: (S,2S,2'S)-N,N'-(2,2'-(4,5-bis(mercaptomethyl)-1,2-phenylene)bis(oxy)bis(ethane-2,1-diyl))bis(2-amino-6-((S)-2,6-diaminohexanamido)hexanamide)

Scheme 24

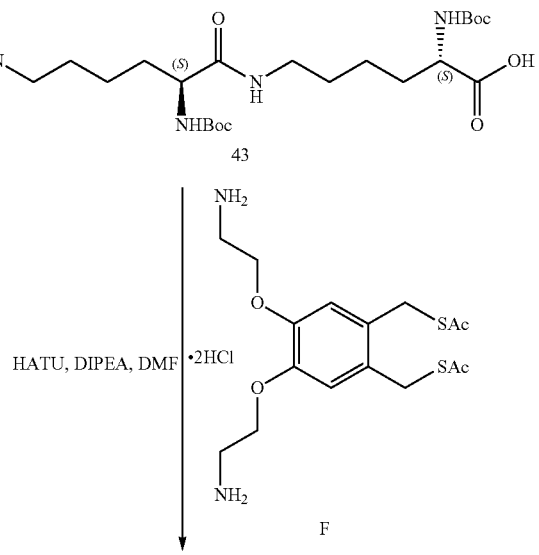

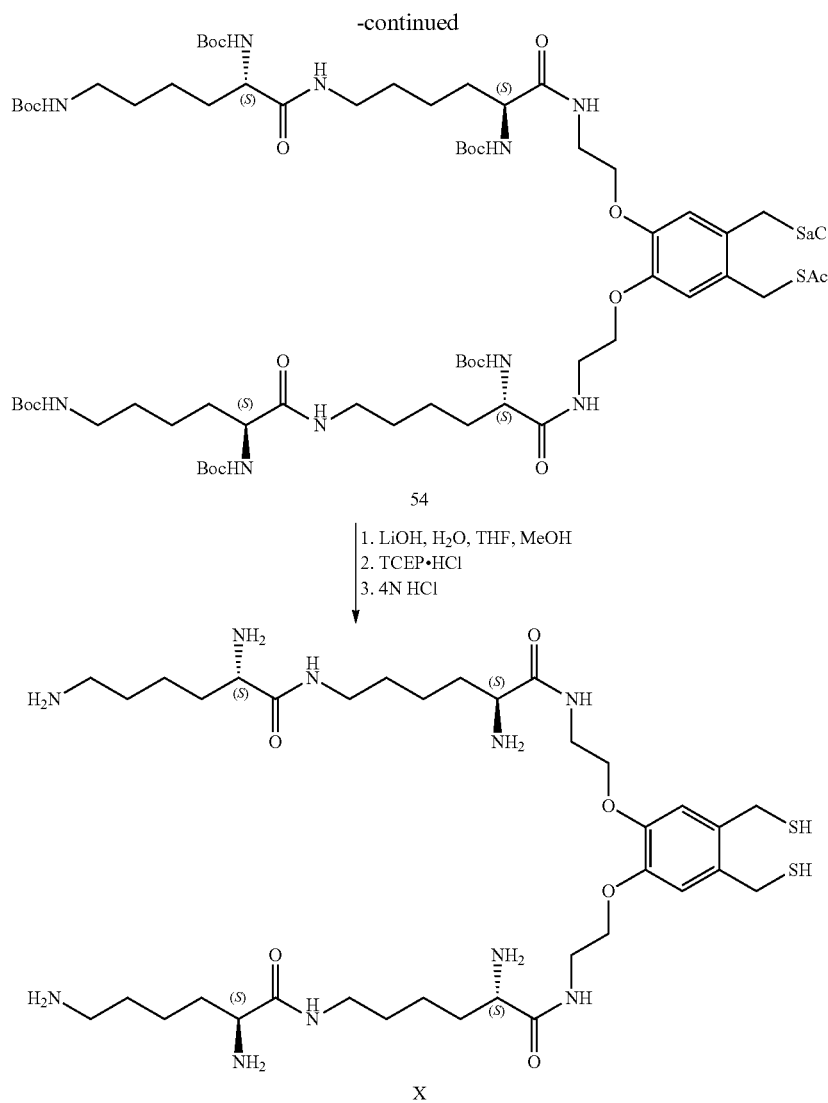

Preparation of Compound 54

Compound B (308 mg, 0.69 mmol) and acid 32 (800 mg, 1.39 mmol) were dissolved in DMF (10 mL) and treated with DIPEA (1.20 mL, 6.90 mmol) and HATU (529 mg, 1.39 mmol). The reaction mixture was stirred at room temperature for 16 h. TLC analysis of the yellow reaction mixture showed the completion of the reaction. After the solvent was removed under reduced pressure, the residue was partitioned between $CH_2Cl_2$ (100 mL) and $NaHCO_3$ (50 mL). The organic layer was separated, washed with brine (50 mL), and dried over $Na_2SO_4$. The organic layer was concentrated and the residue was purified by column chromatography (silica gel, 50% to 80% EtOAc in hexanes) to afford compound 54 (700 mg, 73%) as a yellow solid: $^1$H NMR (400 MHz, $CD_3OD$) δ6.89 (s, 2H), 4.10 (s, 4H), 4.08-3.99 (m, 5H), 3.98-3.89 (m, 2H), 3.65-3.53 (m, 4H), 3.21-3.07 (m, 5H), 3.02 (t, J=7.0 Hz, 4H), 2.32 (s, 6H), 1.78-1.53 (m, 9H), 1.52-1.27 (m, 15H), 1.43 (s, 18H), 1.42 (s, 18), 1.40 (s, 18H).

Preparation of Compound X: (S,2S,2'S)-N,N'-(2,2'-(4,5-bis(mercaptomethyl)-1,2-phenylene)bis(oxy)bis(ethane-2,1-diyl))bis(2-amino-6-((S)-2,6-diaminohexanamido)hexanamide)

A solution of 54 (700 mg, 0.50 mmol) in a mixture of THF (15 mL), methanol (15 mL), and water (15 mL) was charged with solid $LiOH \cdot H_2O$ (84.0 mg, 2.0 mmol) and the reaction mixture was stirred at room temperature for 1 h. The above reaction mixture was charged with TCEP·HCl (72 mg, 0.25 mmol) and stirred for another 1 h. The solvent was removed, the residue was dissolved in $CH_2Cl_2$ (50 mL), and the solution was washed with saturated aqueous $NaHCO_3$ solution (10 mL). The $CH_2Cl_2$ layer was separated and the aqueous layer was extracted with $CH_2Cl_2$ (2×30 mL). The combined organic layers were dried over $Na_2SO_4$, filtered, and concentrated. The residue was dissolved in EtOH (15 mL), and 4 N HCl (15 mL) was added. After stirring at room temperature for 1 h, the reaction mixture was concentrated to afford compound P-2060 (crude HCl salt) as a yellow solid. The crude HCl salt was purified by reverse-phase column chromatography and lyophilized to afford 245 mg (48%) of pure compound P-2060 as a hygroscopic white solid: ¹H NMR (400 MHz, CD₃OD) δ6.96 (s, 2H), 4.12 (t, J=5.5 Hz, 4H), 3.98 (t, J=6.5 Hz, 2H), 3.92 (t, J=6.5 Hz, 2H), 3.79 (s, 4H), 3.71 (td, J=14.5, 5.5 Hz, 2H), 3.61 (td, J=14.1, 5.1 Hz, 2H), 3.22 (td, J=14.7, 7.1 Hz, 2H), 3.12 (td, J=12.3, 6.4 Hz, 2H), 2.96 (t, J=7.4 Hz, 4H), 1.97-1.79 (m, 8H), 1.78-1.68 (m, 4H), 1.61-1.41 (m, 12H); ¹H NMR (400 MHz, DMSO-d₆) δ9.04 (t, J=5.4 Hz, 2H), 8.76 (t, J=5.1 Hz, 2H), 8.44-8.23 (m, 12H), 8.07 (br s, 6H), 6.98 (s, 2H), 4.02 (t, J=5.3 Hz, 4H), 3.91-3.82 (m, 2H), 3.82-3.76 (m, 2H), 3.76 (s, 2H), 3.74 (s, 2H), 3.59-3.40 (m, 5H), 3.11-3.00 (m, 4H), 2.91 (t, J=7.2 Hz, 2H), 2.83-2.71 (m, 4H), 1.85-1.70 (m, 8H), 1.67-1.54 (m, 4H), 1.50-1.28 (m, 12H); HRMS (ESI-MS m/z) calculated for C₃₆H₆₈N₁₀O₆S₂ [M +H]⁺, 801.4843; found 801.4799. Elemental analysis: % calcd C, 42.4; H, 7.31; N, 13.73; found C, 39.42; H, 7.37; N, 12.55.

25. Preparation of Y: (S,2S,2'S)-N,N'-(2,2'-(4,5-bis(mercaptomethyl)-1,2-phenylene)bis(oxy)bis(ethane-2,1-diyl))bis(2-amino-6-((S)-2-amino-6-guanidino-hexanamido)hexanamide)

Scheme 25

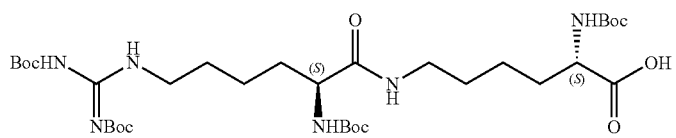

21

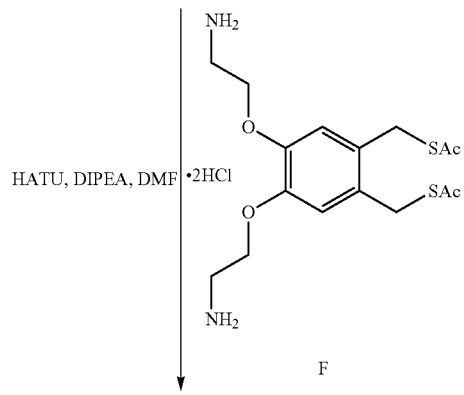

F

HATU, DIPEA, DMF

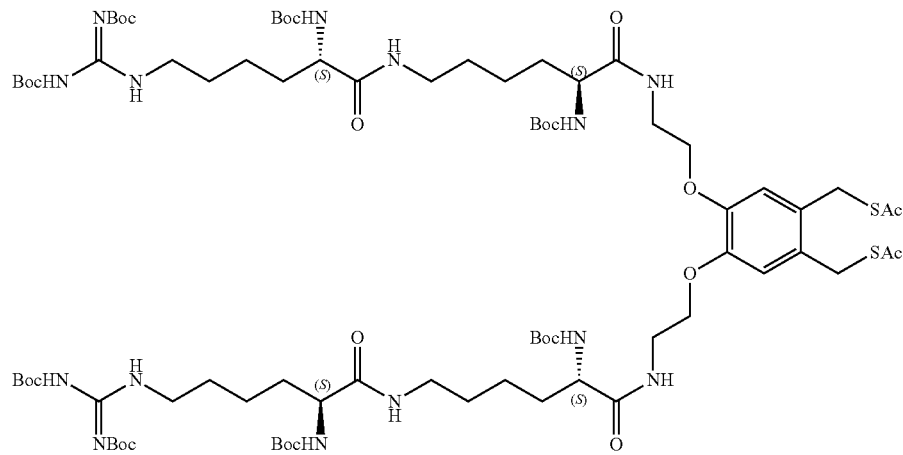

55

1. LiOH, H₂O, THF, MeOH
2. TCEP•HCl
3. 4N HCl

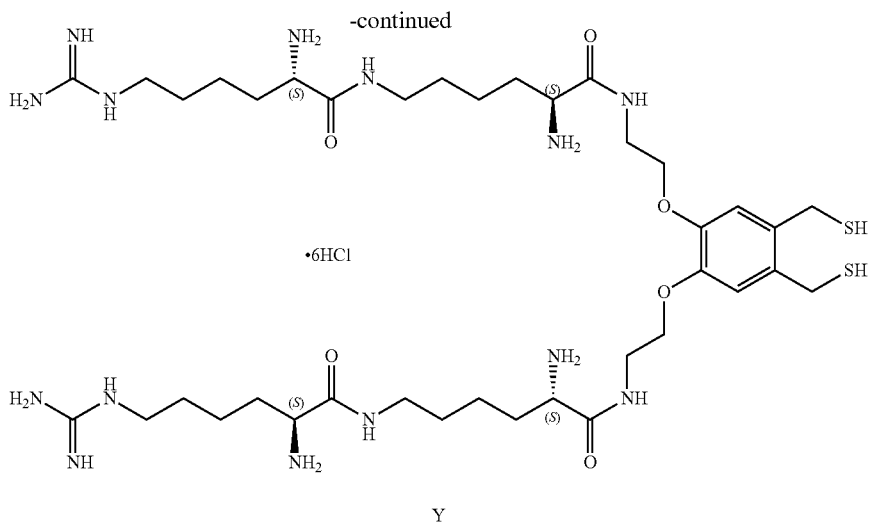

Preparation of Compound 55

Compound F (444 mg, 1.00 mmol) and acid 21 (1.43 g, 2.00 mmol) were dissolved in DMF (10 mL) and treated with DIPEA (1.74 mL, 10.0 mmol) and HATU (760 mg, 2.00 mmol). The reaction mixture was stirred at room temperature for 16 h. TLC analysis of the yellow reaction mixture showed the completion of the reaction. After the solvent was removed under reduced pressure, the residue was partitioned between CH$_2$Cl$_2$ (100 mL) and NaHCO$_3$ (50 mL). The organic layer was separated, washed with brine (50 mL), and dried over Na$_2$SO$_4$. The organic layer was concentrated and the residue was purified by column chromatography (silica gel, 50% to 80% EtOAc in hexanes) to afford compound 55 (810 mg, 48%) as an yellow solid: $^1$H NMR (400 MHz, CD$_3$OD) δ6.89 (s, 2H), 4.10 (s, 4H), 4.07-3.94 (m, 8H), 3.63-3.54 (m, 4H), 3.34 (t, J=7.3 Hz, 4H), 3.20-3.06 (m, 4H), 2.31 (s, 6H), 1.79-1.65 (m, 4H), 1.64-1.54 (m, 10H), 1.50-1.30 (m, 10H), 1.51 (s, 18H), 1.46 (s, 18H), 1.43 (s, 18H), 1.39 (s, 18H).

Preparation of Compound Y: (S,2S,2'S)-N,N'-(2,2'-(4,5-bis(mercaptomethyl)-1,2-phenylene)bis(oxy)bis(ethane-2,1-diyl))bis(2-amino-6-((S)-2-amino-6-guanidinohexanamido)hexanamide)

A solution of 55 (810 mg, 0.48 mmol) in a mixture of THF (15 mL), methanol (15 mL), and water (15 mL) was charged with solid LiOH.H$_2$O (81 mg, 1.92 mmol) and the reaction mixture was stirred at room temperature for 1 h. The above reaction mixture was charged with TCEP.HCl (69 mg, 0.24 mmol) and stirred for another 1 h. The solvent was removed, the residue was dissolved in CH$_2$Cl$_2$ (50 mL), and the solution was washed with saturated aqueous NaHCO$_3$ solution (10 mL). The CH$_2$Cl$_2$ layer was separated and the aqueous layer was extracted with CH$_2$Cl$_2$ (2×30 mL). The combined organic layers were dried over Na$_2$SO$_4$, filtered, and concentrated. The residue was dissolved in EtOH (15 mL), and 4 N HCl (15 mL) was added. After stirring at room temperature for 1 h, the reaction mixture was concentrated to afford compound Y (crude HCl salt) as a yellow solid. The crude HCl salt was purified by reverse-phase column chromatography and lyophilized to afford 290 mg (55%) of pure compound Y as a hygroscopic white solid: $^1$H NMR (400 MHz, CD$_3$OD) δ 6.96 (s, 2H), 4.11 (t, J=5.3 Hz, 4H), 3.95 (t, J=6.5 Hz, 2H), 3.87 (t, J=6.8 Hz, 2H), 3.79 (s, 4H), 3.74-3.66 (m, 2H), 3.65-3.57 (m, 2H), 3.21 (t, J=8.9, 7.2 Hz, 6H), 3.18-3.08 (m, 2H), 1.94-1.78 (m, 8H), 1.69-1.60 (m, 4H), 1.59-1.40 (m, 12H); $^1$H NMR (400 MHz, DMSO-d$_6$) δ9.04 (t, J=5.8 Hz, 2H), 8.75 (t, J=5.5 Hz, 2H), 8.70-8.02 (m, 9H), 7.91 (t, J=4.8 Hz, 2H), 7.77-6.76 (m, 8H), 6.98 (s, 2H), 4.02 (t, J=5.8 Hz, 4H), 3.85 (t, J=6.7 Hz, 2H), 3.76 (t, J=6.5 Hz, 2H), 3.75 (s, 4H), 3.58-3.41 (m, 8H), 3.16-3.08 (m, 4H), 3.08-3.01 (m, 4H), 1.83-1.68 (m, 8H), 1.54-1.28 (m, 16H); HRMS (ESI-MS m/z) calculated for C$_{38}$H$_{72}$N$_{14}$O$_6$S$_2$ [M +H]$^+$, 885.5279; found 885.5304. Elemental analysis: % calcd C, 41.34; H, 7.12; N, 17.76; found C, 39.04; H, 7.32; N, 15.89.

26. Preparation of Z: (2R,2'R)-N,N'-(3,3'-(2-(3,4-bis(mercaptomethyl)phenoxy)ethylazanediyl)bis(propane-3,1-diyl))bis(2-amino-6-guanidinohexanamide)

Scheme 26

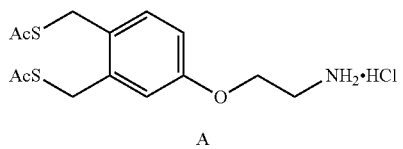

A

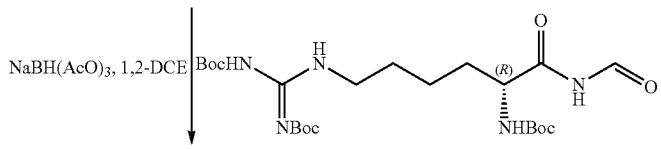

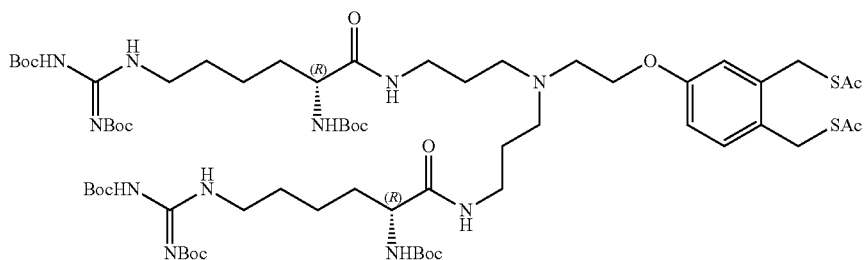

57

1. LiOH, H₂O, THF, MeOH
2. TCEP·HCl
3. 4N HCl

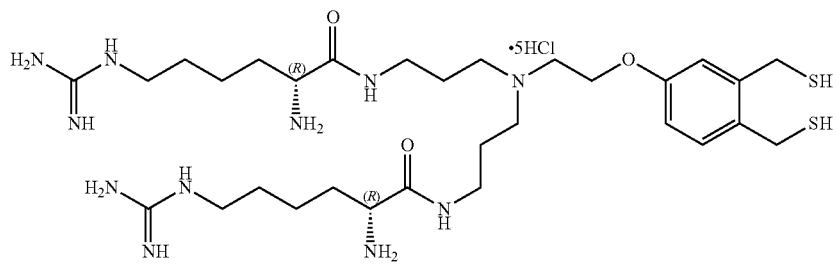

Z

Preparation of Compound 57

Compound A (356 mg, 1.00 mmol) and NaBH(AcO)$_3$ (530 mg, 2.50 mmol) were dissolved in 1,2-DCE (20 mL) and stirred at room temperature for 5 min. Known aldehyde 56 (1.36 g, 2.50 mmol) was added and the reaction mixture was stirred at room temperature for 3 h. TLC analysis (100% EtOAc) of the reaction mixture showed incomplete reaction. The reaction mixture was charged with NaHCO$_3$ solution (25 mL) and extracted with CH$_2$Cl$_2$ (3×50 mL). The organic layer was concentrated and the residue was purified by column chromatography (silica gel, 4% to 6% MeOH in EtOAc to CH$_2$Cl$_2$) to afford compound 57 (1.00 g, mixture) as a white solid, mixture was directly used for the next step: $^1$H NMR (400 MHz, CD$_3$OD) δ 7.21 (d, J=8.8 Hz, 1H), 6.91 (d, J=2.7 Hz, 1H), 6.80 (dd, J=8.8, 2.7 Hz, 1H), 4.13 (s, 2H), 4.12 (s, 2H), 4.05 (t, J=6.0 Hz, 2H), 4.01-3.93 (m, 2H), 3.28-3.23 (m, 4H), 3.38-3.32 (m, 4H), 2.70-2.65 (m, 2H), 2.64-2.52 (m, 4H), 2.33 (s, 3H), 2.31 (s, 3H), 1.77-1.66 (m, 6H), 1.65-1.30 (m, 6H), 1.47-1.32 (m, 4H), 1.51 (s, 18H), 1.46 (s, 18H), 1.42 (s, 18H).

Preparation of Compound Z: (2R,2'R)-N,N'-(3,3'-(2-(3,4-bis(mercaptomethyl)phenoxy)ethylazanediyl)bis(propane-3,1-diyl))bis(2-amino-6-guanidinohexanamide)

A solution of 57 (1.00 g, 0.73 mmol, mixture) in a mixture of THF (20 mL), methanol (20 mL), and water (20 mL) was charged with solid LiOH·H$_2$O (123 mg, 2.92 mmol) and the reaction mixture was stirred at room temperature for 1 h. The above reaction mixture was charged with TCEP·HCl (105 mg, 0.36 mmol) and stirred for another 1 h. The solvent was removed and the residue was partitioned between CH$_2$Cl$_2$ (50 mL) and saturated aqueous NaHCO$_3$ solution (10 mL). The CH$_2$Cl$_2$ layer was separated and the aqueous layer was extracted with CH$_2$Cl$_2$ (2×30 mL). The combined organic layers were dried over Na$_2$SO$_4$, filtered, and concentrated. The residue was dissolved in EtOH (20 mL) and 4 N HCl (20 mL) was added. After stirring at room temperature for 1 h, the reaction mixture was concentrated to afford compound Z (640 mg, crude HCl salt) as a yellow solid. The crude HCl salt (490 mg) was purified by reverse-phase column chromatography and lyophilized to afford 40 mg (8%, over two steps) of pure compound Z as a hygroscopic white solid: $^1$H NMR (400 MHz, CD$_3$OD) δ7.25 (d, J=8.4 Hz, 1H), 7.03 (d, J=2.6 Hz, 1H), 6.90 (dd, J=8.4, 2.6 Hz, 1H), 4.41 (t, J=5.0 Hz, 2H), 3.92 (t, J=6.5 Hz, 2H), 3.85 (s, 2H), 3.82 (s, 2H), 3.73-3.66 (m, 2H), 3.51-3.36 (m, 6H), 3.33 (t, J=7.2 Hz, 2H), 3.22 (t, J=7.7 Hz, 4H), 2.17-2.03 (m, 4H), 1.99-1.79 (m, 4H), 1.69-1.59 (m, 4H), 1.55-1.43 (m, 4H); $^1$H NMR (400 MHz, DMSO-d$_6$) δ 10.75 (br s, 1H), 8.99-8.91 (m, 2H), 8.44-8.26 (m, 5H), 7.81 (t, J=6.0 Hz, 2H), 7.69-6.77 (m, 7H), 7.25 (d, J=8.6 Hz, 1H), 7.01 (d, J=2.4 Hz, 1H), 6.87 (dd, J=8.6, 2.4 Hz, 1H), 4.40 (t, J=5.1 Hz, 2H), 3.80 (s, 2H), 3.77 (s, 2H), 3.84-3.72 (m, 2H), 3.58-3.50 (m, 2H), 3.28-3.17 (m, 8H), 3.15-3.07 (m, 4H), 2.99 (t, J=7.7 Hz, 1H). 2.83 (t, J=7.3 Hz, 1H), 2.03-1.87 (m, 4H), 1.78-1.68 (m, 4H), 1.54-1.42 (m, 4H), 1.39-1.29 (m, 4H); HRMS (ESI-MS m/z) calculated for C$_{30}$H$_{57}$N$_{11}$O$_3$S$_2$ [M+H]$^+$, 684.4166; found 684.4169.

27. Preparation of AA: (S)-2,6-diamino-N-(2-(1,4-dihydrobenzo[d][1,2]dithiin-6-yloxy)ethyl)hexanamide

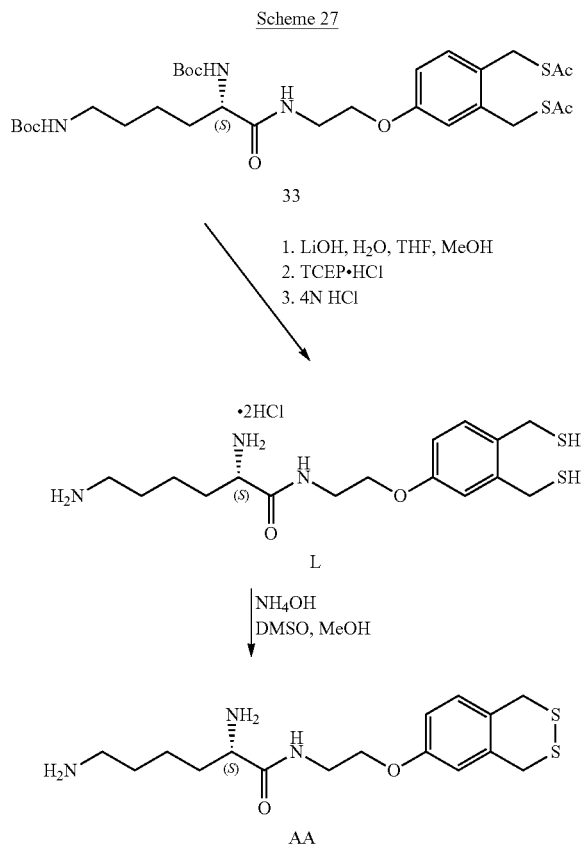

A solution of 33 (320 mg, 0.49 mmol) in a mixture of THF (10 mL), methanol (10 mL), and water (10 mL) was charged with solid LiOH.H$_2$O (105 mg, 2.49 mmol) and the reaction mixture was stirred at room temperature for 1 h. The above reaction mixture was charged with TCEP.HCl (128 mg, 0.45 mmol) and stirred for another 1 h. The solvent was removed and the residue was partitioned between saturated aqueous NaHCO$_3$ solution (10 mL) and CH$_2$Cl$_2$ (50 mL). The CH$_2$Cl$_2$ layer was separated and the aqueous layer was extracted with CH$_2$Cl$_2$ (2×20 mL). The combined organic layers were dried over Na$_2$SO$_4$, filtered, and concentrated to get 300 mg crude product as a white solid. 300 mg crude product was dissolved in EtOH (5.0 mL) and 4 N HCl (15 mL) was added. After stirring at room temperature for 1 h, the reaction mixture was concentrated to afford crude HCl salt (280 mg, crude) which was dissolved in methanol (30 mL) and stirred at room temperature for 48 h in open air (<10% formation of disulfide was observed by LCMS analyses). To the above reaction mixture NH$_4$OH (30% in water, 20 mL) was added and stirred at room temperature for another 72 h in open air (~50% formation of disulfide was observed by LCMS analyses). Then DMSO (1.0 mL) was added to the above reaction mixture and stirring was continued for more 48 h (>90% formation of disulfide was observed by LCMS analyses). Solvent was removed, purified by reverse-phase column chromatography and lyophilized to afford 29 mg (18%, three steps) of pure compound AA as a hygroscopic brown semi-solid: $^1$H NMR (400 MHz, CD$_3$OD) δ7.04 (d, J=8.4 Hz, 1H), 6.78 (dd, J=8.4, 2.6 Hz, 1H), 6.72 (d, J=2.6 Hz, 1H), 4.10-4.04 (m, 2H), 4.03 (s, 2H), 4.00 (s, 2H), 3.78 (t, J=6.8 Hz, 1H), 3.68 (ddd, J=10.4, 5.8, 4.6 Hz, 1H), 3.57 (ddd, J=10.9, 6.4, 4.3 Hz, 1H), 2.83 (dd, J=7.5, 1.5 Hz, 2H), 1.92-1.75 (m, 2H), 1.72-1.60 (m, 2H), 1.53-1.36 (m, 2H); $^1$H NMR (400 MHz, DMSO-d$_6$) δ 8.63 (t, J=5.8 Hz, 1H), 8.40-7.27 (m, 4H), 7.08 (d, J=8.5 Hz, 1H), 6.80 (dd, J=8.5, 2.7 Hz, 1H), 6.75 (d, J=2.7 Hz, 1H), 4.08 (s, 2H), 4.05 (s, 2H), 4.03-3.96 (m, 2H), 3.61 (t, J=6.6 Hz, 1H), 3.56-3.33 (m, 2H), 2.70 (t, J=7.3 Hz, 2H), 1.71-1.60 (m, 2H), 1.57-1.48 (m, 2H), 1.38-1.27 (m, 2H); ESI (m/z) [C$_{16}$H$_{25}$N$_3$O$_2$S$_2$+H]$^+$356.

28. Preparation of BB: (2S,2'S)-N,N'-(2,2'-(1,4-dihydrobenzo[d][1,2]dithiine-6,7-diyl)bis(oxy)bis(ethane-2,1-diyl))bis(2,6-diaminohexanamide)

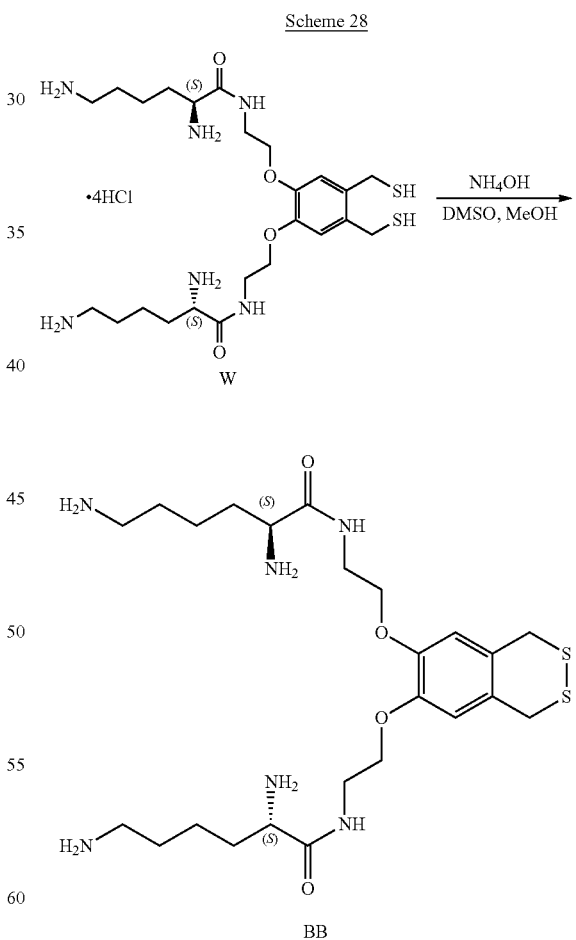

A solution of W (65 mg, 0.09 mmol) in methanol (5.0 mL), was charged with NH$_4$OH (30% in water, 3.0 mL) and DMSO (0.5 mL) and reaction mixture was stirred at room temperature for 96 h in open air (>90% formation of disulfide was observed by LCMS analyses). Solvent was removed, purified by reverse-phase column chromatography and lyophilized to afford 49 mg (96%) of pure compound BB as a hygroscopic white solid: $^1$H NMR (400 MHz, CD$_3$OD) δ6.79 (s, 2H), 4.09 (t, J=5.3 Hz, 4H), 3.98 (s, 4H), 3.95 (t, J=6.6 Hz, 2H), 3.70 (td, J=13.9, 5.5 Hz, 2H), 3.66 (td, J=14.2, 4.8 Hz, 2H), 2.86 (ddd, J=7.5, 6.4, 1.3 Hz, 4H), 2.00-1.81 (m, 4H), 1.75-1.61 (m, 4H), 1.56-1.41 (m, 4H); $^1$H NMR (400 MHz, DMSO-d$_6$) δ8.99 (t, J=4.8 Hz, 2H), 8.40-8.19 (m, 4H), 8.11-7.82 (m, 4H), 6.82 (s, 2H), 4.02 (s, 4H), 4.06-3.95 (m, 5H), 3.90-3.80 (m, 2H), 3.74-3.18 (m, 3H), 2.82-2.62 (m, 4H), 1.83-1.68 (m, 4H), 1.63-1.48 (m, 4H), 1.45-1.25 (m, 4H); HRMS (ESI-MS m/z) calculated for C$_{24}$H$_{42}$N$_6$O$_4$S$_2$ [M+H]$^+$, 543.2787; found 543.2779. Elemental analysis: % calcd C, 53.11; H, 7.8; N, 15.48. found C, 37.21; H, 6.79; N, 11.02.

29. Preparation of CC: (2S,2'S)-N,N'-(2,2'-(1,4-dihydrobenzo[d][1,2]dithiine-6,7-diyl)bis(oxy)bis(ethane-2,1-diyl))bis(2-amino-6-guanidinohexanamide)

A solution of H (55 mg, 0.09 mmol) in methanol (5.0 mL), was charged with NH$_4$OH (30% in water, 3.0 mL) and DMSO (0.5 mL) and reaction mixture was stirred at room temperature for 96 h in open air (>90% formation of disulfide was observed by LCMS analyses). Solvent was removed, purified by reverse-phase column chromatography and lyophilized to afford 15 mg (28%) of pure compound CC as a hygroscopic white solid: $^1$H NMR (400 MHz, CD$_3$OD) δ6.77 (s, 2H), 4.08 (t, J=5.5 Hz, 4H), 3.97 (s, 4H), 3.84 (t, J=7.1 Hz, 2H), 3.68 (dt, J=13.9, 4.8 Hz, 2H), 3.60 (dt, J=13.9, 5.3 Hz, 2H), 3.08 (t, J=7.0 Hz, 4H), 1.93-1.74 (m, 4H), 1.64-1.52 (m, 4H), 1.49-1.38 (m, 4H); $^1$H NMR (400 MHz, DMSO-d$_6$) δ8.96 (t, J=5.5 Hz, 2H), 8.40-8.20 (m, 5H), 7.78 (t, J=6.2 Hz, 2H), 7.67-6.81 (m, 7H), 6.82 (s, 2H), 4.01 (s, 4H), 4.09-3.93 (m, 4H), 3.90-3.77 (m, 2H), 3.58-3.40 (m, 4H), 3.08-3.00 (m, 4H), 1.81-1.66 (m, 4H), 1.52-1.41 (m, 4H), 1.40-1.25 (m, 4H); HRMS (ESI-MS m/z) calculated for C$_{26}$H$_{46}$N$_{10}$O$_4$S$_2$ [M+H]$^+$, 627.3223; found 627.3260.

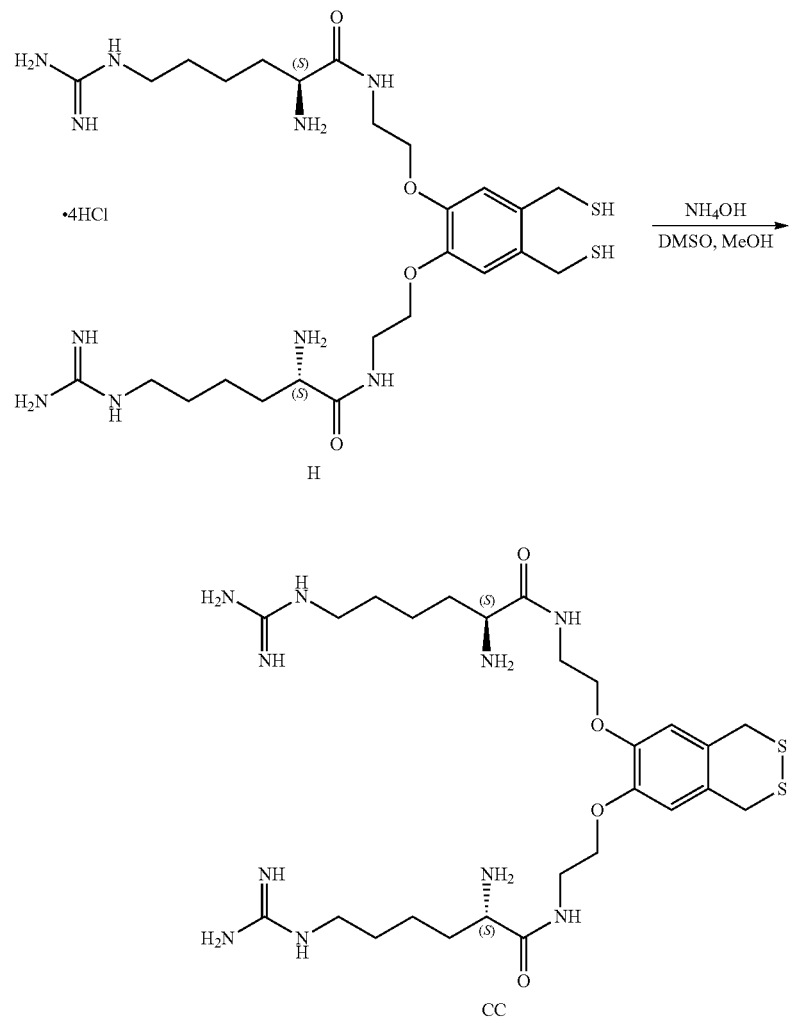

Scheme 29

30. Preparation of DD: (2R,2'R)-N,N'-(2,2'-(1,4-dihydrobenzo[d][1,2]dithiine-6,7-diyl)bis(oxy)bis(ethane-2,1-diyl))bis(2-amino-6-guanidinohexanamide)

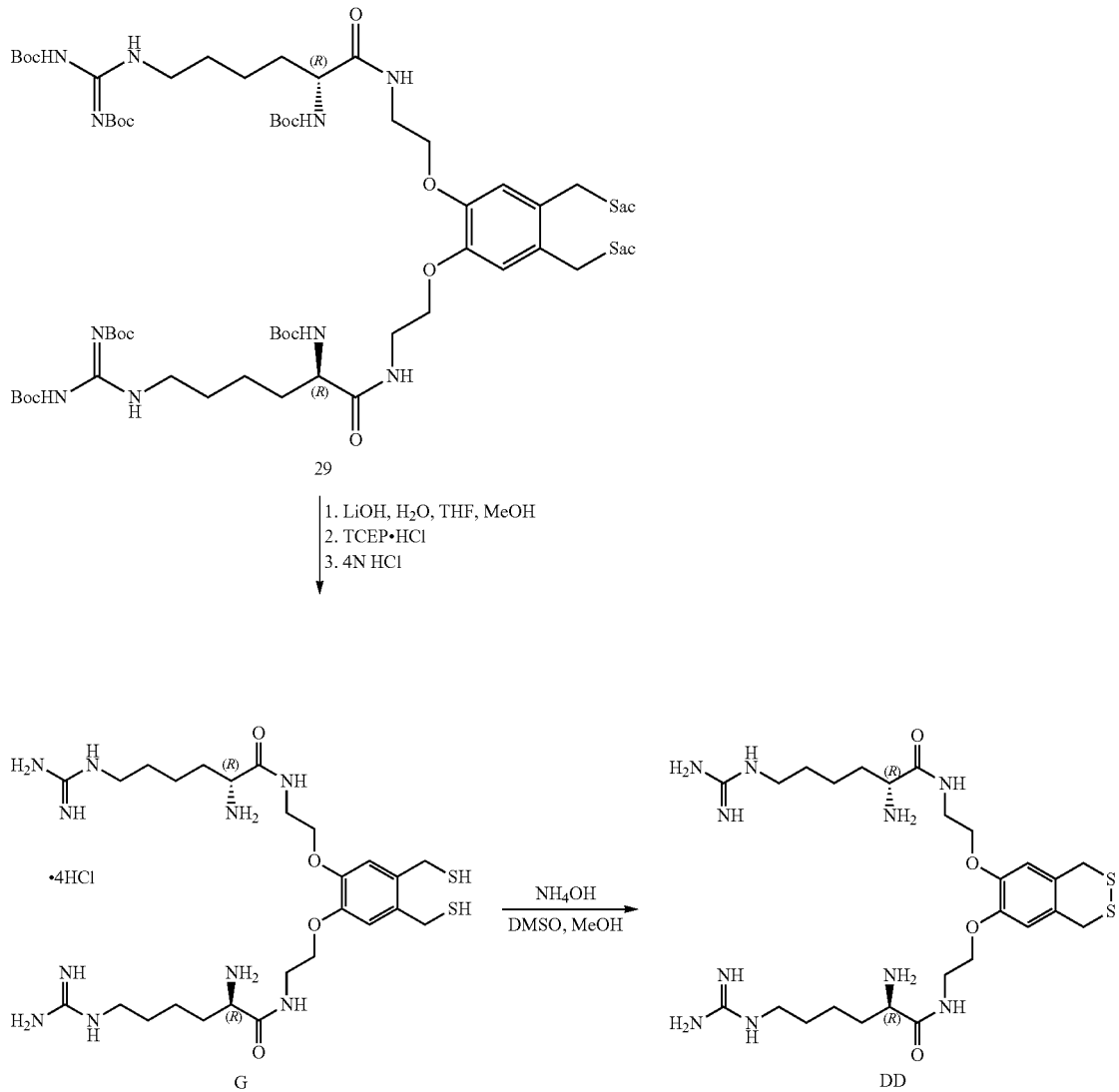

Scheme 30

A solution of 29 (1.31 g, 1.00 mmol) in a mixture of THF (20 mL), methanol (20 mL), and water (20 mL) was charged with solid LiOH.H$_2$O (168 mg, 4.00 mmol) and the reaction mixture was stirred at room temperature for 1 h. The above reaction mixture was charged with TCEP.HCl (143 mg, 0.50 mmol) and stirred for another 1 h. The solvent was removed and the residue was partitioned between CH$_2$Cl$_2$ (50 mL) and saturated aqueous NaHCO$_3$ solution (10 mL). The CH$_2$Cl$_2$ layer was separated and the aqueous layer was extracted with CH$_2$Cl$_2$ (2×30 mL). The combined organic layers were dried over Na$_2$SO$_4$, filtered, and concentrated. The residue was dissolved in EtOH (20 mL) and 4 N HCl (20 mL) was added. After stirring at room temperature for 1 h, the reaction mixture was concentrated to afford compound G (800 mg, crude HCl salt) as a yellow solid. A solution of G (200 mg, 0.25 mmol, crude) in methanol (10 mL), was charged with NH$_4$OH (30% in water, 10 mL) and DMSO (0.5 mL) and reaction mixture was stirred at room temperature for 20 h in open air (>90% formation of disulfide was observed by LCMS analyses). Solvent was removed, purified by reverse-phase column chromatography and lyophilized to afford 56 mg (36%, over two steps) of pure compound P-DD as a hygroscopic white solid: $^1$H NMR (400 MHz, CD$_3$OD) δ6.78 (s, 2H), 4.09 (t, J=5.5 Hz, 4H), 3.98 (s, 4H), 3.98 (t, J=7.3 Hz, 2H), 3.72 (dt, J=13.9, 4.8 Hz, 2H), 3.59 (dt, J=13.9, 5.3 Hz, 2H), 3.08 (t, J=7.0 Hz, 4H), 1.97-1.81 (m, 4H), 1.65-1.54 (m, 4H), 1.53-1.41 (m, 4H); $^1$H NMR (400 MHz, DMSO-d$_6$) δ900 (t, J=5.8 Hz, 2H), 8.31 (br s, 5H), 7.85 (t, J=5.8 Hz, 2H), 7.70-6.68 (m, 7H), 6.83 (s, 2H), 4.01 (s, 4H), 4.05-3.97 (m, 4H), 3.89-3.81 (m, 2H), 3.58-3.40 (m, 4H), 3.10-3.00 (m, 4H), 1.82-1.66 (m, 4H), 1.53-1.40 (m, 4H), 1.40-1.25 (m, 4H); HRMS (ESI-MS m/z) calculated for C$_{26}$H$_{46}$N$_{10}$O$_4$S$_2$ [M+H]$^+$, 627.3223; found 627.3238.

31. Preparation of EE: (R)-2-amino-N-(2-(1,4-dihydrobenzo[d][1,2]dithiin-6-yloxy)ethyl)-6-guanidinohexanamide

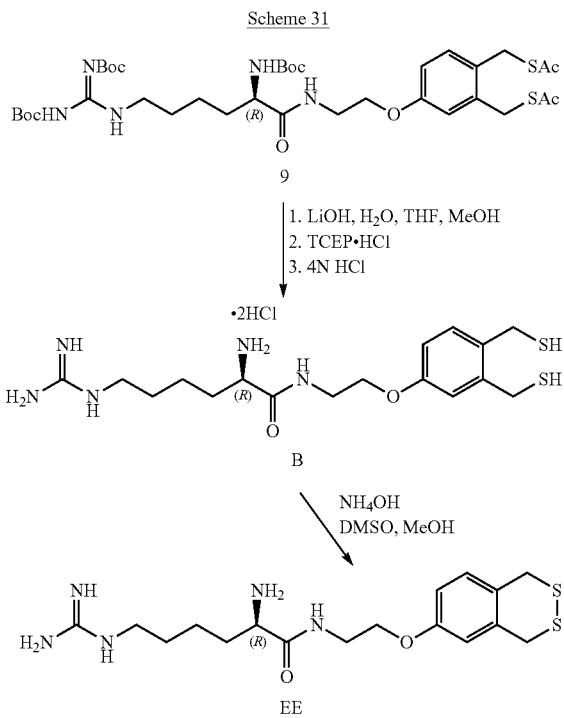

Scheme 31

A solution of 9 (300 mg, 0.38 mmol) in a mixture of THF (15 mL), methanol (15 mL), and water (15 mL) was charged with solid LiOH.H₂O (64 mg, 1.53 mmol) and the reaction mixture was stirred at room temperature for 1 h. The above reaction mixture was charged with TCEP.HCl (54 mg, 0.19 mmol) and stirred for another 1 h. The organic solvent was removed and the residue was partitioned between saturated aqueous NaHCO₃ solution (10 mL) and CH₂Cl₂ (50 mL). The CH₂Cl₂ layer was separated and the aqueous layer was extracted with CH₂Cl₂ (2×30 mL). The combined organic layers were dried over Na₂SO₄, filtered, and concentrated. The final residue was dissolved in EtOH (15 mL) and 4 N HCl (15 mL) was added. After stirring at room temperature for 1 h, the reaction mixture was concentrated to afford compound B (155 mg, crude HCl salt) as a yellow solid. A solution of EE (155 mg, 0.38 mmol, crude) in methanol (10 mL), was charged with NH₄OH (30% in water, 10 mL) and DMSO (0.5 mL) and reaction mixture was stirred at room temperature for 20 h in open air (>90% formation of disulfide was observed by LCMS analyses). Solvent was removed, purified by reverse-phase column chromatography and lyophilized to afford 78 mg (52%, over two steps) of pure compound P-2064 as a hygroscopic white solid: $^1$H NMR (400 MHz, CD₃OD) δ7.03 (d, J=8.4 Hz, 1H), 6.78 (dd, J=8.4, 2.6 Hz, 1H), 6.72 (d, J=2.6 Hz, 1H), 4.07 (ddd, J=6.1, 3.5, 1.6 Hz, 2H), 4.03 (s, 2H), 4.00 (s, 2H), 3.85 (t, J=6.8 Hz, 1H), 3.70 (td, J=14.4, 4.6 Hz, 1H), 3.55 (ddd, J=14.4, 6.6, 4.7 Hz, 1H), 3.05 (t, J=7.4 Hz, 2H), 1.92-1.78 (m, 2H), 1.65-1.52 (m, 2H), 1.50-1.36 (m, 2H); $^1$H NMR (400 MHz, DMSO-d₆) 8.81 (t, J=5.0 Hz, 1H), 8.21 (br s, 3H), 7.82 (br s, 1H), 7.59-6.70 (m, 7H), 7.08 (d, J=8.5 Hz, 1H), 6.81 (dd, J=8.5, 2.7 Hz, 1H), 6.78 (d, J=2.7 Hz, 1H), 4.08 (s, 2H), 4.05 (s, 2H), 4.04-3.98 (m, 2H), 3.75 (t, J=6.8 Hz, 1H), 3.58-3.42 (m, 2H), 3.03 (dd, J=13.0, 6.3 Hz, 2H), 1.76-1.64 (m, 2H), 1.54-1.39 (m, 2H), 1.38-1.27 (m, 2H); HRMS (ESI-MS m/z) calculated for C₁₇H₂₇N₅O₂S₂ [M+H]$^+$, 398.1684; found 398.1674.

32. Preparation of FF: (S,2S,2'S)-N,N'-(2,2'-(1,4-dihydrobenzo[d][1,2]dithiine-6,7-diyl)bis(oxy)bis(ethane-2,1-diyl))bis(2-amino-6-((S)-2,6-diaminohexanamido)hexanamide)

Scheme 32

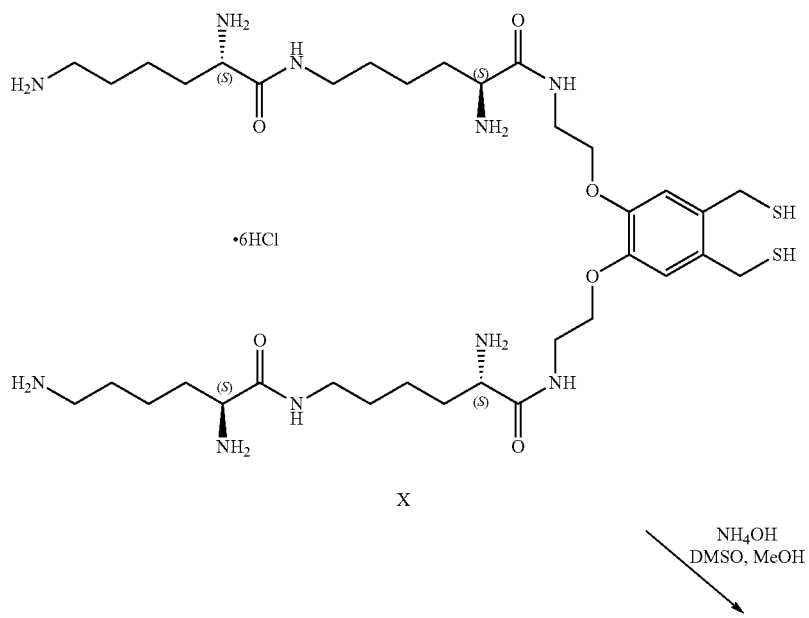

-continued

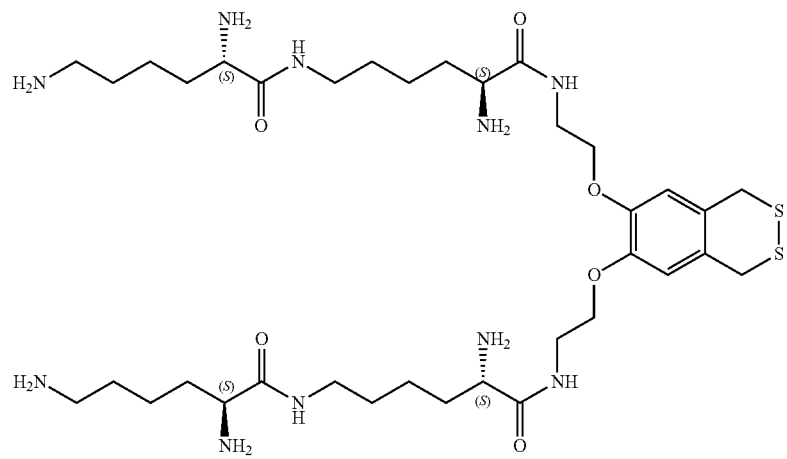

FF

A solution of X (50 mg, 0.05 mmol) in methanol (10 mL), was charged with NH₄OH (30% in water, 10 mL) and DMSO (0.5 mL) and reaction mixture was stirred at room temperature for 16 h in open air (>90% formation of disulfide was observed by LCMS analyses). Solvent was removed, purified by reverse-phase column chromatography and lyophilized to afford 76 mg (49%)* of pure compound FF as a hygroscopic white solid: $^1$H NMR (400 MHz, CD$_3$OD) δ 6.79 (s, 2H), 4.10 (t, J=5.5 Hz, 4H), 3.98 (s, 4H), 3.97 (t, J=6.6 Hz, 2H), 3.91 (t, J=7.1 Hz, 2H), 3.71 (td, J=14.1, 5.5 Hz, 2H), 3.59 (td, J=14.2, 5.1 Hz, 2H), 3.27-3.17 (m, 2H), 3.15-3.07 (m, 2H), 2.96 (dd, J=8.5, 7.6 Hz, 4H), 1.99-1.78 (m, 8H), 1.77-1.68 (m, 4H), 1.61-1.40 (m, 12H); $^1$H NMR (400 MHz, DMSO-d$_6$) δ9.04 (t, J=5.1 Hz, 2H), 8.75 (t, J=5.4 Hz, 2H), 8.23 (br s, 12H), 6.83 (s, 2H), 4.02 (s, 4H), 4.01 (t, J=6.6 Hz, 4H), 3.85 (t, J=6.6 Hz, 2H), 3.77 (t, J=6.3 Hz, 2H), 3.58-3.40 (m, 4H), 3.05 (dd, J=11.6, 6.2 Hz, 4H), 2.75 (t, J=7.5 Hz, 4H), 1.86-1.66 (m, 8H), 1.65-1.51 (m, 4H), 1.50-1.27 (m, 12H); HRMS (ESI-MS m/z) calculated for C$_{36}$H$_{66}$N$_{10}$O$_6$S$_2$ [M+H]$^+$, 799.4686; found 799.4726.

33. Preparation of GG: (S,2S,2'S)-N,N'-(2,2'-(1,4-dihydrobenzo[d][1,2]dithiine-6,7-diyl)bis(oxy)bis(ethane-2,1-diyl))bis(2-amino-6-((S)-2-amino-6-guanidinohexanamido)hexanamide)

Scheme 33

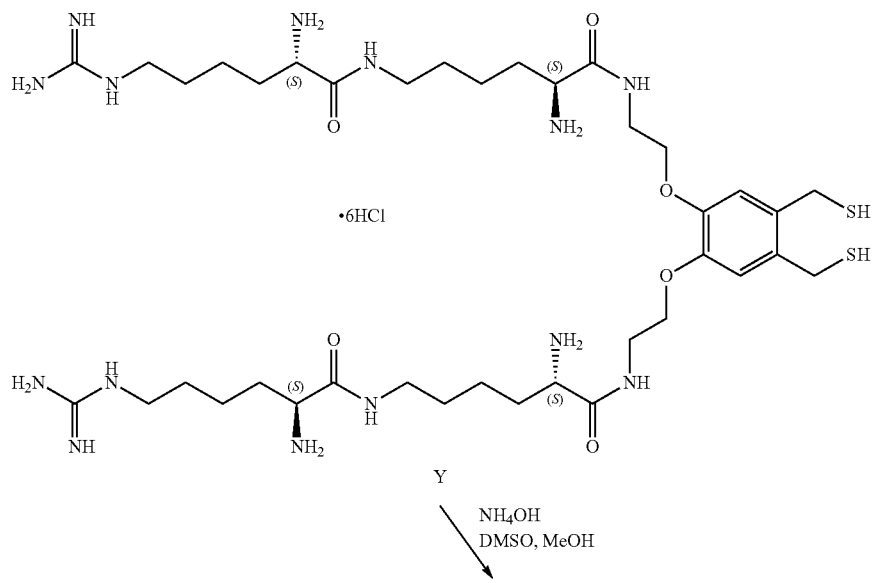

Y

NH₄OH
DMSO, MeOH

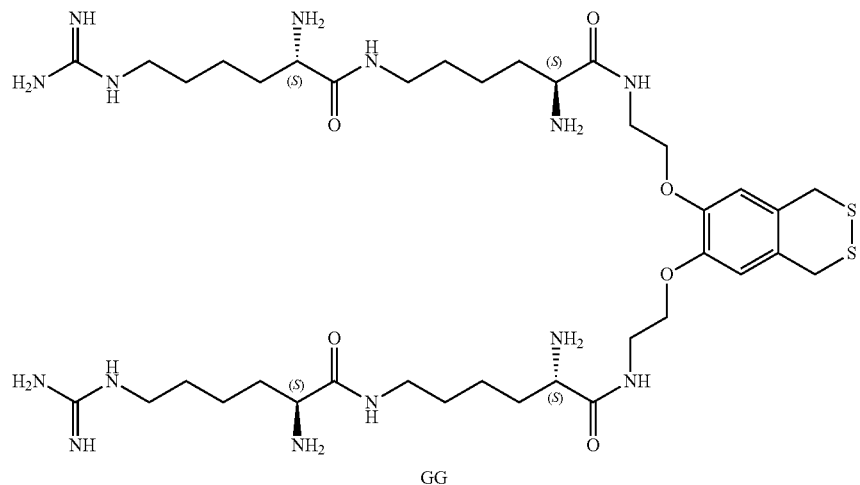

GG

A solution of Y (60 mg, 0.054 mmol) in methanol (10 mL), was charged with NH₄OH (30% in water, 10 mL) and DMSO (0.5 mL) and reaction mixture was stirred at room temperature for 20 h in open air (>90% formation of disulfide was observed by LCMS analyses). Solvent was removed, purified by reverse-phase column chromatography and lyophilized to afford 42 mg (33%)* of pure compound GG as a hygroscopic white solid: $^1$H NMR (400 MHz, CD₃OD) δ6.79 (s, 2H), 4.10 (t, J=5.6 Hz, 4H), 3.98 (s, 4H), 3.97 (t, J=6.7 Hz, 2H), 3.89 (t, J=6.6 Hz, 2H), 3.71 (td, J=14.3, 5.7 Hz, 2H), 3.59 (td, J=14.1, 5.1 Hz, 2H), 3.22 (t, J=6.9 Hz, 4H), 3.19-3.08 (m, 4H), 1.98-1.76 (m, 8H), 1.73-1.60 (m, 4H), 1.60-1.38 (m, 12H); $^1$H NMR (400 MHz DMSO-d₆) δ9.03 (t, J=5.4 Hz, 2H), 8.73 (t, J=5.4 Hz, 2H), 8.40-8.18 (m, 12H), 7.85 (t, J=5.5 Hz, 2H), 7.69-6.83 (m, 7H), 6.83 (s, 2H), 4.02 (s, 4H), 4.01 (t, J=6.2 Hz, 2H), 3.90-3.81 (m, 2H), 3.80-3.71 (m, 2H), 3.58-3.39 (m, 4H), 3.15-3.01 (m, 8H), 1.85-1.64 (m, 8H), 1.58-1.27 (m, 16H); HRMS (ESI-MS m/z) calculated for $C_{38}H_{70}N_{14}O_6S_2$ [M+H]⁺, 883.5122; found 883.5134.

*100 mg of crude P-2061 (obtained after combining impure fractions of SG-SJL-D-87) was also subjected to similar reaction condition for cyclic disulfide formation; after purification by reverse phase column combined with above for lyophilization. *Yield is based on combined starting materials (60 mg+100 mg).

34. Preparation of HH: (R)-2-amino-N-((R)-5-amino-6-(2-(1,4-dihydrobenzo[d][1,2]dithiin-6-yloxy)ethylamino)-6-oxohexyl)-6-guanidinohexanamide Scheme 34

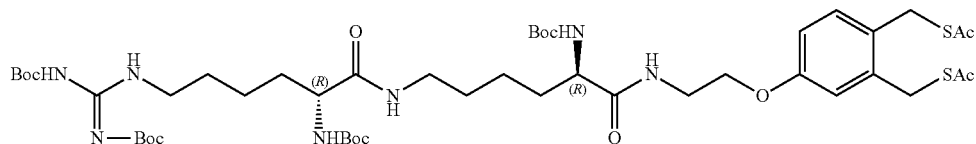

17

1. LiOH, H₂O, THF, MeOH
2. TCEP·HCl
3. 4N HCl

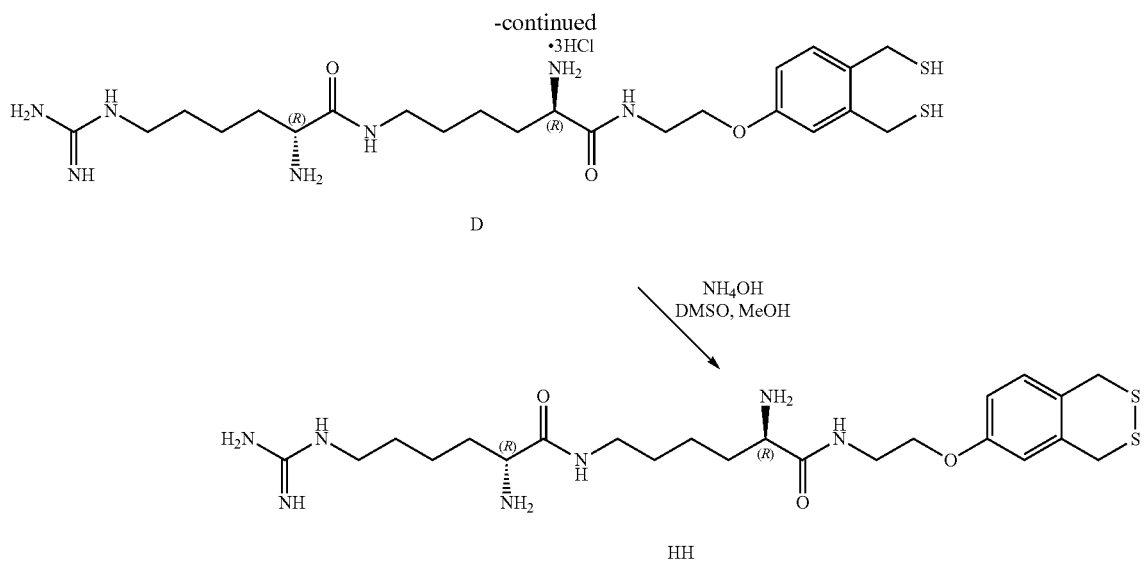

A solution of 17 (1.30 g, 1.28 mmol) in a mixture of THF (20 mL), methanol (20 mL), and water (20 mL) was charged with solid LiOH·H$_2$O (216 mg, 5.14 mmol) and the reaction mixture was stirred at room temperature for 1 h. The above reaction mixture TCEP·HCl (183 mg, 0.64 mmol) was charged with and stirred for another 1 h. The solvent was removed and the residue was partitioned between saturated aqueous NaHCO$_3$ solution (10 mL) and CH$_2$Cl$_2$ (50 mL). The CH$_2$Cl$_2$ layer was separated and the aqueous layer was extracted with CH$_2$Cl$_2$ (2×30 mL). The organic layers were combined, dried over Na$_2$SO$_4$, filtered, and concentrated. The residue was dissolved in EtOH (20 mL) and 4 N HCl (20 mL) was added. After stirring at room temperature for 1 h, the reaction mixture was concentrated to afford compound D (820 mg, crude HCl salt) as a yellow solid. A solution of D (220 mg, 0.34 mmol, crude) in methanol (10 mL), was charged with NH$_4$OH (30% in water, 10 mL) and DMSO (0.1 mL) and reaction mixture was stirred at room temperature for 20 h in open air (>90% formation of disulfide was observed by LCMS analyses). Solvent was removed, purified by reverse-phase column chromatography and lyophilized to afford 30 mg (17%, over two steps) of pure compound P-2067 as a hygroscopic white solid: $^1$H NMR (400 MHz, CD$_3$OD) δ7.04 (d, J=8.4 Hz, 1H), 6.82 (dd, J=8.4, 2.6 Hz, 1H), 6.78 (d, J=2.6 Hz, 1H), 4.10-4.05 (m, 2H), 4.03 (s, 2H), 4.00 (s, 2H), 3.90 (dt, J=6.8, 1.4 Hz, 2H), 3.75-3.67 (m, 1H), 3.59-3.51 (m, 1H), 3.31 (t, J=7.4 Hz, 2H), 3.18-3.06 m, 2H), 1.97-1.72 (m, 4H), 1.71-1.58 (m, 2H), 1.57-1.38 (m, 6H); $^1$H NMR (400 MHz, DMSO-d$_6$) δ8.82 (t, J=5.5 Hz, 1H), 8.66 (t, J=5.4 Hz, 1H), 8.25 (br s, 6H), 7.80 (t, J=5.2 Hz, 1H), 7.66-6.67 (m, 6H), 7.08 (d, J=8.5 Hz, 1H), 6.81 (dd, J=8.5, 2.7 Hz, 1H), 6.76 (d, J=2.7 Hz, 1H), 4.08 (s, 2H), 4.05 (s, 2H), 4.04-3.98 (m, 2H), 3.80-3.69 (m, 2H), 3.62-3.40 (m, 3H), 3.15-2.99 (m, 4H), 1.79-1.65 (m, 4H), 1.53-1.35 (m, 4H), 1.37-1.27 (m, 4H); ESI-MS (m/z) C$_{23}$H$_{39}$N$_7$O$_3$S$_2$+H]$^+$526.

35. Preparation JJ: (2R,2'R)-N,N'-(3,3'-(2-(1,4-dihydrobenzo[d][1,2]dithiin-6-yloxy)ethylazanediyl)bis(propane-3,1-diyl))bis(2-amino-6-guanidinohexanamide)

Scheme 35

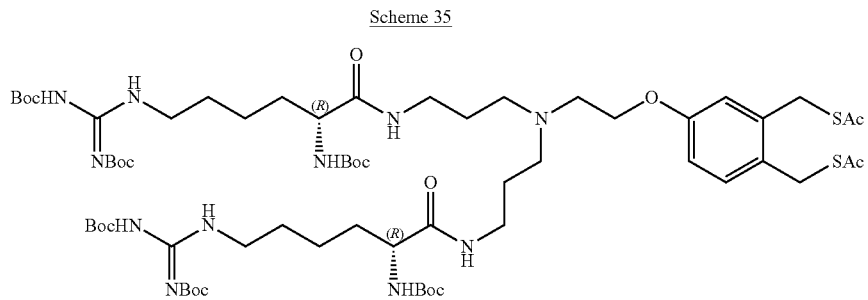

1. LiOH, H$_2$O, THF, MeOH
2. TCEP·HCl
3. 4N HCl

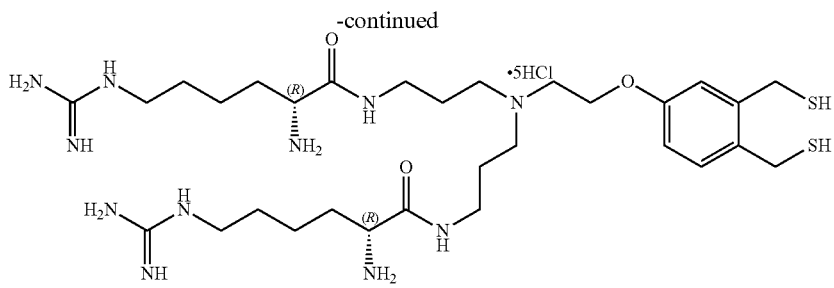

Z

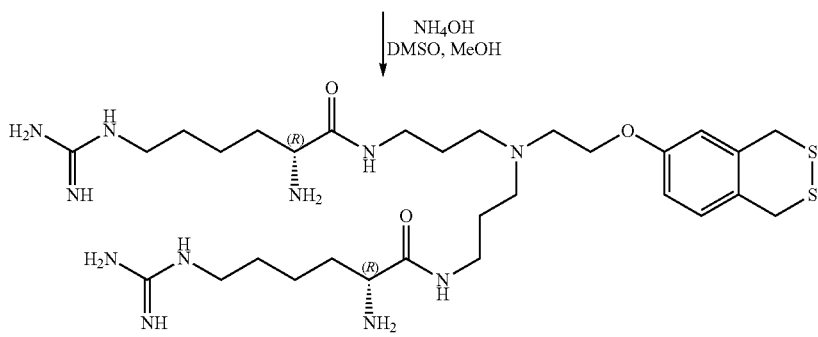

JJ

A solution of 57 (475 mg, 0.35 mmol, mixture) in a mixture of THF (15 mL), methanol (15 mL), and water (15 mL) was charged with solid LiOH.H$_2$O (59 mg, 1.40 mmol) and the reaction mixture was stirred at room temperature for 1 h. The above reaction mixture was charged with TCEP.HCl (50 mg, 0.17 mmol) and stirred for another 1 h. The solvent was removed and the residue was partitioned between CH$_2$Cl$_2$ (50 mL) and saturated aqueous NaHCO$_3$ solution (10 The CH$_2$Cl$_2$ layer was separated and the aqueous layer was extracted with CH$_2$Cl$_2$ (2×30 mL). The combined organic layers were dried over Na$_2$SO$_4$, filtered, and concentrated. The residue was dissolved in EtOH (15 mL) and 4 N HCl (15 mL) was added. After stirring at room temperature for 1 h, the reaction mixture was concentrated to afford compound Z (300 mg, crude HCl salt) as a yellow solid. (200 mg, 0.24 mmol, crude) in methanol (10 mL), was charged with NH$_4$OH (30% in water, 10 mL) and DMSO (0.1 mL) and reaction mixture was stirred at room temperature for 20 h in open air (>90% formation of disulfide was observed by LCMS analyses). Solvent was removed, purified by reverse-phase column chromatography and lyophilized to afford 80 mg (39%, over two steps) of pure compound JJ as a hygroscopic white solid: $^1$H NMR (400 MHz, CD$_3$OD) δ7.09 (d, J=8.4 Hz, 1H), 6.89 (dd, J=8.4, 2.6 Hz, 1H), 6.87 (d, J=2.6 Hz, 1H), 4.40 (t, J=4.8 Hz, 2H), 4.07 (s, 2H), 4.02 (s, 2H), 3.92 (t, J=6.6 Hz, 2H), 3.72-3.66 (m, 2H), 3.51-3.32 (m, 8H), 3.21 (dt, J=7.2, 1.9 Hz, 4H), 2.19-2.02 (m, 4H), 2.00-1.77 (m, 4H), 1.70-1.57 (m, 4H), 1.54-1.42 (m, 4H); $^1$H NMR (400 MHz, DMSO-d$_6$) δ10.83 (br s, 1H), 8.96 (dd, J 102, 5.8 Hz, 2H), 8.37 (br s, 6H), 7.85 (t, J=5.5 Hz, 2H), 7.67-6.78 (m, 7H), 7.11 (d, J=8.6 Hz, 1H), 6.89 (dd, J=8.6, 2.4 Hz, 1H), 6.88 (d, J=2.4 Hz, 1H), 4.40 (t, J=4.6 Hz, 2H), 4.11 (s, 2H), 4.07 (s, 2H), 3.82-3.72 (m, 2H), 3.58-3.50 (m, 2H), 3.31-3.17 (m, 8H), 3.15-3.03 (m, 4H), 2.06-1.87 (m, 4H), 1.79-1.66 (m, 4H), 1.54-1.41 (m, 4H), 1.39-1.26 (m, 4H); HRMS (ESI-MS m/z) calculated for C$_{30}$H$_{55}$N$_{11}$O$_3$S$_2$ [M+H]$^1$, 682.4009; found 682.404.

36. Preparation of (4-(2-aminoethoxy)-1,2-phenylene)dimethanethiol (KK)

Scheme 36

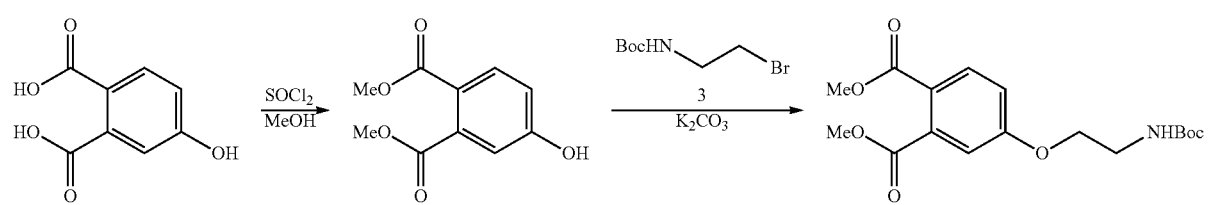

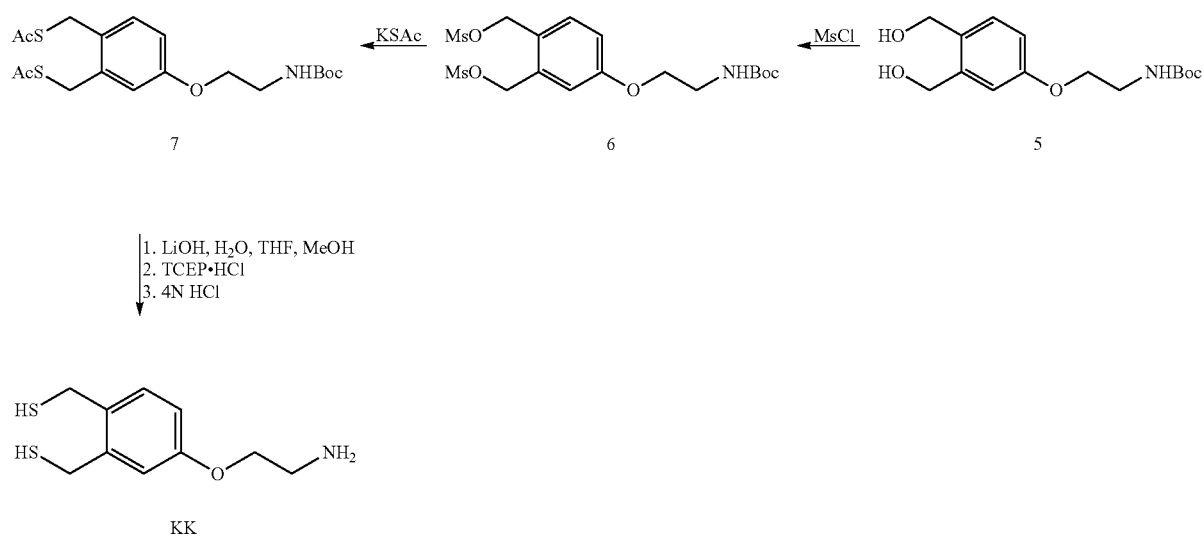
37. Preparation of LL: 1-(2-(3,4-bis(mercaptomethyl)phenoxy)ethyl)guanidine (LL)
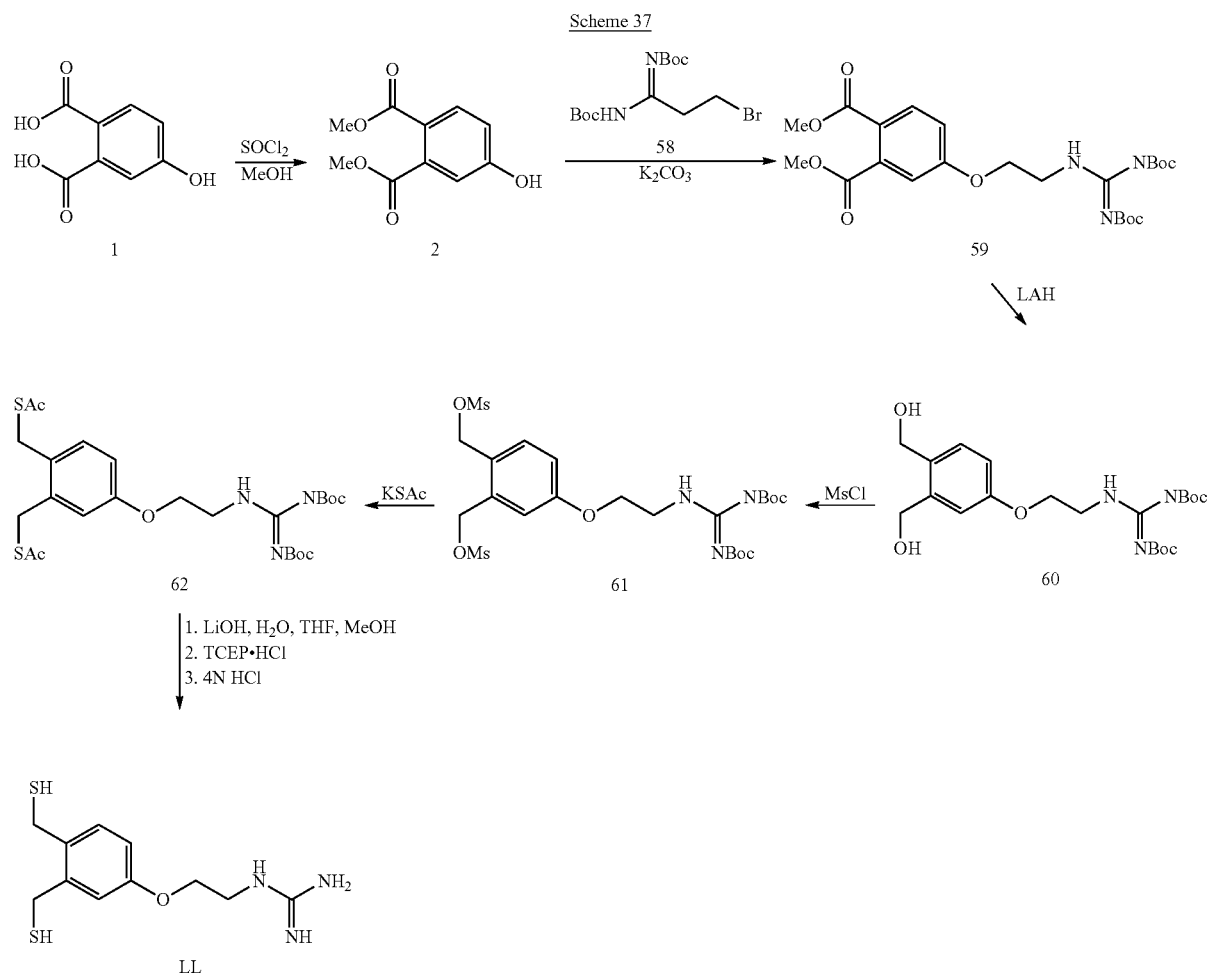

All of the references cited above throughout this application are incorporated herein by reference. In the event of a conflict between the foregoing description and a reference, the description provided herein controls.

That which is claimed is:

1. A compound represented by formula Ia, Ib, Ic or Id:

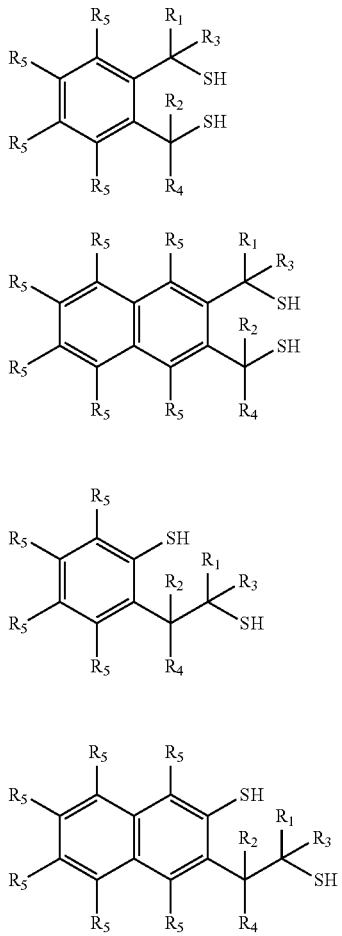

wherein $R^1$ and $R^2$ are each, independently, hydrogen, lower alkyl, halogen or triflouromethyl;

$R^3$ and $R^4$ are each, independently, hydrogen, lower alkyl, hydroxyl-lower alkyl, phenyl, (phenyl)-lower alkyl, (halophenyl)-lower alkyl, ((lower-alkyl)phenyl)-lower-alkyl, ((lower-alkoxy) phenyl)-lower-alkyl, (naphthyl)-lower-alkyl, or (pyridyl)-lower-alkyl;

each $R^5$ is, independently, hydrogen or $-O-(CH_2)_m-NR^7R^7$, with the proviso that at least one $R^5$ group is $-O-(CH_2)_m-NR^7R^7$;

each $R^7$ is, independently, hydrogen, lower alkyl, phenyl, substituted phenyl, lower alkyl phenyl or $-CH_2(CHOR^8)_m-CH_2OR^8$;

each $R^8$ is, independently, hydrogen, lower alkyl, lower alkyl phenyl, $-C(=O)-R^{11}$, glucuronide, 2-tetrahydropyranyl, or

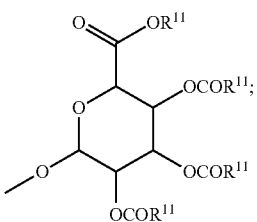

each $R^{11}$ is, independently, hydrogen, lower alkyl, phenyl lower alkyl or substituted phenyl lower alkyl; and each m is, independently, an integer from 1 to 7;

with the proviso that when any $-CHOR^8-$ or $-CH_2OR^8$ groups are located 1,2- or 1,3-with respect to each other, the $R^8$ groups may, optionally, be taken together to form a cyclic mono- or di-substituted 1,3-dioxane or 1,3-dioxolane;

and racemates, enantiomers, diastereomers, tautomers, polymorphs, pseudopolymorphs and pharmaceutically acceptable salts, thereof.

2. The compound of claim 1, which is a pharmaceutically acceptable salt.

3. The compound of claim 1, which is an acid addition salt of an inorganic acid or an organic acid selected from the group consisting of hydrochloric acid, hydrobromic acid, sulfuric acid, phosphoric acid, nitric acid, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalensulfonic acid, methanesulfonic acid, p-toluenesulfonic acid, naphthalenedisulfonic acid, polygalacturonic acid, malonic acid, sulfosalicylic acid, glycolic acid, 2-hydroxy-3-naphthoate, pamoate, salicylic acid, stearic acid, phthalic acid, mandelic acid, and lactic acid.

4. The compound of claim 1, which is a hydrochloride salt.

5. The compound of claim 1, which is represented by the formula:

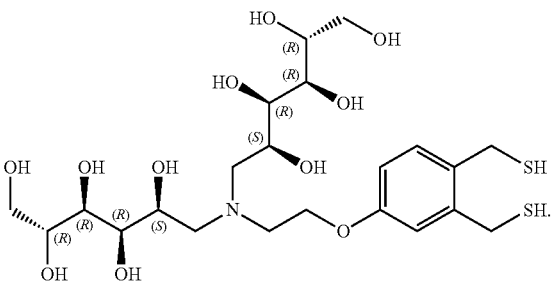

6. The compound of claim 5, which is a pharmaceutically acceptable salt.

7. The compound of claim 5, which is an acid addition salt of an inorganic acid or an organic acid selected from the group consisting of hydrochloric acid, hydrobromic acid, sulfuric acid, phosphoric acid, nitric acid, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalensulfonic acid, methanesulfonic acid, p-toluenesulfonic acid, naphthalenedisulfonic acid, polygalacturonic acid, malonic acid, sulfosalicylic acid, glycolic acid, 2-hydroxy-3-naphthoate, pamoate, salicylic acid, stearic acid, phthalic acid, mandelic acid, and lactic acid.

8. The compound of claim 5, which is a hydrochloride salt.

9. The compound of claim 1, wherein $R^1$, $R^2$, $R^3$ and $R^4$ are hydrogen and one $R^5$ is —O—$(CH_2)_m$—$NR^7R^7$.

10. The compound of claim 9, wherein each $R^7$ is, independently, —$CH_2(CHOR^8)_m$—$CH_2OR^8$.

11. The compound of claim 10, wherein each $R^8$ is hydrogen.

12. The compound of claim 10, which is a pharmaceutically acceptable salt.

13. The compound of claim 10, which is an acid addition salt of an inorganic acid or an organic acid selected from the group consisting of hydrochloric acid, hydrobromic acid, sulfuric acid, phosphoric acid, nitric acid, acetic acid, oxalic acid, tartaric acid, succinic acid, maleic acid, furmaric acid, gluconic acid, citric acid, malic acid, ascorbic acid, benzoic acid, tannic acid, palmitic acid, alginic acid, polyglutamic acid, naphthalensulfonic acid, methanesulfonic acid, p-toluenesulfonic acid, naphthalenedisulfonic acid, polygalacturonic acid, malonic acid, sulfosalicylic acid, glycolic acid, 2-hydroxy-3-naphthoate, pamoate, salicylic acid, stearic acid, phthalic acid, mandelic acid, and lactic acid.

14. The compound of claim 10, which is a hydrochloride salt.

15. A pharmaceutical composition, comprising the compound of claim 1 and a pharmaceutically acceptable carrier.

16. A composition, comprising:
(a) the compound of claim 1 and (b) an osmotically active compound.

17. A method of liquefying mucus from mucosal surfaces, comprising:
administering an effective amount of the compound of claim 1 to a mucosal surface of a subject.

18. A method of treating chronic bronchitis, treating bronchiectasis, treating cystic fibrosis, treating chronic obstructive pulmonary disease, treating asthma, treating sinusitis, treating vaginal dryness, treating dry eye, promoting ocular hydration, promoting corneal hydration, promoting mucus clearance in mucosal surfaces, treating Sjogren's disease, treating distal intestinal obstruction syndrome, treating dry skin, treating esophagitis, treating dry mouth, treating nasal dehydration, treating ventilator-induced pneumonia, treating asthma, treating primary ciliary dyskinesia, treating otitis media, inducing sputum for diagnostic purposes, treating cystinosis, treating emphysema, treating pneumonia, treating constipation, treating chronic diverticulitis, and/or treating rhinosinusitis, comprising:
administering an effective amount of the compound of claim 1 to a subject in need thereof.

19. A method of treating an eye disease characterized by the presence of ocular discharge consisting of administering to a subject in need an effective amount of the compound of claim 1.

20. The method of claim 19, wherein the eye disease is one or more conditions selected from the group consisting of blepharitis, allergies, conjunctivitis, corneal ulcer, trachoma, congenital herpes simplex, corneal abrasions, ectropion, eyelid disorders, gonococcal conjunctivitis, herpetic keratitis, ophthalmitis, Sjogren's Syndrome, or Stevens-Johnson Syndrome.

21. A method of treating a disease ameliorated by increased mucociliary clearance and mucosal hydration comprising administering to a subject in need of increased mucociliary clearance and mucosal hydration an effective amount of an osmolyte and the compound of claim 1.

22. The method of claim 21, wherein the disease is one or more conditions selected from the group consisting of chronic bronchitis, bronchiectasis, cystic fibrosis, asthma, sinusitis, vaginal dryness, dry eye, Sjogren's disease, distal intestinal obstruction syndrome, dry skin, esophagitis, dry mouth (xerostomia), nasal dehydration, asthma, primary ciliary dyskinesia, otitis media, chronic obstructive pulmonary disease, emphysema, pneumonia, diverticulitis, rhinosinusitis, and airborne infections.

23. The method of claim 21, wherein the compound is administered preceding administration of the osmolyte.

24. The method of claim 21, wherein the compound is administered concurrent with administration of the osmolyte.

25. The method of claim 21, wherein the compound is administered following administration of the osmolyte.

26. The method of claim 21, wherein the osmolyte is hypertonic saline or mannitol.

27. The method of claim 21, wherein the osmolyte is sodium chloride which is delivered as a micronized particle of respirable size.

28. The method of claim 21, wherein the effective amount of an osmolyte and the compound is administered by aerosolization using a device capable of delivering the formulation to the nasal passages or pulmonary airway wherein the aerosol is a respirable size.

29. A method of inducing sputum, comprising administering to a subject in need of increased mucociliary clearance and mucosal hydration an effective amount of an osmolyte and the compound of claim 1.

30. A method of prophylactic, post-exposure prophylactic, preventive or therapeutic treatment against diseases or conditions caused by pathogens, comprising administering to a subject in need of increased mucociliary clearance and mucosal an effective amount of the compound of claim 1.

31. The method of claim 30, wherein the pathogen is anthrax or plague.

32. A method for preventing, mitigating, and/or treating deterministic health effects to the respiratory tract and/or other bodily organs caused by respirable aerosols containing radionuclides in a human in need thereof, comprising administering to said human an effective amount of the compound of claim 1, or a pharmaceutically acceptable salt thereof.

33. A method for improving mucus penetration of therapeutic agents comprising administering an effective amount of the compound of claim 1 and a second therapeutic agent.

34. The method of claim 33, wherein the second therapeutic agent is an osmolyte, a sodium channel blocker, a secretogogue, a bronchodilator, an anti-infective, an anti-inflammatory, or a gene carrier.

35. A method for decreasing mucosal inflammation comprising administering an effective amount of the compound of claim 1.

36. A method for decreasing mucosal oxygen free radicals comprising administering an effective amount of the compound of claim 1.

* * * * *